US011450419B1

(12) United States Patent
Esman

(10) Patent No.: US 11,450,419 B1
(45) Date of Patent: Sep. 20, 2022

(54) MEDICATION SECURITY AND HEALTHCARE PRIVACY SYSTEMS

(71) Applicant: Splunk Inc., San Francisco, CA (US)

(72) Inventor: Gleb Esman, San Mateo, CA (US)

(73) Assignee: Splunk Inc., San Francisco, CA (US)

(*) Notice: Subject to any disclaimer, the term of this patent is extended or adjusted under 35 U.S.C. 154(b) by 156 days.

(21) Appl. No.: 16/399,610

(22) Filed: Apr. 30, 2019

(51) Int. Cl.
    G16H 20/13    (2018.01)
    G06F 3/04842  (2022.01)
    G06F 3/0482   (2013.01)

(52) U.S. Cl.
    CPC ........... G16H 20/13 (2018.01); G06F 3/0482 (2013.01); G06F 3/04842 (2013.01)

(58) Field of Classification Search
    CPC .................... G06Q 50/22–24; G16H 20/13
    See application file for complete search history.

(56) References Cited

U.S. PATENT DOCUMENTS

| | | | | |
|---|---|---|---|---|
| 2011/0161108 A1* | 6/2011 | Miller | ............... | G06Q 10/10 705/3 |
| 2013/0006652 A1* | 1/2013 | Vahlberg | ............... | G16H 20/10 705/2 |
| 2013/0070090 A1* | 3/2013 | Bufalini | ............... | G16H 20/13 348/143 |
| 2017/0109497 A1* | 4/2017 | Tribble | ............... | G06F 16/9535 |
| 2018/0039736 A1* | 2/2018 | Williams | ............... | G16H 40/20 |
| 2019/0307647 A1* | 10/2019 | Greenspan | ........... | A61B 5/4833 |
| 2020/0073742 A1* | 3/2020 | Arora | ............... | G01C 21/20 |

OTHER PUBLICATIONS

Traffic Anomaly Detection Using K-Means Clustering; 2007 (Year: 2007).*
Drug diversion and impaired health workers; The Joint Commission; Apr. 2019 (Year: 2019).*
ASHP Guidelines on Safe Use of Automated Dispensing Devices; American Society of Health-System Pharmacists; 2010 (Year: 2010).*
Outlier Detection Using enhanced K-means Clustering Algorithm and Weight Based Center Approach; Manoharan et al.; Apr. 2016 (Year: 2016).*

* cited by examiner

*Primary Examiner* — John A Pauls
(74) *Attorney, Agent, or Firm* — Nicholson De Vos Webster & Elliott LLP

(57) ABSTRACT

Medication security and healthcare privacy analytics systems are described that enable users to search for and process stored healthcare environment data. The medication security and healthcare privacy analytics systems receive and correlate data from a plurality of data sources, including medication dispensing systems, healthcare employee records, and patient records, including user behavior or interaction data with the foregoing data sources. The medication security and healthcare privacy analytics systems include graphical user interfaces (GUIs) that enable users to select elements to filter the processed healthcare environment data and generate visualizations of filtered datasets. The visualizations are created using datasets generated by clustering algorithms and can indicate those users from a plurality of users whose interactions with various systems are anomalous (e.g., indicative of unexpected or non-customary user behavior).

30 Claims, 52 Drawing Sheets

| Time 2935 | Host 2936 | Source 2937 | Source Type 2938 | Event 2939 |
|---|---|---|---|---|
| 10/10/2000 1:55 p.m. | www1 | access.log | access_combined | 127.0.0.1 - - frank [10/Oct/2000:13:55:36-0700] "GET/apache.gif HTTP/1.0" 200 2326 0.0947 |
| 10/10/2000 1:56 p.m. | www2 | access.log | access_combined | 127.0.0.1 - - bob [10/Oct/2000:13:56:36-0700] "GET/mickey_mouse.gif HTTP/1.0" 200 2980 0.0899 |
| 10/10/2000 1:57 p.m. | www2 | access.log | access_combined | 127.0.0.1 - - carlos [10/Oct/2000:13:57:36-0700] "GET/donald_duck.gif HTTP/1.0" 200 2900 0.0857 |
| 10/10/2000 1:58 p.m. | www2 | error.log | apache_error | [Sunday Oct 10 1:58:33 2010] [error] [client 127.10.1.1.015] File does not exist: /home/reba/public_html/images/daffy_duck.gif |

Similar Drugs Access Analysis — 3402

Start Menu ▾ Search ▾ Splunk System ▾ Analyze ▾

Select timeframe:
Between Date-times ▾   Hide Filters

Reset Dashboard

Edit | Export ▾

3400

3404

| _time ◆ | drug_name_short ◆ | patient_id ◆ | user_id ◆ | user_first_name ◆ | user_last_name ◆ | user_department ◆ | user_title ◆ | transaction_subtype ◆ | transaction_type ◆ | seq ◆ | c1 ◆ | c2 ◆ | c3 ◆ |
|---|---|---|---|---|---|---|---|---|---|---|---|---|---|
| 2019-01-17 15:10:12 | ACETAMINOPHEN | Patient_01 | User_01 | John | Doe | Nur - Amb Surg | Registered Nurse | I | I-UN | | | 2 | 1 |
| 2019-01-17 15:09:09 | ACETAMINOPHEN-OXYCODONE | Patient_02 | User_02 | Jane | Doe | Nur - Amb Surg | Registered Nurse | I | I-UN | | | 1 | 2 |
| 2019-02-08 16:12:05 | ACETAMINOPHEN | Patient_03 | User_03 | Joe | Doe | Nur - Amb Surg | Registered Nurse | I | I-UN | | | 2 | 1 |
| 2019-02-08 16:11:54 | ACETAMINOPHEN-OXYCODONE | Patient_04 | User_04 | Jim | Doe | Nur - Amb Surg | Registered Nurse | I | I-UN | | | 1 | 2 |
| 2018-12-09 08:18:29 | ACETAMINOPHEN-OXYCODONE | Patient_05 | User_05 | Jay | Doe | Nur - Crit ER | Registered Nurse | I | I-UN | | | 2 | 1 |
| 2018-12-09 08:18:07 | ACETAMINOPHEN | Patient_06 | User_06 | John | Smith | Nur - Crit ER | Registered Nurse | I | I-UN | | | 1 | 2 |
| 2018-12-17 01:07:58 | ACETAMINOPHEN-OXYCODONE | Patient_07 | User_07 | Jane | Smith | Nur - Crit ER | Registered Nurse | I | I-UN | | | 2 | 1 |
| 2018-12-17 01:07:18 | ACETAMINOPHEN | Patient_08 | User_08 | Joe | Smith | Nur - Crit ER | Registered Nurse | I | I-UN | | | 1 | 2 |
| 2019-01-09 17:51:20 | ACETAMINOPHEN | Patient_09 | User_09 | Jim | Smith | Nursing-4A Surgery | Registered Nurse | I | I-UN | | | 2 | 1 |

FIG. 35

Start Menu   Search   Splunk System ▼   Analyze ▼

Unaccounted Narcotic Removals — 3502

Select timeframe:
Jan 8 through 10, 2019 ▼ | Hide Filters

Reset Dashboard

| # | time_range ⬍ | users_removed ⬍ | drugs ⬍ | patient_id ⬍ | patient_id_local ⬍ | unaccounted_for ⬍ | drugs_removed ⬍ | drugs_administered ⬍ |
|---|---|---|---|---|---|---|---|---|
| 1 | 2019-01-10 17:22:50 - 2019-01-11 00:49:50 | User_01, Anesthesiology, Graduate Staff NUR-2S Neuro ICU, Staff Nurse | HYDROMORPHONE MORPHINE REMIFENTANIL | Patient_01 | Patient_01 | 4 | 5 | 1 |
| 2 | 2019-01-10 22:11:31 - 2019-01-11 02:04:01 | User_02, NUR-8N Surgical SDU, Staff Nurse Pharmacy, Pharmacist | FENTANYL | Patient_02 | Patient_02 | 3 | 3 | 0 |
| 3 | 2019-01-10 22:07:26 - 2019-01-10 22:39:47 | User_03, NUR-8N Surgical SDU, Staff Nurse Pharmacy, Pharmacist | MORPHINE OXYCODONE | Patient_03 | Patient_03 | 2 | 3 | 1 |
| 4 | 2019-01-11 01:30:51 - 2019-01-11 01:43:21 | User_04, Anesthesiology, Nurse Anesthetist | FENTANYL MORPHINE | Patient_04 | Patient_04 | 2 | 2 | 0 |
| 5 | 2019-01-10 19:58:18 - 2019-01-11 00:25:00 | User_05, Anesthesiology, Nurse Anesthetist | FENTANYL HYDROMORPHONE REMIFENTANIL | Patient_05 | Patient_05 | 2 | 3 | 1 |

3500

3504

Edit | Export ▼

FIG. 36

Unjustified Narcotics Administration — 3600
Painkillers/Narcotics administered to the patients with claimed pain score of 2 — 3602

Start Menu | Search | Splunk System ▼ | Analyze ▼
Edit | Export ▼

Select timeframe: Last 7 days ▼ | Hide Filters

Reset Dashboard

| # | user_id ⇅ | times ⇅ | user_department ⇅ | user_title ⇅ | user_first_name ⇅ | user_last_name ⇅ | drugs ⇅ | patients ⇅ | patient_pain_score ⇅ |
|---|---|---|---|---|---|---|---|---|---|
| 1 | User_01 | 9 | Electrophysiology | Staff Nurse | John | Doe | fentaNYL Citrate Inj +R+ | Patient_01 | 0, Numeric 0-10 scale |
| 2 | User_02 | 7 | Interventional Radiology Vascu | Clinical Nurse I | Jane | Doe | fentaNYL Citrate Inj +R+ | Patient_02 | 0, Numeric 0-10 scale |
| 3 | User_03 | 7 | Nur-8W Crit Burn (ICU) | Staff Nurse | Joe | Doe | HYDROmorphone Inj fentaNYL Citrate Inj +R+ oxyCODONE Immediate Release Tab | Patient_03, Patient_06 | 0, Numeric 0-10 scale |
| 4 | User_04 | 6 | Nsg 6N | Registered Nurse | Jim | Doe | HYDROmorphone Inj HYDROmorphone Oral fentaNYL Patch | Patient_04 | 0 |
| 5 | User_05 | 5 | Nsg 3N | Registered Nurse | Jay | Doe | HYDROmorphone 20 mg/ 100 mL NS For PCA NB Morphine Sulfate Inj oxyCODONE Immediate Release Tab oxyCODONE/ Acetaminophen 5/325 mg Tab (Percocet) | Patient_05, Patient_07, Patient_08 | 0 |

FIG. 44B

MEDICATION SECURITY AND HEALTHCARE PRIVACY SYSTEMS

RELATED APPLICATIONS

Any and all applications for which a foreign or domestic priority claim is identified in the Application Data Sheet as filed with the present application are incorporated by reference under 37 CFR 1.57 and made a part of this specification.

FIELD

At least one embodiment of the present disclosure pertains to one or more tools for facilitating searching and analyzing large sets of data to locate data of interest.

BACKGROUND

Information technology (IT) environments can include diverse types of data systems that store large amounts of diverse data types generated by numerous devices. For example, a big data ecosystem may include databases such as MySQL and Oracle databases, cloud computing services such as Amazon web services (AWS), and other data systems that store passively or actively generated data, including machine-generated data ("machine data"). The machine data can include performance data, diagnostic data, or any other data that can be analyzed to diagnose equipment performance problems, monitor user interactions, and to derive other insights.

The large amount and diversity of data systems containing large amounts of structured, semi-structured, and unstructured data relevant to any search query can be massive, and continues to grow rapidly. This technological evolution can give rise to various challenges in relation to managing, understanding and effectively utilizing the data. To reduce the potentially vast amount of data that may be generated, some data systems pre-process data based on anticipated data analysis needs. In particular, specified data items may be extracted from the generated data and stored in a data system to facilitate efficient retrieval and analysis of those data items at a later time. At least some of the remainder of the generated data is typically discarded during pre-processing.

However, storing massive quantities of minimally processed or unprocessed data (collectively and individually referred to as "raw data") for later retrieval and analysis is becoming increasingly more feasible as storage capacity becomes more inexpensive and plentiful. In general, storing raw data and performing analysis on that data later can provide greater flexibility because it enables an analyst to analyze all of the generated data instead of only a fraction of it.

Although the availability of vastly greater amounts of diverse data on diverse data systems provides opportunities to derive new insights, it also gives rise to technical challenges to search and analyze the data. Tools exist that allow an analyst to search data systems separately and collect results over a network for the analyst to derive insights in a piecemeal manner. However, UI tools that allow analysts to quickly search and analyze large set of raw machine data to visually identify data subsets of interest, particularly via straightforward and easy-to-understand sets of tools and search functionality do not exist.

BRIEF DESCRIPTION OF THE DRAWINGS

The present disclosure is illustrated by way of example, and not limitation, in the figures of the accompanying drawings, in which like reference numerals indicate similar elements.

FIG. 29C provides a visual representation of the manner in which a pipelined search language or query operates, in accordance with example embodiments.

FIG. 34 illustrates an example graphical user interface of a medication security analytics application displaying user behavior information of accesses of similar medications in accordance with the disclosed embodiments.

FIG. 35 illustrates an example graphical user interface of a medication security analytics application displaying unaccounted narcotic removals in accordance with the disclosed embodiments.

FIG. 36 illustrates an example graphical user interface of a medication security analytics application displaying unjustified narcotics administration in accordance with the disclosed embodiments.

FIG. 43 is a table of sample data from a medication dispensing system according to some embodiments.

FIGS. 44A-B are tables of sample data from an electronic health records system according to some embodiments.

DETAILED DESCRIPTION

Figure 1:
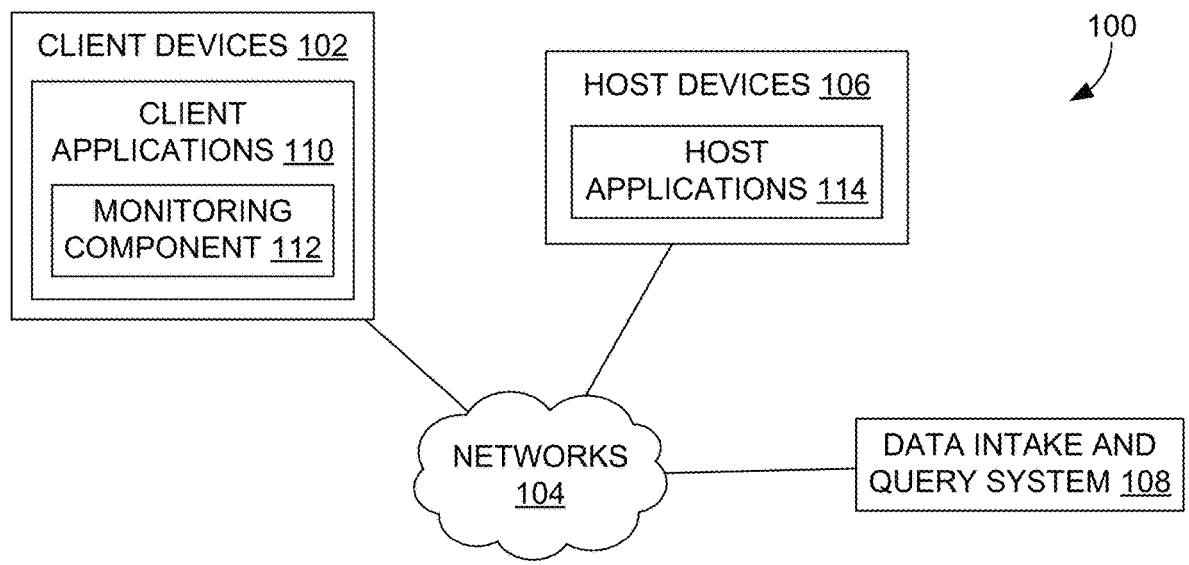
FIG. 1 is a block diagram of an example networked computer environment, in accordance with example embodiments.

Embodiments are described herein according to the following outline:
  1.0. General Overview
  2.0. Operating Environment
    2.1. Host Devices
    2.2. Client Devices
    2.3. Client Device Applications
    2.4. Data Intake and Query System Overview
  3.0. Data Intake and Query System Architecture
    3.1. Gateway
    3.2. Intake System
    3.2.1. Forwarder
    3.2.2. Data Retrieval Subsystem
    3.2.3. Ingestion Buffer
    3.2.4. Streaming Data Processors
    3.3. Indexing System
      3.3.1. Indexing System Manager
      3.3.2. Indexing Nodes
        3.3.2.1. Indexing Node Manager
        3.3.2.2. Partition Manager
        3.3.2.3. Indexer and Data Store
      3.3.3. Bucket Manager
    3.4. Query System
      3.4.1. Query System Manager
      3.4.2. Search Head
        3.4.2.1. Search Master
        3.4.2.2. Search Manager
      3.4.3. Search Nodes 3.4.4. Cache Manager
   3.4.5. Search Node Monitor and Catalog
3.5. Common Storage
3.6. Data Store Catalog
   3.7. Query Acceleration Data Store
   3.8. Metadata Catalog
      3.8.1. Dataset Association Records
      3.8.2. Dataset Configurations
      3.8.3. Rules Configurations
4.0. Data Intake and Query System Functions
4.1. Ingestion
   4.1.1. Publication to Intake Topic(s)
   4.1.2. Transmission to Streaming Data Processors
   4.1.3. Messages Processing
   4.1.4. Transmission to Subscribers
   4.1.5. Data Resiliency and Security
   4.1.6. Message Processing Algorithm
4.2. Indexing
   4.2.1. Containerized Indexing Nodes
   4.2.2. Moving Buckets to Common Storage
   4.2.3. Updating Location Marker in Ingestion Buffer
   4.2.4. Merging Buckets
4.3. Querying
   4.3.1. Containerized Search Nodes
   4.3.2. Identifying Buckets for Search Nodes for Query
   4.3.3. Identifying Buckets for Query Execution
   4.3.4. Identifying Search Nodes for Query Execution
   4.3.5. Hashing Bucket Identifiers for Query Execution
   4.3.6. Obtaining Data for Query Execution
   4.3.7. Caching Search Results
4.4. Querying Using Metadata Catalog
   4.4.1. Metadata Catalog Data Flow
   4.4.2. Example Metadata Catalog Processing
   4.4.3. Metadata Catalog Flows
4.5. Data Ingestion, Indexing, and Storage Flow
   4.5.1. Input
   4.5.2. Parsing
   4.5.3. Indexing
4.6. Query Processing Flow
4.7. Pipelined Search Language
4.8. Field Extraction
5.0. Medication Security and Healthcare Privacy Analytics Applications
   5.1. Medication Security Analytics Interfaces
   5.2. Healthcare Privacy Analytics Interfaces
1.0. General Overview Modern data centers and other computing environments can comprise anywhere from a few host computer systems to thousands of systems configured to process data, service requests from remote clients, and perform numerous other computational tasks. During operation, various components within these computing environments often generate significant volumes of machine data. Machine data is any data produced by a machine or component in an information technology (IT) environment and that reflects activity in the IT environment. For example, machine data can be raw machine data that is generated by various components in IT environments, such as servers, sensors, routers, mobile devices, Internet of Things (IoT) devices, etc. Machine data can include system logs, network packet data, sensor data, application program data, error logs, stack traces, system performance data, etc. In general, machine data can also include performance data, diagnostic information, and many other types of data that can be analyzed to diagnose performance problems, monitor user interactions, and to derive other insights.

A number of tools are available to analyze machine data. In order to reduce the size of the potentially vast amount of machine data that may be generated, many of these tools typically pre-process the data based on anticipated data-analysis needs. For example, pre-specified data items may be extracted from the machine data and stored in a database to facilitate efficient retrieval and analysis of those data items at search time. However, the rest of the machine data typically is not saved and is discarded during pre-processing. As storage capacity becomes progressively cheaper and more plentiful, there are fewer incentives to discard these portions of machine data and many reasons to retain more of the data.

This plentiful storage capacity is presently making it feasible to store massive quantities of minimally processed machine data for later retrieval and analysis. In general, storing minimally processed machine data and performing analysis operations at search time can provide greater flexibility because it enables an analyst to search all of the machine data, instead of searching only a pre-specified set of data items. This may enable an analyst to investigate different aspects of the machine data that previously were unavailable for analysis.

However, analyzing and searching massive quantities of machine data presents a number of challenges. For example, a data center, servers, or network appliances may generate many different types and formats of machine data (e.g., system logs, network packet data (e.g., wire data, etc.), sensor data, application program data, error logs, stack traces, system performance data, operating system data, virtualization data, etc.) from thousands of different components, which can collectively be very time-consuming to analyze. In another example, mobile devices may generate large amounts of information relating to data accesses, application performance, operating system performance, network performance, etc. There can be millions of mobile devices that report these types of information.

These challenges can be addressed by using an event-based data intake and query system, such as the SPLUNK® ENTERPRISE system developed by Splunk Inc. of San Francisco, Calif. The SPLUNK® ENTERPRISE system is the leading platform for providing real-time operational intelligence that enables organizations to collect, index, and search machine data from various websites, applications, servers, networks, and mobile devices that power their businesses. The data intake and query system is particularly useful for analyzing data which is commonly found in system log files, network data, and other data input sources. Although many of the techniques described herein are explained with reference to a data intake and query system similar to the SPLUNK® ENTERPRISE system, these techniques are also applicable to other types of data systems.

In the data intake and query system, machine data are collected and stored as "events". An event comprises a portion of machine data and is associated with a specific point in time. The portion of machine data may reflect activity in an IT environment and may be produced by a component of that IT environment, where the events may be searched to provide insight into the IT environment, thereby improving the performance of components in the IT environment. Events may be derived from "time series data," where the time series data comprises a sequence of data points (e.g., performance measurements from a computer system, etc.) that are associated with successive points in time. In general, each event has a portion of machine data that is associated with a timestamp that is derived from the portion of machine data in the event. A timestamp of an event may be determined through interpolation between temporally proximate events having known timestamps or may be determined based on other configurable rules for associating timestamps with events.

In some instances, machine data can have a predefined format, where data items with specific data formats are stored at predefined locations in the data. For example, the machine data may include data associated with fields in a database table. In other instances, machine data may not have a predefined format (e.g., may not be at fixed, predefined locations), but may have repeatable (e.g., non-random) patterns. This means that some machine data can comprise various data items of different data types that may be stored at different locations within the data. For example, when the data source is an operating system log, an event can include one or more lines from the operating system log containing machine data that includes different types of performance and diagnostic information associated with a specific point in time (e.g., a timestamp).

Examples of components which may generate machine data from which events can be derived include, but are not limited to, web servers, application servers, databases, firewalls, routers, operating systems, and software applications that execute on computer systems, mobile devices, sensors, Internet of Things (IoT) devices, etc. The machine data generated by such data sources can include, for example and without limitation, server log files, activity log files, configuration files, messages, network packet data, performance measurements, sensor measurements, etc.

The data intake and query system uses a flexible schema to specify how to extract information from events. A flexible schema may be developed and redefined as needed. Note that a flexible schema may be applied to events "on the fly," when it is needed (e.g., at search time, index time, ingestion time, etc.). When the schema is not applied to events until search time, the schema may be referred to as a "late-binding schema."

During operation, the data intake and query system receives machine data from any type and number of sources (e.g., one or more system logs, streams of network packet data, sensor data, application program data, error logs, stack traces, system performance data, etc.). The system parses the machine data to produce events each having a portion of machine data associated with a timestamp. The system stores the events in a data store. The system enables users to run queries against the stored events to, for example, retrieve events that meet criteria specified in a query, such as criteria indicating certain keywords or having specific values in defined fields. As used herein, the term "field" refers to a location in the machine data of an event containing one or more values for a specific data item. A field may be referenced by a field name associated with the field. As will be described in more detail herein, a field is defined by an extraction rule (e.g., a regular expression) that derives one or more values or a sub-portion of text from the portion of machine data in each event to produce a value for the field for that event. The set of values produced are semantically-related (such as IP address), even though the machine data in each event may be in different formats (e.g., semantically-related values may be in different positions in the events derived from different sources).

As described above, the system stores the events in a data store. The events stored in the data store are field-searchable, where field-searchable herein refers to the ability to search the machine data (e.g., the raw machine data) of an event based on a field specified in search criteria. For example, a search having criteria that specifies a field name "UserID" may cause the system to field-search the machine data of events to identify events that have the field name "UserID." In another example, a search having criteria that specifies a field name "UserID" with a corresponding field value "12345" may cause the system to field-search the machine data of events to identify events having that field-value pair (e.g., field name "UserID" with a corresponding field value of "12345"). Events are field-searchable using one or more configuration files associated with the events. Each configuration file includes one or more field names, where each field name is associated with a corresponding extraction rule and a set of events to which that extraction rule applies. The set of events to which an extraction rule applies may be identified by metadata associated with the set of events. For example, an extraction rule may apply to a set of events that are each associated with a particular host, source, or source type. When events are to be searched based on a particular field name specified in a search, the system uses one or more configuration files to determine whether there is an extraction rule for that particular field name that applies to each event that falls within the criteria of the search. If so, the event is considered as part of the search results (and additional processing may be performed on that event based on criteria specified in the search). If not, the next event is similarly analyzed, and so on.

As noted above, the data intake and query system utilizes a late-binding schema while performing queries on events. One aspect of a late-binding schema is applying extraction rules to events to extract values for specific fields during search time. More specifically, the extraction rule for a field can include one or more instructions that specify how to extract a value for the field from an event. An extraction rule can generally include any type of instruction for extracting values from events. In some cases, an extraction rule comprises a regular expression, where a sequence of characters form a search pattern. An extraction rule comprising a regular expression is referred to herein as a regex rule. The system applies a regex rule to an event to extract values for a field associated with the regex rule, where the values are extracted by searching the event for the sequence of characters defined in the regex rule.

In the data intake and query system, a field extractor may be configured to automatically generate extraction rules for certain fields in the events when the events are being created, indexed, or stored, or possibly at a later time. Alternatively, a user may manually define extraction rules for fields using a variety of techniques. In contrast to a conventional schema for a database system, a late-binding schema is not defined at data ingestion time. Instead, the late-binding schema can be developed on an ongoing basis until the time a query is actually executed. This means that extraction rules for the fields specified in a query may be provided in the query itself, or may be located during execution of the query. Hence, as a user learns more about the data in the events, the user can continue to refine the late-binding schema by adding new fields, deleting fields, or modifying the field extraction rules for use the next time the schema is used by the system. Because the data intake and query system maintains the underlying machine data and uses a late-binding schema for searching the machine data, it enables a user to continue investigating and learn valuable insights about the machine data.

In some embodiments, a common field name may be used to reference two or more fields containing equivalent and/or similar data items, even though the fields may be associated with different types of events that possibly have different data formats and different extraction rules. By enabling a common field name to be used to identify equivalent and/or similar fields from different types of events generated by disparate data sources, the system facilitates use of a "common information model" (CIM) across the disparate data sources (further discussed with respect to FIG. 31A).

In some embodiments, the configuration files and/or extraction rules described above can be stored in a catalog, such as a metadata catalog. In certain embodiments, the content of the extraction rules can be stored as rules or actions in the metadata catalog. For example, the identification of the data to which the extraction rule applies can be referred to a rule and the processing of the data can be referred to as an action.

2.0. Operating Environment

FIG. 1 is a block diagram of an example networked computer environment 100, in accordance with example embodiments. It will be understood that FIG. 1 represents one example of a networked computer system and other embodiments may use different arrangements.

The networked computer environment 100 comprises one or more computing devices. These one or more computing devices comprise any combination of hardware and software configured to implement the various logical components described herein. For example, the one or more computing devices may include one or more memories that store instructions for implementing the various components described herein, one or more hardware processors configured to execute the instructions stored in the one or more memories, and various data repositories in the one or more memories for storing data structures utilized and manipulated by the various components.

In some embodiments, one or more client devices 102 are coupled to one or more host devices 106 and a data intake and query system 108 via one or more networks 104. Networks 104 broadly represent one or more LANs, WANs, cellular networks (e.g., LTE, HSPA, 3G, and other cellular technologies), and/or networks using any of wired, wireless, terrestrial microwave, or satellite links, and may include the public Internet.

2.1. Host Devices

In the illustrated embodiment, a networked computer environment 100 includes one or more host devices 106. Host devices 106 may broadly include any number of computers, virtual machine instances, and/or data centers that are configured to host or execute one or more instances of host applications 114. In general, a host device 106 may be involved, directly or indirectly, in processing requests received from client devices 102. Each host device 106 may comprise, for example, one or more of a network device, a web server, an application server, a database server, etc. A collection of host devices 106 may be configured to implement a network-based service. For example, a provider of a network-based service may configure one or more host devices 106 and host applications 114 (e.g., one or more web servers, application servers, database servers, etc.) to collectively implement the network-based application.

In general, client devices 102 communicate with one or more host applications 114 to exchange information. The communication between a client device 102 and a host application 114 may, for example, be based on the Hypertext Transfer Protocol (HTTP) or any other network protocol. Content delivered from the host application 114 to a client device 102 may include, for example, HTML documents, media content, etc. The communication between a client device 102 and host application 114 may include sending various requests and receiving data packets. For example, in general, a client device 102 or application running on a client device may initiate communication with a host application 114 by making a request for a specific resource (e.g., based on an HTTP request), and the application server may respond with the requested content stored in one or more response packets.

In the illustrated embodiment, one or more of host applications 114 may generate various types of performance data during operation, including event logs, network data, sensor data, and other types of machine data. For example, a host application 114 comprising a web server may generate one or more web server logs in which details of interactions between the web server and any number of client devices 102 is recorded. As another example, a host device 106 comprising a router may generate one or more router logs that record information related to network traffic managed by the router. As yet another example, a host application 114 comprising a database server may generate one or more logs that record information related to requests sent from other host applications 114 (e.g., web servers or application servers) for data managed by the database server.

2.2. Client Devices

Client devices 102 of FIG. 1 represent any computing device capable of interacting with one or more host devices 106 via a network 104. Examples of client devices 102 may include, without limitation, smart phones, tablet computers, handheld computers, wearable devices, laptop computers, desktop computers, servers, portable media players, gaming devices, and so forth. In general, a client device 102 can provide access to different content, for instance, content provided by one or more host devices 106, etc. Each client device 102 may comprise one or more client applications 110, described in more detail in a separate section hereinafter.

2.3. Client Device Applications

In some embodiments, each client device 102 may host or execute one or more client applications 110 that are capable of interacting with one or more host devices 106 via one or more networks 104. For instance, a client application 110 may be or comprise a web browser that a user may use to navigate to one or more websites or other resources provided by one or more host devices 106. As another example, a client application 110 may comprise a mobile application or "app." For example, an operator of a network-based service hosted by one or more host devices 106 may make available one or more mobile apps that enable users of client devices 102 to access various resources of the network-based service. As yet another example, client applications 110 may include background processes that perform various operations without direct interaction from a user. A client application 110 may include a "plug-in" or "extension" to another application, such as a web browser plug-in or extension.

In some embodiments, a client application 110 may include a monitoring component 112. At a high level, the monitoring component 112 comprises a software component or other logic that facilitates generating performance data related to a client device's operating state, including monitoring network traffic sent and received from the client device and collecting other device and/or application-specific information. Monitoring component 112 may be an integrated component of a client application 110, a plug-in, an extension, or any other type of add-on component. Monitoring component 112 may also be a stand-alone process.

In some embodiments, a monitoring component 112 may be created when a client application 110 is developed, for example, by an application developer using a software development kit (SDK). The SDK may include custom monitoring code that can be incorporated into the code implementing a client application 110. When the code is converted to an executable application, the custom code implementing the monitoring functionality can become part of the application itself.

In some embodiments, an SDK or other code for implementing the monitoring functionality may be offered by a provider of a data intake and query system, such as a system 108. In such cases, the provider of the system 108 can implement the custom code so that performance data generated by the monitoring functionality is sent to the system 108 to facilitate analysis of the performance data by a developer of the client application or other users.

In some embodiments, the custom monitoring code may be incorporated into the code of a client application 110 in a number of different ways, such as the insertion of one or more lines in the client application code that call or otherwise invoke the monitoring component 112. As such, a developer of a client application 110 can add one or more lines of code into the client application 110 to trigger the monitoring component 112 at desired points during execution of the application. Code that triggers the monitoring component may be referred to as a monitor trigger. For instance, a monitor trigger may be included at or near the beginning of the executable code of the client application 110 such that the monitoring component 112 is initiated or triggered as the application is launched, or included at other points in the code that correspond to various actions of the client application, such as sending a network request or displaying a particular interface.

In some embodiments, the monitoring component 112 may monitor one or more aspects of network traffic sent and/or received by a client application 110. For example, the monitoring component 112 may be configured to monitor data packets transmitted to and/or from one or more host applications 114. Incoming and/or outgoing data packets can be read or examined to identify network data contained within the packets, for example, and other aspects of data packets can be analyzed to determine a number of network performance statistics. Monitoring network traffic may enable information to be gathered particular to the network performance associated with a client application 110 or set of applications.

In some embodiments, network performance data refers to any type of data that indicates information about the network and/or network performance. Network performance data may include, for instance, a URL requested, a connection type (e.g., HTTP, HTTPS, etc.), a connection start time, a connection end time, an HTTP status code, request length, response length, request headers, response headers, connection status (e.g., completion, response time(s), failure, etc.), and the like. Upon obtaining network performance data indicating performance of the network, the network performance data can be transmitted to a data intake and query system 108 for analysis.

Upon developing a client application 110 that incorporates a monitoring component 112, the client application 110 can be distributed to client devices 102. Applications generally can be distributed to client devices 102 in any manner, or they can be pre-loaded. In some cases, the application may be distributed to a client device 102 via an application marketplace or other application distribution system. For instance, an application marketplace or other application distribution system might distribute the application to a client device based on a request from the client device to download the application.

Examples of functionality that enables monitoring performance of a client device are described in U.S. patent application Ser. No. 14/524,748, entitled "UTILIZING PACKET HEADERS TO MONITOR NETWORK TRAFFIC IN ASSOCIATION WITH A CLIENT DEVICE", filed on 27 Oct. 2014, and which is hereby incorporated by reference in its entirety for all purposes.

In some embodiments, the monitoring component 112 may also monitor and collect performance data related to one or more aspects of the operational state of a client application 110 and/or client device 102. For example, a monitoring component 112 may be configured to collect device performance information by monitoring one or more client device operations, or by making calls to an operating system and/or one or more other applications executing on a client device 102 for performance information. Device performance information may include, for instance, a current wireless signal strength of the device, a current connection type and network carrier, current memory performance information, a geographic location of the device, a device orientation, and any other information related to the operational state of the client device.

In some embodiments, the monitoring component 112 may also monitor and collect other device profile information including, for example, a type of client device, a manufacturer, and model of the device, versions of various software applications installed on the device, and so forth.

In general, a monitoring component 112 may be configured to generate performance data in response to a monitor trigger in the code of a client application 110 or other triggering application event, as described above, and to store the performance data in one or more data records. Each data record, for example, may include a collection of field-value pairs, each field-value pair storing a particular item of performance data in association with a field for the item. For example, a data record generated by a monitoring component 112 may include a "networkLatency" field (not shown in the Figure) in which a value is stored. This field indicates a network latency measurement associated with one or more network requests. The data record may include a "state" field to store a value indicating a state of a network connection, and so forth for any number of aspects of collected performance data.

2.4. Data Intake and Query System Overview

The data intake and query system 108 can process and store data received data from the data sources client devices 102 or host devices 106, and execute queries on the data in response to requests received from one or more computing devices. In some cases, the data intake and query system 108 can generate events from the received data and store the events in buckets in a common storage system. In response to received queries, the data intake and query system can assign one or more search nodes to search the buckets in the common storage.

In certain embodiments, the data intake and query system 108 can include various components that enable it to provide stateless services or enable it to recover from an unavailable or unresponsive component without data loss in a time efficient manner. For example, the data intake and query system 108 can store contextual information about its various components in a distributed way such that if one of the components becomes unresponsive or unavailable, the data intake and query system 108 can replace the unavailable component with a different component and provide the replacement component with the contextual information. In this way, the data intake and query system 108 can quickly recover from an unresponsive or unavailable component while reducing or eliminating the loss of data that was being processed by the unavailable component.

3.0. Data Intake and Query System Architecture

Figure 2:
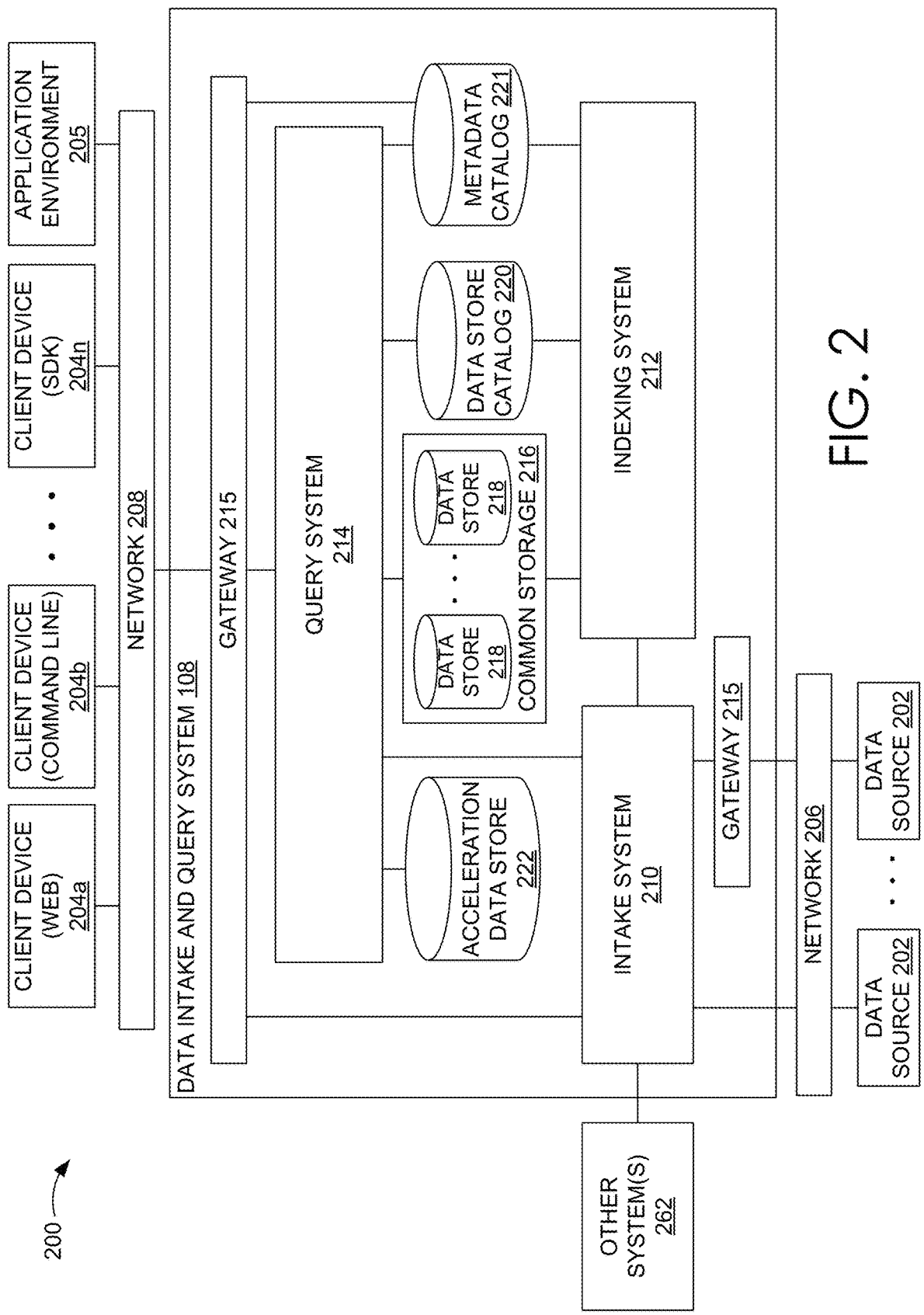
FIG. 2 is a block diagram of an example data intake and query system, in accordance with example embodiments.

FIG. 2 is a block diagram of an embodiment of a data processing environment 200. In the illustrated embodiment, the environment 200 includes data sources 202, client devices 204a, 204b . . . 204n (generically referred to as client device(s) 204), and an application environment 205, in communication with a data intake and query system 108 via networks 206, 208, respectively. The networks 206, 208 may be the same network, may correspond to the network 104, or may be different networks. Further, the networks 206, 208 may be implemented as one or more LANs, WANs, cellular networks, intranetworks, and/or internetworks using any of wired, wireless, terrestrial microwave, satellite links, etc., and may include the Internet.

Each data source 202 broadly represents a distinct source of data that can be consumed by the data intake and query system 108. Examples of data sources 202 include, without limitation, data files, directories of files, data sent over a network, event logs, registries, streaming data services (examples of which can include, by way of non-limiting example, Amazon's Simple Queue Service ("SQS") or Kinesis™ services, devices executing Apache Kafka™ software, or devices implementing the Message Queue Telemetry Transport (MQTT) protocol, Microsoft Azure EventHub, Google Cloud PubSub, devices implementing the Java Message Service (JMS) protocol, devices implementing the Advanced Message Queuing Protocol (AMQP)), performance metrics, cloud-based services (e.g., AWS, Microsoft Azure, Google Cloud, etc.), operating-system-level virtualization environments (e.g., Docker), container orchestration systems (e.g., Kubernetes), virtual machines using full virtualization or paravirtualization, or other virtualization technique or isolated execution environments.

As illustrated in FIG. 2, in some embodiments, the data sources 202 can communicate with the data to the intake system 210 via the network 206 without passing through the gateway 215. As a non-limiting example, if the intake system 210 receives the data from a data source 202 via a forwarder 302 (described in greater detail below), the intake system 210 may receive the data via the network 206 without going through the gateway 215. In certain embodiments, the data sources 202 can communicate the data to the intake system 210 via the network 206 using the gateway 215. As another non-limiting example, if the intake system 210 receives the data from a data source 202 via a HTTP intake point 322 (described in greater detail below), it may receive the data via the gateway 215. Accordingly, it will be understood that a variety of methods can be used to receive data from the data sources 202 via the network 206 or via the network 206 and the gateway 215.

The client devices 204 can be implemented using one or more computing devices in communication with the data intake and query system 108, and represent some of the different ways in which computing devices can submit queries to the data intake and query system 108. For example, the client device 204a is illustrated as communicating over an Internet (Web) protocol with the data intake and query system 108, the client device 204b is illustrated as communicating with the data intake and query system 108 via a command line interface, and the client device 204n is illustrated as communicating with the data intake and query system 108 via a software developer kit (SDK). However, it will be understood that the client devices 204 can communicate with and submit queries to the data intake and query system 108 in a variety of ways. For example, the client devices 204 can use one or more executable applications or programs from the application environment 205 to interface with the data intake and query system 108. The application environment 205 can include tools, software modules (e.g., computer executable instructions to perform a particular function), etc., to enable application developers to create computer executable applications to interface with the data intake and query system 108. For example, application developers can identify particular data that is of particular relevance to them. The application developers can use the application environment 205 to build a particular application to interface with the data intake and query system 108 to obtain the relevant data that they seek, process the relevant data, and display it in a manner that is consumable by a user. The applications developed using the application environment 205 can include their own backend services, middleware logic, front-end user interface, etc., and can provide facilities for ingesting use case specific data and interacting with that data.

As a non-limiting example, an application developed using the application environment 205 can include a custom web-user interface that may or may not leverage one or more UI components provided by the application environment 205. The application could include middle-ware business logic, on a middle-ware platform of the developer's choice. Furthermore, the applications implemented using the application environment 205 can be instantiated and execute in a different isolated execution environment. As a non-limiting example, in embodiments where the data intake and query system 108 is implemented in a kubernetes cluster, the applications developed using the application environment 205 can execute in a different kubernetes cluster (or other isolated execution environment system) and interact with the data intake and query system 108 via the gateway 215.

The data intake and query system 108 can process and store data received data from the data sources 202 and execute queries on the data in response to requests received from the client devices 204. In the illustrated embodiment, the data intake and query system 108 includes a gateway 209, an intake system 210, an indexing system 212, a query system 214, common storage 216 including one or more data stores 218, a data store catalog 220, and a query acceleration data store 222.

As will be described in greater detail herein, the gateway 215 can provide an interface between one or more components of the data intake and query system 108 and other systems or computing devices, such as, but not limited to, client devices 204, the application environment 205, one or more data sources 202, and/or other systems 262. In some embodiments, the gateway 215 can be implemented using an application programming interface (API). In certain embodiments, the gateway 215 can be implemented using a representational state transfer API (REST API).

As mentioned, the data intake and query system 108 can receive data from different sources 202. In some cases, the data sources 202 can be associated with different tenants or customers. Further, each tenant may be associated with one or more indexes, hosts, sources, sourcetypes, or users. For example, company ABC, Inc. can correspond to one tenant and company XYZ, Inc. can correspond to a different tenant. While the two companies may be unrelated, each company may have a main index and test index associated with it, as well as one or more data sources or systems (e.g., billing system, CRM system, etc.). The data intake and query system 108 can concurrently receive and process the data from the various systems and sources of ABC, Inc. and XYZ, Inc.

In certain cases, although the data from different tenants can be processed together or concurrently, the data intake and query system 108 can take steps to avoid combining or co-mingling data from the different tenants. For example, the data intake and query system 108 can assign a tenant identifier for each tenant and maintain a separation between the data using the tenant identifier. In some cases, the tenant identifier can be assigned to the data at the data sources 202, or can be assigned to the data by the data intake and query system 108 at ingest.

As will be described in greater detail herein, at least with reference to FIGS. 3A and 3B, the intake system 210 can receive data from the data sources 202, perform one or more preliminary processing operations on the data, and communicate the data to the indexing system 212, query system 214, or to other systems 262 (which may include, for example, data processing systems, telemetry systems, real-time analytics systems, data stores, databases, etc., any of which may be operated by an operator of the data intake and query system 108 or a third party). The intake system 210 can receive data from the data sources 202 in a variety of formats or structures. In some embodiments, the received data corresponds to raw machine data, structured or unstructured data, correlation data, data files, directories of files, data sent over a network, event logs, registries, messages published to streaming data sources, performance metrics, sensor data, image and video data, etc. The intake system 210 can process the data based on the form in which it is received. In some cases, the intake system 210 can utilize one or more rules to process data and to make the data available to downstream systems (e.g., the indexing system 212, query system 214, etc.). Illustratively, the intake system 210 can enrich the received data. For example, the intake system may add one or more fields to the data received from the data sources 202, such as fields denoting the host, source, sourcetype, index, or tenant associated with the incoming data. In certain embodiments, the intake system 210 can perform additional processing on the incoming data, such as transforming structured data into unstructured data (or vice versa), identifying timestamps associated with the data, removing extraneous data, parsing data, indexing data, separating data, categorizing data, routing data based on criteria relating to the data being routed, and/or performing other data transformations, etc.

As will be described in greater detail herein, at least with reference to FIG. 4, the indexing system 212 can process the data and store it, for example, in common storage 216. As part of processing the data, the indexing system can identify timestamps associated with the data, organize the data into buckets or time series buckets, convert editable buckets to non-editable buckets, store copies of the buckets in common storage 216, merge buckets, generate indexes of the data, etc. In addition, the indexing system 212 can update the data store catalog 220 with information related to the buckets (pre-merged or merged) or data that is stored in common storage 216, and can communicate with the intake system 210 about the status of the data storage.

As will be described in greater detail herein, at least with reference to FIG. 5, the query system 214 can receive queries that identify a set of data to be processed and a manner of processing the set of data from one or more client devices 204, process the queries to identify the set of data, and execute the query on the set of data. In some cases, as part of executing the query, the query system 214 can use the data store catalog 220 to identify the set of data to be processed or its location in common storage 216 and/or can retrieve data from common storage 216 or the query acceleration data store 222. In addition, in some embodiments, the query system 214 can store some or all of the query results in the query acceleration data store 222.

As mentioned and as will be described in greater detail below, the common storage 216 can be made up of one or more data stores 218 storing data that has been processed by the indexing system 212. The common storage 216 can be configured to provide high availability, highly resilient, low loss data storage. In some cases, to provide the high availability, highly resilient, low loss data storage, the common storage 216 can store multiple copies of the data in the same and different geographic locations and across different types of data stores (e.g., solid state, hard drive, tape, etc.). Further, as data is received at the common storage 216 it can be automatically replicated multiple times according to a replication factor to different data stores across the same and/or different geographic locations. In some embodiments, the common storage 216 can correspond to cloud storage, such as Amazon Simple Storage Service (S3) or Elastic Block Storage (EBS), Google Cloud Storage, Microsoft Azure Storage, etc.

In some embodiments, indexing system 212 can read to and write from the common storage 216. For example, the indexing system 212 can copy buckets of data from its local or shared data stores to the common storage 216. In certain embodiments, the query system 214 can read from, but cannot write to, the common storage 216. For example, the query system 214 can read the buckets of data stored in common storage 216 by the indexing system 212, but may not be able to copy buckets or other data to the common storage 216. In some embodiments, the intake system 210 does not have access to the common storage 216. However, in some embodiments, one or more components of the intake system 210 can write data to the common storage 216 that can be read by the indexing system 212.

As described herein, in some embodiments, data in the data intake and query system 108 (e.g., in the data stores of the indexers of the indexing system 212, common storage 216, or search nodes of the query system 214) can be stored in one or more time series buckets. Each bucket can include raw machine data associated with a time stamp and additional information about the data or bucket, such as, but not limited to, one or more filters, indexes (e.g., TSIDX, inverted indexes, keyword indexes, etc.), bucket summaries, etc. In some embodiments, the bucket data and information about the bucket data is stored in one or more files. For example, the raw machine data, filters, indexes, bucket summaries, etc. can be stored in respective files in or associated with a bucket. In certain cases, the group of files can be associated together to form the bucket.

The data store catalog 220 can store information about the data stored in common storage 216, such as, but not limited to an identifier for a set of data or buckets, a location of the set of data, tenants or indexes associated with the set of data, timing information about the data, etc. For example, in embodiments where the data in common storage 216 is stored as buckets, the data store catalog 220 can include a bucket identifier for the buckets in common storage 216, a location of or path to the bucket in common storage 216, a time range of the data in the bucket (e.g., range of time between the first-in-time event of the bucket and the last-in-time event of the bucket), a tenant identifier identifying a customer or computing device associated with the bucket, and/or an index (also referred to herein as a partition)

associated with the bucket, etc. In certain embodiments, the data intake and query system 108 includes multiple data store catalogs 220. For example, in some embodiments, the data intake and query system 108 can include a data store catalog 220 for each tenant (or group of tenants), each partition of each tenant (or group of indexes), etc. In some cases, the data intake and query system 108 can include a single data store catalog 220 that includes information about buckets associated with multiple or all of the tenants associated with the data intake and query system 108.

The indexing system 212 can update the data store catalog 220 as the indexing system 212 stores data in common storage 216. Furthermore, the indexing system 212 or other computing device associated with the data store catalog 220 can update the data store catalog 220 as the information in the common storage 216 changes (e.g., as buckets in common storage 216 are merged, deleted, etc.). In addition, as described herein, the query system 214 can use the data store catalog 220 to identify data to be searched or data that satisfies at least a portion of a query. In some embodiments, the query system 214 makes requests to and receives data from the data store catalog 220 using an application programming interface ("API").

As will be described in greater detail herein, at least with reference to FIGS. 6 and 22-27, the metadata catalog 221 can store information about datasets used or supported by the data intake and query system 108 and/or one or more rules that indicate which data in a dataset to process and how to process the data from the dataset. The information about the datasets can include configuration information, such as, but not limited to the type of the dataset, access and authorization information for the dataset, location information for the dataset, physical and logical names or other identifiers for the dataset, etc. The rules can indicate how different data of a dataset is to be processed and/or how to extract fields or field values from different data of a dataset.

The metadata catalog 221 can also include one or more dataset association records. The dataset association records can indicate how to refer to a particular dataset (e.g., a name or other identifier for the dataset) and/or identify associations or relationships between the particular dataset and one or more rules or other datasets. In some embodiments, a dataset association record can be similar to a namespace in that it can indicate a scope of one or more datasets and the manner in which to reference the one or more datasets. As a non-limiting example, one dataset association record can identify four datasets: a main index, a test index, a username collection, and a username lookup. The dataset association record can also identify one or more rules for one or more of the datasets. For example, one rule can indicate that for data with the sourcetype "foo" from the main index, multiple actions are to take place, such as, extracting a field value for a "UID" field, and using the username lookup to identify a username associated with the extracted "UID" field value. The actions of the rule can provide specific guidance as to how to extract the field value for the "UID" field from the sourcetype "foo" data in the main index and how to perform the lookup of the username.

As described herein, the query system 214 can use the metadata catalog 221 to, among other things, interpret dataset identifiers in a query, verify/authenticate a user's permissions and/or authorizations for different datasets, identify additional processing as part of the query, identify one or more datasets from which to retrieve data as part of the query (also referred to herein as dataset sources), determine how to extract data from datasets, identify configurations/definitions/dependencies to be used by search nodes to execute the query, etc.

In certain embodiments, the query system 214 can use the metadata catalog 221 to provide a stateless search service. For example, the query system 214 can use the metadata catalog 221 to dynamically determine the dataset configurations and rule configurations to be used to execute a query (also referred to herein as the query configuration parameters) and communicate the query configuration parameters to one or more search heads 504. If the query system 214 determines that an assigned search head becomes unavailable, the query system 214 can communicate the dynamically determined query configuration parameters (and query to be executed) to another search head 504 without data loss and/or with minimal time loss.

In some embodiments, the metadata catalog 221 can be implemented using a database system, such as, but not limited to, a relational database system (non-limiting commercial examples: DynamoDB, Aurora DB, etc.). In certain embodiments, the database system can include entries for the different datasets, rules, and/or dataset association records.

The query acceleration data store 222 can store the results or partial results of queries, or otherwise be used to accelerate queries. For example, if a user submits a query that has no end date, the system can query system 214 can store an initial set of results in the query acceleration data store 222. As additional query results are determined based on additional data, the additional results can be combined with the initial set of results, and so on. In this way, the query system 214 can avoid re-searching all of the data that may be responsive to the query and instead search the data that has not already been searched.

In some environments, a user of a data intake and query system 108 may install and configure, on computing devices owned and operated by the user, one or more software applications that implement some or all of these system components. For example, a user may install a software application on server computers owned by the user and configure each server to operate as one or more of intake system 210, indexing system 212, query system 214, common storage 216, data store catalog 220, or query acceleration data store 222, etc. This arrangement generally may be referred to as an "on-premises" solution. That is, the system 108 is installed and operates on computing devices directly controlled by the user of the system. Some users may prefer an on-premises solution because it may provide a greater level of control over the configuration of certain aspects of the system (e.g., security, privacy, standards, controls, etc.). However, other users may instead prefer an arrangement in which the user is not directly responsible for providing and managing the computing devices upon which various components of system 108 operate.

In certain embodiments, one or more of the components of a data intake and query system 108 can be implemented in a remote distributed computing system. In this context, a remote distributed computing system or cloud-based service can refer to a service hosted by one more computing resources that are accessible to end users over a network, for example, by using a web browser or other application on a client device to interface with the remote computing resources. For example, a service provider may provide a data intake and query system 108 by managing computing resources configured to implement various aspects of the system (e.g., intake system 210, indexing system 212, query system 214, common storage 216, data store catalog 220, or query acceleration data store 222, etc.) and by providing access to the system to end users via a network. Typically, a user may pay a subscription or other fee to use such a service. Each subscribing user of the cloud-based service may be provided with an account that enables the user to configure a customized cloud-based system based on the user's preferences. When implemented as a cloud-based service, various components of the system 108 can be implemented using containerization or operating-system-level virtualization, or other virtualization technique. For example, one or more components of the intake system 210, indexing system 212, or query system 214 can be implemented as separate software containers or container instances. Each container instance can have certain resources (e.g., memory, processor, etc.) of the underlying host computing system assigned to it, but may share the same operating system and may use the operating system's system call interface. Each container may provide an isolated execution environment on the host system, such as by providing a memory space of the host system that is logically isolated from memory space of other containers. Further, each container may run the same or different computer applications concurrently or separately, and may interact with each other. Although reference is made herein to containerization and container instances, it will be understood that other virtualization techniques can be used. For example, the components can be implemented using virtual machines using full virtualization or paravirtualization, etc. Thus, where reference is made to "containerized" components, it should be understood that such components may additionally or alternatively be implemented in other isolated execution environments, such as a virtual machine environment.

3.1. Gateway

As described herein, the gateway 215 can provide an interface between one or more components of the data intake and query system 108 (non-limiting examples: one or more components of the intake system 210, one or more components of the indexing system 212, one or more components of the query system 214, common storage 216, the data store catalog 220, the metadata catalog 221 and/or the acceleration data store 222), and other systems or computing devices, such as, but not limited to, client devices 204, the application environment 205, one or more data sources 202, and/or other systems 262 (not illustrated). In some cases, one or more components of the data intake and query system 108 can include their own API. In such embodiments, the gateway 215 can communicate with the API of a component of the data intake and query system 108. Accordingly, the gateway 215 can translate requests received from an external device into a command understood by the API of the specific component of the data intake and query system 108. In this way, the gateway 215 can provide an interface between external devices and the API of the devices of the data intake and query system 108.

In some embodiments, the gateway 215 can be implemented using an API, such as the REST API. In some such embodiments, the client devices 204 can communicate via one or more commands, such as GET, PUT, etc. However, it will be understood that the gateway 215 can be implemented in a variety of ways to enable the external devices and/or systems to interface with one or more components of the data intake and query system 108.

In certain embodiments, a client device 204 can provide control parameters to the data intake and query system 108 via the gateway 215. As a non-limiting example, using the gateway 215, a client device 204 can provide instructions to the metadata catalog 221, the intake system 210, indexing system 212, and/or the query system 214. For example, using the gateway 215, a client device 204 can instruct the metadata catalog 221 to add/modify/delete a dataset association record, dataset, rule, configuration, and/or action, etc. As another example, using the gateway 215, a client device 204 can provide a query to the query system 214 and receive results. As yet another example, using the gateway 215, a client device 204 can provide processing instructions to the intake system 210. As yet another example, using the gateway 215, one or more data sources 202 can provide data to the intake system 210. In some embodiments, one or more components of the intake system 210 can receive data from a data source 202 via the gateway 215. For example, in some embodiments, data received by the HTTP intake point 322 and/or custom intake points 332 (described in greater detail below) of the intake system 210 can be received via the gateway 215.

As mentioned, upon receipt of a request or command from an external device, the gateway 215 can determine the component of the data intake and query system 108 (or service) to handle the request. Furthermore, in some cases, the gateway 215 can translate the request or command received from the external device into a command that can be interpreted by the component of the data intake and query system 108.

In some cases, the gateway 215 can expose a subset of components and/or a limited number of features of the components of the data intake and query system 108 to the external devices. For example, for the query system 214, the gateway 215, may expose the ability to submit queries but may not expose the ability to configure certain components of the query system 214, such as the search node catalog 510, search node monitor 508, and/or cache manager 516 (described in greater detail below). However, it will be understood that the gateway 215 can be configured to expose fewer or more components and/or fewer or more functions for the different components as desired. By limiting the components or commands for the components of the data intake and query system, the gateway 215 can provide improved security for the data intake and query system 108.

In addition to limiting the components or functions made available to external systems, the gateway 215 can provide authentication and/or authorization functionality. For example, with each request or command received by a client device and/or data source 202, the gateway 215 can authenticate the computing device from which the requester command was received and/or determine whether the requester has sufficient permissions or authorizations to make the request. In this way, the Gateway 215 can provide additional security for the data intake and query system 108.

3.2. Intake System

As detailed below, data may be ingested at the data intake and query system 108 through an intake system 210 configured to conduct preliminary processing on the data, and make the data available to downstream systems or components, such as the indexing system 212, query system 214, third party systems, etc.

Figure 3A:
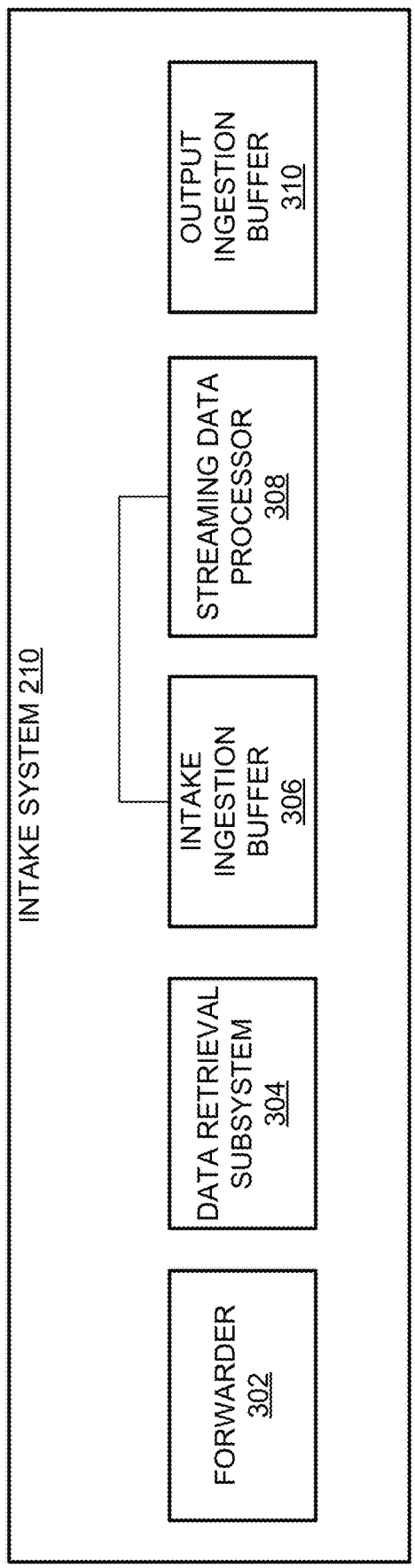
FIG. 3A is a block diagram of one embodiment an intake system.

One example configuration of an intake system 210 is shown in FIG. 3A. As shown in FIG. 3A, the intake system 210 includes a forwarder 302, a data retrieval subsystem 304, an intake ingestion buffer 306, a streaming data processor 308, and an output ingestion buffer 310. As described in detail below, the components of the intake system 210 may be configured to process data according to a streaming data model, such that data ingested into the data intake and query system 108 is processed rapidly (e.g., within seconds or minutes of initial reception at the intake system 210) and made available to downstream systems or components. The initial processing of the intake system 210 may include search or analysis of the data ingested into the intake system 210. For example, the initial processing can transform data ingested into the intake system 210 sufficiently, for example, for the data to be searched by a query system 214, thus enabling "real-time" searching for data on the data intake and query system 108 (e.g., without requiring indexing of the data). Various additional and alternative uses for data processed by the intake system 210 are described below.

Although shown as separate components, the forwarder 302, data retrieval subsystem 304, intake ingestion buffer 306, streaming data processors 308, and output ingestion buffer 310, in various embodiments, may reside on the same machine or be distributed across multiple machines in any combination. In one embodiment, any or all of the components of the intake system can be implemented using one or more computing devices as distinct computing devices or as one or more container instances or virtual machines across one or more computing devices. It will be appreciated by those skilled in the art that the intake system 210 may have more of fewer components than are illustrated in FIGS. 3A and 3B. In addition, the intake system 210 could include various web services and/or peer-to-peer network configurations or inter container communication network provided by an associated container instantiation or orchestration platform. Thus, the intake system 210 of FIGS. 3A and 3B should be taken as illustrative. For example, in some embodiments, components of the intake system 210, such as the ingestion buffers 306 and 310 and/or the streaming data processors 308, may be executed by one more virtual machines implemented in a hosted computing environment. A hosted computing environment may include one or more rapidly provisioned and released computing resources, which computing resources may include computing, networking and/or storage devices. A hosted computing environment may also be referred to as a cloud computing environment. Accordingly, the hosted computing environment can include any proprietary or open source extensible computing technology, such as Apache Flink or Apache Spark, to enable fast or on-demand horizontal compute capacity scaling of the streaming data processor 308.

In some embodiments, some or all of the elements of the intake system 210 (e.g., forwarder 302, data retrieval subsystem 304, intake ingestion buffer 306, streaming data processors 308, and output ingestion buffer 310, etc.) may reside on one or more computing devices, such as servers, which may be communicatively coupled with each other and with the data sources 202, query system 214, indexing system 212, or other components. In other embodiments, some or all of the elements of the intake system 210 may be implemented as worker nodes as disclosed in U.S. patent application Ser. Nos. 15/665,159, 15/665,148, 15/665,187, 15/665,248, 15/665,197, 15/665,279, 15/665,302, and 15/665,339, each of which is incorporated by reference herein in its entirety (hereinafter referred to as "the Incorporated Applications").

As noted above, the intake system 210 can function to conduct preliminary processing of data ingested at the data intake and query system 108. As such, the intake system 210 illustratively includes a forwarder 302 that obtains data from a data source 202 and transmits the data to a data retrieval subsystem 304. The data retrieval subsystem 304 may be configured to convert or otherwise format data provided by the forwarder 302 into an appropriate format for inclusion at the intake ingestion buffer and transmit the message to the intake ingestion buffer 306 for processing. Thereafter, a streaming data processor 308 may obtain data from the intake ingestion buffer 306, process the data according to one or more rules, and republish the data to either the intake ingestion buffer 306 (e.g., for additional processing) or to the output ingestion buffer 310, such that the data is made available to downstream components or systems. In this manner, the intake system 210 may repeatedly or iteratively process data according to any of a variety of rules, such that the data is formatted for use on the data intake and query system 108 or any other system. As discussed below, the intake system 210 may be configured to conduct such processing rapidly (e.g., in "real-time" with little or no perceptible delay), while ensuring resiliency of the data.

3.2.1. Forwarder

The forwarder 302 can include or be executed on a computing device configured to obtain data from a data source 202 and transmit the data to the data retrieval subsystem 304. In some implementations, the forwarder 302 can be installed on a computing device associated with the data source 202 or directly on the data source 202. While a single forwarder 302 is illustratively shown in FIG. 3A, the intake system 210 may include a number of different forwarders 302. Each forwarder 302 may illustratively be associated with a different data source 202. A forwarder 302 initially may receive the data as a raw data stream generated by the data source 202. For example, a forwarder 302 may receive a data stream from a log file generated by an application server, from a stream of network data from a network device, or from any other source of data. In some embodiments, a forwarder 302 receives the raw data and may segment the data stream into "blocks", possibly of a uniform data size, to facilitate subsequent processing steps. The forwarder 302 may additionally or alternatively modify data received, prior to forwarding the data to the data retrieval subsystem 304. Illustratively, the forwarder 202 may "tag" metadata for each data block, such as by specifying a source, source type, or host associated with the data, or by appending one or more timestamp or time ranges to each data block.

In some embodiments, a forwarder 302 may comprise a service accessible to data sources 202 via a network 206. For example, one type of forwarder 302 may be capable of consuming vast amounts of real-time data from a potentially large number of data sources 202. The forwarder 302 may, for example, comprise a computing device which implements multiple data pipelines or "queues" to handle forwarding of network data to data retrieval subsystems 304.

3.2.2. Data Retrieval Subsystem

The data retrieval subsystem 304 illustratively corresponds to a computing device which obtains data (e.g., from the forwarder 302), and transforms the data into a format suitable for publication on the intake ingestion buffer 306. Illustratively, where the forwarder 302 segments input data into discrete blocks, the data retrieval subsystem 304 may generate a message for each block, and publish the message to the intake ingestion buffer 306. Generation of a message for each block may include, for example, formatting the data of the message in accordance with the requirements of a streaming data system implementing the intake ingestion buffer 306, the requirements of which may vary according to the streaming data system. In one embodiment, the intake ingestion buffer 306 formats messages according to the protocol buffers method of serializing structured data. Thus, the intake ingestion buffer 306 may be configured to convert data from an input format into a protocol buffer format. Where a forwarder 302 does not segment input data into discrete blocks, the data retrieval subsystem 304 may itself segment the data. Similarly, the data retrieval subsystem 304 may append metadata to the input data, such as a source, source type, or host associated with the data.

Generation of the message may include "tagging" the message with various information, which may be included as metadata for the data provided by the forwarder 302, and determining a "topic" for the message, under which the message should be published to the intake ingestion buffer 306. In general, the "topic" of a message may reflect a categorization of the message on a streaming data system. Illustratively, each topic may be associated with a logically distinct queue of messages, such that a downstream device or system may "subscribe" to the topic in order to be provided with messages published to the topic on the streaming data system.

In one embodiment, the data retrieval subsystem 304 may obtain a set of topic rules (e.g., provided by a user of the data intake and query system 108 or based on automatic inspection or identification of the various upstream and downstream components of the data intake and query system 108) that determine a topic for a message as a function of the received data or metadata regarding the received data. For example, the topic of a message may be determined as a function of the data source 202 from which the data stems. After generation of a message based on input data, the data retrieval subsystem can publish the message to the intake ingestion buffer 306 under the determined topic.

While the data retrieval subsystem 304 is depicted in FIG. 3A as obtaining data from the forwarder 302, the data retrieval subsystem 304 may additionally or alternatively obtain data from other sources, such as from the data source 202 and/or via the gateway 209. In some instances, the data retrieval subsystem 304 may be implemented as a plurality of intake points, each functioning to obtain data from one or more corresponding data sources (e.g., the forwarder 302, data sources 202, or any other data source), generate messages corresponding to the data, determine topics to which the messages should be published, and to publish the messages to one or more topics of the intake ingestion buffer 306.

Figure 3B:
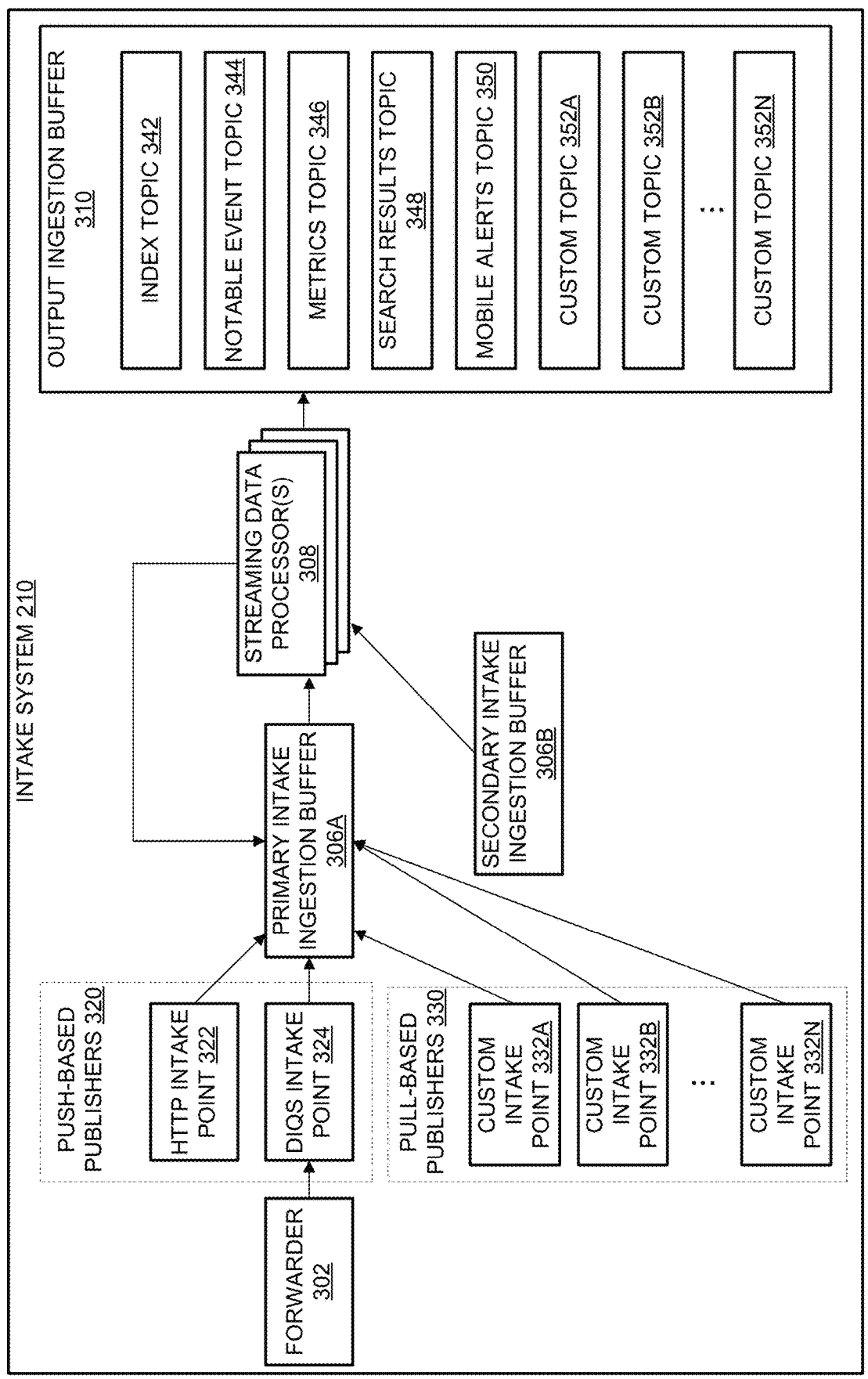
FIG. 3B is a block diagram of another embodiment of an intake system.

One illustrative set of intake points implementing the data retrieval subsystem 304 is shown in FIG. 3B. Specifically, as shown in FIG. 3B, the data retrieval subsystem 304 of FIG. 3A may be implemented as a set of push-based publishers 320 or a set of pull-based publishers 330. The illustrative push-based publishers 320 operate on a "push" model, such that messages are generated at the push-based publishers 320 and transmitted to an intake ingestion buffer 306 (shown in FIG. 3B as primary and secondary intake ingestion buffers 306A and 306B, which are discussed in more detail below). As will be appreciated by one skilled in the art, "push" data transmission models generally correspond to models in which a data source determines when data should be transmitted to a data target. A variety of mechanisms exist to provide "push" functionality, including "true push" mechanisms (e.g., where a data source independently initiates transmission of information) and "emulated push" mechanisms, such as "long polling" (a mechanism whereby a data target initiates a connection with a data source, but allows the data source to determine within a timeframe when data is to be transmitted to the data source).

As shown in FIG. 3B, the push-based publishers 320 illustratively include an HTTP intake point 322 and a data intake and query system (DIQS) intake point 324. The HTTP intake point 322 can include a computing device configured to obtain HTTP-based data (e.g., as JavaScript Object Notation, or JSON messages) to format the HTTP-based data as a message, to determine a topic for the message (e.g., based on fields within the HTTP-based data), and to publish the message to the primary intake ingestion buffer 306A. Similarly, the DIQS intake point 324 can be configured to obtain data from a forwarder 324, to format the forwarder data as a message, to determine a topic for the message, and to publish the message to the primary intake ingestion buffer 306A. In this manner, the DIQS intake point 324 can function in a similar manner to the operations described with respect to the data retrieval subsystem 304 of FIG. 3A.

In addition to the push-based publishers 320, one or more pull-based publishers 330 may be used to implement the data retrieval subsystem 304. The pull-based publishers 330 may function on a "pull" model, whereby a data target (e.g., the primary intake ingestion buffer 306A) functions to continuously or periodically (e.g., each n seconds) query the pull-based publishers 330 for new messages to be placed on the primary intake ingestion buffer 306A. In some instances, development of pull-based systems may require less coordination of functionality between a pull-based publisher 330 and the primary intake ingestion buffer 306A. Thus, for example, pull-based publishers 330 may be more readily developed by third parties (e.g., other than a developer of the data intake a query system 108), and enable the data intake and query system 108 to ingest data associated with third party data sources 202. Accordingly, FIG. 3B includes a set of custom intake points 332A through 332N, each of which functions to obtain data from a third-party data source 202, format the data as a message for inclusion in the primary intake ingestion buffer 306A, determine a topic for the message, and make the message available to the primary intake ingestion buffer 306A in response to a request (a "pull") for such messages.

While the pull-based publishers 330 are illustratively described as developed by third parties, push-based publishers 320 may also in some instances be developed by third parties. Additionally or alternatively, pull-based publishers may be developed by the developer of the data intake and query system 108. To facilitate integration of systems potentially developed by disparate entities, the primary intake ingestion buffer 306A may provide an API through which an intake point may publish messages to the primary intake ingestion buffer 306A. Illustratively, the API may enable an intake point to "push" messages to the primary intake ingestion buffer 306A, or request that the primary intake ingestion buffer 306A "pull" messages from the intake point. Similarly, the streaming data processors 308 may provide an API through which ingestions buffers may register with the streaming data processors 308 to facilitate pre-processing of messages on the ingestion buffers, and the output ingestion buffer 310 may provide an API through which the streaming data processors 308 may publish messages or through which downstream devices or systems may subscribe to topics on the output ingestion buffer 310. Furthermore, any one or more of the intake points 322 through 332N may provide an API through which data sources 202 may submit data to the intake points. Thus, any one or more of the components of FIGS. 3A and 3B may be made available via APIs to enable integration of systems potentially provided by disparate parties.

The specific configuration of publishers 320 and 330 shown in FIG. 3B is intended to be illustrative in nature. For example, the specific number and configuration of intake points may vary according to embodiments of the present application. In some instances, one or more components of the intake system 210 may be omitted. For example, a data source 202 may in some embodiments publish messages to an intake ingestion buffer 306, and thus an intake point 332 may be unnecessary. Other configurations of the intake system 210 are possible.

3.2.3. Ingestion Buffer

The intake system 210 is illustratively configured to ensure message resiliency, such that data is persisted in the event of failures within the intake system 310. Specifically, the intake system 210 may utilize one or more ingestion buffers, which operate to resiliently maintain data received at the intake system 210 until the data is acknowledged by downstream systems or components. In one embodiment, resiliency is provided at the intake system 210 by use of ingestion buffers that operate according to a publish-subscribe ("pub-sub") message model. In accordance with the pub-sub model, data ingested into the data intake and query system 108 may be atomized as "messages," each of which is categorized into one or more "topics." An ingestion buffer can maintain a queue for each such topic, and enable devices to "subscribe" to a given topic. As messages are published to the topic, the ingestion buffer can function to transmit the messages to each subscriber, and ensure message resiliency until at least each subscriber has acknowledged receipt of the message (e.g., at which point the ingestion buffer may delete the message). In this manner, the ingestion buffer may function as a "broker" within the pub-sub model. A variety of techniques to ensure resiliency at a pub-sub broker are known in the art, and thus will not be described in detail herein. In one embodiment, an ingestion buffer is implemented by a streaming data source. As noted above, examples of streaming data sources include (but are not limited to) Amazon's Simple Queue Service ("SQS") or Kinesis™ services, devices executing Apache Kafka™ software, or devices implementing the Message Queue Telemetry Transport (MQTT) protocol. Any one or more of these example streaming data sources may be utilized to implement an ingestion buffer in accordance with embodiments of the present disclosure.

With reference to FIG. 3A, the intake system 210 may include at least two logical ingestion buffers: an intake ingestion buffer 306 and an output ingestion buffer 310. As noted above, the intake ingestion buffer 306 can be configured to receive messages from the data retrieval subsystem 304 and resiliently store the message. The intake ingestion buffer 306 can further be configured to transmit the message to the streaming data processors 308 for processing. As further described below, the streaming data processors 308 can be configured with one or more data transformation rules to transform the messages, and republish the messages to one or both of the intake ingestion buffer 306 and the output ingestion buffer 310. The output ingestion buffer 310, in turn, may make the messages available to various subscribers to the output ingestion buffer 310, which subscribers may include the query system 214, the indexing system 212, or other third-party devices (e.g., client devices 102, host devices 106, etc.).

Both the input ingestion buffer 306 and output ingestion buffer 310 may be implemented on a streaming data source, as noted above. In one embodiment, the intake ingestion buffer 306 operates to maintain source-oriented topics, such as topics for each data source 202 from which data is obtained, while the output ingestion buffer operates to maintain content-oriented topics, such as topics to which the data of an individual message pertains. As discussed in more detail below, the streaming data processors 308 can be configured to transform messages from the intake ingestion buffer 306 (e.g., arranged according to source-oriented topics) and publish the transformed messages to the output ingestion buffer 310 (e.g., arranged according to content-oriented topics). In some instances, the streaming data processors 308 may additionally or alternatively republish transformed messages to the intake ingestion buffer 306, enabling iterative or repeated processing of the data within the message by the streaming data processors 308.

While shown in FIG. 3A as distinct, these ingestion buffers 306 and 310 may be implemented as a common ingestion buffer. However, use of distinct ingestion buffers may be beneficial, for example, where a geographic region in which data is received differs from a region in which the data is desired. For example, use of distinct ingestion buffers may beneficially allow the intake ingestion buffer 306 to operate in a first geographic region associated with a first set of data privacy restrictions, while the output ingestion buffer 308 operates in a second geographic region associated with a second set of data privacy restrictions. In this manner, the intake system 210 can be configured to comply with all relevant data privacy restrictions, ensuring privacy of data processed at the data intake and query system 108.

Moreover, either or both of the ingestion buffers 306 and 310 may be implemented across multiple distinct devices, as either a single or multiple ingestion buffers. Illustratively, as shown in FIG. 3B, the intake system 210 may include both a primary intake ingestion buffer 306A and a secondary intake ingestion buffer 306B. The primary intake ingestion buffer 306A is illustratively configured to obtain messages from the data retrieval subsystem 304 (e.g., implemented as a set of intake points 322 through 332N). The secondary intake ingestion buffer 306B is illustratively configured to provide an additional set of messages (e.g., from other data sources 202). In one embodiment, the primary intake ingestion buffer 306A is provided by an administrator or developer of the data intake and query system 108, while the secondary intake ingestion buffer 306B is a user-supplied ingestion buffer (e.g., implemented externally to the data intake and query system 108).

As noted above, an intake ingestion buffer 306 may in some embodiments categorize messages according to source-oriented topics (e.g., denoting a data source 202 from which the message was obtained). In other embodiments, an intake ingestion buffer 306 may in some embodiments categorize messages according to intake-oriented topics (e.g., denoting the intake point from which the message was obtained). The number and variety of such topics may vary, and thus are not shown in FIG. 3B. In one embodiment, the intake ingestion buffer 306 maintains only a single topic (e.g., all data to be ingested at the data intake and query system 108).

The output ingestion buffer 310 may in one embodiment categorize messages according to content-centric topics (e.g., determined based on the content of a message). Additionally or alternatively, the output ingestion buffer 310 may categorize messages according to consumer-centric topics (e.g., topics intended to store messages for consumption by a downstream device or system). An illustrative number of topics are shown in FIG. 3B, as topics 342 through 352N. Each topic may correspond to a queue of messages (e.g., in accordance with the pub-sub model) relevant to the corresponding topic. As described in more detail below, the streaming data processors 308 may be configured to process messages from the intake ingestion buffer 306 and determine which topics of the topics 342 through 352N into which to place the messages. For example, the index topic 342 may be intended to store messages holding data that should be consumed and indexed by the indexing system 212. The notable event topic 344 may be intended to store messages holding data that indicates a notable event at a data source 202 (e.g., the occurrence of an error or other notable event). The metrics topic 346 may be intended to store messages holding metrics data for data sources 202. The search results topic 348 may be intended to store messages holding data responsive to a search query. The mobile alerts topic 350 may be intended to store messages holding data for which an end user has requested alerts on a mobile device. A variety of custom topics 352A through 352N may be intended to hold data relevant to end-user-created topics.

As will be described below, by application of message transformation rules at the streaming data processors 308, the intake system 210 may divide and categorize messages from the intake ingestion buffer 306, partitioning the message into output topics relevant to a specific downstream consumer. In this manner, specific portions of data input to the data intake and query system 108 may be "divided out" and handled separately, enabling different types of data to be handled differently, and potentially at different speeds. Illustratively, the index topic 342 may be configured to include all or substantially all data included in the intake ingestion buffer 306. Given the volume of data, there may be a significant delay (e.g., minutes or hours) before a downstream consumer (e.g., the indexing system 212) processes a message in the index topic 342. Thus, for example, searching data processed by the indexing system 212 may incur significant delay.

Conversely, the search results topic 348 may be configured to hold only messages corresponding to data relevant to a current query. Illustratively, on receiving a query from a client device 204, the query system 214 may transmit to the intake system 210 a rule that detects, within messages from the intake ingestion buffer 306A, data potentially relevant to the query. The streaming data processors 308 may republish these messages within the search results topic 348, and the query system 214 may subscribe to the search results topic 348 in order to obtain the data within the messages. In this manner, the query system 214 can "bypass" the indexing system 212 and avoid delay that may be caused by that system, thus enabling faster (and potentially real time) display of search results.

While shown in FIGS. 3A and 3B as a single output ingestion buffer 310, the intake system 210 may in some instances utilize multiple output ingestion buffers 310.

3.2.4. Streaming Data Processors

As noted above, the streaming data processors 308 may apply one or more rules to process messages from the intake ingestion buffer 306A into messages on the output ingestion buffer 310. These rules may be specified, for example, by an end user of the data intake and query system 108 or may be automatically generated by the data intake and query system 108 (e.g., in response to a user query).

Illustratively, each rule may correspond to a set of selection criteria indicating messages to which the rule applies, as well as one or more processing sub-rules indicating an action to be taken by the streaming data processors 308 with respect to the message. The selection criteria may include any number or combination of criteria based on the data included within a message or metadata of the message (e.g., a topic to which the message is published). In one embodiment, the selection criteria are formatted in the same manner or similarly to extraction rules, discussed in more detail below. For example, selection criteria may include regular expressions that derive one or more values or a sub-portion of text from the portion of machine data in each message to produce a value for the field for that message. When a message is located within the intake ingestion buffer 308 that matches the selection criteria, the streaming data processors 308 may apply the processing rules to the message. Processing sub-rules may indicate, for example, a topic of the output ingestion buffer 310 into which the message should be placed. Processing sub-rules may further indicate transformations, such as field or unit normalization operations, to be performed on the message. Illustratively, a transformation may include modifying data within the message, such as altering a format in which the data is conveyed (e.g., converting millisecond timestamps values to microsecond timestamp values, converting imperial units to metric units, etc.), or supplementing the data with additional information (e.g., appending an error descriptor to an error code). In some instances, the streaming data processors 308 may be in communication with one or more external data stores (the locations of which may be specified within a rule) that provide information used to supplement or enrich messages processed at the streaming data processors 308. For example, a specific rule may include selection criteria identifying an error code within a message of the primary ingestion buffer 306A, and specifying that when the error code is detected within a message, that the streaming data processors 308 should conduct a lookup in an external data source (e.g., a database) to retrieve the human-readable descriptor for that error code, and inject the descriptor into the message. In this manner, rules may be used to process, transform, or enrich messages.

The streaming data processors 308 may include a set of computing devices configured to process messages from the intake ingestion buffer 306 at a speed commensurate with a rate at which messages are placed into the intake ingestion buffer 306. In one embodiment, the number of streaming data processors 308 used to process messages may vary based on a number of messages on the intake ingestion buffer 306 awaiting processing. Thus, as additional messages are queued into the intake ingestion buffer 306, the number of streaming data processors 308 may be increased to ensure that such messages are rapidly processed. In some instances, the streaming data processors 308 may be extensible on a per topic basis. Thus, individual devices implementing the streaming data processors 308 may subscribe to different topics on the intake ingestion buffer 306, and the number of devices subscribed to an individual topic may vary according to a rate of publication of messages to that topic (e.g., as measured by a backlog of messages in the topic). In this way, the intake system 210 can support ingestion of massive amounts of data from numerous data sources 202.

In some embodiments, an intake system may comprise a service accessible to client devices 102 and host devices 106 via a network 104. For example, one type of forwarder may be capable of consuming vast amounts of real-time data from a potentially large number of client devices 102 and/or host devices 106. The forwarder may, for example, comprise a computing device which implements multiple data pipelines or "queues" to handle forwarding of network data to indexers. A forwarder may also perform many of the functions that are performed by an indexer. For example, a forwarder may perform keyword extractions on raw data or parse raw data to create events. A forwarder may generate time stamps for events. Additionally or alternatively, a forwarder may perform routing of events to indexers. Data store 212 may contain events derived from machine data from a variety of sources all pertaining to the same component in an IT environment, and this data may be produced by the machine in question or by other components in the IT environment.

3.3. Indexing System

Figure 4:
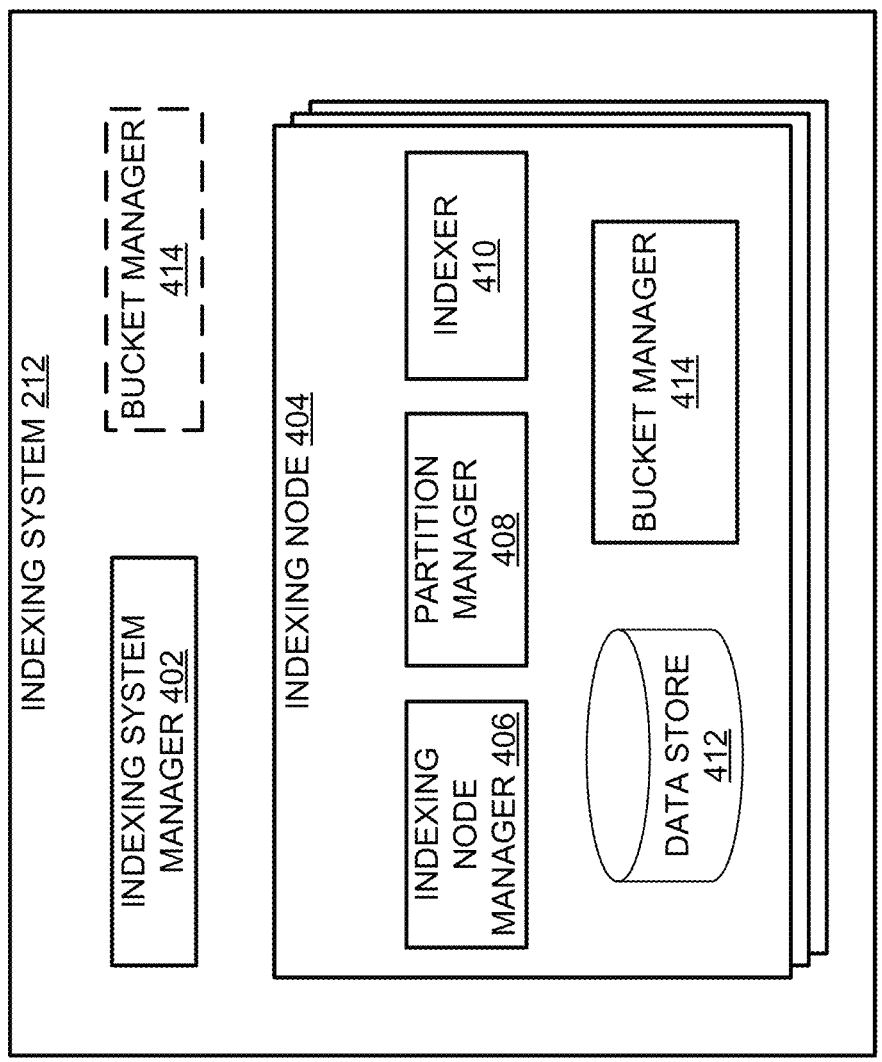
FIG. 4 is a block diagram illustrating an embodiment of an indexing system of the data intake and query system.

FIG. 4 is a block diagram illustrating an embodiment of an indexing system 212 of the data intake and query system 108. The indexing system 212 can receive, process, and store data from multiple data sources 202, which may be associated with different tenants, users, etc. Using the received data, the indexing system can generate events that include a portion of machine data associated with a timestamp and store the events in buckets based on one or more of the timestamps, tenants, indexes, etc., associated with the data. Moreover, the indexing system 212 can include various components that enable it to provide a stateless indexing service, or indexing service that is able to rapidly recover without data loss if one or more components of the indexing system 212 become unresponsive or unavailable.

In the illustrated embodiment, the indexing system 212 includes an indexing system manager 402 and one or more indexing nodes 404. However, it will be understood that the indexing system 212 can include fewer or more components. For example, in some embodiments, the common storage 216 or data store catalog 220 can form part of the indexing system 212, etc.

As described herein, each of the components of the indexing system 212 can be implemented using one or more computing devices as distinct computing devices or as one or more container instances or virtual machines across one or more computing devices. For example, in some embodiments, the indexing system manager 402 and indexing nodes 404 can be implemented as distinct computing devices with separate hardware, memory, and processors. In certain embodiments, the indexing system manager 402 and indexing nodes 404 can be implemented on the same or across different computing devices as distinct container instances, with each container having access to a subset of the resources of a host computing device (e.g., a subset of the memory or processing time of the processors of the host computing device), but sharing a similar operating system. In some cases, the components can be implemented as distinct virtual machines across one or more computing devices, where each virtual machine can have its own unshared operating system but shares the underlying hardware with other virtual machines on the same host computing device.

3.3.1. Indexing System Manager

As mentioned, the indexing system manager 402 can monitor and manage the indexing nodes 404, and can be implemented as a distinct computing device, virtual machine, container, container of a pod, or a process or thread associated with a container. In certain embodiments, the indexing system 212 can include one indexing system manager 402 to manage all indexing nodes 404 of the indexing system 212. In some embodiments, the indexing system 212 can include multiple indexing system managers 402. For example, an indexing system manager 402 can be instantiated for each computing device (or group of computing devices) configured as a host computing device for multiple indexing nodes 404.

The indexing system manager 402 can handle resource management, creation/destruction of indexing nodes 404, high availability, load balancing, application upgrades/rollbacks, logging and monitoring, storage, networking, service discovery, and performance and scalability, and otherwise handle containerization management of the containers of the indexing system 212. In certain embodiments, the indexing system manager 402 can be implemented using Kubernetes or Swarm.

In some cases, the indexing system manager 402 can monitor the available resources of a host computing device and request additional resources in a shared resource environment, based on workload of the indexing nodes 404 or create, destroy, or reassign indexing nodes 404 based on workload. Further, the indexing system manager 402 system can assign indexing nodes 404 to handle data streams based on workload, system resources, etc.

3.3.2. Indexing Nodes

The indexing nodes 404 can include one or more components to implement various functions of the indexing system 212. In the illustrated embodiment, the indexing node 404 includes an indexing node manager 406, partition manager 408, indexer 410, data store 412, and bucket manager 414. As described herein, the indexing nodes 404 can be implemented on separate computing devices or as containers or virtual machines in a virtualization environment.

In some embodiments, an indexing node 404, and can be implemented as a distinct computing device, virtual machine, container, container of a pod, or a process or thread associated with a container, or using multiple-related containers. In certain embodiments, such as in a Kubernetes deployment, each indexing node 404 can be implemented as a separate container or pod. For example, one or more of the components of the indexing node 404 can be implemented as different containers of a single pod, e.g., on a containerization platform, such as Docker, the one or more components of the indexing node can be implemented as different Docker containers managed by synchronization platforms such as Kubernetes or Swarm. Accordingly, reference to a containerized indexing node 404 can refer to the indexing node 404 as being a single container or as one or more components of the indexing node 404 being implemented as different, related containers or virtual machines.

3.3.2.1. Indexing Node Manager

The indexing node manager 406 can manage the processing of the various streams or partitions of data by the indexing node 404, and can be implemented as a distinct computing device, virtual machine, container, container of a pod, or a process or thread associated with a container. For example, in certain embodiments, as partitions or data streams are assigned to the indexing node 404, the indexing node manager 406 can generate one or more partition manager(s) 408 to manage each partition or data stream. In some cases, the indexing node manager 406 generates a separate partition manager 408 for each partition or shard that is processed by the indexing node 404. In certain embodiments, the partition can correspond to a topic of a data stream of the ingestion buffer 310. Each topic can be configured in a variety of ways. For example, in some embodiments, a topic may correspond to data from a particular data source 202, tenant, index/partition, or sourcetype. In this way, in certain embodiments, the indexing system 212 can discriminate between data from different sources or associated with different tenants, or indexes/partitions. For example, the indexing system 212 can assign more indexing nodes 404 to process data from one topic (associated with one tenant) than another topic (associated with another tenant), or store the data from one topic more frequently to common storage 216 than the data from a different topic, etc.

In some embodiments, the indexing node manager 406 monitors the various shards of data being processed by the indexing node 404 and the read pointers or location markers for those shards. In some embodiments, the indexing node manager 406 stores the read pointers or location marker in one or more data stores, such as but not limited to, common storage 216, DynamoDB, S3, or another type of storage system, shared storage system, or networked storage system, etc. As the indexing node 404 processes the data and the markers for the shards are updated by the intake system 210, the indexing node manager 406 can be updated to reflect the changes to the read pointers or location markers. In this way, if a particular partition manager 408 becomes unresponsive or unavailable, the indexing node manager 406 can generate a new partition manager 408 to handle the data stream without losing context of what data is to be read from the intake system 210. Accordingly, in some embodiments, by using the ingestion buffer 310 and tracking the location of the location markers in the shards of the ingestion buffer, the indexing system 212 can aid in providing a stateless indexing service.

In some embodiments, the indexing node manager 406 is implemented as a background process, or daemon, on the indexing node 404 and the partition manager(s) 408 are implemented as threads, copies, or forks of the background process. In some cases, an indexing node manager 406 can copy itself, or fork, to create a partition manager 408 or cause a template process to copy itself, or fork, to create each new partition manager 408, etc. This may be done for multithreading efficiency or for other reasons related to containerization and efficiency of managing indexers 410. In certain embodiments, the indexing node manager 406 generates a new process for each partition manager 408. In some cases, by generating a new process for each partition manager 408, the indexing node manager 408 can support multiple language implementations and be language agnostic. For example, the indexing node manager 408 can generate a process for a partition manager 408 in python and create a second process for a partition manager 408 in golang, etc.

3.3.2.2. Partition Manager

As mentioned, the partition manager(s) 408 can manage the processing of one or more of the partitions or shards of a data stream processed by an indexing node 404 or the indexer 410 of the indexing node 404, and can be implemented as a distinct computing device, virtual machine, container, container of a pod, or a process or thread associated with a container.

In some cases, managing the processing of a partition or shard can include, but it not limited to, communicating data from a particular shard to the indexer 410 for processing, monitoring the indexer 410 and the size of the data being processed by the indexer 410, instructing the indexer 410 to move the data to common storage 216, and reporting the storage of the data to the intake system 210. For a particular shard or partition of data from the intake system 210, the indexing node manager 406 can assign a particular partition manager 408. The partition manager 408 for that partition can receive the data from the intake system 210 and forward or communicate that data to the indexer 410 for processing.

In some embodiments, the partition manager 408 receives data from a pub-sub messaging system, such as the ingestion buffer 310. As described herein, the ingestion buffer 310 can have one or more streams of data and one or more shards or partitions associated with each stream of data. Each stream of data can be separated into shards and/or other partitions or types of organization of data. In certain cases, each shard can include data from multiple tenants, indexes/partition, etc. In some cases, each shard can correspond to data associated with a particular tenant, index/partition, source, sourcetype, etc. Accordingly, the indexing system 212 can include a partition manager 408 for individual tenants, indexes/partitions, sources, sourcetypes, etc. In this way, the indexing system 212 can manage and process the data differently. For example, the indexing system 212 can assign more indexing nodes 404 to process data from one tenant than another tenant, or store buckets associated with one tenant or partition/index more frequently to common storage 216 than buckets associated with a different tenant or partition/index, etc.

Accordingly, in some embodiments, a partition manager 408 receives data from one or more of the shards or partitions of the ingestion buffer 310. The partition manager 408 can forward the data from the shard to the indexer 410 for processing. In some cases, the amount of data coming into a shard may exceed the shard's throughput. For example, 4 MB/s of data may be sent to an ingestion buffer 310 for a particular shard, but the ingestion buffer 310 may be able to process only 2 MB/s of data per shard. Accordingly, in some embodiments, the data in the shard can include a reference to a location in storage where the indexing system 212 can retrieve the data. For example, a reference pointer to data can be placed in the ingestion buffer 310 rather than putting the data itself into the ingestion buffer. The reference pointer can reference a chunk of data that is larger than the throughput of the ingestion buffer 310 for that shard. In this way, the data intake and query system 108 can increase the throughput of individual shards of the ingestion buffer 310. In such embodiments, the partition manager 408 can obtain the reference pointer from the ingestion buffer 310 and retrieve the data from the referenced storage for processing. In some cases, the referenced storage to which reference pointers in the ingestion buffer 310 may point can correspond to the common storage 216 or other cloud or local storage. In some implementations, the chunks of data to which the reference pointers refer may be directed to common storage 216 from intake system 210, e.g., streaming data processor 308 or ingestion buffer 310.

As the indexer 410 processes the data, stores the data in buckets, and generates indexes of the data, the partition manager 408 can monitor the indexer 410 and the size of the data on the indexer 410 (inclusive of the data store 412) associated with the partition. The size of the data on the indexer 410 can correspond to the data that is actually received from the particular partition of the intake system 210, as well as data generated by the indexer 410 based on the received data (e.g., inverted indexes, summaries, etc.), and may correspond to one or more buckets. For instance, the indexer 410 may have generated one or more buckets for each tenant and/or partition associated with data being processed in the indexer 410.

Based on a bucket roll-over policy, the partition manager 408 can instruct the indexer 410 to convert editable groups of data or buckets to non-editable groups or buckets and/or copy the data associated with the partition to common storage 216. In some embodiments, the bucket roll-over policy can indicate that the data associated with the particular partition, which may have been indexed by the indexer 410 and stored in the data store 412 in various buckets, is to be copied to common storage 216 based on a determination that the size of the data associated with the particular partition satisfies a threshold size. In some cases, the bucket roll-over policy can include different threshold sizes for different partitions. In other implementations the bucket roll-over policy may be modified by other factors, such as an identity of a tenant associated with indexing node 404, system resource usage, which could be based on the pod or other container that contains indexing node 404, or one of the physical hardware layers with which the indexing node 404 is running, or any other appropriate factor for scaling and system performance of indexing nodes 404 or any other system component.

In certain embodiments, the bucket roll-over policy can indicate data is to be copied to common storage 216 based on a determination that the amount of data associated with all partitions (or a subset thereof) of the indexing node 404 satisfies a threshold amount. Further, the bucket roll-over policy can indicate that the one or more partition managers 408 of an indexing node 404 are to communicate with each other or with the indexing node manager 406 to monitor the amount of data on the indexer 410 associated with all of the partitions (or a subset thereof) assigned to the indexing node 404 and determine that the amount of data on the indexer 410 (or data store 412) associated with all the partitions (or a subset thereof) satisfies a threshold amount. Accordingly, based on the bucket roll-over policy, one or more of the partition managers 408 or the indexing node manager 406 can instruct the indexer 410 to convert editable buckets associated with the partitions (or subsets thereof) to non-editable buckets and/or store the data associated with the partitions (or subset thereof) in common storage 216.

In certain embodiments, the bucket roll-over policy can indicate that buckets are to be converted to non-editable buckets and stored in common storage based on a collective size of buckets satisfying a threshold size. In some cases, the bucket roll-over policy can use different threshold sizes for conversion and storage. For example, the bucket roll-over policy can use a first threshold size to indicate when editable buckets are to be converted to non-editable buckets (e.g., stop writing to the buckets) and a second threshold size to indicate when the data (or buckets) are to be stored in common storage 216. In certain cases, the bucket roll-over policy can indicate that the partition manager(s) 408 are to send a single command to the indexer 410 that causes the indexer 410 to convert editable buckets to non-editable buckets and store the buckets in common storage 216.

Based on an acknowledgement that the data associated with a partition (or multiple partitions as the case may be) has been stored in common storage 216, the partition manager 408 can communicate to the intake system 210, either directly, or through the indexing node manager 406, that the data has been stored and/or that the location marker or read pointer can be moved or updated. In some cases, the partition manager 408 receives the acknowledgement that the data has been stored from common storage 216 and/or from the indexer 410. In certain embodiments, which will be described in more detail herein, the intake system 210 does not receive communication that the data stored in intake system 210 has been read and processed until after that data has been stored in common storage 216.

The acknowledgement that the data has been stored in common storage 216 can also include location information about the data within the common storage 216. For example, the acknowledgement can provide a link, map, or path to the copied data in the common storage 216. Using the information about the data stored in common storage 216, the partition manager 408 can update the data store catalog 220. For example, the partition manager 408 can update the data store catalog 220 with an identifier of the data (e.g., bucket identifier, tenant identifier, partition identifier, etc.), the location of the data in common storage 216, a time range associated with the data, etc. In this way, the data store catalog 220 can be kept up-to-date with the contents of the common storage 216.

Moreover, as additional data is received from the intake system 210, the partition manager 408 can continue to communicate the data to the indexer 410, monitor the size or amount of data on the indexer 410, instruct the indexer 410 to copy the data to common storage 216, communicate the successful storage of the data to the intake system 210, and update the data store catalog 220.

As a non-limiting example, consider the scenario in which the intake system 210 communicates data from a particular shard or partition to the indexing system 212. The intake system 210 can track which data it has sent and a location marker for the data in the intake system 210 (e.g., a marker that identifies data that has been sent to the indexing system 212 for processing).

As described herein, the intake system 210 can retain or persistently make available the sent data until the intake system 210 receives an acknowledgement from the indexing system 212 that the sent data has been processed, stored in persistent storage (e.g., common storage 216), or is safe to be deleted. In this way, if an indexing node 404 assigned to process the sent data becomes unresponsive or is lost, e.g., due to a hardware failure or a crash of the indexing node manager 406 or other component, process, or daemon, the data that was sent to the unresponsive indexing node 404 will not be lost. Rather, a different indexing node 404 can obtain and process the data from the intake system 210.

As the indexing system 212 stores the data in common storage 216, it can report the storage to the intake system 210. In response, the intake system 210 can update its marker to identify different data that has been sent to the indexing system 212 for processing, but has not yet been stored. By moving the marker, the intake system 210 can indicate that the previously-identified data has been stored in common storage 216, can be deleted from the intake system 210 or, otherwise, can be allowed to be overwritten, lost, etc.

With reference to the example above, in some embodiments, the indexing node manager 406 can track the marker used by the ingestion buffer 310, and the partition manager 408 can receive the data from the ingestion buffer 310 and forward it to an indexer 410 for processing (or use the data in the ingestion buffer to obtain data from a referenced storage location and forward the obtained data to the indexer). The partition manager 408 can monitor the amount of data being processed and instruct the indexer 410 to copy the data to common storage 216. Once the data is stored in common storage 216, the partition manager 408 can report the storage to the ingestion buffer 310, so that the ingestion buffer 310 can update its marker. In addition, the indexing node manager 406 can update its records with the location of the updated marker. In this way, if partition manager 408 become unresponsive or fails, the indexing node manager 406 can assign a different partition manager 408 to obtain the data from the data stream without losing the location information, or if the indexer 410 becomes unavailable or fails, the indexing node manager 406 can assign a different indexer 410 to process and store the data.

3.3.2.3. Indexer and Data Store

As described herein, the indexer 410 can be the primary indexing execution engine, and can be implemented as a distinct computing device, container, container within a pod, etc. For example, the indexer 410 can tasked with parsing, processing, indexing, and storing the data received from the intake system 210 via the partition manager(s) 408. Specifically, in some embodiments, the indexer 410 can parse the incoming data to identify timestamps, generate events from the incoming data, group and save events into buckets, generate summaries or indexes (e.g., time series index, inverted index, keyword index, etc.) of the events in the buckets, and store the buckets in common storage 216.

In some cases, one indexer 410 can be assigned to each partition manager 408, and in certain embodiments, one indexer 410 can receive and process the data from multiple (or all) partition mangers 408 on the same indexing node 404 or from multiple indexing nodes 404.

In some embodiments, the indexer 410 can store the events and buckets in the data store 412 according to a bucket creation policy. The bucket creation policy can indicate how many buckets the indexer 410 is to generate for the data that it processes. In some cases, based on the bucket creation policy, the indexer 410 generates at least one bucket for each tenant and index (also referred to as a partition) associated with the data that it processes. For example, if the indexer 410 receives data associated with three tenants A, B, C, each with two indexes X, Y, then the indexer 410 can generate at least six buckets: at least one bucket for each of Tenant A::Index X, Tenant A::Index Y, Tenant B::Index X, Tenant B::Index Y, Tenant C::Index X, and Tenant C::Index Y. Additional buckets may be generated for a tenant/partition pair based on the amount of data received that is associated with the tenant/partition pair. However, it will be understood that the indexer 410 can generate buckets using a variety of policies. For example, the indexer 410 can generate one or more buckets for each tenant, partition, source, sourcetype, etc.

In some cases, if the indexer 410 receives data that it determines to be "old," e.g., based on a timestamp of the data or other temporal determination regarding the data, then it can generate a bucket for the "old" data. In some embodiments, the indexer 410 can determine that data is "old," if the data is associated with a timestamp that is earlier in time by a threshold amount than timestamps of other data in the corresponding bucket (e.g., depending on the bucket creation policy, data from the same partition and/or tenant) being processed by the indexer 410. For example, if the indexer 410 is processing data for the bucket for Tenant A::Index X having timestamps on 4/23 between 16:23:56 and 16:46:32 and receives data for the Tenant A::Index X bucket having a timestamp on 4/22 or on 4/23 at 08:05:32, then it can determine that the data with the earlier timestamps is "old" data and generate a new bucket for that data. In this way, the indexer 410 can avoid placing data in the same bucket that creates a time range that is significantly larger than the time range of other buckets, which can decrease the performance of the system as the bucket could be identified as relevant for a search more often than it otherwise would.

The threshold amount of time used to determine if received data is "old," can be predetermined or dynamically determined based on a number of factors, such as, but not limited to, time ranges of other buckets, amount of data being processed, timestamps of the data being processed, etc. For example, the indexer 410 can determine an average time range of buckets that it processes for different tenants and indexes. If incoming data would cause the time range of a bucket to be significantly larger (e.g., 25%, 50%, 75%, double, or other amount) than the average time range, then the indexer 410 can determine that the data is "old" data, and generate a separate bucket for it. By placing the "old" bucket in a separate bucket, the indexer 410 can reduce the instances in which the bucket is identified as storing data that may be relevant to a query. For example, by having a smaller time range, the query system 214 may identify the bucket less frequently as a relevant bucket then if the bucket had the large time range due to the "old" data. Additionally, in a process that will be described in more detail herein, time-restricted searches and search queries may be executed more quickly because there may be fewer buckets to search for a particular time range. In this manner, computational efficiency of searching large amounts of data can be improved. Although described with respect detecting "old" data, the indexer 410 can use similar techniques to determine that "new" data should be placed in a new bucket or that a time gap between data in a bucket and "new" data is larger than a threshold amount such that the "new" data should be stored in a separate bucket.

Once a particular bucket satisfies a size threshold, the indexer 410 can store the bucket in or copy the bucket to common storage 216. In certain embodiments, the partition manager 408 can monitor the size of the buckets and instruct the indexer 410 to copy the bucket to common storage 216. The threshold size can be predetermined or dynamically determined.

In certain embodiments, the partition manager 408 can monitor the size of multiple, or all, buckets associated with the partition being managed by the partition manager 408, and based on the collective size of the buckets satisfying a threshold size, instruct the indexer 410 to copy the buckets associated with the partition to common storage 216. In certain cases, one or more partition managers 408 or the indexing node manager 406 can monitor the size of buckets across multiple, or all partitions, associated with the indexing node 404, and instruct the indexer to copy the buckets to common storage 216 based on the size of the buckets satisfying a threshold size.

As described herein, buckets in the data store 412 that are being edited by the indexer 410 can be referred to as hot buckets or editable buckets. For example, the indexer 410 can add data, events, and indexes to editable buckets in the data store 412, etc. Buckets in the data store 412 that are no longer edited by the indexer 410 can be referred to as warm buckets or non-editable buckets. In some embodiments, once the indexer 410 determines that a hot bucket is to be copied to common storage 216, it can convert the hot (editable) bucket to a warm (non-editable) bucket, and then move or copy the warm bucket to the common storage 216. Once the warm bucket is moved or copied to common storage 216, the indexer 410 can notify the partition manager 408 that the data associated with the warm bucket has been processed and stored. As mentioned, the partition manager 408 can relay the information to the intake system 210. In addition, the indexer 410 can provide the partition manager 408 with information about the buckets stored in common storage 216, such as, but not limited to, location information, tenant identifier, index identifier, time range, etc. As described herein, the partition manager 408 can use this information to update the data store catalog 220.

3.3.3. Bucket Manager

The bucket manager 414 can manage the buckets stored in the data store 412, and can be implemented as a distinct computing device, virtual machine, container, container of a pod, or a process or thread associated with a container. In some cases, the bucket manager 414 can be implemented as part of the indexer 410, indexing node 404, or as a separate component of the indexing system 212.

As described herein, the indexer 410 stores data in the data store 412 as one or more buckets associated with different tenants, indexes, etc. In some cases, the contents of the buckets are not searchable by the query system 214 until they are stored in common storage 216. For example, the query system 214 may be unable to identify data responsive to a query that is located in hot (editable) buckets in the data store 412 and/or the warm (non-editable) buckets in the data store 412 that have not been copied to common storage 216. Thus, query results may be incomplete or inaccurate, or slowed as the data in the buckets of the data store 412 are copied to common storage 216.

To decrease the delay between processing and/or indexing the data and making that data searchable, the indexing system 212 can use a bucket roll-over policy that instructs the indexer 410 to convert hot buckets to warm buckets more frequently (or convert based on a smaller threshold size) and/or copy the warm buckets to common storage 216. While converting hot buckets to warm buckets more frequently or based on a smaller storage size can decrease the lag between processing the data and making it searchable, it can increase the storage size and overhead of buckets in common storage 216. For example, each bucket may have overhead associated with it, in terms of storage space required, processor power required, or other resource requirement. Thus, more buckets in common storage 216 can result in more storage used for overhead than for storing data, which can lead to increased storage size and costs. In addition, a larger number of buckets in common storage 216 can increase query times, as the opening of each bucket as part of a query can have certain processing overhead or time delay associated with it.

To decrease search times and reduce overhead and storage associated with the buckets (while maintaining a reduced delay between processing the data and making it searchable), the bucket manager 414 can monitor the buckets stored in the data store 412 and/or common storage 216 and merge buckets according to a bucket merge policy. For example, the bucket manager 414 can monitor and merge warm buckets stored in the data store 412 before, after, or concurrently with the indexer copying warm buckets to common storage 216.

The bucket merge policy can indicate which buckets are candidates for a merge or which bucket to merge (e.g., based on time ranges, size, tenant/partition or other identifiers), the number of buckets to merge, size or time range parameters for the merged buckets, and/or a frequency for creating the merged buckets. For example, the bucket merge policy can indicate that a certain number of buckets are to be merged, regardless of size of the buckets. As another non-limiting example, the bucket merge policy can indicate that multiple buckets are to be merged until a threshold bucket size is reached (e.g., 750 MB, or 1 GB, or more). As yet another non-limiting example, the bucket merge policy can indicate that buckets having a time range within a set period of time (e.g., 30 sec, 1 min., etc.) are to be merged, regardless of the number or size of the buckets being merged.

In addition, the bucket merge policy can indicate which buckets are to be merged or include additional criteria for merging buckets. For example, the bucket merge policy can indicate that only buckets having the same tenant identifier and/or partition are to be merged, or set constraints on the size of the time range for a merged bucket (e.g., the time range of the merged bucket is not to exceed an average time range of buckets associated with the same source, tenant, partition, etc.). In certain embodiments, the bucket merge policy can indicate that buckets that are older than a threshold amount (e.g., one hour, one day, etc.) are candidates for a merge or that a bucket merge is to take place once an hour, once a day, etc. In certain embodiments, the bucket merge policy can indicate that buckets are to be merged based on a determination that the number or size of warm buckets in the data store 412 of the indexing node 404 satisfies a threshold number or size, or the number or size of warm buckets associated with the same tenant identifier and/or partition satisfies the threshold number or size. It will be understood, that the bucket manager 414 can use any one or any combination of the aforementioned or other criteria for the bucket merge policy to determine when, how, and which buckets to merge.

Once a group of buckets are merged into one or more merged buckets, the bucket manager 414 can copy or instruct the indexer 406 to copy the merged buckets to common storage 216. Based on a determination that the merged buckets are successfully copied to the common storage 216, the bucket manager 414 can delete the merged buckets and the buckets used to generate the merged buckets (also referred to herein as unmerged buckets or pre-merged buckets) from the data store 412.

In some cases, the bucket manager 414 can also remove or instruct the common storage 216 to remove corresponding pre-merged buckets from the common storage 216 according to a bucket management policy. The bucket management policy can indicate when the pre-merged buckets are to be deleted or designated as able to be overwritten from common storage 216.

In some cases, the bucket management policy can indicate that the pre-merged buckets are to be deleted immediately, once any queries relying on the pre-merged buckets are completed, after a predetermined amount of time, etc. In some cases, the pre-merged buckets may be in use or identified for use by one or more queries. Removing the pre-merged buckets from common storage 216 in the middle of a query may cause one or more failures in the query system 214 or result in query responses that are incomplete or erroneous. Accordingly, the bucket management policy, in some cases, can indicate to the common storage 216 that queries that arrive before a merged bucket is stored in common storage 216 are to use the corresponding pre-merged buckets and queries that arrive after the merged bucket is stored in common storage 216 are to use the merged bucket.

Further, the bucket management policy can indicate that once queries using the pre-merged buckets are completed, the buckets are to be removed from common storage 216. However, it will be understood that the bucket management policy can indicate removal of the buckets in a variety of ways. For example, per the bucket management policy, the common storage 216 can remove the buckets after on one or more hours, one day, one week, etc., with or without regard to queries that may be relying on the pre-merged buckets. In some embodiments, the bucket management policy can indicate that the pre-merged buckets are to be removed without regard to queries relying on the pre-merged buckets and that any queries relying on the pre-merged buckets are to be redirected to the merged bucket.

In addition to removing the pre-merged buckets and merged bucket from the data store 412 and removing or instructing common storage 216 to remove the pre-merged buckets from the data store(s) 218, the bucket manger 414 can update the data store catalog 220 or cause the indexer 410 or partition manager 408 to update the data store catalog 220 with the relevant changes. These changes can include removing reference to the pre-merged buckets in the data store catalog 220 and/or adding information about the merged bucket, including, but not limited to, a bucket, tenant, and/or partition identifier associated with the merged bucket, a time range of the merged bucket, location information of the merged bucket in common storage 216, etc. In this way, the data store catalog 220 can be kept up-to-date with the contents of the common storage 216.

3.4. Query System

Figure 5:
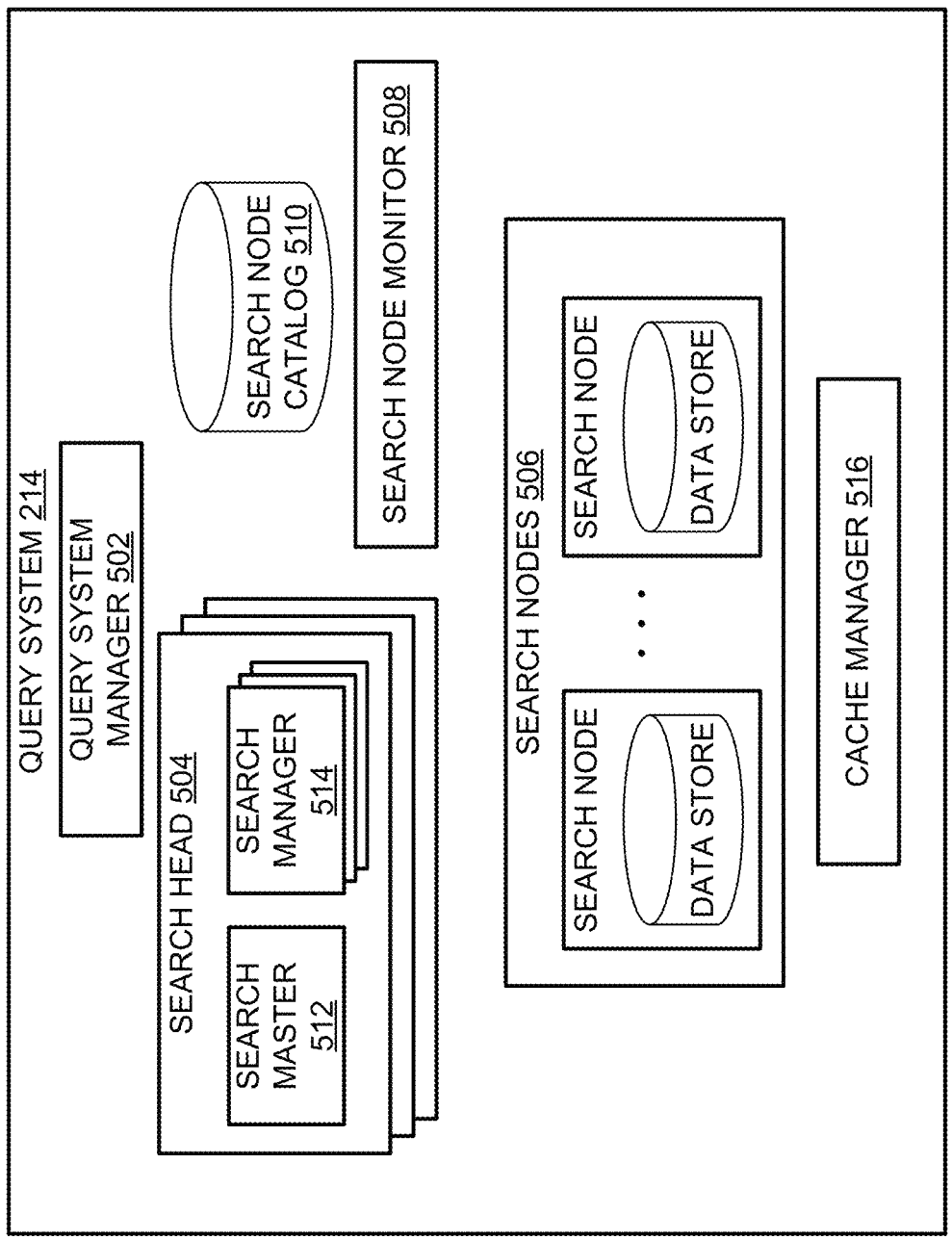
FIG. 5 is a block diagram illustrating an embodiment of a query system of the data intake and query system.

FIG. 5 is a block diagram illustrating an embodiment of a query system 214 of the data intake and query system 108. The query system 214 can receive, process, and execute queries from multiple client devices 204, which may be associated with different tenants, users, etc. Similarly, the query system 214 can execute the queries on data from the intake system 210, indexing system 212, common storage 216, acceleration data store 222, or other system. Moreover, the query system 214 can include various components that enable it to provide a stateless or state-free search service, or search service that is able to rapidly recover without data loss if one or more components of the query system 214 become unresponsive or unavailable.

In the illustrated embodiment, the query system 214 includes one or more query system managers 502 (collectively or individually referred to as query system manager 502), one or more search heads 504 (collectively or individually referred to as search head 504 or search heads 504), one or more search nodes 506 (collectively or individually referred to as search node 506 or search nodes 506), a search node monitor 508, and a search node catalog 510. However, it will be understood that the query system 214 can include fewer or more components as desired. For example, in some embodiments, the common storage 216, data store catalog 220, or query acceleration data store 222 can form part of the query system 214, etc.

As described herein, each of the components of the query system 214 can be implemented using one or more computing devices as distinct computing devices or as one or more container instances or virtual machines across one or more computing devices. For example, in some embodiments, the query system manager 502, search heads 504, and search nodes 506 can be implemented as distinct computing devices with separate hardware, memory, and processors. In certain embodiments, the query system manager 502, search heads 504, and search nodes 506 can be implemented on the same or across different computing devices as distinct container instances, with each container having access to a subset of the resources of a host computing device (e.g., a subset of the memory or processing time of the processors of the host computing device), but sharing a similar operating system. In some cases, the components can be implemented as distinct virtual machines across one or more computing devices, where each virtual machine can have its own unshared operating system but shares the underlying hardware with other virtual machines on the same host computing device.

3.4.1. Query System Manager

As mentioned, the query system manager 502 can monitor and manage the search heads 504 and search nodes 506, and can be implemented as a distinct computing device, virtual machine, container, container of a pod, or a process or thread associated with a container. For example, the query system manager 502 can determine which search head 504 is to handle an incoming query or determine whether to generate an additional search node 506 based on the number of queries received by the query system 214 or based on another search node 506 becoming unavailable or unresponsive. Similarly, the query system manager 502 can determine that additional search heads 504 should be generated to handle an influx of queries or that some search heads 504 can be de-allocated or terminated based on a reduction in the number of queries received.

In certain embodiments, the query system 214 can include one query system manager 502 to manage all search heads 504 and search nodes 506 of the query system 214. In some embodiments, the query system 214 can include multiple query system managers 502. For example, a query system manager 502 can be instantiated for each computing device (or group of computing devices) configured as a host computing device for multiple search heads 504 and/or search nodes 506.

Moreover, the query system manager 502 can handle resource management, creation, assignment, or destruction of search heads 504 and/or search nodes 506, high availability, load balancing, application upgrades/rollbacks, logging and monitoring, storage, networking, service discovery, and performance and scalability, and otherwise handle containerization management of the containers of the query system 214. In certain embodiments, the query system manager 502 can be implemented using Kubernetes or Swarm. For example, in certain embodiments, the query system manager 502 may be part of a sidecar or sidecar container, that allows communication between various search nodes 506, various search heads 504, and/or combinations thereof.

In some cases, the query system manager 502 can monitor the available resources of a host computing device and/or request additional resources in a shared resource environment, based on workload of the search heads 504 and/or search nodes 506 or create, destroy, or reassign search heads 504 and/or search nodes 506 based on workload. Further, the query system manager 502 system can assign search heads 504 to handle incoming queries and/or assign search nodes 506 to handle query processing based on workload, system resources, etc.

3.4.2. Search Head

As described herein, the search heads 504 can manage the execution of queries received by the query system 214. For example, the search heads 504 can parse the queries to identify the set of data to be processed and the manner of processing the set of data, identify the location of the data (non-limiting examples: intake system 210, common storage 216, acceleration data store 222, etc.), identify tasks to be performed by the search head and tasks to be performed by the search nodes 506, distribute the query (or sub-queries corresponding to the query) to the search nodes 506, apply extraction rules to the set of data to be processed, aggregate search results from the search nodes 506, store the search results in the query acceleration data store 222, return search results to the client device 204, etc.

As described herein, the search heads 504 can be implemented on separate computing devices or as containers or virtual machines in a virtualization environment. In some embodiments, the search heads 504 may be implemented using multiple-related containers. In certain embodiments, such as in a Kubernetes deployment, each search head 504 can be implemented as a separate container or pod. For example, one or more of the components of the search head 504 can be implemented as different containers of a single pod, e.g., on a containerization platform, such as Docker, the one or more components of the indexing node can be implemented as different Docker containers managed by synchronization platforms such as Kubernetes or Swarm. Accordingly, reference to a containerized search head 504 can refer to the search head 504 as being a single container or as one or more components of the search head 504 being implemented as different, related containers.

In the illustrated embodiment, the search head 504 includes a search master 512 and one or more search managers 514 to carry out its various functions. However, it will be understood that the search head 504 can include fewer or more components as desired. For example, the search head 504 can include multiple search masters 512.

3.4.2.1. Search Master

The search master 512 can manage the execution of the various queries assigned to the search head 504, and can be implemented as a distinct computing device, virtual machine, container, container of a pod, or a process or thread associated with a container. For example, in certain embodiments, as the search head 504 is assigned a query, the search master 512 can generate one or more search manager(s) 514 to manage the query. In some cases, the search master 512 generates a separate search manager 514 for each query that is received by the search head 504. In addition, once a query is completed, the search master 512 can handle the termination of the corresponding search manager 514.

In certain embodiments, the search master 512 can track and store the queries assigned to the different search managers 514. Accordingly, if a search manager 514 becomes unavailable or unresponsive, the search master 512 can generate a new search manager 514 and assign the query to the new search manager 514. In this way, the search head 504 can increase the resiliency of the query system 214, reduce delay caused by an unresponsive component, and can aid in providing a stateless searching service.

In some embodiments, the search master 512 is implemented as a background process, or daemon, on the search head 504 and the search manager(s) 514 are implemented as threads, copies, or forks of the background process. In some cases, a search master 512 can copy itself, or fork, to create a search manager 514 or cause a template process to copy itself, or fork, to create each new search manager 514, etc., in order to support efficient multithreaded implementations 3.4.2.2. Search Manager As mentioned, the search managers 514 can manage the processing and execution of the queries assigned to the search head 504, and can be implemented as a distinct computing device, virtual machine, container, container of a pod, or a process or thread associated with a container. In some embodiments, one search manager 514 manages the processing and execution of one query at a time. In such embodiments, if the search head 504 is processing one hundred queries, the search master 512 can generate one hundred search managers 514 to manage the one hundred queries. Upon completing an assigned query, the search manager 514 can await assignment to a new query or be terminated.

As part of managing the processing and execution of a query, and as described herein, a search manager 514 can parse the query to identify the set of data and the manner in which the set of data is to be processed (e.g., the transformations that are to be applied to the set of data), determine tasks to be performed by the search manager 514 and tasks to be performed by the search nodes 506, identify search nodes 506 that are available to execute the query, map search nodes 506 to the set of data that is to be processed, instruct the search nodes 506 to execute the query and return results, aggregate and/or transform the search results from the various search nodes 506, and provide the search results to a user and/or to the query acceleration data store 222.

In some cases, to aid in identifying the set of data to be processed, the search manager 514 can consult the data store catalog 220 (depicted in FIG. 2). As described herein, the data store catalog 220 can include information regarding the data stored in common storage 216. In some cases, the data store catalog 220 can include bucket identifiers, a time range, and a location of the buckets in common storage 216. In addition, the data store catalog 220 can include a tenant identifier and partition identifier for the buckets. This information can be used to identify buckets that include data that satisfies at least a portion of the query.

As a non-limiting example, consider a search manager 514 that has parsed a query to identify the following filter criteria that is used to identify the data to be processed: time range: past hour, partition: sales, tenant: ABC, Inc., keyword: Error. Using the received filter criteria, the search manager 514 can consult the data store catalog 220. Specifically, the search manager 514 can use the data store catalog 220 to identify buckets associated with the_sales partition and the tenant ABC, Inc. and that include data from the past hour. In some cases, the search manager 514 can obtain bucket identifiers and location information from the data store catalog 220 for the buckets storing data that satisfies at least the aforementioned filter criteria. In certain embodiments, if the data store catalog 220 includes keyword pairs, it can use the keyword: Error to identify buckets that have at least one event that include the keyword Error.

Using the bucket identifiers and/or the location information, the search manager 514 can assign one or more search nodes 506 to search the corresponding buckets. Accordingly, the data store catalog 220 can be used to identify relevant buckets and reduce the number of buckets that are to be searched by the search nodes 506. In this way, the data store catalog 220 can decrease the query response time of the data intake and query system 108.

In some embodiments, the use of the data store catalog 220 to identify buckets for searching can contribute to the statelessness of the query system 214 and search head 504. For example, if a search head 504 or search manager 514 becomes unresponsive or unavailable, the query system manager 502 or search master 512, as the case may be, can spin up or assign an additional resource (new search head 504 or new search manager 514) to execute the query. As the bucket information is persistently stored in the data store catalog 220, data lost due to the unavailability or unresponsiveness of a component of the query system 214 can be recovered by using the bucket information in the data store catalog 220.

In certain embodiments, to identify search nodes 506 that are available to execute the query, the search manager 514 can consult the search node catalog 510. As described herein, the search node catalog 510 can include information regarding the search nodes 506. In some cases, the search node catalog 510 can include an identifier for each search node 506, as well as utilization and availability information. For example, the search node catalog 510 can identify search nodes 506 that are instantiated but are unavailable or unresponsive. In addition, the search node catalog 510 can identify the utilization rate of the search nodes 506. For example, the search node catalog 510 can identify search nodes 506 that are working at maximum capacity or at a utilization rate that satisfies utilization threshold, such that the search node 506 should not be used to execute additional queries for a time.

In addition, the search node catalog 510 can include architectural information about the search nodes 506. For example, the search node catalog 510 can identify search nodes 506 that share a data store and/or are located on the same computing device, or on computing devices that are co-located.

Accordingly, in some embodiments, based on the receipt of a query, a search manager 514 can consult the search node catalog 510 for search nodes 506 that are available to execute the received query. Based on the consultation of the search node catalog 510, the search manager 514 can determine which search nodes 506 to assign to execute the query.

The search manager 514 can map the search nodes 506 to the data that is to be processed according to a search node mapping policy. The search node mapping policy can indicate how search nodes 506 are to be assigned to data (e.g., buckets) and when search nodes 506 are to be assigned to (and instructed to search) the data or buckets.

In some cases, the search manager 514 can map the search nodes 506 to buckets that include data that satisfies at least a portion of the query. For example, in some cases, the search manager 514 can consult the data store catalog 220 to obtain bucket identifiers of buckets that include data that satisfies at least a portion of the query, e.g., as a non-limiting example, to obtain bucket identifiers of buckets that include data associated with a particular time range. Based on the identified buckets and search nodes 506, the search manager 514 can dynamically assign (or map) search nodes 506 to individual buckets according to a search node mapping policy.

In some embodiments, the search node mapping policy can indicate that the search manager 514 is to assign all buckets to search nodes 506 as a single operation. For example, where ten buckets are to be searched by five search nodes 506, the search manager 514 can assign two buckets to a first search node 506, two buckets to a second search node 506, etc. In another embodiment, the search node mapping policy can indicate that the search manager 514 is to assign buckets iteratively. For example, where ten buckets are to be searched by five search nodes 506, the search manager 514 can initially assign five buckets (e.g., one buckets to each search node 506), and assign additional buckets to each search node 506 as the respective search nodes 506 complete the execution on the assigned buckets.

Retrieving buckets from common storage 216 to be searched by the search nodes 506 can cause delay or may use a relatively high amount of network bandwidth or disk read/write bandwidth. In some cases, a local or shared data store associated with the search nodes 506 may include a copy of a bucket that was previously retrieved from common storage 216. Accordingly, to reduce delay caused by retrieving buckets from common storage 216, the search node mapping policy can indicate that the search manager 514 is to assign, preferably assign, or attempt to assign the same search node 506 to search the same bucket over time. In this way, the assigned search node 506 can keep a local copy of the bucket on its data store (or a data store shared between multiple search nodes 506) and avoid the processing delays associated with obtaining the bucket from the common storage 216.

In certain embodiments, the search node mapping policy can indicate that the search manager 514 is to use a consistent hash function or other function to consistently map a bucket to a particular search node 506. The search manager 514 can perform the hash using the bucket identifier obtained from the data store catalog 220, and the output of the hash can be used to identify the search node 506 assigned to the bucket. In some cases, the consistent hash function can be configured such that even with a different number of search nodes 506 being assigned to execute the query, the output will consistently identify the same search node 506, or have an increased probability of identifying the same search node 506.

In some embodiments, the query system 214 can store a mapping of search nodes 506 to bucket identifiers. The search node mapping policy can indicate that the search manager 514 is to use the mapping to determine whether a particular bucket has been assigned to a search node 506. If the bucket has been assigned to a particular search node 506 and that search node 506 is available, then the search manager 514 can assign the bucket to the search node 506. If the bucket has not been assigned to a particular search node 506, the search manager 514 can use a hash function to identify a search node 506 for assignment. Once assigned, the search manager 514 can store the mapping for future use.

In certain cases, the search node mapping policy can indicate that the search manager 514 is to use architectural information about the search nodes 506 to assign buckets. For example, if the identified search node 506 is unavailable or its utilization rate satisfies a threshold utilization rate, the search manager 514 can determine whether an available search node 506 shares a data store with the unavailable search node 506. If it does, the search manager 514 can assign the bucket to the available search node 506 that shares the data store with the unavailable search node 506. In this way, the search manager 514 can reduce the likelihood that the bucket will be obtained from common storage 216, which can introduce additional delay to the query while the bucket is retrieved from common storage 216 to the data store shared by the available search node 506.

In some instances, the search node mapping policy can indicate that the search manager 514 is to assign buckets to search nodes 506 randomly, or in a simple sequence (e.g., a first search nodes 506 is assigned a first bucket, a second search node 506 is assigned a second bucket, etc.). In other instances, as discussed, the search node mapping policy can indicate that the search manager 514 is to assign buckets to search nodes 506 based on buckets previously assigned to a search nodes 506, in a prior or current search. As mentioned above, in some embodiments each search node 506 may be associated with a local data store or cache of information (e.g., in memory of the search nodes 506, such as random access memory LRAM" 1, disk-based cache, a data store, or other form of storage). Each search node 506 can store copies of one or more buckets from the common storage 216 within the local cache, such that the buckets may be more rapidly searched by search nodes 506. The search manager 514 (or cache manager 516) can maintain or retrieve from search nodes 506 information identifying, for each relevant search node 506, what buckets are copied within local cache of the respective search nodes 506. In the event that the search manager 514 determines that a search node 506 assigned to execute a search has within its data store or local cache a copy of an identified bucket, the search manager 514 can preferentially assign the search node 506 to search that locally-cached bucket.

In still more embodiments, according to the search node mapping policy, search nodes 506 may be assigned based on overlaps of computing resources of the search nodes 506. For example, where a containerized search node 506 is to retrieve a bucket from common storage 216 (e.g., where a local cached copy of the bucket does not exist on the search node 506), such retrieval may use a relatively high amount of network bandwidth or disk read/write bandwidth. Thus, assigning a second containerized search node 506 instantiated on the same host computing device might be expected to strain or exceed the network or disk read/write bandwidth of the host computing device. For this reason, in some embodiments, according to the search node mapping policy, the search manager 514 can assign buckets to search nodes 506 such that two containerized search nodes 506 on a common host computing device do not both retrieve buckets from common storage 216 at the same time.

Further, in certain embodiments, where a data store that is shared between multiple search nodes 506 includes two buckets identified for the search, the search manager 514 can, according to the search node mapping policy, assign both such buckets to the same search node 506 or to two different search nodes 506 that share the data store, such that both buckets can be searched in parallel by the respective search nodes 506.

The search node mapping policy can indicate that the search manager 514 is to use any one or any combination of the above-described mechanisms to assign buckets to search nodes 506. Furthermore, the search node mapping policy can indicate that the search manager 514 is to prioritize assigning search nodes 506 to buckets based on any one or any combination of: assigning search nodes 506 to process buckets that are in a local or shared data store of the search nodes 506, maximizing parallelization (e.g., assigning as many different search nodes 506 to execute the query as are available), assigning search nodes 506 to process buckets with overlapping timestamps, maximizing individual search node 506 utilization (e.g., ensuring that each search node 506 is searching at least one bucket at any given time, etc.), or assigning search nodes 506 to process buckets associated with a particular tenant, user, or other known feature of data stored within the bucket (e.g., buckets holding data known to be used in time-sensitive searches may be prioritized). Thus, according to the search node mapping policy, the search manager 514 can dynamically alter the assignment of buckets to search nodes 506 to increase the parallelization of a search, and to increase the speed and efficiency with which the search is executed.

It will be understood that the search manager 514 can assign any search node 506 to search any bucket. This flexibility can decrease query response time as the search manager can dynamically determine which search nodes 506 are best suited or available to execute the query on different buckets. Further, if one bucket is being used by multiple queries, the search manager 515 can assign multiple search nodes 506 to search the bucket. In addition, in the event a search node 506 becomes unavailable or unresponsive, the search manager 514 can assign a different search node 506 to search the buckets assigned to the unavailable search node 506.

As part of the query execution, the search manager 514 can instruct the search nodes 506 to execute the query (or sub-query) on the assigned buckets. As described herein, the search manager 514 can generate specific queries or sub-queries for the individual search nodes 506. The search nodes 506 can use the queries to execute the query on the buckets assigned thereto.

In some embodiments, the search manager 514 stores the sub-queries and bucket assignments for the different search nodes 506. Storing the sub-queries and bucket assignments can contribute to the statelessness of the query system 214. For example, in the event an assigned search node 506 becomes unresponsive or unavailable during the query execution, the search manager 514 can re-assign the sub-query and bucket assignments of the unavailable search node 506 to one or more available search nodes 506 or identify a different available search node 506 from the search node catalog 510 to execute the sub-query. In certain embodiments, the query system manager 502 can generate an additional search node 506 to execute the sub-query of the unavailable search node 506. Accordingly, the query system 214 can quickly recover from an unavailable or unresponsive component without data loss and while reducing or minimizing delay.

During the query execution, the search manager 514 can monitor the status of the assigned search nodes 506. In some cases, the search manager 514 can ping or set up a communication link between it and the search nodes 506 assigned to execute the query. As mentioned, the search manager 514 can store the mapping of the buckets to the search nodes 506. Accordingly, in the event a particular search node 506 becomes unavailable for his unresponsive, the search manager 514 can assign a different search node 506 to complete the execution of the query for the buckets assigned to the unresponsive search node 506.

In some cases, as part of the status updates to the search manager 514, the search nodes 506 can provide the search manager with partial results and information regarding the buckets that have been searched. In response, the search manager 514 can store the partial results and bucket information in persistent storage. Accordingly, if a search node 506 partially executes the query and becomes unresponsive or unavailable, the search manager 514 can assign a different search node 506 to complete the execution, as described above. For example, the search manager 514 can assign a search node 506 to execute the query on the buckets that were not searched by the unavailable search node 506. In this way, the search manager 514 can more quickly recover from an unavailable or unresponsive search node 506 without data loss and while reducing or minimizing delay.

As the search manager 514 receives query results from the different search nodes 506, it can process the data. In some cases, the search manager 514 processes the partial results as it receives them. For example, if the query includes a count, the search manager 514 can increment the count as it receives the results from the different search nodes 506. In certain cases, the search manager 514 waits for the complete results from the search nodes before processing them. For example, if the query includes a command that operates on a result set, or a partial result set, e.g., a stats command (e.g., a command that calculates one or more aggregate statistics over the results set, e.g., average, count, or standard deviation, as examples), the search manager 514 can wait for the results from all the search nodes 506 before executing the stats command.

As the search manager 514 processes the results or completes processing the results, it can store the results in the query acceleration data store 222 or communicate the results to a client device 204. As described herein, results stored in the query acceleration data store 222 can be combined with other results over time. For example, if the query system 212 receives an open-ended query (e.g., no set end time), the search manager 515 can store the query results over time in the query acceleration data store 222. Query results in the query acceleration data store 222 can be updated as additional query results are obtained. In this manner, if an open-ended query is run at time B, query results may be stored from initial time A to time B. If the same open-ended query is run at time C, then the query results from the prior open-ended query can be obtained from the query acceleration data store 222 (which gives the results from time A to time B), and the query can be run from time B to time C and combined with the prior results, rather than running the entire query from time A to time C. In this manner, the computational efficiency of ongoing search queries can be improved.

3.4.3. Search Nodes

As described herein, the search nodes 506 can be the primary query execution engines for the query system 214, and can be implemented as distinct computing devices, virtual machines, containers, container of a pods, or processes or threads associated with one or more containers. Accordingly, each search node 506 can include a processing device and a data store, as depicted at a high level in FIG. 5. Depending on the embodiment, the processing device and data store can be dedicated to the search node (e.g., embodiments where each search node is a distinct computing device) or can be shared with other search nodes or components of the data intake and query system 108 (e.g., embodiments where the search nodes are implemented as containers or virtual machines or where the shared data store is a networked data store, etc.).

In some embodiments, the search nodes 506 can obtain and search buckets identified by the search manager 514 that include data that satisfies at least a portion of the query, identify the set of data within the buckets that satisfies the query, perform one or more transformations on the set of data, and communicate the set of data to the search manager 514. Individually, a search node 506 can obtain the buckets assigned to it by the search manager 514 for a particular query, search the assigned buckets for a subset of the set of data, perform one or more transformation on the subset of data, and communicate partial search results to the search manager 514 for additional processing and combination with the partial results from other search nodes 506.

In some cases, the buckets to be searched may be located in a local data store of the search node 506 or a data store that is shared between multiple search nodes 506. In such cases, the search nodes 506 can identify the location of the buckets and search the buckets for the set of data that satisfies the query.

In certain cases, the buckets may be located in the common storage 216. In such cases, the search nodes 506 can search the buckets in the common storage 216 and/or copy the buckets from the common storage 216 to a local or shared data store and search the locally stored copy for the set of data. As described herein, the cache manager 516 can coordinate with the search nodes 506 to identify the location of the buckets (whether in a local or shared data store or in common storage 216) and/or obtain buckets stored in common storage 216.

Once the relevant buckets (or relevant files of the buckets) are obtained, the search nodes 506 can search their contents to identify the set of data to be processed. In some cases, upon obtaining a bucket from the common storage 216, a search node 306 can decompress the bucket from a compressed format, and accessing one or more files stored within the bucket. In some cases, the search node 306 references a bucket summary or manifest to locate one or more portions (e.g., records or individual files) of the bucket that potentially contain information relevant to the search.

In some cases, the search nodes 506 can use all of the files of a bucket to identify the set of data. In certain embodiments, the search nodes 506 use a subset of the files of a bucket to identify the set of data. For example, in some cases, a search node 506 can use an inverted index, bloom filter, or bucket summary or manifest to identify a subset of the set of data without searching the raw machine data of the bucket. In certain cases, the search node 506 uses the inverted index, bloom filter, bucket summary, and raw machine data to identify the subset of the set of data that satisfies the query.

In some embodiments, depending on the query, the search nodes 506 can perform one or more transformations on the data from the buckets. For example, the search nodes 506 may perform various data transformations, scripts, and processes, e.g., a count of the set of data, etc.

As the search nodes 506 execute the query, they can provide the search manager 514 with search results. In some cases, a search node 506 provides the search manager 514 results as they are identified by the search node 506, and updates the results over time. In certain embodiments, a search node 506 waits until all of its partial results are gathered before sending the results to the search manager 504.

In some embodiments, the search nodes 506 provide a status of the query to the search manager 514. For example, an individual search node 506 can inform the search manager 514 of which buckets it has searched and/or provide the search manager 514 with the results from the searched buckets. As mentioned, the search manager 514 can track or store the status and the results as they are received from the search node 506. In the event the search node 506 becomes unresponsive or unavailable, the tracked information can be used to generate and assign a new search node 506 to execute the remaining portions of the query assigned to the unavailable search node 506.

3.4.4. Cache Manager

As mentioned, the cache manager 516 can communicate with the search nodes 506 to obtain or identify the location of the buckets assigned to the search nodes 506, and can be implemented as a distinct computing device, virtual machine, container, container of a pod, or a process or thread associated with a container.

In some embodiments, based on the receipt of a bucket assignment, a search node 506 can provide the cache manager 516 with an identifier of the bucket that it is to search, a file associated with the bucket that it is to search, and/or a location of the bucket. In response, the cache manager 516 can determine whether the identified bucket or file is located in a local or shared data store or is to be retrieved from the common storage 216.

As mentioned, in some cases, multiple search nodes 506 can share a data store. Accordingly, if the cache manager 516 determines that the requested bucket is located in a local or shared data store, the cache manager 516 can provide the search node 506 with the location of the requested bucket or file. In certain cases, if the cache manager 516 determines that the requested bucket or file is not located in the local or shared data store, the cache manager 516 can request the bucket or file from the common storage 216, and inform the search node 506 that the requested bucket or file is being retrieved from common storage 216.

In some cases, the cache manager 516 can request one or more files associated with the requested bucket prior to, or in place of, requesting all contents of the bucket from the common storage 216. For example, a search node 506 may request a subset of files from a particular bucket. Based on the request and a determination that the files are located in common storage 216, the cache manager 516 can download or obtain the identified files from the common storage 216.

In some cases, based on the information provided from the search node 506, the cache manager 516 may be unable to uniquely identify a requested file or files within the common storage 216. Accordingly, in certain embodiments, the cache manager 516 can retrieve a bucket summary or manifest file from the common storage 216 and provide the bucket summary to the search node 506. In some cases, the cache manager 516 can provide the bucket summary to the search node 506 while concurrently informing the search node 506 that the requested files are not located in a local or shared data store and are to be retrieved from common storage 216.

Using the bucket summary, the search node 506 can uniquely identify the files to be used to execute the query. Using the unique identification, the cache manager 516 can request the files from the common storage 216. Accordingly, rather than downloading the entire contents of the bucket from common storage 216, the cache manager 516 can download those portions of the bucket that are to be used by the search node 506 to execute the query. In this way, the cache manager 516 can decrease the amount of data sent over the network and decrease the search time.

As a non-limiting example, a search node 506 may determine that an inverted index of a bucket is to be used to execute a query. For example, the search node 506 may determine that all the information that it needs to execute the query on the bucket can be found in an inverted index associated with the bucket. Accordingly, the search node 506 can request the file associated with the inverted index of the bucket from the cache manager 516. Based on a determination that the requested file is not located in a local or shared data store, the cache manager 516 can determine that the file is located in the common storage 216.

As the bucket may have multiple inverted indexes associated with it, the information provided by the search node 506 may be insufficient to uniquely identify the inverted index within the bucket. To address this issue, the cache manager 516 can request a bucket summary or manifest from the common storage 216, and forward it to the search node 506. The search node 506 can analyze the bucket summary to identify the particular inverted index that is to be used to execute the query, and request the identified particular inverted index from the cache manager 516 (e.g., by name and/or location). Using the bucket manifest and/or the information received from the search node 506, the cache manager 516 can obtain the identified particular inverted index from the common storage 216. By obtaining the bucket manifest and downloading the requested inverted index instead of all inverted indexes or files of the bucket, the cache manager 516 can reduce the amount of data communicated over the network and reduce the search time for the query.

In some cases, when requesting a particular file, the search node 506 can include a priority level for the file. For example, the files of a bucket may be of different sizes and may be used more or less frequently when executing queries. For example, the bucket manifest may be a relatively small file. However, if the bucket is searched, the bucket manifest can be a relatively valuable file (and frequently used) because it includes a list or index of the various files of the bucket. Similarly, a bloom filter of a bucket may be a relatively small file but frequently used as it can relatively quickly identify the contents of the bucket. In addition, an inverted index may be used more frequently than raw data of a bucket to satisfy a query.

Accordingly, to improve retention of files that are commonly used in a search of a bucket, the search node 506 can include a priority level for the requested file. The cache manager 516 can use the priority level received from the search node 506 to determine how long to keep or when to evict the file from the local or shared data store. For example, files identified by the search node 506 as having a higher priority level can be stored for a greater period of time than files identified as having a lower priority level.

Furthermore, the cache manager 516 can determine what data and how long to retain the data in the local or shared data stores of the search nodes 506 based on a bucket caching policy. In some cases, the bucket caching policy can rely on any one or any combination of the priority level received from the search nodes 506 for a particular file, least recently used, most recent in time, or other policies to indicate how long to retain files in the local or shared data store.

In some instances, according to the bucket caching policy, the cache manager 516 or other component of the query system 214 (e.g., the search master 512 or search manager 514) can instruct search nodes 506 to retrieve and locally cache copies of various buckets from the common storage 216, independently of processing queries. In certain embodiments, the query system 214 is configured, according to the bucket caching policy, such that one or more buckets from the common storage 216 (e.g., buckets associated with a tenant or partition of a tenant) or each bucket from the common storage 216 is locally cached on at least one search node 506.

In some embodiments, according to the bucket caching policy, the query system 214 is configured such that at least one bucket from the common storage 216 is locally cached on at least two search nodes 506. Caching a bucket on at least two search nodes 506 may be beneficial, for example, in instances where different queries both require searching the bucket (e.g., because the at least search nodes 506 may process their respective local copies in parallel). In still other embodiments, the query system 214 is configured, according to the bucket caching policy, such that one or more buckets from the common storage 216 or all buckets from the common storage 216 are locally cached on at least a given number n of search nodes 506, wherein n is defined by a replication factor on the system 108. For example, a replication factor of five may be established to ensure that five copies of a bucket are locally cached across different search nodes 506.

In certain embodiments, the search manager 514 (or search master 512) can assign buckets to different search nodes 506 based on time. For example, buckets that are less than one day old can be assigned to a first group of search nodes 506 for caching, buckets that are more than one day but less than one week old can be assigned to a different group of search nodes 506 for caching, and buckets that are more than one week old can be assigned to a third group of search nodes 506 for caching. In certain cases, the first group can be larger than the second group, and the second group can be larger than the third group. In this way, the query system 214 can provide better/faster results for queries searching data that is less than one day old, and so on, etc. It will be understood that the search nodes can be grouped and assigned buckets in a variety of ways. For example, search nodes 506 can be grouped based on a tenant identifier, index, etc. In this way, the query system 212 can dynamically provide faster results based any one or any number of factors.

In some embodiments, when a search node 506 is added to the query system 214, the cache manager 516 can, based on the bucket caching policy, instruct the search node 506 to download one or more buckets from common storage 216 prior to receiving a query. In certain embodiments, the cache manager 516 can instruct the search node 506 to download specific buckets, such as most recent in time buckets, buckets associated with a particular tenant or partition, etc. In some cases, the cache manager 516 can instruct the search node 506 to download the buckets before the search node 506 reports to the search node monitor 508 that it is available for executing queries. It will be understood that other components of the query system 214 can implement this functionality, such as, but not limited to the query system manager 502, search node monitor 508, search manager 514, or the search nodes 506 themselves.

In certain embodiments, when a search node 506 is removed from the query system 214 or becomes unresponsive or unavailable, the cache manager 516 can identify the buckets that the removed search node 506 was responsible for and instruct the remaining search nodes 506 that they will be responsible for the identified buckets. In some cases, the remaining search nodes 506 can download the identified buckets from common storage 516 or retrieve them from the data store associated with the removed search node 506.

In some cases, the cache manager 516 can change the bucket-search node 506 assignments, such as when a search node 506 is removed or added. In certain embodiments, based on a reassignment, the cache manager 516 can inform a particular search node 506 to remove buckets to which it is no longer assigned, reduce the priority level of the buckets, etc. In this way, the cache manager 516 can make it so the reassigned bucket will be removed more quickly from the search node 506 than it otherwise would without the reassignment. In certain embodiments, the search node 506 that receives the new for the bucket can retrieve the bucket from the now unassigned search node 506 and/or retrieve the bucket from common storage 216.

3.4.5. Search Node Monitor and Catalog

The search node monitor 508 can monitor search nodes and populate the search node catalog 510 with relevant information, and can be implemented as a distinct computing device, virtual machine, container, container of a pod, or a process or thread associated with a container.

In some cases, the search node monitor 508 can ping the search nodes 506 over time to determine their availability, responsiveness, and/or utilization rate. In certain embodiments, each search node 506 can include a monitoring module that provides performance metrics or status updates about the search node 506 to the search node monitor 508. For example, the monitoring module can indicate the amount of processing resources in use by the search node 506, the utilization rate of the search node 506, the amount of memory used by the search node 506, etc. In certain embodiments, the search node monitor 508 can determine that a search node 506 is unavailable or failing based on the data in the status update or absence of a state update from the monitoring module of the search node 506.

Using the information obtained from the search nodes 506, the search node monitor 508 can populate the search node catalog 510 and update it over time. As described herein, the search manager 514 can use the search node catalog 510 to identify search nodes 506 available to execute a query. In some embodiments, the search manager 514 can communicate with the search node catalog 510 using an API.

As the availability, responsiveness, and/or utilization change for the different search nodes 506, the search node monitor 508 can update the search node catalog 510. In this way, the search node catalog 510 can retain an up-to-date list of search nodes 506 available to execute a query.

Furthermore, as search nodes 506 are instantiated (or at other times), the search node monitor 508 can update the search node catalog 510 with information about the search node 506, such as, but not limited to its computing resources, utilization, network architecture (identification of machine where it is instantiated, location with reference to other search nodes 506, computing resources shared with other search nodes 506, such as data stores, processors, I/O, etc.), etc.

3.5. Common Storage

Returning to FIG. 2, the common storage 216 can be used to store data indexed by the indexing system 212, and can be implemented using one or more data stores 218.

In some systems, the same computing devices (e.g., indexers) operate both to ingest, index, store, and search data. The use of an indexer to both ingest and search information may be beneficial, for example, because an indexer may have ready access to information that it has ingested, and can quickly access that information for searching purposes. However, use of an indexer to both ingest and search information may not be desirable in all instances. As an illustrative example, consider an instance in which ingested data is organized into buckets, and each indexer is responsible for maintaining buckets within a data store corresponding to the indexer. Illustratively, a set of ten indexers may maintain 100 buckets, distributed evenly across ten data stores (each of which is managed by a corresponding indexer). Information may be distributed throughout the buckets according to a load-balancing mechanism used to distribute information to the indexers during data ingestion. In an idealized scenario, information responsive to a query would be spread across the 100 buckets, such that each indexer may search their corresponding ten buckets in parallel, and provide search results to a search head. However, it is expected that this idealized scenario may not always occur, and that there will be at least some instances in which information responsive to a query is unevenly distributed across data stores. As one example, consider a query in which responsive information exists within ten buckets, all of which are included in a single data store associated with a single indexer. In such an instance, a bottleneck may be created at the single indexer, and the effects of parallelized searching across the indexers may be minimized. To increase the speed of operation of search queries in such cases, it may therefore be desirable to store data indexed by the indexing system 212 in common storage 216 that can be accessible to any one or multiple components of the indexing system 212 or the query system 214.

Common storage 216 may correspond to any data storage system accessible to the indexing system 212 and the query system 214. For example, common storage 216 may correspond to a storage area network (SAN), network attached storage (NAS), other network-accessible storage system (e.g., a hosted storage system, such as Amazon S3 or EBS provided by Amazon, Inc., Google Cloud Storage, Microsoft Azure Storage, etc., which may also be referred to as "cloud" storage), or combination thereof. The common storage 216 may include, for example, hard disk drives (HDDs), solid state storage devices (SSDs), or other substantially persistent or non-transitory media. Data stores 218 within common storage 216 may correspond to physical data storage devices (e.g., an individual HDD) or a logical storage device, such as a grouping of physical data storage devices or a containerized or virtualized storage device hosted by an underlying physical storage device. In some embodiments, the common storage 216 may also be referred to as a shared storage system or shared storage environment as the data stores 218 may store data associated with multiple customers, tenants, etc., or across different data intake and query systems 108 or other systems unrelated to the data intake and query systems 108.

The common storage 216 can be configured to provide high availability, highly resilient, low loss data storage. In some cases, to provide the high availability, highly resilient, low loss data storage, the common storage 216 can store multiple copies of the data in the same and different geographic locations and across different types of data stores (e.g., solid state, hard drive, tape, etc.). Further, as data is received at the common storage 216 it can be automatically replicated multiple times according to a replication factor to different data stores across the same and/or different geographic locations.

In one embodiment, common storage 216 may be multi-tiered, with each tier providing more rapid access to information stored in that tier. For example, a first tier of the common storage 216 may be physically co-located with the indexing system 212 or the query system 214 and provide rapid access to information of the first tier, while a second tier may be located in a different physical location (e.g., in a hosted or "cloud" computing environment) and provide less rapid access to information of the second tier.

Distribution of data between tiers may be controlled by any number of algorithms or mechanisms. In one embodiment, a first tier may include data generated or including timestamps within a threshold period of time (e.g., the past seven days), while a second tier or subsequent tiers includes data older than that time period. In another embodiment, a first tier may include a threshold amount (e.g., n terabytes) or recently accessed data, while a second tier stores the remaining less recently accessed data.

In one embodiment, data within the data stores 218 is grouped into buckets, each of which is commonly accessible to the indexing system 212 and query system 214. The size of each bucket may be selected according to the computational resources of the common storage 216 or the data intake and query system 108 overall. For example, the size of each bucket may be selected to enable an individual bucket to be relatively quickly transmitted via a network, without introducing excessive additional data storage requirements due to metadata or other overhead associated with an individual bucket. In one embodiment, each bucket is 750 megabytes in size. Further, as mentioned, in some embodiments, some buckets can be merged to create larger buckets.

As described herein, each bucket can include one or more files, such as, but not limited to, one or more compressed or uncompressed raw machine data files, metadata files, filter files, indexes files, bucket summary or manifest files, etc. In addition, each bucket can store events including raw machine data associated with a timestamp.

As described herein, the indexing nodes 404 can generate buckets during indexing and communicate with common storage 216 to store the buckets. For example, data may be provided to the indexing nodes 404 from one or more ingestion buffers of the intake system 210 The indexing nodes 404 can process the information and store it as buckets in common storage 216, rather than in a data store maintained by an individual indexer or indexing node. Thus, the common storage 216 can render information of the data intake and query system 108 commonly accessible to elements of the system 108. As described herein, the common storage 216 can enable parallelized searching of buckets to occur independently of the operation of indexing system 212.

As noted above, it may be beneficial in some instances to separate data indexing and searching. Accordingly, as described herein, the search nodes 506 of the query system 214 can search for data stored within common storage 216. The search nodes 506 may therefore be communicatively attached (e.g., via a communication network) with the common storage 216, and be enabled to access buckets within the common storage 216.

Further, as described herein, because the search nodes 506 in some instances are not statically assigned to individual data stores 218 (and thus to buckets within such a data store 218), the buckets searched by an individual search node 506 may be selected dynamically, to increase the parallelization with which the buckets can be searched. For example, consider an instance where information is stored within 100 buckets, and a query is received at the data intake and query system 108 for information within ten buckets. Unlike a scenario in which buckets are statically assigned to an indexer, which could result in a bottleneck if the ten relevant buckets are associated with the same indexer, the ten buckets holding relevant information may be dynamically distributed across multiple search nodes 506. Thus, if ten search nodes 506 are available to process a query, each search node 506 may be assigned to retrieve and search within one bucket greatly increasing parallelization when compared to the low-parallelization scenarios (e.g., where a single indexer is required to search all ten buckets).

Moreover, because searching occurs at the search nodes 506 rather than at the indexing system 212, indexing resources can be allocated independently to searching operations. For example, search nodes 506 may be executed by a separate processor or computing device than indexing nodes 404, enabling computing resources available to search nodes 506 to scale independently of resources available to indexing nodes 404. Additionally, the impact on data ingestion and indexing due to above-average volumes of search query requests is reduced or eliminated, and similarly, the impact of data ingestion on search query result generation time also is reduced or eliminated.

As will be appreciated in view of the above description, the use of a common storage 216 can provide many advantages within the data intake and query system 108. Specifically, use of a common storage 216 can enable the system 108 to decouple functionality of data indexing by indexing nodes 404 with functionality of searching by search nodes 506. Moreover, because buckets containing data are accessible by each search node 506, a search manager 514 can dynamically allocate search nodes 506 to buckets at the time of a search in order to increase parallelization. Thus, use of a common storage 216 can substantially improve the speed and efficiency of operation of the system 108.

3.6. Data Store Catalog

The data store catalog 220 can store information about the data stored in common storage 216, and can be implemented using one or more data stores. In some embodiments, the data store catalog 220 can be implemented as a portion of the common storage 216 and/or using similar data storage techniques (e.g., local or cloud storage, multi-tiered storage, etc.). In another implementation, the data store catalog 22—may utilize a database, e.g., a relational database engine, such as commercially-provided relational database services, e.g., Amazon's Aurora. In some implementations, the data store catalog 220 may use an API to allow access to register buckets, and to allow query system 214 to access buckets. In other implementations, data store catalog 220 may be implemented through other means, and maybe stored as part of common storage 216, or another type of common storage, as previously described. In various implementations, requests for buckets may include a tenant identifier and some form of user authentication, e.g., a user access token that can be authenticated by authentication service. In various implementations, the data store catalog 220 may store one data structure, e.g., table, per tenant, for the buckets associated with that tenant, one data structure per partition of each tenant, etc. In other implementations, a single data structure, e.g., a single table, may be used for all tenants, and unique tenant IDs may be used to identify buckets associated with the different tenants.

As described herein, the data store catalog 220 can be updated by the indexing system 212 with information about the buckets or data stored in common storage 216. For example, the data store catalog can store an identifier for a sets of data in common storage 216, a location of the sets of data in common storage 216, tenant or indexes associated with the sets of data, timing information about the sets of data, etc. In embodiments where the data in common storage 216 is stored as buckets, the data store catalog 220 can include a bucket identifier for the buckets in common storage 216, a location of or path to the buckets in common storage 216, a time range of the data in the bucket (e.g., range of time between the first-in-time event of the bucket and the last-in-time event of the bucket), a tenant identifier identifying a customer or computing device associated with the bucket, and/or an index or partition associated with the bucket, etc.

In certain embodiments, the data store catalog 220 can include an indication of a location of a copy of a bucket found in one or more search nodes 506. For example, as buckets are copied to search nodes 506, the query system 214 can update the data store catalog 220 with information about which search nodes 506 include a copy of the buckets. This information can be used by the query system 214 to assign search nodes 506 to buckets as part of a query.

In certain embodiments, the data store catalog 220 can function as an index or inverted index of the buckets stored in common storage 216. For example, the data store catalog 220 can provide location and other information about the buckets stored in common storage 216. In some embodiments, the data store catalog 220 can provide additional information about the contents of the buckets. For example, the data store catalog 220 can provide a list of sources, sourcetypes, or hosts associated with the data in the buckets.

In certain embodiments, the data store catalog 220 can include one or more keywords found within the data of the buckets. In such embodiments, the data store catalog can be similar to an inverted index, except rather than identifying specific events associated with a particular host, source, sourcetype, or keyword, it can identify buckets with data associated with the particular host, source, sourcetype, or keyword.

In some embodiments, the query system 214 (e.g., search head 504, search master 512, search manager 514, etc.) can communicate with the data store catalog 220 as part of processing and executing a query. In certain cases, the query system 214 communicates with the data store catalog 220 using an API. As a non-limiting example, the query system 214 can provide the data store catalog 220 with at least a portion of the query or one or more filter criteria associated with the query. In response, the data store catalog 220 can provide the query system 214 with an identification of buckets that store data that satisfies at least a portion of the query. In addition, the data store catalog 220 can provide the query system 214 with an indication of the location of the identified buckets in common storage 216 and/or in one or more local or shared data stores of the search nodes 506.

Accordingly, using the information from the data store catalog 220, the query system 214 can reduce (or filter) the amount of data or number of buckets to be searched. For example, using tenant or partition information in the data store catalog 220, the query system 214 can exclude buckets associated with a tenant or a partition, respectively, that is not to be searched. Similarly, using time range information, the query system 214 can exclude buckets that do not satisfy a time range from a search. In this way, the data store catalog 220 can reduce the amount of data to be searched and decrease search times.

As mentioned, in some cases, as buckets are copied from common storage 216 to search nodes 506 as part of a query, the query system 214 can update the data store catalog 220 with the location information of the copy of the bucket. The query system 214 can use this information to assign search nodes 506 to buckets. For example, if the data store catalog 220 indicates that a copy of a bucket in common storage 216 is stored in a particular search node 506, the query system 214 can assign the particular search node to the bucket. In this way, the query system 214 can reduce the likelihood that the bucket will be retrieved from common storage 216. In certain embodiments, the data store catalog 220 can store an indication that a bucket was recently downloaded to a search node 506. The query system 214 for can use this information to assign search node 506 to that bucket.

3.7. Query Acceleration Data Store

With continued reference to FIG. 2, the query acceleration data store 222 can be used to store query results or datasets for accelerated access, and can be implemented as, a distributed in-memory database system, storage subsystem, local or networked storage (e.g., cloud storage), and so on, which can maintain (e.g., store) datasets in both low-latency memory (e.g., random access memory, such as volatile or non-volatile memory) and longer-latency memory (e.g., solid state storage, disk drives, and so on). In some embodiments, to increase efficiency and response times, the accelerated data store 222 can maintain particular datasets in the low-latency memory, and other datasets in the longer-latency memory. For example, in some embodiments, the datasets can be stored in-memory (non-limiting examples: RAM or volatile memory) with disk spillover (non-limiting examples: hard disks, disk drive, non-volatile memory, etc.). In this way, the query acceleration data store 222 can be used to serve interactive or iterative searches. In some cases, datasets which are determined to be frequently accessed by a user can be stored in the lower-latency memory. Similarly, datasets of less than a threshold size can be stored in the lower-latency memory.

In certain embodiments, the search manager 514 or search nodes 506 can store query results in the query acceleration data store 222. In some embodiments, the query results can correspond to partial results from one or more search nodes 506 or to aggregated results from all the search nodes 506 involved in a query or the search manager 514. In such embodiments, the results stored in the query acceleration data store 222 can be served at a later time to the search head 504, combined with additional results obtained from a later query, transformed or further processed by the search nodes 506 or search manager 514, etc. For example, in some cases, such as where a query does not include a termination date, the search manager 514 can store initial results in the acceleration data store 222 and update the initial results as additional results are received. At any time, the initial results, or iteratively updated results can be provided to a client device 204, transformed by the search nodes 506 or search manager 514, etc.

As described herein, a user can indicate in a query that particular datasets or results are to be stored in the query acceleration data store 222. The query can then indicate operations to be performed on the particular datasets. For subsequent queries directed to the particular datasets (e.g., queries that indicate other operations for the datasets stored in the acceleration data store 222), the search nodes 506 can obtain information directly from the query acceleration data store 222.

Additionally, since the query acceleration data store 222 can be utilized to service requests from different client devices 204, the query acceleration data store 222 can implement access controls (e.g., an access control list) with respect to the stored datasets. In this way, the stored datasets can optionally be accessible only to users associated with requests for the datasets. Optionally, a user who provides a query can indicate that one or more other users are authorized to access particular requested datasets. In this way, the other users can utilize the stored datasets, thus reducing latency associated with their queries.

In some cases, data from the intake system 210 (e.g., ingested data buffer 310, etc.) can be stored in the acceleration data store 222. In such embodiments, the data from the intake system 210 can be transformed by the search nodes 506 or combined with data in the common storage 216.

Furthermore, in some cases, if the query system 214 receives a query that includes a request to process data in the query acceleration data store 222, as well as data in the common storage 216, the search manager 514 or search nodes 506 can begin processing the data in the query acceleration data store 222, while also obtaining and processing the other data from the common storage 216. In this way, the query system 214 can rapidly provide initial results for the query, while the search nodes 506 obtain and search the data from the common storage 216.

It will be understood that the data intake and query system 108 can include fewer or more components as desired. For example, in some embodiments, the system 108 does not include an acceleration data store 222. Further, it will be understood that in some embodiments, the functionality described herein for one component can be performed by another component. For example, the search master 512 and search manager 514 can be combined as one component, etc.

3.8. Metadata Catalog

Figure 6:
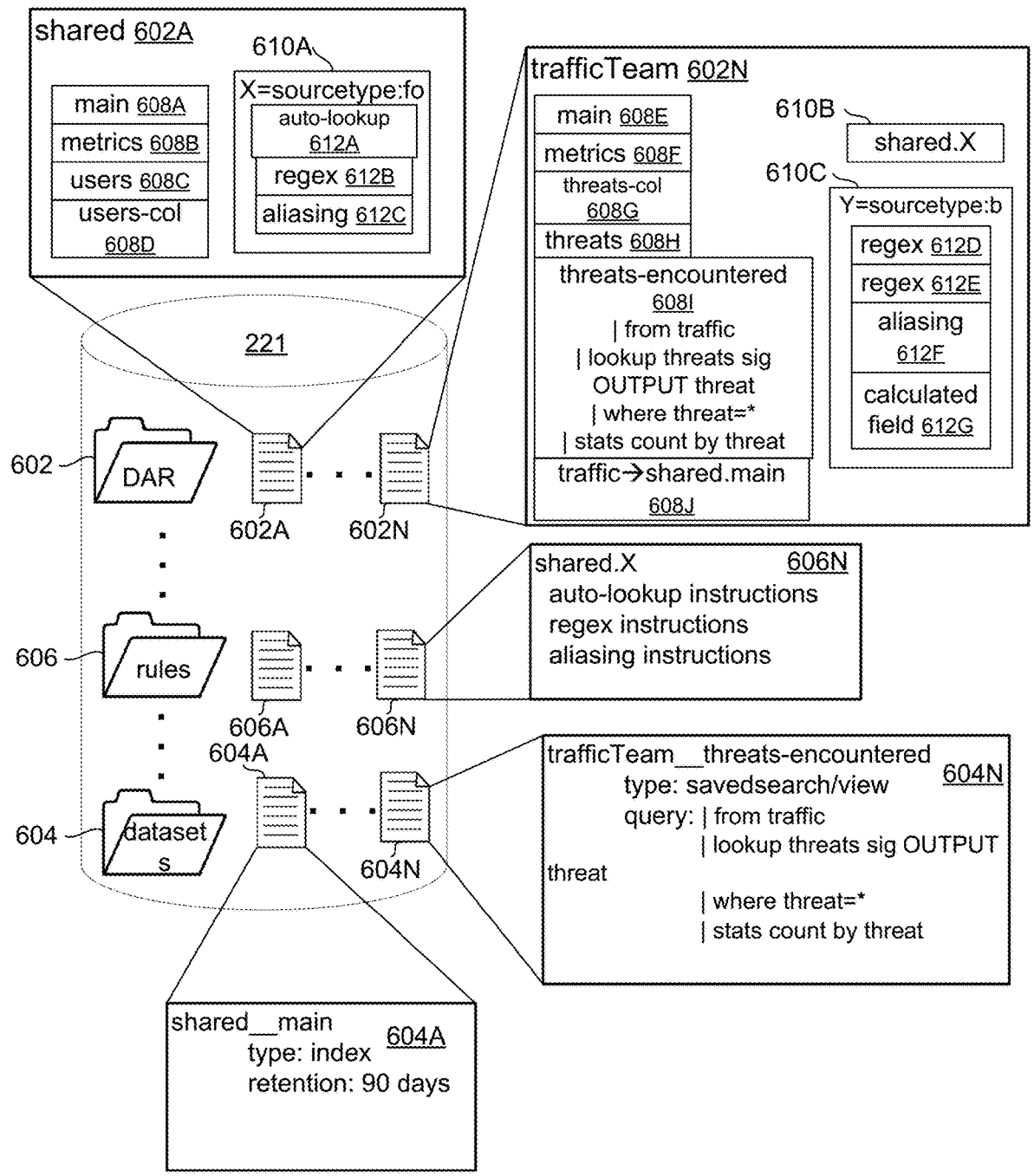
FIG. 6 is a block diagram illustrating an embodiment of a metadata catalog.

FIG. 6 is a block diagram illustrating an embodiment of a metadata catalog 221. The metadata catalog 221 can be implemented using one or more data stores, databases, computing devices, or the like. In some embodiments, the metadata catalog 221 is implemented using one or more relational databases, such as, but not limited to, Dynamo DB and/or Aurora DB.

As described herein, the metadata catalog 221 can store information about datasets and/or rules used or supported by the data intake and query system 108. Furthermore, the metadata catalog 221 can be used to, among other things, interpret dataset identifiers in a query, verify/authenticate a user's permissions and/or authorizations for different datasets, identify additional processing as part of the query, identify one or more dataset sources from which to retrieve data as part of the query, determine how to extract data from datasets, identify configurations/definitions/dependencies to be used by search nodes to execute the query, etc.

In certain embodiments, the query system 214 can use the metadata catalog 221 to dynamically determine the dataset configurations and rule configurations to be used to execute the query (also referred to herein as the query configuration parameters). In certain embodiments, the query system 214 can use the dynamically determined query configuration parameters to provide a stateless search experience. For example, if the query system 214 determines that search heads 504 are to be used to process a query or if an assigned search head 504 becomes unavailable, the query system 214 can communicate the dynamically determined query configuration parameters (and query to be executed) to another search head 504 without data loss and/or with minimal time loss.

In the illustrated embodiment, the metadata catalog 221 stores one or more dataset association records 602, one or more dataset configurations 604, and one or more rules configurations 606. It will be understood, that the metadata catalog 221 can store more or less information as desired. Although shown in the illustrated embodiment as belonging to different folders or files, it will be understood, that the various dataset association records 602 datasets configurations 604, and rules configurations 606 can be stored in the same file, directory, and/or database. For example, in certain embodiments, the metadata catalog 221 can include one or more entries in a database for each dataset association record 602, dataset, and/or rule. Moreover, in certain embodiments, the dataset configurations 604 and/or the rules configurations 606 can be included as part of the dataset association records 602.

In some cases, the metadata catalog 221 may not store separate dataset association records 602. Rather the datasets association records 602 shown in FIG. 6 can be considered logical associations between one or more dataset configurations 604 and/or one or more rules configurations 606. In some such embodiments, the logical association can be determined based on the identifier of each dataset configuration 604 and/or rules configuration 606. For example, the dataset configurations 604 and rules configurations 606 that begin with "shared," can be considered part of the "shared" dataset association record 602A (even if such a record does not physically exist on a data store) and the dataset configurations 604 and rules configurations 606 that begin with "trafficTeam," can be considered part of the "trafficTeam" dataset association record 602N.

In some embodiments, a user can modify the metadata catalog 221 via the gateway 215. For example, the gateway 215 can receive instruction from client device 204 to add/modify/delete dataset association records 602, dataset configurations 604, and/or rule configurations 606. The information received via the gateway 215 can be used by the metadata catalog 221 to create, modify, or delete a dataset association record 602, dataset configuration 604, and/or a rule configuration 606. However, it will be understood that the metadata catalog 221 can be modified in a variety of ways and/or without using the gateway 215.

3.8.1. Dataset Association Records

As described herein, the dataset association records 602 can indicate how to refer to one or more datasets (e.g., provide a name or other identifier for the datasets), identify associations or relationships between a particular dataset and one or more rules or other datasets and/or indicate the scope or definition of a dataset. Accordingly, a dataset association record 602 can include or identify one or more datasets 608 and/or rules 610.

In certain embodiments, a dataset association record 602 can provide a mechanism to avoid conflicts in dataset and/or rule identifiers. For example, different dataset association records 602 can use the same name to refer to different datasets, however, the data intake and query system 108 can differentiate the datasets with the same name based on the dataset association record 602 with which the different datasets are associated. Accordingly, in some embodiments, a dataset can be identified using a logical identifier or name and/or a physical identifier or name. The logical identifier may refer to a particular dataset in the context of a particular dataset association record 602. The physical identifier may be used by the data intake and query system 108 to uniquely identify the dataset from other datasets supported or used by the data intake and query system 108.

In some embodiments, the data intake and query system 108 can determine a physical identifier for a dataset using an identifier of the dataset association record 602 with which the dataset is associated. For example, the data intake and query system 108 can determine the physical name for a dataset by appending the name of the dataset association record 602 to the name of the dataset. For example, if the name of the dataset is "main" and it is associated with or part of the "shared" dataset association record 602, the data intake and query system 108 can generate a physical name for the dataset as "shared.main" or "shared_main." In this way, if another dataset association record 602 "test" includes a "main" dataset, the "main" dataset from the "shared" dataset association record will not conflict with the "main" dataset from the "test" dataset association record (identified as "test. main" or "test_main"). It will be understood that a variety of ways can be used to generate or determine a physical name for a dataset.

In some embodiments, the dataset association records 602 can also be used to limit or restrict access to datasets and/or rules. For example, if a user uses one dataset association record 602 they may be unable to access or use datasets and/or rules from another dataset association record 602. In some such embodiments, if a query identifies a dataset association record 602 for use but references datasets or rules of another dataset association record 602, the data intake and query system 108 can indicate an error.

In certain embodiments, datasets and/or rules can be inherited from one dataset association record 602 to another dataset association record 602. Inheriting a dataset and/or rule can enable a dataset association record 602 to use the referenced dataset and/or rule. In certain embodiments, when inheriting a dataset and/or rule 610, the inherited dataset and/or rule 610 can be given a different name for use in the dataset association record 602. For example, a "main" dataset in one dataset association record can be inherited to another dataset association record and renamed "traffic." However, it will be understood that in some embodiments, the inherited dataset 608 and/or rule 610 can retain the same name.

Accordingly, in some embodiments, the logical identifier for a dataset can vary depending on the dataset association record 602 used, but the physical identifier for the dataset may not change. For example, if the "main" dataset from the "shared" dataset association record is inherited by the "test" dataset association record and renamed as "traffic," the same dataset may be referenced as "main" when using the "shared" dataset association record and may be referenced as "traffic" when using the "test" dataset association record. However, in either case, the data intake and query system 108 can recognize that regardless of the logical identifier used, both datasets refer to the shared_main dataset.

In some embodiments, one or more datasets and/or rules can be inherited automatically. For example, consider a scenario where a rule from the "main" dataset association record 602 is inherited by the "test" dataset association record and references dataset "users." In such a scenario, even if the dataset "users" is not explicitly inherited by the "test" dataset association record 602, the "users" dataset can be inherited by the "test" dataset association record 602. In this way, the data intake and query system 108 can reduce the likelihood that an error occurs when an inherited dataset and/or rule references a dataset and/or rule that was not explicitly inherited.

In certain cases, when a dataset and/or rule is automatically inherited, the data intake and query system 108 can provide limited functionality with respect to the automatically inherited dataset and/or rule. For example, by explicitly inheriting a dataset and/or rule, a user may be able to reference the dataset and/or rule in a query, whereas if the dataset and/or rule is automatically inherited, a user may not be able to reference the dataset and/or rule the query. However, the data intake and query system 108 may be able to reference the automatically inherited dataset and/or rule in order to execute a query without errors.

Datasets of a dataset association record 602 can be associated with a dataset type. A dataset type can be used to differentiate how to interact with the dataset. In some embodiments, datasets of the same type can have similar characteristics or be interacted with in a similar way. For example, index datasets may be searchable, collection datasets may be searchable via a lookup dataset, view datasets may include query parameters or query, etc. Non-limiting examples of dataset types include, but are not limited to: index (or partition), view, lookup, collections, metrics interactions, action service, interactions, four hexagonal coordinate systems, etc.

In certain embodiments, some datasets can include, refer to, or interact with data of the data intake and query system 108, which may also be referred to herein as dataset sources. For example, index or partition datasets can include data stored in buckets as described herein. Similarly, collection datasets can include collected data and lookup datasets can be used to interact with the collected data in collection datasets.

In some embodiments, some datasets can include or refer to other datasets. For example, view datasets can refer to one or more other datasets. In some embodiments, a view dataset can include a query or saved search that identifies a set of data and how to process the set of data. As mentioned, in some cases, a dataset 608 in a dataset association record 602 can be imported or inherited from another dataset association record 602. In some such cases, if the dataset association record 602 includes an inherited dataset 608, it can identify the dataset 608 as an inherited dataset and/or it can identify the dataset 608 as having the same dataset type as the corresponding dataset 608 from the other dataset association record 602.

Rules of a dataset association record 602 can identify data and one or more actions that are to be performed on the identified data. The rule can identify the data in a variety of ways. In some embodiments, the rule can use a field-value pair, index, or other metadata to identify data that is to be processed according to the actions of the rule. For example, a rule can indicate that the data intake and query system 108 is to perform three processes or extraction rules on data from index "main" with a field-value pair "sourcetype:foo."

The actions of a rule can indicate a particular process that is to be applied to the data. Similar to dataset types, each action can have an action type. Action of the same type can have a similar characteristic or perform a similar process on the data. Non-limiting examples of action types include regex, aliasing, auto-lookup, and calculated field.

Regex actions can indicate a particular extraction rule that is to be used to extract a particular field value from a field of the identified data. Auto-lookup actions can indicate a particular lookup that is to take place using data extracted from an event to identify related information stored elsewhere. For example, an auto-lookup can indicate that when a UID value is extracted from an event, it is to be compared with a data collection that relates UIDs to usernames to identify the username associated with the UID. Aliasing actions can indicate how to relate fields from different data. For example, one sourcetype may include usernames in a "customer" field and another sourcetype may include usernames in a "user" field. An aliasing action can associate the two field names together or associate both field names with another field name, such as "username." Calculated field actions can indicate how to calculate a field from data in an event. For example, a calculated field may indicate that an average is to be calculated from the various numbers in an event and assigned to the field name "score_avg." It will be understood that additional actions can be used to process or extract information from the data as desired.

In the illustrated embodiment of FIG. 6, two dataset association records 602A, 602N (also referred to herein as dataset association record(s) 602), two dataset configurations 604A, 604N (also referred to herein as dataset configuration(s) 604), and two rule configurations 606A, 606N (also referred to herein as rule configuration(s) 606) are shown. However, it will be understood that fewer or more dataset association records 602 dataset configurations 604, and/or rule definitions 606 can be included in the metadata catalog 221.

As mentioned, each dataset association record 602 can include a name (or other identifier) for the dataset association record 602, an identification of one or more datasets 608 associated with the dataset association record 602, and one or more rules 610. As described herein, the datasets 608 of a dataset association record 602 can be native to the dataset association record 602 or inherited from another dataset association record 602. Similarly, rules of a dataset association record 602 can be native to the dataset association record 602 and/or inherited from another dataset association record 602.

In the illustrated embodiment, the name of the dataset association record 602A is "shared" and includes the "main" dataset 608A, "metrics" dataset 608B, "users" dataset 608C, and "users-col" dataset 608D. In addition, the "main" dataset 608A and "metrics" dataset 608B are index datasets, the "users" dataset 608C is a lookup dataset associated with the collection "users-col" dataset 608D. In addition, in the illustrated embodiment, dataset association record 602A includes the "X" rule 610A associated with the "main" dataset 608A. The "X" rule 610A uses a field-value pair "sourcetype:foo" to identify data that is to be processed according to an "autolookup" action 612A, "regex" action 612B, and "aliasing" action 612C. Accordingly, in some embodiments, when data from the "main" dataset 608A is accessed, the actions 612A, 612B, 612C of the "X" rule 610A are applied to data of the sourcetype "foo."

Similar to the dataset association record 602A, the dataset association record 602N includes a name ("trafficTeam") and various native index datasets 608E, 608F ("main" and "metrics," respectevely), a collection dataset 608G ("threats-col") and a lookup dataset 608H ("threats"), and a native rule 610C ("Y"). In addition, the dataset association record 602 includes a view dataset 608I ("threats-encountered"). The "threats-encountered" dataset 608I includes a query "|from traffic SEP lookup threats sig OUTPUT threat| where threat=*| stats count by threat" that references two other datasets 608J, 608H ("traffic" and "threats"). Thus, when the "threats-encountered" dataset 608I is referenced, the data intake and query system 108 can process and execute the identified query.

The dataset association record 602N also includes an inherited "traffic" dataset 608J and an inherited "shared.X" rule 610B. In the illustrated embodiment, the "traffic" dataset 608J corresponds to the "main" dataset 608A from the "shared" dataset association record 602A. As described herein, in some embodiments, to associate the "main" dataset 608A (from the "shared" dataset association record 602A) with the "traffic" dataset 608J (from the "trafficTeam" dataset association record 602N), the name of the dataset association record 602A ("shared") is placed in front of the name of the dataset 608A ("main"). However it will be understood that a variety of ways can be used to associate a dataset 608 from one dataset association record 602 with the dataset 608 from another dataset association record 602. As described herein, by inheriting the dataset "main" dataset 608A, a user using the dataset association record 602 and can reference the "main" dataset 608A and/or access the data in the "main" dataset 608A.

Similar to the "main" dataset 608A, the "X" rule 610A is also inherited by the "trafficTeam" dataset association record 602N as the "shared.X" rule 610B. As described herein, by inheriting "X" rule 610A, a user using the "trafficTeam" dataset association record 602N can use the "X" rule 610A. Furthermore, in some embodiments, if the "X" rule 610A (or a dataset) references other datasets, such as, the "users" dataset 608C and the "users-col" dataset 608D, these datasets can be automatically inherited by the "trafficTeam" dataset association record 602N. However, a user may not be able to reference these automatically inherited rules (datasets) in a query.

3.8.2. Dataset Configurations

The dataset configurations 604 can include the configuration and/or access information for the datasets associated with the dataset association records 602 or otherwise used or supported by the data intake and query system 108. In certain embodiments, the metadata catalog 221 includes the dataset configurations 604 for all of the datasets 608 used or supported by the data intake and query system 108 in one or more files or entries. In some embodiments, the metadata catalog 221 includes a separate file or entry for each dataset 608 or dataset configuration 604.

The dataset configuration 604 for each dataset 608 can identify a physical and/or logical name for the dataset, a dataset type, authorization and/or access indicating users that can access the dataset, etc. Furthermore, depending on the dataset type, each dataset configuration 604 can indicate custom fields or characteristics associated with the dataset. For example, in the illustrated embodiment, the "shared_main" dataset configuration 604A for the "shared_main" dataset 608A indicates that it is an index data type. In addition, the dataset configuration 604N includes a retention period indicating the length of time in which data associated with the "shared_main" dataset 608A is to be retained by the data intake and query system 108. As another example, in the illustrated embodiment, the "trafficTeam_threats-encountered" dataset configuration 604N for the "trafficTeam_threats-encountered" dataset 608I indicates that it is a view type of dataset. In addition, the dataset configuration 604N includes the query for the "trafficTeam_threats-encountered" dataset 608I. It will be understood the more or less information can be included in each dataset configuration 604.

Although not illustrated in FIG. 6, it will be understood that the metadata catalog 221 can include a separate dataset configuration 604 for the datasets 608B, 608C, 608D, 608E, 608F, 608G, 608H, and 608J. In some embodiments, the dataset configuration 604 for the "traffic" dataset 608J (or other inherited datasets) can indicate that the "traffic" dataset 608J is an inherited version of the "shared_main" dataset 608A. In certain cases, the dataset configuration 604 for the "traffic" dataset 608J can include a reference to the dataset configuration 604 for the "shared_main" dataset 608A and/or can include all of the configuration information for the "shared_main" dataset 608A. In certain embodiments, the metadata catalog 221 may omit a separate dataset configuration 604 for the "traffic" dataset 608J because that dataset is an inherited dataset of the "main" dataset 608A from the "share" dataset association record 602A.

As described herein, although the dataset association records 602A, 602N each include a "main" dataset 608B, 608E and a "metrics" dataset 608B, 608F, the data intake and query system 108 can differentiate between the datasets from the different dataset association records based on the dataset association record 602 associated with the datasets. For example, the metadata catalog 221 can include separate dataset configurations 604 for the "shared.main" dataset 608A, "trafficTeam.main" dataset 608E, "shared.metrics" dataset 608B, and the "trafficTeam.metrics" dataset 608F.

3.8.3. Rules Configurations

The rules configurations 606 can include the rules, actions, and instructions for executing the rules and actions for the rules referenced of the dataset association records 602 or otherwise used or supported by the data intake and query system 108. In some embodiments, the metadata catalog 221 includes a separate file or entry for each rule configuration 606. In certain embodiments, the metadata catalog 221 includes the rule configurations 606 for all of the rules 610 in one or more files or entries.

In the illustrated embodiment, a rules configurations 606N is shown for the "shared.X" rule 610A. The rules configuration 606N can include the specific parameters and instructions for the "shared.X" rule 610A. For example, the rules configuration 606N can identify the data that satisfies the rule (sourcetype:foo of the "main" dataset 608A). In addition, the rules configuration 606N can include the specific parameters and instructions for the actions associated with the rule. For example, for the "regex" action 612B, the rules configuration 606N can indicate how to parse data with a sourcetype "foo" to identify a field value for a "customerID" field, etc. With continued reference to the example, for the "aliasing" action 612C, the rules configuration 606N can indicate that the "customerID" field corresponds to a "userNumber" field in data with a sourcetype "roo." Similarly, for the "auto-lookup" action 612A, the rules configuration 606N can indicate that the field value for the "customerID" field can be used to lookup a customer name using the "users" dataset 608C and "users-col" dataset 608D.

Similar to the dataset configurations 604, the metadata catalog 221 can include rules configurations 606 for the various rules 610 of the dataset association table 602 or other rules supported for use by the data intake and query system 108. For example, the metadata catalog 221 can include rules configuration 606 for the "shared.X" rule 610A and the "trafficTeam.Y" rule 610C.

4.0. Data Intake and Query System Functions

As described herein, the various components of the data intake and query system 108 can perform a variety of functions associated with the intake, indexing, storage, and querying of data from a variety of sources. It will be understood that any one or any combination of the functions described herein can be combined as part of a single routine or method. For example, a routine can include any one or any combination of one or more data ingestion functions, one or more indexing functions, and/or one or more searching functions.

4.1. Ingestion

Figure 7:
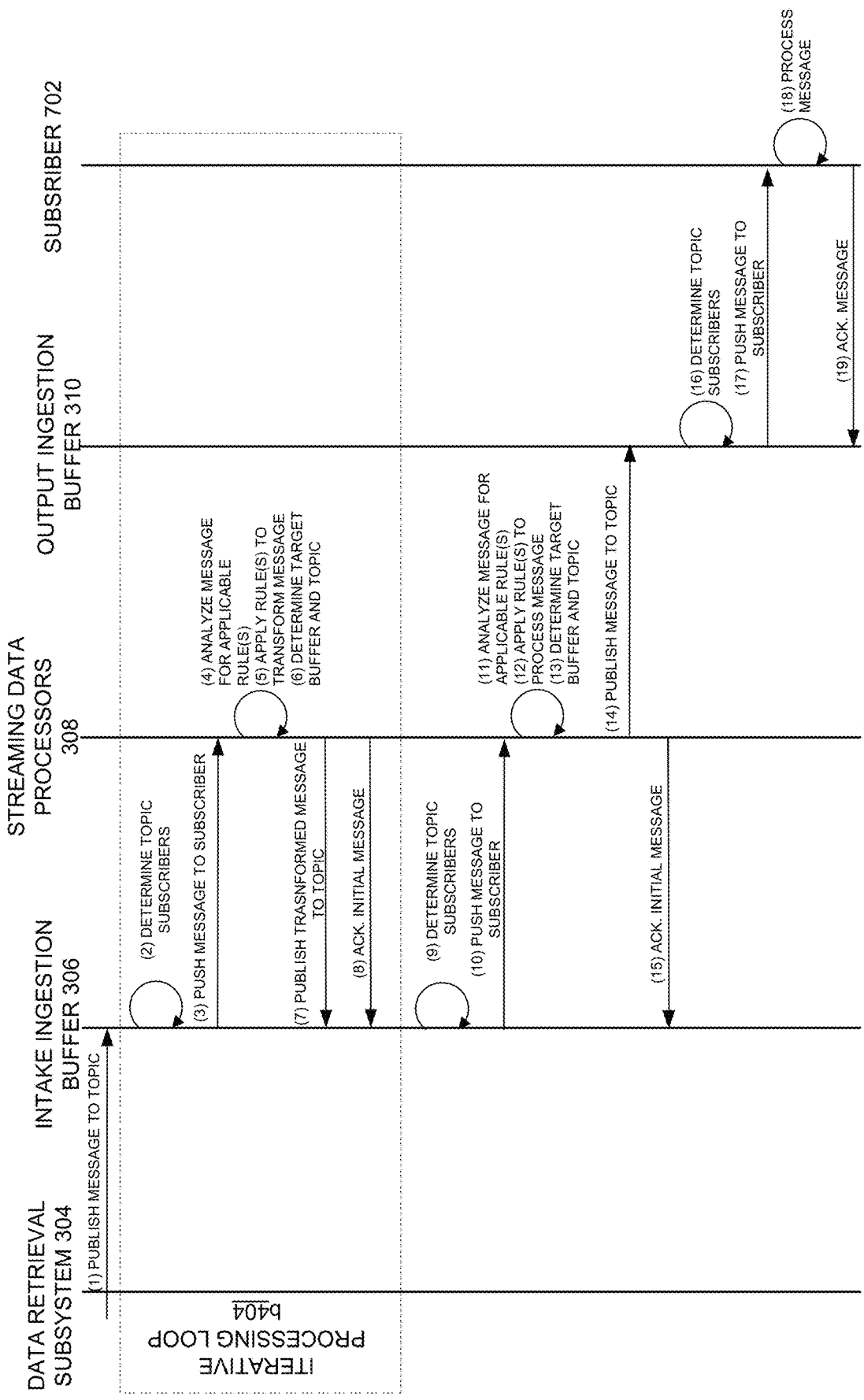
FIG. 7 is a flow diagram depicting illustrative interactions for processing data through an intake system, in accordance with example embodiments.

As discussed above, ingestion into the data intake and query system 108 can be facilitated by an intake system 210, which functions to process data according to a streaming data model, and make the data available as messages on an output ingestion buffer 310, categorized according to a number of potential topics. Messages may be published to the output ingestion buffer 310 by a streaming data processors 308, based on preliminary processing of messages published to an intake ingestion buffer 306. The intake ingestion buffer 306 is, in turn, populated with messages by one or more publishers, each of which may represent an intake point for the data intake and query system 108. The publishers may collectively implement a data retrieval subsystem 304 for the data intake and query system 108, which subsystem 304 functions to retrieve data from a data source 202 and publish the data in the form of a message on the intake ingestion buffer 306. A flow diagram depicting an illustrative embodiment for processing data at the intake system 210 is shown at FIG. 7. While the flow diagram is illustratively described with respect to a single message, the same or similar interactions may be used to process multiple messages at the intake system 210.

4.1.1. Publication to Intake Topic(s)

As shown in FIG. 7, processing of data at the intake system 210 can illustratively begin at (1), where a data retrieval subsystem 304 or a data source 202 publishes a message to a topic at the intake ingestion buffer 306. Generally described, the data retrieval subsystem 304 may include either or both push-based and pull-based publishers. Push-based publishers can illustratively correspond to publishers which independently initiate transmission of messages to the intake ingestion buffer 306. Pull-based publishes can illustratively correspond to publishers which await an inquiry by the intake ingestion buffer 306 for messages to be published to the buffer 306. The publication of a message at (1) is intended to include publication under either push- or pull-based models.

As discussed above, the data retrieval subsystem 304 may generate the message based on data received from a forwarder 302 and/or from one or more data sources 202. In some instances, generation of a message may include converting a format of the data into a format suitable for publishing on the intake ingestion buffer 306. Generation of a message may further include determining a topic for the message. In one embodiment, the data retrieval subsystem 304 selects a topic based on a data source 202 from which the data is received, or based on the specific publisher (e.g., intake point) on which the message is generated. For example, each data source 202 or specific publisher may be associated with a particular topic on the intake ingestion buffer 306 to which corresponding messages are published. In some instances, the same source data may be used to generate multiple messages to the intake ingestion buffer 306 (e.g., associated with different topics).

4.1.2. Transmission to Streaming Data Processors

After receiving a message from a publisher, the intake ingestion buffer 306, at (2), determines subscribers to the topic. For the purposes of example, it will be associated that at least one device of the streaming data processors 308 has subscribed to the topic (e.g., by previously transmitting to the intake ingestion buffer 306 a subscription request). As noted above, the streaming data processors 308 may be implemented by a number of (logically or physically) distinct devices. As such, the streaming data processors 308, at (2), may operate to determine which devices of the streaming data processors 308 have subscribed to the topic (or topics) to which the message was published.

Thereafter, at (3), the intake ingestion buffer 306 publishes the message to the streaming data processors 308 in accordance with the pub-sub model. This publication may correspond to a "push" model of communication, whereby an ingestion buffer determines topic subscribers and initiates transmission of messages within the topic to the subscribers. While interactions of FIG. 7 are described with reference to such a push model, in some embodiments a pull model of transmission may additionally or alternatively be used. Illustratively, rather than an ingestion buffer determining topic subscribers and initiating transmission of messages for the topic to a subscriber (e.g., the streaming data processors 308), an ingestion buffer may enable a subscriber to query for unread messages for a topic, and for the subscriber to initiate transmission of the messages from the ingestion buffer to the subscriber. Thus, an ingestion buffer (e.g., the intake ingestion buffer 306) may enable subscribers to "pull" messages from the buffer. As such, interactions of FIG. 7 (e.g., including interactions (2) and (3) as well as (9), (10), (16), and (17) described below) may be modified to include pull-based interactions (e.g., whereby a subscriber queries for unread messages and retrieves the messages from an appropriate ingestion buffer).

4.1.3. Messages Processing

On receiving a message, the streaming data processors 308, at (4), analyze the message to determine one or more rules applicable to the message. As noted above, rules maintained at the streaming data processors 308 can generally include selection criteria indicating messages to which the rule applies. This selection criteria may be formatted in the same manner or similarly to extraction rules, discussed in more detail below, and may include any number or combination of criteria based on the data included within a message or metadata of the message, such as regular expressions based on the data or metadata.

On determining that a rule is applicable to the message, the streaming data processors 308 can apply to the message one or more processing sub-rules indicated within the rule. Processing sub-rules may include modifying data or metadata of the message. Illustratively, processing sub-rules may edit or normalize data of the message (e.g., to convert a format of the data) or inject additional information into the message (e.g., retrieved based on the data of the message). For example, a processing sub-rule may specify that the data of the message be transformed according to a transformation algorithmically specified within the sub-rule. Thus, at (5), the streaming data processors 308 applies the sub-rule to transform the data of the message.

In addition or alternatively, processing sub-rules can specify a destination of the message after the message is processed at the streaming data processors 308. The destination may include, for example, a specific ingestion buffer (e.g., intake ingestion buffer 306, output ingestion buffer 310, etc.) to which the message should be published, as well as the topic on the ingestion buffer to which the message should be published. For example, a particular rule may state that messages including metrics within a first format (e.g., imperial units) should have their data transformed into a second format (e.g., metric units) and be republished to the intake ingestion buffer 306. At such, at (6), the streaming data processors 308 can determine a target ingestion buffer and topic for the transformed message based on the rule determined to apply to the message. Thereafter, the streaming data processors 308 publishes the message to the destination buffer and topic.

For the purposes of illustration, the interactions of FIG. 7 assume that, during an initial processing of a message, the streaming data processors 308 determines (e.g., according to a rule of the data processor) that the message should be republished to the intake ingestion buffer 306, as shown at (7). The streaming data processors 308 further acknowledges the initial message to the intake ingestion buffer 306, at (8), thus indicating to the intake ingestion buffer 306 that the streaming data processors 308 has processed the initial message or published it to an intake ingestion buffer. The intake ingestion buffer 306 may be configured to maintain a message until all subscribers have acknowledged receipt of the message. Thus, transmission of the acknowledgement at (8) may enable the intake ingestion buffer 306 to delete the initial message.

It is assumed for the purposes of these illustrative interactions that at least one device implementing the streaming data processors 308 has subscribed to the topic to which the transformed message is published. Thus, the streaming data processors 308 is expected to again receive the message (e.g., as previously transformed the streaming data processors 308), determine whether any rules apply to the message, and process the message in accordance with one or more applicable rules. In this manner, interactions (2) through (8) may occur repeatedly, as designated in FIG. 7 by the iterative processing loop 402. By use of iterative processing, the streaming data processors 308 may be configured to progressively transform or enrich messages obtained at data sources 202. Moreover, because each rule may specify only a portion of the total transformation or enrichment of a message, rules may be created without knowledge of the entire transformation. For example, a first rule may be provided by a first system to transform a message according to the knowledge of that system (e.g., transforming an error code into an error descriptor), while a second rule may process the message according to the transformation (e.g., by detecting that the error descriptor satisfies alert criteria). Thus, the streaming data processors 308 enable highly granulized processing of data without requiring an individual entity (e.g., user or system) to have knowledge of all permutations or transformations of the data.

After completion of the iterative processing loop 402, the interactions of FIG. 7 proceed to interaction (9), where the intake ingestion buffer 306 again determines subscribers of the message. The intake ingestion buffer 306, at (10), the transmits the message to the streaming data processors 308, and the streaming data processors 308 again analyze the message for applicable rules, process the message according to the rules, determine a target ingestion buffer and topic for the processed message, and acknowledge the message to the intake ingestion buffer 306, at interactions (11), (12), (13), and (15). These interactions are similar to interactions (4), (5), (6), and (8) discussed above, and therefore will not be re-described. However, in contrast to interaction (13), the streaming data processors 308 may determine that a target ingestion buffer for the message is the output ingestion buffer 310. Thus, the streaming data processors 308, at (14), publishes the message to the output ingestion buffer 310, making the data of the message available to a downstream system.

FIG. 7 illustrates one processing path for data at the streaming data processors 308. However, other processing paths may occur according to embodiments of the present disclosure. For example, in some instances, a rule applicable to an initially published message on the intake ingestion buffer 306 may cause the streaming data processors 308 to publish the message out ingestion buffer 310 on first processing the data of the message, without entering the iterative processing loop 402. Thus, interactions (2) through (8) may be omitted.

In other instances, a single message published to the intake ingestion buffer 306 may spawn multiple processing paths at the streaming data processors 308. Illustratively, the streaming data processors 308 may be configured to maintain a set of rules, and to independently apply to a message all rules applicable to the message. Each application of a rule may spawn an independent processing path, and potentially a new message for publication to a relevant ingestion buffer. In other instances, the streaming data processors 308 may maintain a ranking of rules to be applied to messages, and may be configured to process only a highest ranked rule which applies to the message. Thus, a single message on the intake ingestion buffer 306 may result in a single message or multiple messages published by the streaming data processors 308, according to the configuration of the streaming data processors 308 in applying rules.

As noted above, the rules applied by the streaming data processors 308 may vary during operation of those processors 308. For example, the rules may be updated as user queries are received (e.g., to identify messages whose data is relevant to those queries). In some instances, rules of the streaming data processors 308 may be altered during the processing of a message, and thus the interactions of FIG. 7 may be altered dynamically during operation of the streaming data processors 308.

While the rules above are described as making various illustrative alterations to messages, various other alterations are possible within the present disclosure. For example, rules in some instances be used to remove data from messages, or to alter the structure of the messages to conform to the format requirements of a downstream system or component. Removal of information may be beneficial, for example, where the messages include private, personal, or confidential information which is unneeded or should not be made available by a downstream system. In some instances, removal of information may include replacement of the information with a less confidential value. For example, a mailing address may be considered confidential information, whereas a postal code may not be. Thus, a rule may be implemented at the streaming data processors 308 to replace mailing addresses with a corresponding postal code, to ensure confidentiality. Various other alterations will be apparent in view of the present disclosure.

4.1.4. Transmission to Subscribers

As discussed above, the rules applied by the streaming data processors 308 may eventually cause a message containing data from a data source 202 to be published to a topic on an output ingestion buffer 310, which topic may be specified, for example, by the rule applied by the streaming data processors 308. The output ingestion buffer 310 may thereafter make the message available to downstream systems or components. These downstream systems or components are generally referred to herein as "subscribers." For example, the indexing system 212 may subscribe to an indexing topic 342, the query system 214 may subscribe to a search results topic 348, a client device 102 may subscribe to a custom topic 352A, etc. In accordance with the pub-sub model, the output ingestion buffer 310 may transmit each message published to a topic to each subscriber of that topic, and resiliently store the messages until acknowledged by each subscriber (or potentially until an error is logged with respect to a subscriber). As noted above, other models of communication are possible and contemplated within the present disclosure. For example, rather than subscribing to a topic on the output ingestion buffer 310 and allowing the output ingestion buffer 310 to initiate transmission of messages to the subscriber 702, the output ingestion buffer 310 may be configured to allow a subscriber 702 to query the buffer 310 for messages (e.g., unread messages, new messages since last transmission, etc.), and to initiate transmission of those messages form the buffer 310 to the subscriber 702. In some instances, such querying may remove the need for the subscriber 702 to separately "subscribe" to the topic.

Accordingly, at (16), after receiving a message to a topic, the output ingestion buffer 310 determines the subscribers to the topic (e.g., based on prior subscription requests transmitted to the output ingestion buffer 310). At (17), the output ingestion buffer 310 transmits the message to a subscriber 402. Thereafter, the subscriber may process the message at (18). Illustrative examples of such processing are described below, and may include (for example) preparation of search results for a client device 204, indexing of the data at the indexing system 212, and the like. After processing, the subscriber can acknowledge the message to the output ingestion buffer 310, thus confirming that the message has been processed at the subscriber.

4.1.5. Data Resiliency and Security

In accordance with embodiments of the present disclosure, the interactions of FIG. 7 may be ordered such that resiliency is maintained at the intake system 210. Specifically, as disclosed above, data streaming systems (which may be used to implement ingestion buffers) may implement a variety of techniques to ensure the resiliency of messages stored at such systems, absent systematic or catastrophic failures. Thus, the interactions of FIG. 7 may be ordered such that data from a data source 202 is expected or guaranteed to be included in at least one message on an ingestion system until confirmation is received that the data is no longer required.

For example, as shown in FIG. 7, interaction (8)—wherein the streaming data processors 308 acknowledges receipt of an initial message at the intake ingestion buffer 306—can illustratively occur after interaction (7)—wherein the streaming data processors 308 republishes the data to the intake ingestion buffer 306. Similarly, interaction (15)—wherein the streaming data processors 308 acknowledges receipt of an initial message at the intake ingestion buffer 306—can illustratively occur after interaction (14)—wherein the streaming data processors 308 republishes the data to the intake ingestion buffer 306. This ordering of interactions can ensure, for example, that the data being processed by the streaming data processors 308 is, during that processing, always stored at the ingestion buffer 306 in at least one message. Because an ingestion buffer 306 can be configured to maintain and potentially resend messages until acknowledgement is received from each subscriber, this ordering of interactions can ensure that, should a device of the streaming data processors 308 fail during processing, another device implementing the streaming data processors 308 can later obtain the data and continue the processing.

Similarly, as shown in FIG. 7, each subscriber 402 may be configured to acknowledge a message to the output ingestion buffer 310 after processing for the message is completed. In this manner, should a subscriber 402 fail after receiving a message but prior to completing processing of the message, the processing of the subscriber 402 can be restarted to successfully process the message. Thus, the interactions of FIG. 7 can maintain resiliency of data on the intake system 108 commensurate with the resiliency provided by an individual ingestion buffer 306.

While message acknowledgement is described herein as an illustrative mechanism to ensure data resiliency at an intake system 210, other mechanisms for ensuring data resiliency may additionally or alternatively be used.

As will be appreciated in view of the present disclosure, the configuration and operation of the intake system 210 can further provide high amounts of security to the messages of that system. Illustratively, the intake ingestion buffer 306 or output ingestion buffer 310 may maintain an authorization record indicating specific devices or systems with authorization to publish or subscribe to a specific topic on the ingestion buffer. As such, an ingestion buffer may ensure that only authorized parties are able to access sensitive data. In some instances, this security may enable multiple entities to utilize the intake system 210 to manage confidential information, with little or no risk of that information being shared between the entities. The managing of data or processing for multiple entities is in some instances referred to as "multi-tenancy."

Illustratively, a first entity may publish messages to a first topic on the intake ingestion buffer 306, and the intake ingestion buffer 306 may verify that any intake point or data source 202 publishing to that first topic be authorized by the first entity to do so. The streaming data processors 308 may maintain rules specific to the first entity, which the first entity may illustrative provide through authenticated session on an interface (e.g., GUI, API, command line interface (CLI), etc.). The rules of the first entity may specify one or more entity-specific topics on the output ingestion buffer 310 to which messages containing data of the first entity should be published by the streaming data processors 308. The output ingestion buffer 310 may maintain authorization records for such entity-specific topics, thus restricting messages of those topics to parties authorized by the first entity. In this manner, data security for the first entity can be ensured across the intake system 210. Similar operations may be performed for other entities, thus allowing multiple entities to separately and confidentially publish data to and retrieve data from the intake system.

4.1.6. Message Processing Algorithm

Figure 8:
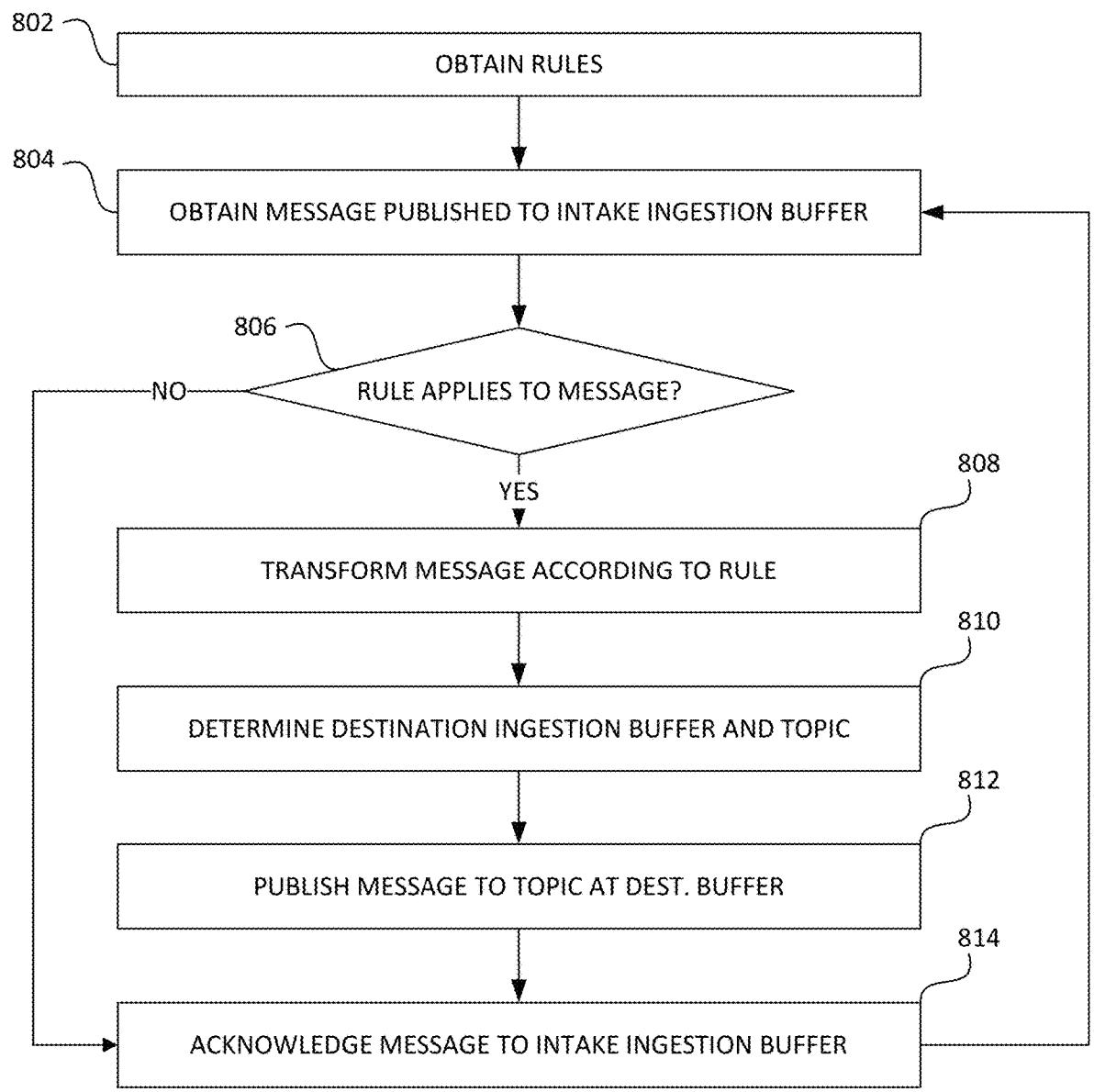
FIG. 8 is a flowchart depicting an illustrative routine for processing data at an intake system, according to example embodiments.

With reference to FIG. 8, an illustrative algorithm or routine for processing messages at the intake system 210 will be described in the form of a flowchart. The routine begins at block b102, where the intake system 210 obtains one or more rules for handling messages enqueued at an intake ingestion buffer 306. As noted above, the rules may, for example, be human-generated, or may be automatically generated based on operation of the data intake and query system 108 (e.g., in response to user submission of a query to the system 108).

At block 804, the intake system 210 obtains a message at the intake ingestion buffer 306. The message may be published to the intake ingestion buffer 306, for example, by the data retrieval subsystem 304 (e.g., working in conjunction with a forwarder 302) and reflect data obtained from a data source 202.

At block 806, the intake system 210 determines whether any obtained rule applies to the message. Illustratively, the intake system 210 (e.g., via the streaming data processors 308) may apply selection criteria of each rule to the message to determine whether the message satisfies the selection criteria. Thereafter, the routine varies according to whether a rule applies to the message. If no rule applies, the routine can continue to block 814, where the intake system 210 transmits an acknowledgement for the message to the intake ingestion buffer 306, thus enabling the buffer 306 to discard the message (e.g., once all other subscribers have acknowledged the message). In some variations of the routine, a "default rule" may be applied at the intake system 210, such that all messages are processed as least according to the default rule. The default rule may, for example, forward the message to an indexing topic 342 for processing by an indexing system 212. In such a configuration, block 806 may always evaluate as true.

In the instance that at least one rule is determined to apply to the message, the routine continues to block 808, where the intake system 210 (e.g., via the streaming data processors 308) transforms the message as specified by the applicable rule. For example, a processing sub-rule of the applicable rule may specify that data or metadata of the message be converted from one format to another via an algorithmic transformation. As such, the intake system 210 may apply the algorithmic transformation to the data or metadata of the message at block 808 to transform the data or metadata of the message. In some instances, no transformation may be specified within intake system 210, and thus block 808 may be omitted.

At block 810, the intake system 210 determines a destination ingestion buffer to which to publish the (potentially transformed) message, as well as a topic to which the message should be published. The destination ingestion buffer and topic may be specified, for example, in processing sub-rules of the rule determined to apply to the message. In one embodiment, the destination ingestion buffer and topic may vary according to the data or metadata of the message. In another embodiment, the destination ingestion buffer and topic may be fixed with respect to a particular rule.

At block 812, the intake system 210 publishes the (potentially transformed) message to the determined destination ingestion buffer and topic. The determined destination ingestion buffer may be, for example, the intake ingestion buffer 306 or the output ingestion buffer 310. Thereafter, at block 814, the intake system 210 acknowledges the initial message on the intake ingestion buffer 306, thus enabling the intake ingestion buffer 306 to delete the message.

Thereafter, the routine returns to block 804, where the intake system 210 continues to process messages from the intake ingestion buffer 306. Because the destination ingestion buffer determined during a prior implementation of the routine may be the intake ingestion buffer 306, the routine may continue to process the same underlying data within multiple messages published on that buffer 306 (thus implementing an iterative processing loop with respect to that data). The routine may then continue to be implemented during operation of the intake system 210, such that data published to the intake ingestion buffer 306 is processed by the intake system 210 and made available on an output ingestion buffer 310 to downstream systems or components.

While the routine of FIG. 8 is described linearly, various implementations may involve concurrent or at least partially parallel processing. For example, in one embodiment, the intake system 210 is configured to process a message according to all rules determined to apply to that message. Thus for example if at block 806 five rules are determined to apply to the message, the intake system 210 may implement five instances of blocks 808 through 814, each of which may transform the message in different ways or publish the message to different ingestion buffers or topics. These five instances may be implemented in serial, parallel, or a combination thereof. Thus, the linear description of FIG. 8 is intended simply for illustrative purposes.

While the routine of FIG. 8 is described with respect to a single message, in some embodiments streaming data processors 308 may be configured to process multiple messages concurrently or as a batch. Similarly, all or a portion of the rules used by the streaming data processors 308 may apply to sets or batches of messages. Illustratively, the streaming data processors 308 may obtain a batch of messages from the intake ingestion buffer 306 and process those messages according to a set of "batch" rules, whose criteria and/or processing sub-rules apply to the messages of the batch collectively. Such rules may, for example, determine aggregate attributes of the messages within the batch, sort messages within the batch, group subsets of messages within the batch, and the like. In some instances, such rules may further alter messages based on aggregate attributes, sorting, or groupings. For example, a rule may select the third messages within a batch, and perform a specific operation on that message. As another example, a rule may determine how many messages within a batch are contained within a specific group of messages. Various other examples for batch-based rules will be apparent in view of the present disclosure. Batches of messages may be determined based on a variety of criteria. For example, the streaming data processors 308 may batch messages based on a threshold number of messages (e.g., each thousand messages), based on timing (e.g., all messages received over a ten minute window), or based on other criteria (e.g., the lack of new messages posted to a topic within a threshold period of time).

4.2. Indexing

Figure 9:
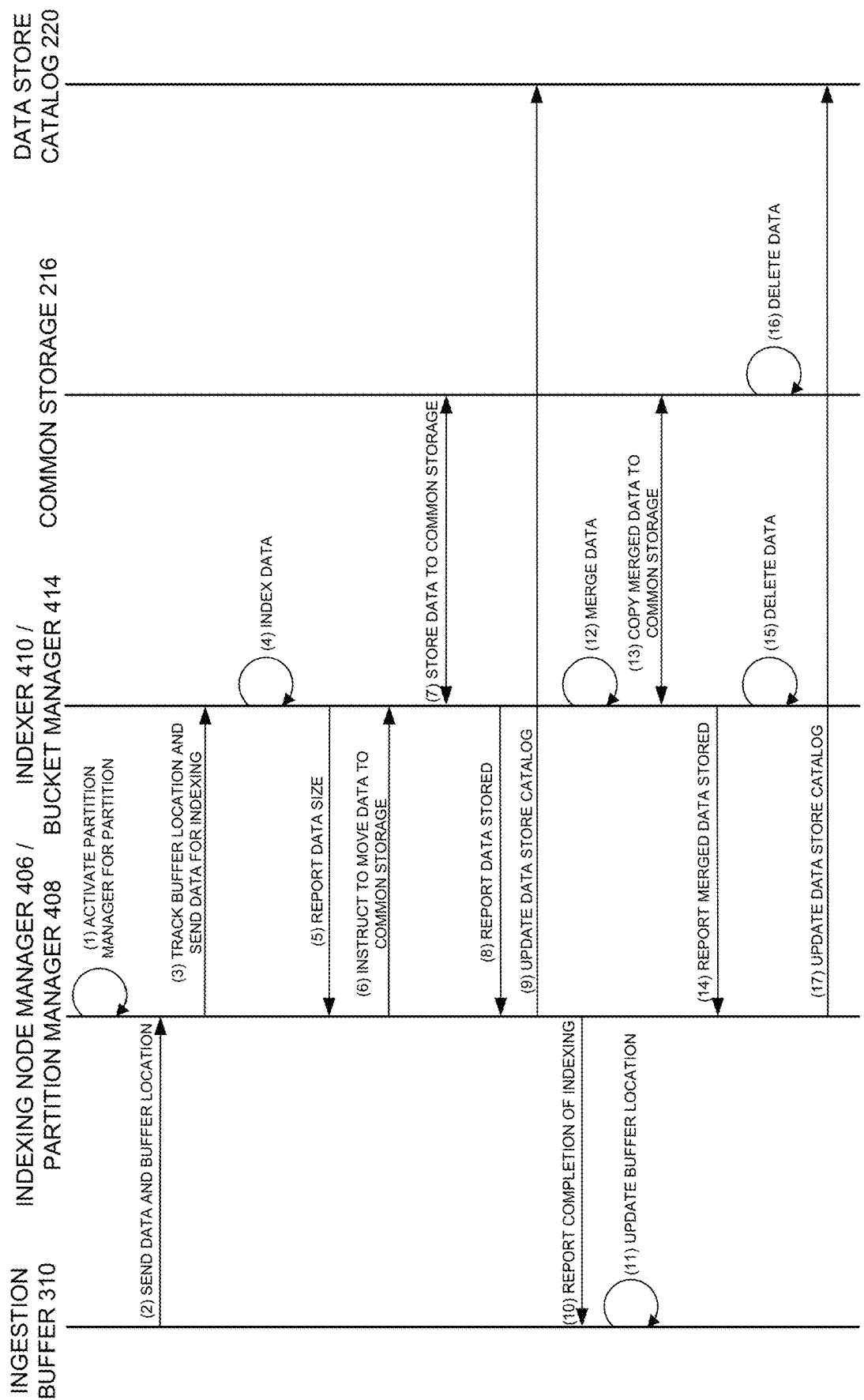
FIG. 9 is a data flow diagram illustrating an embodiment of the data flow and communications between a variety of the components of the data intake and query system during indexing.

FIG. 9 is a data flow diagram illustrating an embodiment of the data flow and communications between a variety of the components of the data intake and query system 108 during indexing. Specifically, FIG. 9 is a data flow diagram illustrating an embodiment of the data flow and communications between an ingestion buffer 310, an indexing node manager 406 or partition manager 408, an indexer 410, common storage 216, and the data store catalog 220. However, it will be understood, that in some of embodiments, one or more of the functions described herein with respect to FIG. 9 can be omitted, performed in a different order and/or performed by a different component of the data intake and query system 108. Accordingly, the illustrated embodiment and description should not be construed as limiting.

At (1), the indexing node manager 406 activates a partition manager 408 for a partition. As described herein, the indexing node manager 406 can activate a partition manager 408 for each partition or shard that is processed by an indexing node 404. In some embodiments, the indexing node manager 406 can activate the partition manager 408 based on an assignment of a new partition to the indexing node 404 or a partition manager 408 becoming unresponsive or unavailable, etc.

In some embodiments, the partition manager 408 can be a copy of the indexing node manager 406 or a copy of a template process. In certain embodiments, the partition manager 408 can be instantiated in a separate container from the indexing node manager 406.

At (2), the ingestion buffer 310 sends data and a buffer location to the indexing node 404. As described herein, the data can be raw machine data, performance metrics data, correlation data, JSON blobs, XML data, data in a datamodel, report data, tabular data, streaming data, data exposed in an API, data in a relational database, etc. The buffer location can correspond to a marker in the ingestion buffer 310 that indicates the point at which the data within a partition has been communicated to the indexing node 404. For example, data before the marker can correspond to data that has not been communicated to the indexing node 404, and data after the marker can correspond to data that has been communicated to the indexing node. In some cases, the marker can correspond to a set of data that has been communicated to the indexing node 404, but for which no indication has been received that the data has been stored. Accordingly, based on the marker, the ingestion buffer 310 can retain a portion of its data persistently until it receives confirmation that the data can be deleted or has been stored in common storage 216.

At (3), the indexing node manager 406 tracks the buffer location and the partition manager 408 communicates the data to the indexer 410. As described herein, the indexing node manager 406 can track (and/or store) the buffer location for the various partitions received from the ingestion buffer 310. In addition, as described herein, the partition manager 408 can forward the data received from the ingestion buffer 310 to the indexer 410 for processing. In various implementations, as previously described, the data from ingestion buffer 310 that is sent to the indexer 410 may include a path to stored data, e.g., data stored in common storage 216 or another common store, which is then retrieved by the indexer 410 or another component of the indexing node 404.

At (4), the indexer 410 processes the data. As described herein, the indexer 410 can perform a variety of functions, enrichments, or transformations on the data as it is indexed. For example, the indexer 410 can parse the data, identify events from the data, identify and associate timestamps with the events, associate metadata or one or more field values with the events, group events (e.g., based on time, partition, and/or tenant ID, etc.), etc. Furthermore, the indexer 410 can generate buckets based on a bucket creation policy and store the events in the hot buckets, which may be stored in data store 412 of the indexing node 404 associated with that indexer 410 (see FIG. 4).

At (5), the indexer 410 reports the size of the data being indexed to the partition manager 408. In some cases, the indexer 410 can routinely provide a status update to the partition manager 408 regarding the data that is being processed by the indexer 410.

The status update can include, but is not limited to the size of the data, the number of buckets being created, the amount of time since the buckets have been created, etc. In some embodiments, the indexer 410 can provide the status update based on one or more thresholds being satisfied (e.g., one or more threshold sizes being satisfied by the amount of data being processed, one or more timing thresholds being satisfied based on the amount of time the buckets have been created, one or more bucket number thresholds based on the number of buckets created, the number of hot or warm buckets, number of buckets that have not been stored in common storage 216, etc.).

In certain cases, the indexer 410 can provide an update to the partition manager 408 regarding the size of the data that is being processed by the indexer 410 in response to one or more threshold sizes being satisfied. For example, each time a certain amount of data is added to the indexer 410 (e.g., 5 MB, 10 MB, etc.), the indexer 410 can report the updated size to the partition manager 408. In some cases, the indexer 410 can report the size of the data stored thereon to the partition manager 408 once a threshold size is satisfied.

In certain embodiments, the indexer 408 reports the size of the date being indexed to the partition manager 408 based on a query by the partition manager 408. In certain embodiments, the indexer 410 and partition manager 408 maintain an open communication link such that the partition manager 408 is persistently aware of the amount of data on the indexer 410.

In some cases, a partition manager 408 monitors the data processed by the indexer 410. For example, the partition manager 408 can track the size of the data on the indexer 410 that is associated with the partition being managed by the partition manager 408. In certain cases, one or more partition managers 408 can track the amount or size of the data on the indexer 410 that is associated with any partition being managed by the indexing node manager 406 or that is associated with the indexing node 404.

At (6), the partition manager 408 instructs the indexer 410 to copy the data to common storage 216. As described herein, the partition manager 408 can instruct the indexer 410 to copy the data to common storage 216 based on a bucket roll-over policy. As described herein, in some cases, the bucket roll-over policy can indicate that one or more buckets are to be rolled over based on size. Accordingly, in some embodiments, the partition manager 408 can instruct the indexer 410 to copy the data to common storage 216 based on a determination that the amount of data stored on the indexer 410 satisfies a threshold amount. The threshold amount can correspond to the amount of data associated with the partition that is managed by the partition manager 408 or the amount of data being processed by the indexer 410 for any partition.

In some cases, the partition manager 408 can instruct the indexer 410 to copy the data that corresponds to the partition being managed by the partition manager 408 to common storage 216 based on the size of the data that corresponds to the partition satisfying the threshold amount. In certain embodiments, the partition manager 408 can instruct the indexer 410 to copy the data associated with any partition being processed by the indexer 410 to common storage 216 based on the amount of the data from the partitions that are being processed by the indexer 410 satisfying the threshold amount.

In some embodiments, (5) and/or (6) can be omitted. For example, the indexer 410 can monitor the data stored thereon. Based on the bucket roll-over policy, the indexer 410 can determine that the data is to be copied to common storage 216. Accordingly, in some embodiments, the indexer 410 can determine that the data is to be copied to common storage 216 without communication with the partition manager 408.

At (7), the indexer 410 copies and/or stores the data to common storage 216. As described herein, in some cases, as the indexer 410 processes the data, it generates events and stores the events in hot buckets. In response to receiving the instruction to move the data to common storage 216, the indexer 410 can convert the hot buckets to warm buckets, and copy or move the warm buckets to the common storage 216.

As part of storing the data to common storage 216, the indexer 410 can verify or obtain acknowledgements that the data is stored successfully. In some embodiments, the indexer 410 can determine information regarding the data stored in the common storage 216. For example, the information can include location information regarding the data that was stored to the common storage 216, bucket identifiers of the buckets that were copied to common storage 216, as well as additional information, e.g., in implementations in which the ingestion buffer 310 uses sequences of records as the form for data storage, the list of record sequence numbers that were used as part of those buckets that were copied to common storage 216.

At (8), the indexer 410 reports or acknowledges to the partition manager 408 that the data is stored in the common storage 216. In various implementations, this can be in response to periodic requests from the partition manager 408 to the indexer 410 regarding which buckets and/or data have been stored to common storage 216. The indexer 410 can provide the partition manager 408 with information regarding the data stored in common storage 216 similar to the data that is provided to the indexer 410 by the common storage 216. In some cases, (8) can be replaced with the common storage 216 acknowledging or reporting the storage of the data to the partition manager 408.

At (9), the partition manager 408 updates the data store catalog 220. As described herein, the partition manager 408 can update the data store catalog 220 with information regarding the data or buckets stored in common storage 216. For example, the partition manager 408 can update the data store catalog 220 to include location information, a bucket identifier, a time range, and tenant and partition information regarding the buckets copied to common storage 216, etc. In this way, the data store catalog 220 can include up-to-date information regarding the buckets stored in common storage 216.

At (10), the partition manager 408 reports the completion of the storage to the ingestion buffer 310, and at (11), the ingestion buffer 310 updates the buffer location or marker. Accordingly, in some embodiments, the ingestion buffer 310 can maintain its marker until it receives an acknowledgement that the data that it sent to the indexing node 404 has been indexed by the indexing node 404 and stored to common storage 216. In addition, the updated buffer location or marker can be communicated to and stored by the indexing node manager 406. In this way, a data intake and query system 108 can use the ingestion buffer 310 to provide a stateless environment for the indexing system 212. For example, as described herein, if an indexing node 404 or one of its components (e.g., indexing node manager 486, partition manager 408, indexer) becomes unavailable or unresponsive before data from the ingestion buffer 310 is copied to common storage 216, the indexing system 212 can generate or assign a new indexing node 404 (or component), to process the data that was assigned to the now unavailable indexing node 404 (or component) while reducing, minimizing, or eliminating data loss.

At (12), a bucket manager 414, which may form part of the indexer 410, the indexing node 404, or indexing system 212, merges multiple buckets into one or more merged buckets. As described herein, to reduce delay between processing data and making that data available for searching, the indexer 410 can convert smaller hot buckets to warm buckets and copy the warm buckets to common storage 216. However, as smaller buckets in common storage 216 can result in increased overhead and storage costs, the bucket manager 414 can monitor warm buckets in the indexer 410 and merge the warm buckets into one or more merged buckets.

In some cases, the bucket manager 414 can merge the buckets according to a bucket merge policy. As described herein, the bucket merge policy can indicate which buckets are candidates for a merge (e.g., based on time ranges, size, tenant/partition or other identifiers, etc.), the number of buckets to merge, size or time range parameters for the merged buckets, a frequency for creating the merged buckets, etc.

At (13), the bucket manager 414 stores and/or copies the merged data or buckets to common storage 216, and obtains information about the merged buckets stored in common storage 216. Similar to (7), the obtained information can include information regarding the storage of the merged buckets, such as, but not limited to, the location of the buckets, one or more bucket identifiers, tenant or partition identifiers, etc. At (14), the bucket manager 414 reports the storage of the merged data to the partition manager 408, similar to the reporting of the data storage at (8).

At (15), the indexer 410 deletes data from the data store (e.g., data store 412). As described herein, once the merged buckets have been stored in common storage 216, the indexer 410 can delete corresponding buckets that it has stored locally. For example, the indexer 410 can delete the merged buckets from the data store 412, as well as the pre-merged buckets (buckets used to generate the merged buckets). By removing the data from the data store 412, the indexer 410 can free up additional space for additional hot buckets, warm buckets, and/or merged buckets.

At (16), the common storage 216 deletes data according to a bucket management policy. As described herein, once the merged buckets have been stored in common storage 216, the common storage 216 can delete the pre-merged buckets stored therein. In some cases, as described herein, the common storage 216 can delete the pre-merged buckets immediately, after a predetermined amount of time, after one or more queries relying on the pre-merged buckets have completed, or based on other criteria in the bucket management policy, etc. In certain embodiments, a controller at the common storage 216 handles the deletion of the data in common storage 216 according to the bucket management policy. In certain embodiments, one or more components of the indexing node 404 delete the data from common storage 216 according to the bucket management policy. However, for simplicity, reference is made to common storage 216 performing the deletion.

At (17), the partition manager 408 updates the data store catalog 220 with the information about the merged buckets. Similar to (9), the partition manager 408 can update the data store catalog 220 with the merged bucket information. The information can include, but is not limited to, the time range of the merged buckets, location of the merged buckets in common storage 216, a bucket identifier for the merged buckets, tenant and partition information of the merged buckets, etc. In addition, as part of updating the data store catalog 220, the partition manager 408 can remove reference to the pre-merged buckets. Accordingly, the data store catalog 220 can be revised to include information about the merged buckets and omit information about the pre-merged buckets. In this way, as the search managers 514 request information about buckets in common storage 216 from the data store catalog 220, the data store catalog 220 can provide the search managers 514 with the merged bucket information.

As mentioned previously, in some of embodiments, one or more of the functions described herein with respect to FIG. 9 can be omitted, performed in a variety of orders and/or performed by a different component of the data intake and query system 108. For example, the partition manager 408 can (9) update the data store catalog 220 before, after, or concurrently with the deletion of the data in the (15) indexer 410 or (16) common storage 216. Similarly, in certain embodiments, the indexer 410 can (12) merge buckets before, after, or concurrently with (7)-(11), etc.

4.2.1. Containerized Indexing Nodes

Figure 10:
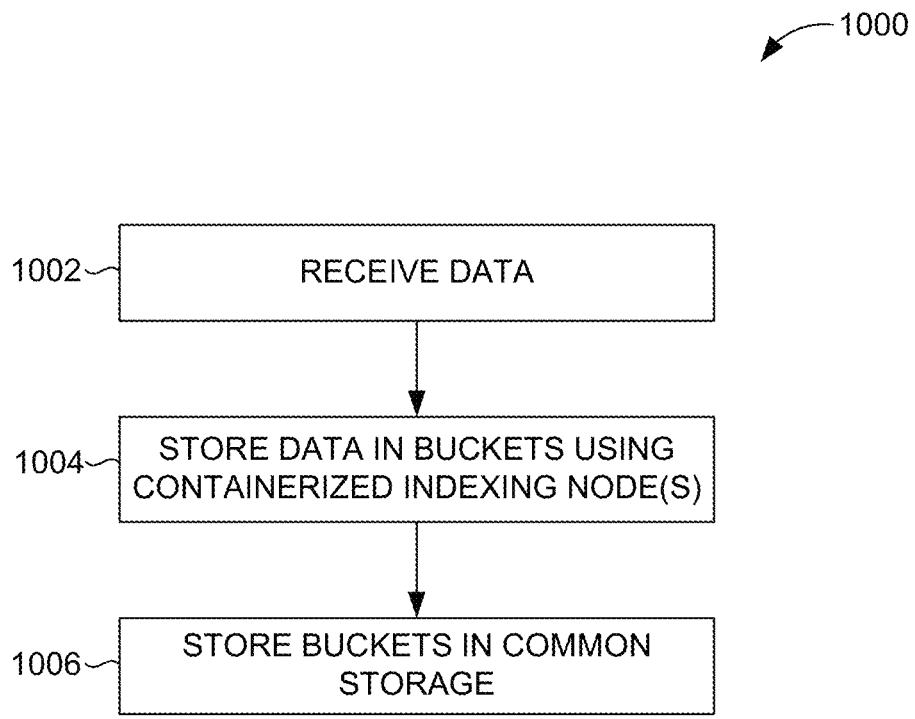
FIG. 10 is a flow diagram illustrative of an embodiment of a routine implemented by an indexing system to store data in common storage.

FIG. 10 is a flow diagram illustrative of an embodiment of a routine 1000 implemented by the indexing system 212 to store data in common storage 216. Although described as being implemented by the indexing system 212, it will be understood that the elements outlined for routine 1000 can be implemented by one or more computing devices/components that are associated with the data intake and query system 108, such as, but not limited to, the indexing manager 402, the indexing node 404, indexing node manager 406, the partition manager 408, the indexer 410, the bucket manager 414, etc. Thus, the following illustrative embodiment should not be construed as limiting.

At block 1002, the indexing system 212 receives data. As described herein, the system 312 can receive data from a variety of sources in various formats. For example, as described herein, the data received can be machine data, performance metrics, correlated data, etc.

At block 1004, the indexing system 212 stores the data in buckets using one or more containerized indexing nodes 404. As described herein, the indexing system 212 can include multiple containerized indexing nodes 404 to receive and process the data. The containerized indexing nodes 404 can enable the indexing system 212 to provide a highly extensible and dynamic indexing service. For example, based on resource availability and/or workload, the indexing system 212 can instantiate additional containerized indexing nodes 404 or terminate containerized indexing nodes 404. Further, multiple containerized indexing nodes 404 can be instantiated on the same computing device, and share the resources of the computing device.

As described herein, each indexing node 404 can be implemented using containerization or operating-system-level virtualization, or other virtualization technique. For example, the indexing node 404, or one or more components of the indexing node 404 can be implemented as separate containers or container instances. Each container instance can have certain resources (e.g., memory, processor, etc.) of the underlying computing system assigned to it, but may share the same operating system and may use the operating system's system call interface. Further, each container may run the same or different computer applications concurrently or separately, and may interact with each other. It will be understood that other virtualization techniques can be used. For example, the containerized indexing nodes 404 can be implemented using virtual machines using full virtualization or paravirtualization, etc.

In some embodiments, the indexing node 404 can be implemented as a group of related containers or a pod, and the various components of the indexing node 404 can be implemented as related containers of a pod. Further, the indexing node 404 can assign different containers to execute different tasks. For example, one container of a containerized indexing node 404 can receive the incoming data and forward it to a second container for processing, etc. The second container can generate buckets for the data, store the data in buckets, and communicate the buckets to common storage 216. A third container of the containerized indexing node 404 can merge the buckets into merged buckets and store the merged buckets in common storage. However, it will be understood that the containerized indexing node 404 can be implemented in a variety of configurations. For example, in some cases, the containerized indexing node 404 can be implemented as a single container and can include multiple processes to implement the tasks described above by the three containers. Any combination of containerization and processed can be used to implement the containerized indexing node 404 as desired.

In some embodiments, the containerized indexing node 404 processes the received data (or the data obtained using the received data) and stores it in buckets. As part of the processing, the containerized indexing node 404 can determine information about the data (e.g., host, source, sourcetype), extract or identify timestamps, associated metadata fields with the data, extract keywords, transform the data, identify and organize the data into events having raw machine data associated with a timestamp, etc. In some embodiments, the containerized indexing node 404 uses one or more configuration files and/or extraction rules to extract information from the data or events.

In addition, as part of processing and storing the data, the containerized indexing node 404 can generate buckets for the data according to a bucket creation policy. As described herein, the containerized indexing node 404 can concurrently generate and fill multiple buckets with the data that it processes. In some embodiments, the containerized indexing node 404 generates buckets for each partition or tenant associated with the data that is being processed. In certain embodiments, the indexing node 404 stores the data or events in the buckets based on the identified timestamps.

Furthermore, containerized indexing node 404 can generate one or more indexes associated with the buckets, such as, but not limited to, one or more inverted indexes, TSIDXs, keyword indexes, etc. The data and the indexes can be stored in one or more files of the buckets. In addition, the indexing node 404 can generate additional files for the buckets, such as, but not limited to, one or more filter files, a bucket summary, or manifest, etc.

At block 1006, the indexing node 404 stores buckets in common storage 216. As described herein, in certain embodiments, the indexing node 404 stores the buckets in common storage 216 according to a bucket roll-over policy. In some cases, the buckets are stored in common storage 216 in one or more directories based on an index/partition or tenant associated with the buckets. Further, the buckets can be stored in a time series manner to facilitate time series searching as described herein. Additionally, as described herein, the common storage 216 can replicate the buckets across multiple tiers and data stores across one or more geographical locations.

Fewer, more, or different blocks can be used as part of the routine 1000. In some cases, one or more blocks can be omitted. For example, in some embodiments, the containerized indexing node 404 or a indexing system manager 402 can monitor the amount of data received by the indexing system 212. Based on the amount of data received and/or a workload or utilization of the containerized indexing node 404, the indexing system 212 can instantiate an additional containerized indexing node 404 to process the data.

In some cases, the containerized indexing node 404 can instantiate a container or process to manage the processing and storage of data from an additional shard or partition of data received from the intake system. For example, as described herein, the containerized indexing node 404 can instantiate a partition manager 408 for each partition or shard of data that is processed by the containerized indexing node 404.

In certain embodiments, the indexing node 404 can delete locally stored buckets. For example, once the buckets are stored in common storage 216, the indexing node 404 can delete the locally stored buckets. In this way, the indexing node 404 can reduce the amount of data stored thereon.

As described herein, the indexing node 404 can merge buckets and store merged buckets in the common storage 216. In some cases, as part of merging and storing buckets in common storage 216, the indexing node 404 can delete locally storage pre-merged buckets (buckets used to generate the merged buckets) and/or the merged buckets or can instruct the common storage 216 to delete the pre-merged buckets. In this way, the indexing node 404 can reduce the amount of data stored in the indexing node 404 and/or the amount of data stored in common storage 216.

In some embodiments, the indexing node 404 can update a data store catalog 220 with information about pre-merged or merged buckets stored in common storage 216. As described herein, the information can identify the location of the buckets in common storage 216 and other information, such as, but not limited to, a partition or tenant associated with the bucket, time range of the bucket, etc. As described herein, the information stored in the data store catalog 220 can be used by the query system 214 to identify buckets to be searched as part of a query.

Furthermore, it will be understood that the various blocks described herein with reference to FIG. 10 can be implemented in a variety of orders, or can be performed concurrently. For example, the indexing node 404 can concurrently convert buckets and store them in common storage 216, or concurrently receive data from a data source and process data from the data source, etc.

4.2.2. Moving Buckets to Common Storage

Figure 11:
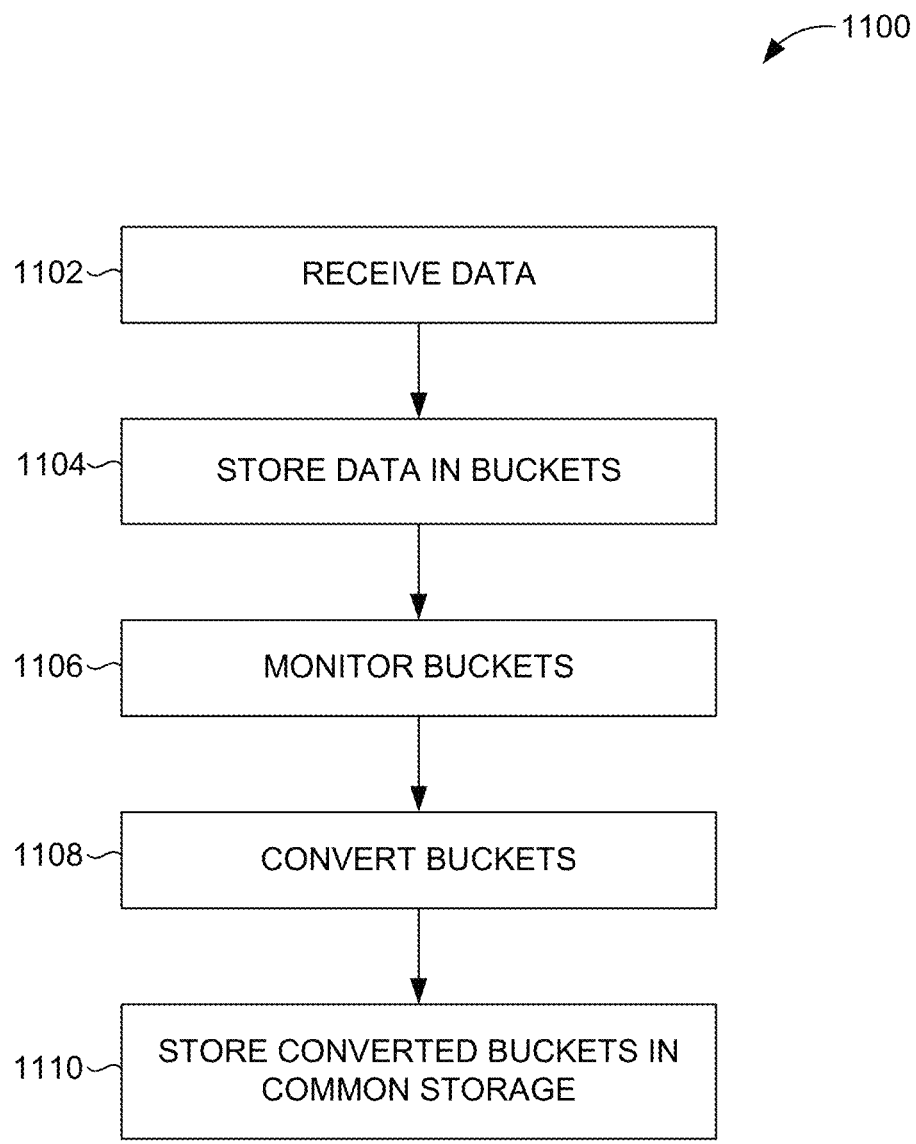
FIG. 11 is a flow diagram illustrative of an embodiment of a routine implemented by an indexing system to store data in common storage.

FIG. 11 is a flow diagram illustrative of an embodiment of a routine 1000 implemented by the indexing node 404 to store data in common storage 216. Although described as being implemented by the indexing node 404, it will be understood that the elements outlined for routine 1000 can be implemented by one or more computing devices/components that are associated with the data intake and query system 108, such as, but not limited to, the indexing manager 402, the indexing node manager 406, the partition manager 408, the indexer 410, the bucket manager 414, etc. Thus, the following illustrative embodiment should not be construed as limiting.

At block 1102, the indexing node 404 receives data. As described herein, the indexing node 404 can receive data from a variety of sources in various formats. For example, as described herein, the data received can be machine data, performance metrics, correlated data, etc.

Further, as described herein, the indexing node 404 can receive data from one or more components of the intake system 210 (e.g., the ingesting buffer 310, forwarder 302, etc.) or other data sources 202. In some embodiments, the indexing node 404 can receive data from a shard or partition of the ingestion buffer 310. Further, in certain cases, the indexing node 404 can generate a partition manager 408 for each shard or partition of a data stream. In some cases, the indexing node 404 receives data from the ingestion buffer 310 that references or points to data stored in one or more data stores, such as a data store 218 of common storage 216, or other network accessible data store or cloud storage. In such embodiments, the indexing node 404 can obtain the data from the referenced data store using the information received from the ingestion buffer 310.

At block 1104, the indexing node 404 stores data in buckets. In some embodiments, the indexing node 404 processes the received data (or the data obtained using the received data) and stores it in buckets. As part of the processing, the indexing node 404 can determine information about the data (e.g., host, source, sourcetype), extract or identify timestamps, associated metadata fields with the data, extract keywords, transform the data, identify and organize the data into events having raw machine data associated with a timestamp, etc. In some embodiments, the indexing node 404 uses one or more configuration files and/or extraction rules to extract information from the data or events.

In addition, as part of processing and storing the data, the indexing node 404 can generate buckets for the data according to a bucket creation policy. As described herein, the indexing node 404 can concurrently generate and fill multiple buckets with the data that it processes. In some embodiments, the indexing node 404 generates buckets for each partition or tenant associated with the data that is being processed. In certain embodiments, the indexing node 404 stores the data or events in the buckets based on the identified timestamps.

Furthermore, indexing node 404 can generate one or more indexes associated with the buckets, such as, but not limited to, one or more inverted indexes, TSIDXs, keyword indexes, bloom filter files, etc. The data and the indexes can be stored in one or more files of the buckets. In addition, the indexing node 404 can generate additional files for the buckets, such as, but not limited to, one or more filter files, a buckets summary, or manifest, etc.

At block 1106, the indexing node 404 monitors the buckets. As described herein, the indexing node 404 can process significant amounts of data across a multitude of buckets, and can monitor the size or amount of data stored in individual buckets, groups of buckets or all the buckets that it is generating and filling. In certain embodiments, one component of the indexing node 404 can monitor the buckets (e.g., partition manager 408), while another component fills the buckets (e.g., indexer 410).

In some embodiments, as part of monitoring the buckets, the indexing node 404 can compare the individual size of the buckets or the collective size of multiple buckets with a threshold size. Once the threshold size is satisfied, the indexing node 404 can determine that the buckets are to be stored in common storage 216. In certain embodiments, the indexing node 404 can monitor the amount of time that has passed since the buckets have been stored in common storage 216. Based on a determination that a threshold amount of time has passed, the indexing node 404 can determine that the buckets are to be stored in common storage 216. Further, it will be understood that the indexing node 404 can use a bucket roll-over policy and/or a variety of techniques to determine when to store buckets in common storage 216.

At block 1108, the indexing node 404 converts the buckets. In some cases, as part of preparing the buckets for storage in common storage 216, the indexing node 404 can convert the buckets from editable buckets to non-editable buckets. In some cases, the indexing node 404 convert hot buckets to warm buckets based on the bucket roll-over policy. The bucket roll-over policy can indicate that buckets are to be converted from hot to warm buckets based on a predetermined period of time, one or more buckets satisfying a threshold size, the number of hot buckets, etc. In some cases, based on the bucket roll-over policy, the indexing node 404 converts hot buckets to warm buckets based on a collective size of multiple hot buckets satisfying a threshold size. The multiple hot buckets can correspond to any one or any combination of randomly selected hot buckets, hot buckets associated with a particular partition or shard (or partition manager 408), hot buckets associated with a particular tenant or partition, all hot buckets in the data store 412 or being processed by the indexer 410, etc.

At block 1110, the indexing node 404 stores the converted buckets in a data store. As described herein, the indexing node 404 can store the buckets in common storage 216 or other location accessible to the query system 214. In some cases, the indexing node 404 stores a copy of the buckets in common storage 416 and retains the original bucket in its data store 412. In certain embodiments, the indexing node 404 stores a copy of the buckets in common storage and deletes any reference to the original buckets in its data store 412.

Furthermore, as described herein, in some cases, the indexing node 404 can store the one or more buckets based on the bucket roll-over policy. In addition to indicating when buckets are to be converted from hot buckets to warm buckets, the bucket roll-over policy can indicate when buckets are to be stored in common storage 216. In some cases, the bucket roll-over policy can use the same or different policies or thresholds to indicate when hot buckets are to be converted to warm and when buckets are to be stored in common storage 216.

In certain embodiments, the bucket roll-over policy can indicate that buckets are to be stored in common storage 216 based on a collective size of buckets satisfying a threshold size. As mentioned, the threshold size used to determine that the buckets are to be stored in common storage 216 can be the same as or different from the threshold size used to determine that editable buckets should be converted to non-editable buckets. Accordingly, in certain embodiments, based on a determination that the size of the one or more buckets have satisfied a threshold size, the indexing node 404 can convert the buckets to non-editable buckets and store the buckets in common storage 216.

Other thresholds and/or other factors or combinations of thresholds and factors can be used as part of the bucket roll-over policy. For example, the bucket roll-over policy can indicate that buckets are to be stored in common storage 216 based on the passage of a threshold amount of time. As yet another example, bucket roll-over policy can indicate that buckets are to be stored in common storage 216 based on the number of buckets satisfying a threshold number.

It will be understood that the bucket roll-over policy can use a variety of techniques or thresholds to indicate when to store the buckets in common storage 216. For example, in some cases, the bucket roll-over policy can use any one or any combination of a threshold time period, threshold number of buckets, user information, tenant or partition information, query frequency, amount of data being received, time of day or schedules, etc., to indicate when buckets are to be stored in common storage 216 (and/or converted to non-editable buckets). In some cases, the bucket roll-over policy can use different priorities to determine how to store the buckets, such as, but not limited to, minimizing or reducing time between processing and storage to common storage 216, maximizing or increasing individual bucket size, etc. Furthermore, the bucket roll-over policy can use dynamic thresholds to indicate when buckets are to be stored in common storage 216.

As mentioned, in some cases, based on an increased query frequency, the bucket roll-over policy can indicate that buckets are to be moved to common storage 216 more frequently by adjusting one more thresholds used to determine when the buckets are to be stored to common storage 216 (e.g., threshold size, threshold number, threshold time, etc.).

In addition, the bucket roll-over policy can indicate that different sets of buckets are to be rolled-over differently or at different rates or frequencies. For example, the bucket roll-over policy can indicate that buckets associated with a first tenant or partition are to be rolled over according to one policy and buckets associated with a second tenant or partition are to be rolled over according to a different policy. The different policies may indicate that the buckets associated with the first tenant or partition are to be stored more frequently to common storage 216 than the buckets associated with the second tenant or partition. Accordingly, the bucket roll-over policy can use one set of thresholds (e.g., threshold size, threshold number, and/or threshold time, etc.)

to indicate when the buckets associated with the first tenant or partition are to be stored in common storage 216 and a different set of thresholds for the buckets associated with the second tenant or partition.

As another non-limiting example, consider a scenario in which buckets from a partition _main are being queried more frequently than bucket from the partition _test. The bucket roll-over policy can indicate that based on the increased frequency of queries for buckets from partition _main, buckets associated with partition _main should be moved more frequently to common storage 216, for example, by adjusting the threshold size used to determine when to store the buckets in common storage 216. In this way, the query system 214 can obtain relevant search results more quickly for data associated with the _main partition. Further, if the frequency of queries for buckets from the _main partition decreases, the data intake and query system 108 can adjust the threshold accordingly. In addition, the bucket roll-over policy may indicate that the changes are only for buckets associated with the partition _main or that the changes are to be made for all buckets, or all buckets associated with a particular tenant that is associated with the partition _main, etc.

Furthermore, as mentioned, the bucket roll-over policy can indicate that buckets are to be stored in common storage 216 at different rates or frequencies based on time of day. For example, the data intake and query system 108 can adjust the thresholds so that the buckets are moved to common storage 216 more frequently during working hours and less frequently during non-working hours. In this way, the delay between processing and making the data available for searching during working hours can be reduced, and can decrease the amount of merging performed on buckets generated during non-working hours. In other cases, the data intake and query system 108 can adjust the thresholds so that the buckets are moved to common storage 216 less frequently during working hours and more frequently during non-working hours.

As mentioned, the bucket roll-over policy can indicate that based on an increased rate at which data is received, buckets are to be moved to common storage more (or less) frequently. For example, if the bucket roll-over policy initially indicates that the buckets are to be stored every millisecond, as the rate of data received by the indexing node 404 increases, the amount of data received during each millisecond can increase, resulting in more data waiting to be stored. As such, in some cases, the bucket roll-over policy can indicate that the buckets are to be stored more frequently in common storage 216. Further, in some cases, such as when a collective bucket size threshold is used, an increased rate at which data is received may overburden the indexing node 404 due to the overhead associated with copying each bucket to common storage 216. As such, in certain cases, the bucket roll-over policy can use a larger collective bucket size threshold to indicate that the buckets are to be stored in common storage 216. In this way, the bucket roll-over policy can reduce the ratio of overhead to data being stored.

Similarly, the bucket roll-over policy can indicate that certain users are to be treated differently. For example, if a particular user is logged in, the bucket roll-over policy can indicate that the buckets in an indexing node 404 are to be moved to common storage 216 more or less frequently to accommodate the user's preferences, etc. Further, as mentioned, in some embodiments, the data intake and query system 108 may indicate that only those buckets associated with the user (e.g., based on tenant information, indexing information, user information, etc.) are to be stored more or less frequently.

Furthermore, the bucket roll-over policy can indicate whether, after copying buckets to common storage 216, the locally stored buckets are to be retained or discarded. In some cases, the bucket roll-over policy can indicate that the buckets are to be retained for merging. In certain cases, the bucket roll-over policy can indicate that the buckets are to be discarded.

Fewer, more, or different blocks can be used as part of the routine 1000. In some cases, one or more blocks can be omitted. For example, in certain embodiments, the indexing node 404 may not convert the buckets before storing them. As another example, the routine 1000 can include notifying the data source, such as the intake system, that the buckets have been uploaded to common storage, merging buckets and uploading merged buckets to common storage, receiving identifying information about the buckets in common storage 216 and updating a data store catalog 220 with the received information, etc.

Furthermore, it will be understood that the various blocks described herein with reference to FIG. 11 can be implemented in a variety of orders, or can be performed concurrently. For example, the indexing node 404 can concurrently convert buckets and store them in common storage 216, or concurrently receive data from a data source and process data from the data source, etc.

4.2.3. Updating Location Marker in Ingestion Buffer

Figure 12:
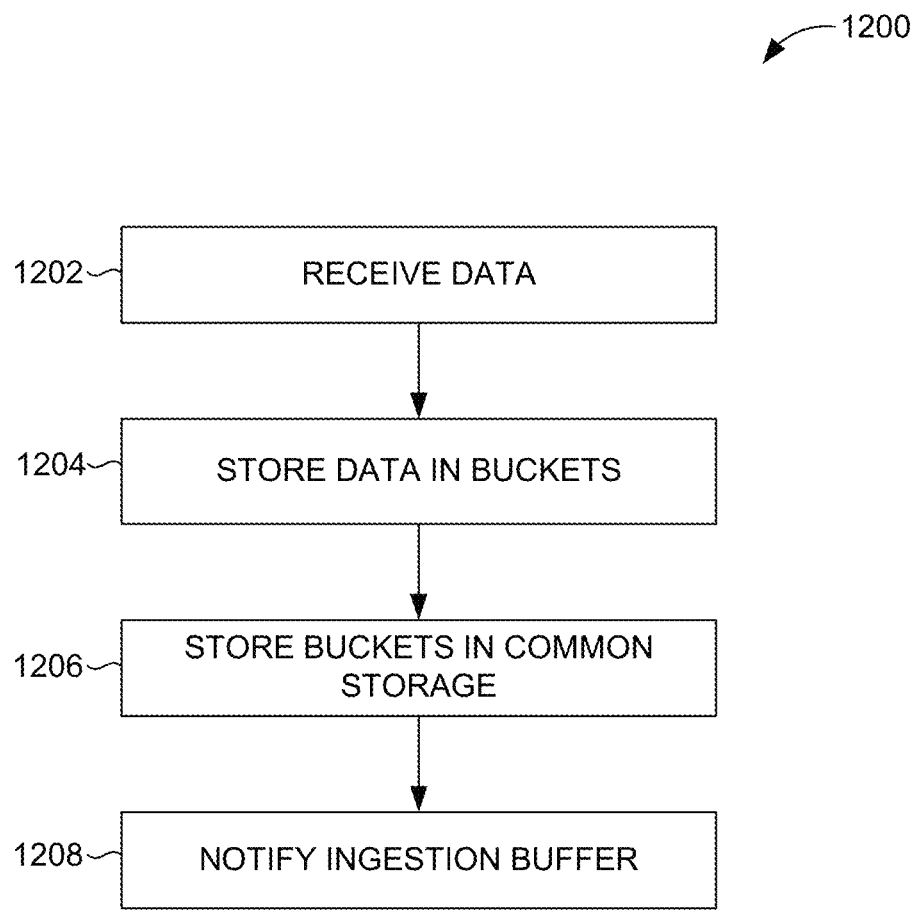
FIG. 12 is a flow diagram illustrative of an embodiment of a routine implemented by an indexing node to update a location marker in an ingestion buffer.

FIG. 12 is a flow diagram illustrative of an embodiment of a routine 1200 implemented by the indexing node 404 to update a location marker in an ingestion buffer, e.g., ingestion buffer 310. Although described as being implemented by the indexing node 404, it will be understood that the elements outlined for routine 1200 can be implemented by one or more computing devices/components that are associated with the data intake and query system 108, such as, but not limited to, the indexing manager 402, the indexing node manager 406, the partition manager 408, the indexer 410, the bucket manager 414, etc. Thus, the following illustrative embodiment should not be construed as limiting. Moreover, although the example refers to updating a location marker in ingestion buffer 310, other implementations can include other ingestion components with other types of location tracking that can be updated in a similar manner as the location marker.

At block 1202, the indexing node 404 receives data. As described in greater detail above with reference to block 1102, the indexing node 404 can receive a variety of types of data from a variety of sources.

In some embodiments, the indexing node 404 receives data from an ingestion buffer 310. As described herein, the ingestion buffer 310 can operate according to a pub-sub messaging service. As such, the ingestion buffer 310 can communicate data to the indexing node 404, and also ensure that the data is available for additional reads until it receives an acknowledgement from the indexing node 404 that the data can be removed.

In some cases, the ingestion buffer 310 can use one or more read pointers or location markers to track the data that has been communicated to the indexing node 404 but that has not been acknowledged for removal. As the ingestion buffer 310 receives acknowledgments from the indexing node 404, it can update the location markers. In some cases, such as where the ingestion buffer 310 uses multiple partitions or shards to provide the data to the indexing node 404, the ingestion buffer 310 can include at least one location marker for each partition or shard. In this way, the ingestion buffer 310 can separately track the progress of the data reads in the different shards.

In certain embodiments, the indexing node 404 can receive (and/or store) the location markers in addition to or as part of the data received from the ingestion buffer 310. Accordingly, the indexing node 404 can track the location of the data in the ingestion buffer 310 that the indexing node 404 has received from the ingestion buffer 310. In this way, if an indexer 410 or partition manager 408 becomes unavailable or fails, the indexing node 404 can assign a different indexer 410 or partition manager 408 to process or manage the data from the ingestion buffer 310 and provide the indexer 410 or partition manager 408 with a location from which the indexer 410 or partition manager 408 can obtain the data.

At block 1204, the indexing node 404 stores the data in buckets. As described in greater detail above with reference to block 1104 of FIG. 11, as part of storing the data in buckets, the indexing node 404 can parse the data, generate events, generate indexes of the data, compress the data, etc. In some cases, the indexing node 404 can store the data in hot or warm buckets and/or convert hot buckets to warm buckets based on the bucket roll-over policy.

At block 1206, the indexing node 404 stores buckets in common storage 216. As described herein, in certain embodiments, the indexing node 404 stores the buckets in common storage 216 according to the bucket roll-over policy. In some cases, the buckets are stored in common storage 216 in one or more directories based on an index/partition or tenant associated with the buckets. Further, the buckets can be stored in a time series manner to facilitate time series searching as described herein. Additionally, as described herein, the common storage 216 can replicate the buckets across multiple tiers and data stores across one or more geographical locations. In some cases, in response to the storage, the indexing node 404 receives an acknowledgement that the data was stored. Further, the indexing node 404 can receive information about the location of the data in common storage, one or more identifiers of the stored data, etc. The indexing node 404 can use this information to update the data store catalog 220.

At block 1208, the indexing node 404 notifies an ingestion buffer 310 that the data has been stored in common storage 216. As described herein, in some cases, the ingestion buffer 310 can retain location markers for the data that it sends to the indexing node 404. The ingestion buffer 310 can use the location markers to indicate that the data sent to the indexing node 404 is to be made persistently available to the indexing system 212 until the ingestion buffer 310 receives an acknowledgement from the indexing node 404 that the data has been stored successfully. In response to the acknowledgement, the ingestion buffer 310 can update the location marker(s) and communicate the updated location markers to the indexing node 404. The indexing node 404 can store updated location markers for use in the event one or more components of the indexing node 404 (e.g., partition manager 408, indexer 410) become unavailable or fail. In this way, the ingestion buffer 310 and the location markers can aid in providing a stateless indexing service.

Fewer, more, or different blocks can be used as part of the routine 1200. In some cases, one or more blocks can be omitted. For example, in certain embodiments, the indexing node 404 can update the data store catalog 220 with information about the buckets created by the indexing node 404 and/or stored in common storage 216, as described herein.

Furthermore, it will be understood that the various blocks described herein with reference to FIG. 12 can be implemented in a variety of orders. In some cases, the indexing node 404 can implement some blocks concurrently or change the order as desired. For example, the indexing node 404 can concurrently receive data, store other data in buckets, and store buckets in common storage.

4.2.4. Merging Buckets

Figure 13:
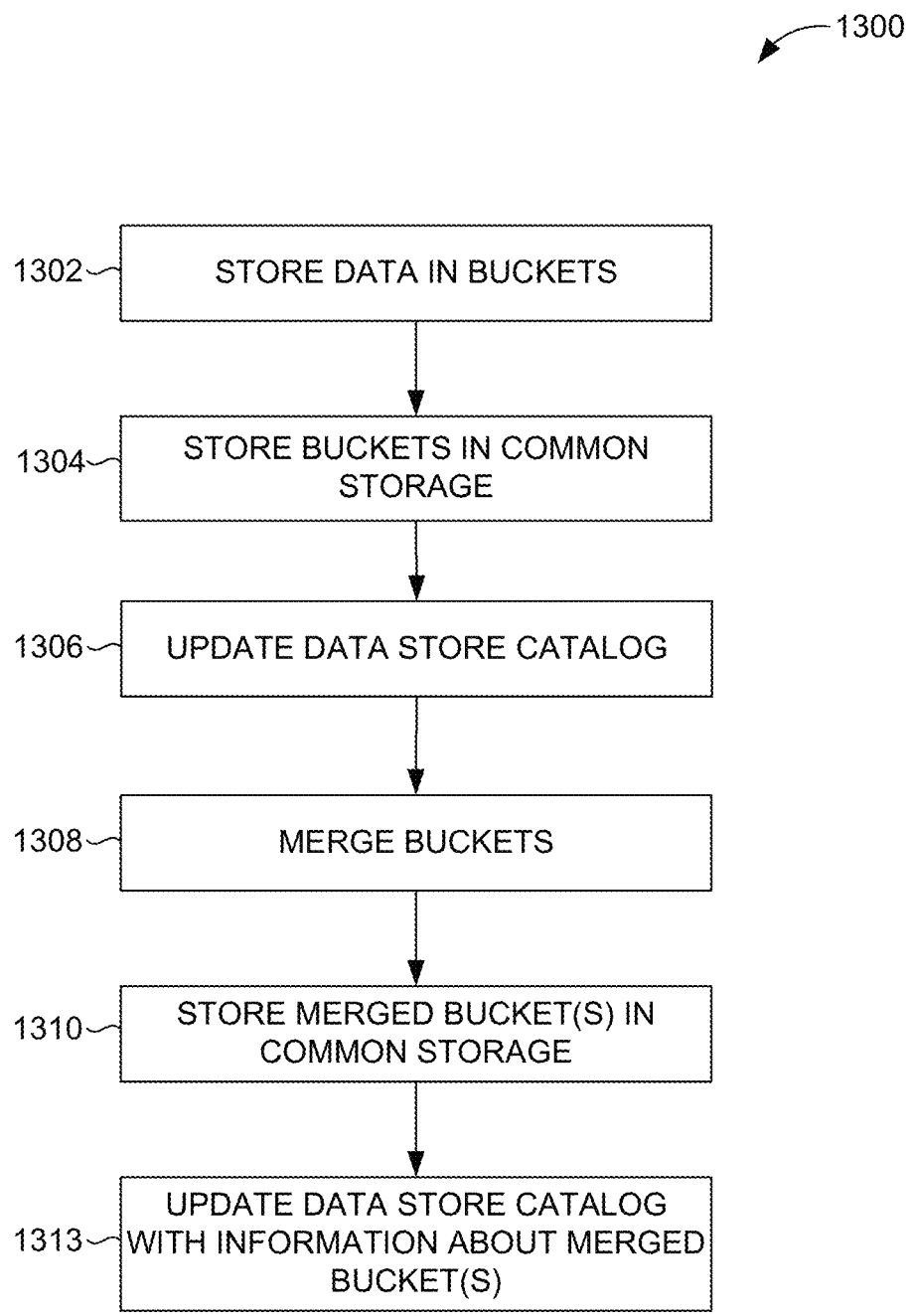
FIG. 13 is a flow diagram illustrative of an embodiment of a routine implemented by an indexing node to merge buckets.

FIG. 13 is a flow diagram illustrative of an embodiment of a routine 1300 implemented by the indexing node 404 to merge buckets. Although described as being implemented by the indexing node 404, it will be understood that the elements outlined for routine 1300 can be implemented by one or more computing devices/components that are associated with the data intake and query system 108, such as, but not limited to, the indexing manager 402, the indexing node manager 406, the partition manager 408, the indexer 410, the bucket manager 414, etc. Thus, the following illustrative embodiment should not be construed as limiting.

At block 1302, the indexing node 404 stores data in buckets. As described herein, the indexing node 404 can process various types of data from a variety of sources. Further, the indexing node 404 can create one or more buckets according to a bucket creation policy and store the data in the store the data in one or more buckets. In addition, in certain embodiments, the indexing node 404 can convert hot or editable buckets to warm or non-editable buckets according to a bucket roll-over policy.

At block 1304, the indexing node 404 stores buckets in common storage 216. As described herein, the indexing node 404 can store the buckets in common storage 216 according to the bucket roll-over policy. In some cases, the buckets are stored in common storage 216 in one or more directories based on an index/partition or tenant associated with the buckets. Further, the buckets can be stored in a time series manner to facilitate time series searching as described herein. Additionally, as described herein, the common storage 216 can replicate the buckets across multiple tiers and data stores across one or more geographical locations.

At block 1306, the indexing node 404 updates the data store catalog 220. As described herein, in some cases, in response to the storage, the indexing node 404 receives an acknowledgement that the data was stored. Further, the indexing node 404 can receive information about the location of the data in common storage, one or more identifiers of the stored data, etc. The received information can be used by the indexing node 404 to update the data store catalog 220. In addition, the indexing node 404 can provide the data store catalog 220 with any one or any combination of the tenant or partition associated with the bucket, a time range of the events in the bucket, one or more metadata fields of the bucket (e.g., host, source, sourcetype, etc.), etc. In this way, the data store catalog 220 can store up-to-date information about the buckets in common storage 216. Further, this information can be used by the query system 214 to identify relevant buckets for a query.

In some cases, the indexing node 404 can update the data store catalog 220 before, after, or concurrently with storing the data to common storage 216. For example, as buckets are created by the indexing node 404, the indexing node 404 can update the data store catalog 220 with information about the created buckets, such as, but not limited to, a partition or tenant associated with the bucket, a time range or initial time (e.g., time of earliest-in-time timestamp), etc. In addition, the indexing node 404 can include an indication that the bucket is a hot bucket or editable bucket and that the contents of the bucket are not (yet) available for searching or in the common storage 216.

As the bucket is filled with events or data, the indexing node 404 can update the data store catalog 220 with additional information about the bucket (e.g., updated time range based on additional events, size of the bucket, number of events in the bucket, certain keywords or metadata from the bucket, such as, but not limited to a host, source, or sourcetype associated with different events in the bucket, etc.). Further, once the bucket is uploaded to common storage 216, the indexing node 404 can complete the entry for the bucket, such as, by providing a completed time range, location information of the bucket in common storage 216, completed keyword or metadata information as desired, etc.

The information in the data store catalog 220 can be used by the query system 214 to execute queries. In some cases, based on the information in the data store catalog 220 about buckets that are not yet available for searching, the query system 214 can wait until the data is available for searching before completing the query or inform a user that some data that may be relevant has not been processed or that the results will be updated. Further, in some cases, the query system 214 can inform the indexing system 212 about the bucket, and the indexing system 212 can cause the indexing node 404 to store the bucket in common storage 216 sooner than it otherwise would without the communication from the query system 214.

In addition, the indexing node 404 can update the data store catalog 220 with information about buckets to be merged. For example, once one or more buckets are identified for merging, the indexing node 404 can update an entry for the buckets in the data store catalog 220 indicating that they are part of a merge operation and/or will be replaced. In some cases, as part of the identification, the data store catalog 220 can provide information about the entries to the indexing node 404 for merging. As the entries may have summary information about the buckets, the indexing node 404 can use the summary information to generate a merged entry for the data store catalog 220 as opposed to generating the summary information from the merged data itself. In this way, the information from the data store catalog 220 can increase the efficiency of a merge operation by the indexing node 404.

At block 1308, the indexing node 404 merges buckets. In some embodiments, the indexing node 404 can merge buckets according to a bucket merge policy. As described herein, the bucket merge policy can indicate which buckets to merge, when to merge buckets and one or more parameters for the merged buckets (e.g., time range for the merged buckets, size of the merged buckets, etc.). For example, the bucket merge policy can indicate that only buckets associated with the same tenant identifier and/or partition can be merged. As another example, the bucket merge policy can indicate that only buckets that satisfy a threshold age (e.g., have existed or been converted to warm buckets for more than a set period of time) are eligible for a merge. Similarly, the bucket merge policy can indicate that each merged bucket must be at least 750 MB or no greater than 1 GB, or cannot have a time range that exceeds a predetermined amount or is larger than 75% of other buckets. The other buckets can refer to one or more buckets in common storage 216 or similar buckets (e.g., buckets associated with the same tenant, partition, host, source, or sourcetype, etc.). In certain cases, the bucket merge policy can indicate that buckets are to be merged based on a schedule (e.g., during non-working hours) or user login (e.g., when a particular user is not logged in), etc. In certain embodiments, the bucket merge policy can indicate that bucket merges can be adjusted dynamically. For example, based on the rate of incoming data or queries, the bucket merge policy can indicate that buckets are to be merged more or less frequently, etc. In some cases, the bucket merge policy can indicate that due to increased processing demands by other indexing nodes 404 or other components of an indexing node 404, such as processing and storing buckets, that bucket merges are to occur less frequently so that the computing resources used to merge buckets can be redirected to other tasks. It will be understood that a variety of priorities and policies can be used as part of the bucket merge policy.

At block 1310, the indexing node 404 stores the merged buckets in common storage 216. In certain embodiments, the indexing node 404 can store the merged buckets based on the bucket merge policy. For example, based on the bucket merge policy indicating that merged buckets are to satisfy a size threshold, the indexing node 404 can store a merged bucket once it satisfies the size threshold. Similarly, the indexing node 404 can store the merged buckets after a predetermined amount of time or during non-working hours, etc., per the bucket merge policy.

In response to the storage of the merged buckets in common storage 216, the indexing node 404 can receive an acknowledgement that the merged buckets have been stored. In some cases, the acknowledgement can include information about the merged buckets, including, but not limited to, a storage location in common storage 216, identifier, etc.

At block 1312, the indexing node 404 updates the data store catalog 220. As described herein, the indexing node 404 can store information about the merged buckets in the data store catalog. 220. The information can be similar to the information stored in the data store catalog 220 for the pre-merged buckets (buckets used to create the merged buckets). For example, in some cases, the indexing node 404 can store any one or any combination of the following in the data store catalog: the tenant or partition associated with the merged buckets, a time range of the merged bucket, the location information of the merged bucket in common storage 216, metadata fields associated with the bucket (e.g., host, source, sourcetype), etc. As mentioned, the information about the merged buckets in the data store catalog 220 can be used by the query system 214 to identify relevant buckets for a search. Accordingly, in some embodiments, the data store catalog 220 can be used in a similar fashion as an inverted index, and can include similar information (e.g., time ranges, field-value pairs, keyword pairs, location information, etc.). However, instead of providing information about individual events in a bucket, the data store catalog 220 can provide information about individual buckets in common storage 216.

In some cases, the indexing node 404 can retrieve information from the data store catalog 220 about the pre-merged buckets and use that information to generate information about the merged bucket(s) for storage in the data store catalog 220. For example, the indexing node 404 can use the time ranges of the pre-merged buckets to generate a merged time range, identify metadata fields associated with the different events in the pre-merged buckets, etc. In certain embodiments, the indexing node 404 can generate the information about the merged buckets for the data store catalog 220 from the merged data itself without retrieving information about the pre-merged buckets from the data store catalog 220.

In certain embodiments, as part of updating the data store catalog 220 with information about the merged buckets, the indexing node 404 can delete the information in the data store catalog 220 about the pre-merged buckets. For example, once the merged bucket is stored in common storage 216, the merged bucket can be used for queries. As such, the information about the pre-merged buckets can be removed so that the query system 214 does not use the pre-merged buckets to execute a query.

Fewer, more, or different blocks can be used as part of the routine 1300. In some cases, one or more blocks can be omitted. For example, in certain embodiments, the indexing node 404 can delete locally stored buckets. In some cases, the indexing node 404 deletes any buckets used to form merged buckets and/or the merged buckets. In this way, the indexing node 404 can reduce the amount of data stored in the indexing node 404.

In certain embodiments, the indexing node 404 can instruct the common storage 216 to delete buckets or delete the buckets in common storage according to a bucket management policy. For example, the indexing node 404 can instruct the common storage 216 to delete any buckets used to generate the merged buckets. Based on the bucket management policy, the common storage 216 can remove the buckets. As described herein, the bucket management policy can indicate when buckets are to be removed from common storage 216. For example, the bucket management policy can indicate that buckets are to be removed from common storage 216 after a predetermined amount of time, once any queries relying on the pre-merged buckets are completed, etc.

By removing buckets from common storage 216, the indexing node 404 can reduce the size or amount of data stored in common storage 216 and improve search times. For example, in some cases, large buckets can increase search times as there are fewer buckets for the query system 214 to search. By another example, merging buckets after indexing allows optimal or near-optimal bucket sizes for search (e.g., performed by query system 214) and index (e.g., performed by indexing system 212) to be determined independently or near-independently.

Furthermore, it will be understood that the various blocks described herein with reference to FIG. 13 can be implemented in a variety of orders. In some cases, the indexing node 404 can implement some blocks concurrently or change the order as desired. For example, the indexing node 404 can concurrently merge buckets while updating an ingestion buffer 310 about the data stored in common storage 216 or updating the data store catalog 220. As another example, the indexing node 404 can delete data about the pre-merged buckets locally and instruct the common storage 216 to delete the data about the pre-merged buckets while concurrently updating the data store catalog 220 about the merged buckets. In some embodiments, the indexing node 404 deletes the pre-merged bucket data entries in the data store catalog 220 prior to instructing the common storage 216 to delete the buckets. In this way, the data indexing node 404 can reduce the risk that a query relies on information in the data store catalog 220 that does not reflect the data stored in the common storage 216.

4.3. Querying

Figure 14:
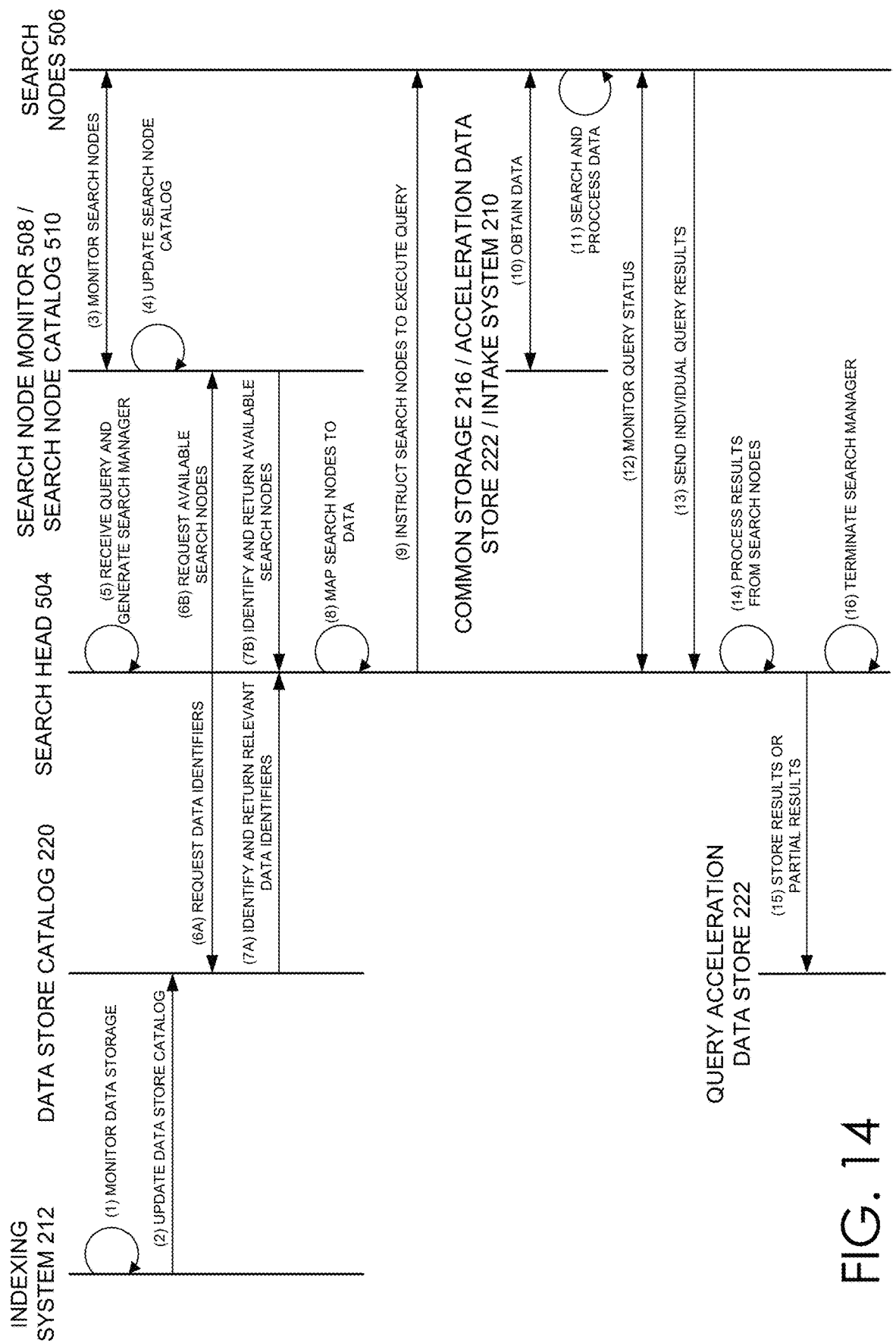
FIG. 14 is a data flow diagram illustrating an embodiment of the data flow and communications between a variety of the components of the data intake and query system during execution of a query.

FIG. 14 is a data flow diagram illustrating an embodiment of the data flow and communications between a variety of the components of the data intake and query system 108 during execution of a query. Specifically, FIG. 14 is a data flow diagram illustrating an embodiment of the data flow and communications between the indexing system 212, the data store catalog 220, a search head 504, a search node monitor 508, search node catalog 510, search nodes 506, common storage 216, and the query acceleration data store 222. However, it will be understood, that in some of embodiments, one or more of the functions described herein with respect to FIG. 14 can be omitted, performed in a different order and/or performed by a different component of the data intake and query system 108. Accordingly, the illustrated embodiment and description should not be construed as limiting.

Further, it will be understood that the various functions described herein with respect to FIG. 14 can be performed by one or more distinct components of the data intake and query system 108. For example, for simplicity, reference is made to a search head 504 performing one or more functions. However, it will be understood that these functions can be performed by one or more components of the search head 504, such as, but not limited to, the search master 512 and/or the search manager 514. Similarly, reference is made to the indexing system 212 performing one or more functions. However, it will be understood that the functions identified as being performed by the indexing system 212 can be performed by one or more components of the indexing system 212.

At (1) and (2), the indexing system 212 monitors the storage of processed data and updates the data store catalog 220 based on the monitoring. As described herein, one or more components of the indexing system 212, such as the partition manager 408 and/or the indexer 410 can monitor the storage of data or buckets to common storage 216. As the data is stored in common storage 216, the indexing system 212 can obtain information about the data stored in the common storage 216, such as, but not limited to, location information, bucket identifiers, tenant identifier (e.g., for buckets that are single tenant) etc. The indexing system 212 can use the received information about the data stored in common storage 216 to update the data store catalog 220.

Furthermore, as described herein, in some embodiments, the indexing system 212 can merge buckets into one or more merged buckets, store the merged buckets in common storage 216, and update the data store catalog to 220 with the information about the merged buckets stored in common storage 216.

At (3) and (4), the search node monitor 508 monitors the search nodes 506 and updates the search node catalog 510. As described herein, the search node monitor 508 can monitor the availability, responsiveness, and/or utilization rate of the search nodes 506. Based on the status of the search nodes 506, the search node monitor 508 can update the search node catalog 510. In this way, the search node catalog 510 can retain information regarding a current status of each of the search nodes 506 in the query system 214.

At (5), the search head 504 receives a query and generates a search manager 514. As described herein, in some cases, a search master 512 can generate the search manager 514. For example, the search master 512 can spin up or instantiate a new process, container, or virtual machine, or copy itself to generate the search manager 514, etc. As described herein, in some embodiments, the search manager 514 can perform one or more of functions described herein with reference to FIG. 14 as being performed by the search head 504 to process and execute the query.

The search head 504 (6A) requests data identifiers from the data store catalog 220 and (6B) requests an identification of available search nodes from the search node catalog 510. As described, the data store catalog 220 can include information regarding the data stored in common storage 216 and the search node catalog 510 can include information regarding the search nodes 506 of the query system 214. Accordingly, the search head 504 can query the respective catalogs to identify data or buckets that include data that satisfies at least a portion of the query and search nodes available to execute the query. In some cases, these requests can be done concurrently or in any order.

At (7A), the data store catalog 220 provides the search head 504 with an identification of data that satisfies at least a portion of the query. As described herein, in response to the request from the search head 504, the data store catalog 220 can be used to identify and return identifiers of buckets in common storage 216 and/or location information of data in common storage 216 that satisfy at least a portion of the query or at least some filter criteria (e.g., buckets associated with an identified tenant or partition or that satisfy an identified time range, etc.).

In some cases, as the data store catalog 220 can routinely receive updates by the indexing system 212, it can implement a read-write lock while it is being queried by the search head 504. Furthermore, the data store catalog 220 can store information regarding which buckets were identified for the search. In this way, the data store catalog 220 can be used by the indexing system 212 to determine which buckets in common storage 216 can be removed or deleted as part of a merge operation.

At (7B), the search node catalog 510 provides the search head 504 with an identification of available search nodes 506. As described herein, in response to the request from the search head 504, the search node catalog 510 can be used to identify and return identifiers for search nodes 506 that are available to execute the query.

At (8) the search head 504 maps the identified search nodes 506 to the data according to a search node mapping policy. In some cases, per the search node mapping policy, the search head 504 can dynamically map search nodes 506 to the identified data or buckets. As described herein, the search head 504 can map the identified search nodes 506 to the identified data or buckets at one time or iteratively as the buckets are searched according to the search node mapping policy. In certain embodiments, per the search node mapping policy, the search head 504 can map the identified search nodes 506 to the identified data based on previous assignments, data stored in a local or shared data store of one or more search heads 506, network architecture of the search nodes 506, a hashing algorithm, etc.

In some cases, as some of the data may reside in a local or shared data store between the search nodes 506, the search head 504 can attempt to map that was previously assigned to a search node 506 to the same search node 506. In certain embodiments, to map the data to the search nodes 506, the search head 504 uses the identifiers, such as bucket identifiers, received from the data store catalog 220. In some embodiments, the search head 504 performs a hash function to map a bucket identifier to a search node 506. In some cases, the search head 504 uses a consistent hash algorithm to increase the probability of mapping a bucket identifier to the same search node 506.

In certain embodiments, the search head 504 or query system 214 can maintain a table or list of bucket mappings to search nodes 506. In such embodiments, per the search node mapping policy, the search head 504 can use the mapping to identify previous assignments between search nodes and buckets. If a particular bucket identifier has not been assigned to a search node 506, the search head 504 can use a hash algorithm to assign it to a search node 506. In certain embodiments, prior to using the mapping for a particular bucket, the search head 504 can confirm that the search node 506 that was previously assigned to the particular bucket is available for the query. In some embodiments, if the search node 506 is not available for the query, the search head 504 can determine whether another search node 506 that shares a data store with the unavailable search node 506 is available for the query. If the search head 504 determines that an available search node 506 shares a data store with the unavailable search node 506, the search head 504 can assign the identified available search node 506 to the bucket identifier that was previously assigned to the now unavailable search node 506.

At (9), the search head 504 instructs the search nodes 506 to execute the query. As described herein, based on the assignment of buckets to the search nodes 506, the search head 504 can generate search instructions for each of the assigned search nodes 506. These instructions can be in various forms, including, but not limited to, JSON, DAG, etc. In some cases, the search head 504 can generate sub-queries for the search nodes 506. Each sub-query or instructions for a particular search node 506 generated for the search nodes 506 can identify the buckets that are to be searched, the filter criteria to identify a subset of the set of data to be processed, and the manner of processing the subset of data. Accordingly, the instructions can provide the search nodes 506 with the relevant information to execute their particular portion of the query.

At (10), the search nodes 506 obtain the data to be searched. As described herein, in some cases the data to be searched can be stored on one or more local or shared data stores of the search nodes 506. In some embodiments, the data to be searched is located in the intake system 210 and/or the acceleration data store 222. In certain embodiments, the data to be searched is located in the common storage 216. In such embodiments, the search nodes 506 or a cache manager 516 can obtain the data from the common storage 216.

In some cases, the cache manager 516 can identify or obtain the data requested by the search nodes 506. For example, if the requested data is stored on the local or shared data store of the search nodes 506, the cache manager 516 can identify the location of the data for the search nodes 506. If the requested data is stored in common storage 216, the cache manager 516 can obtain the data from the common storage 216. As another example, if the requested data is stored in the intake system 210 and/or the acceleration data store 222, the cache manager 516 can obtain the data from the intake system 210 and/or the acceleration data store 222.

As described herein, in some embodiments, the cache manager 516 can obtain a subset of the files associated with the bucket to be searched by the search nodes 506. For example, based on the query, the search node 506 can determine that a subset of the files of a bucket are to be used to execute the query. Accordingly, the search node 506 can request the subset of files, as opposed to all files of the bucket. The cache manager 516 can download the subset of files from common storage 216 and provide them to the search node 506 for searching.

In some embodiments, such as when a search node 506 cannot uniquely identify the file of a bucket to be searched, the cache manager 516 can download a bucket summary or manifest that identifies the files associated with the bucket. The search node 506 can use the bucket summary or manifest to uniquely identify the file to be used in the query. The common storage 216 can then obtain that uniquely identified file from common storage 216.

At (11), the search nodes 506 search and process the data. As described herein, the sub-queries or instructions received from the search head 504 can instruct the search nodes 506 to identify data within one or more buckets and perform one or more transformations on the data. Accordingly, each search node 506 can identify a subset of the set of data to be processed and process the subset of data according to the received instructions. This can include searching the contents of one or more inverted indexes of a bucket or the raw machine data or events of a bucket, etc. In some embodiments, based on the query or sub-query, a search node 506 can perform one or more transformations on the data received from each bucket or on aggregate data from the different buckets that are searched by the search node 506.

At (12), the search head 504 monitors the status of the query of the search nodes 506. As described herein, the search nodes 506 can become unresponsive or fail for a variety of reasons (e.g., network failure, error, high utilization rate, etc.). Accordingly, during execution of the query, the search head 504 can monitor the responsiveness and availability of the search nodes 506. In some cases, this can be done by pinging or querying the search nodes 506, establishing a persistent communication link with the search nodes 506, or receiving status updates from the search nodes 506. In some cases, the status can indicate the buckets that have been searched by the search nodes 506, the number or percentage of remaining buckets to be searched, the percentage of the query that has been executed by the search node 506, etc. In some cases, based on a determination that a search node 506 has become unresponsive, the search head 504 can assign a different search node 506 to complete the portion of the query assigned to the unresponsive search node 506.

In certain embodiments, depending on the status of the search nodes 506, the search manager 514 can dynamically assign or re-assign buckets to search nodes 506. For example, as search nodes 506 complete their search of buckets assigned to them, the search manager 514 can assign additional buckets for search. As yet another example, if one search node 506 is 95% complete with its search while another search node 506 is less than 50% complete, the query manager can dynamically assign additional buckets to the search node 506 that is 95% complete or re-assign buckets from the search node 506 that is less than 50% complete to the search node that is 95% complete. In this way, the search manager 514 can improve the efficiency of how a computing system performs searches through the search manager 514 increasing parallelization of searching and decreasing the search time.

At (13), the search nodes 506 send individual query results to the search head 504. As described herein, the search nodes 506 can send the query results as they are obtained from the buckets and/or send the results once they are completed by a search node 506. In some embodiments, as the search head 504 receives results from individual search nodes 506, it can track the progress of the query. For example, the search head 504 can track which buckets have been searched by the search nodes 506. Accordingly, in the event a search node 506 becomes unresponsive or fails, the search head 504 can assign a different search node 506 to complete the portion of the query assigned to the unresponsive search node 506. By tracking the buckets that have been searched by the search nodes and instructing different search node 506 to continue searching where the unresponsive search node 506 left off, the search head 504 can reduce the delay caused by a search node 506 becoming unresponsive, and can aid in providing a stateless searching service.

At (14), the search head 504 processes the results from the search nodes 506. As described herein, the search head 504 can perform one or more transformations on the data received from the search nodes 506. For example, some queries can include transformations that cannot be completed until the data is aggregated from the different search nodes 506. In some embodiments, the search head 504 can perform these transformations.

At (15), the search head 504 stores results in the query acceleration data store 222. As described herein, in some cases some, all, or a copy of the results of the query can be stored in the query acceleration data store 222. The results stored in the query acceleration data store 222 can be combined with other results already stored in the query acceleration data store 222 and/or be combined with subsequent results. For example, in some cases, the query system 214 can receive ongoing queries, or queries that do not have a predetermined end time. In such cases, as the search head 504 receives a first set of results, it can store the first set of results in the query acceleration data store 222. As subsequent results are received, the search head 504 can add them to the first set of results, and so forth. In this way, rather than executing the same or similar query data across increasingly larger time ranges, the query system 214 can execute the query across a first time range and then aggregate the results of the query with the results of the query across the second time range. In this way, the query system can reduce the amount of queries and the size of queries being executed and can provide query results in a more time efficient manner.

At (16), the search head 504 terminates the search manager 514. As described herein, in some embodiments a search head 504 or a search master 512 can generate a search manager 514 for each query assigned to the search head 504. Accordingly, in some embodiments, upon completion of a search, the search head 504 or search master 512 can terminate the search manager 514. In certain embodiments, rather than terminating the search manager 514 upon completion of a query, the search head 504 can assign the search manager 514 to a new query.

As mentioned previously, in some of embodiments, one or more of the functions described herein with respect to FIG. 14 can be omitted, performed in a variety of orders and/or performed by a different component of the data intake and query system 108. For example, the search head 504 can monitor the status of the query throughout its execution by the search nodes 506 (e.g., during (10), (11), and (13)). Similarly, (1) and (2) can be performed concurrently, (3) and (4) can be performed concurrently, and all can be performed before, after, or concurrently with (5). Similarly, steps (6A) and (6B) and steps (7A) and (7B) can be performed before, after, or concurrently with each other. Further, (6A) and (7A) can be performed before, after, or concurrently with (7A) and (7B). As yet another example, (10), (11), and (13) can be performed concurrently. For example, a search node 506 can concurrently receive one or more files for one bucket, while searching the content of one or more files of a second bucket and sending query results for a third bucket to the search head 504. Similarly, the search head 504 can (8) map search nodes 506 to buckets while concurrently (9) generating instructions for and instructing other search nodes 506 to begin execution of the query. In some cases, such as when the set of data is from the intake system 210 or the acceleration data store 222, (6A) and (7A) can be omitted. Furthermore, in some such cases, the data may be obtained (10) from the intake system 210 and/or the acceleration data store 222.

4.3.1. Containerized Search Nodes

Figure 15:
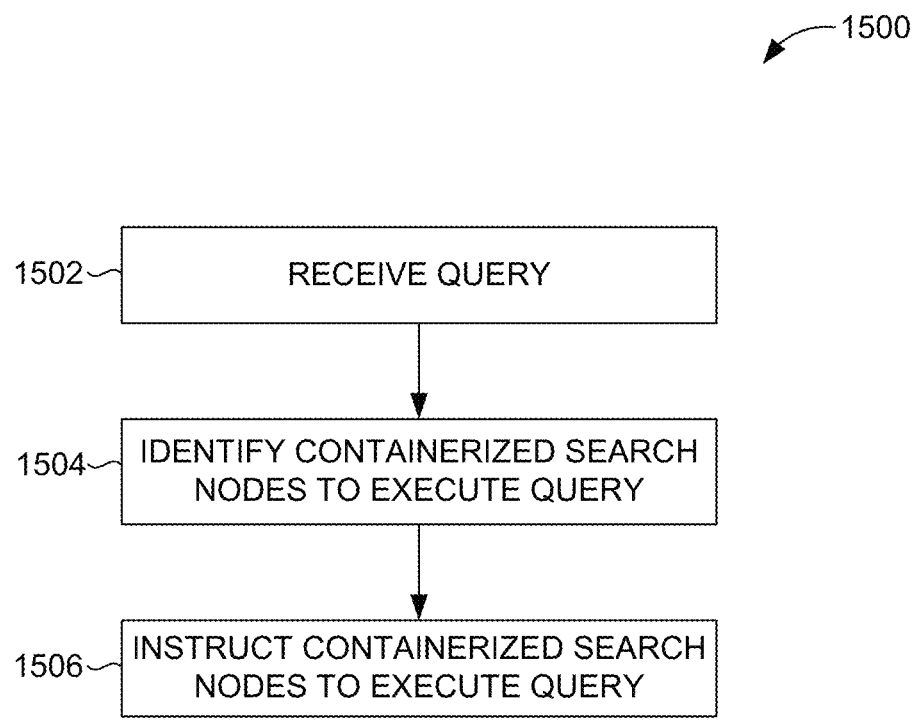
FIG. 15 is a flow diagram illustrative of an embodiment of a routine implemented by a query system to execute a query.

FIG. 15 is a flow diagram illustrative of an embodiment of a routine 1500 implemented by the query system 214 to execute a query. Although described as being implemented by the search head 504, it will be understood that the elements outlined for routine 1500 can be implemented by one or more computing devices/components that are associated with the data intake and query system 108, such as, but not limited to, the query system manager 502, the search head 504, the search master 512, the search manager 514, the search nodes 506, etc. Thus, the following illustrative embodiment should not be construed as limiting.

At block 1502, the search manager 514 receives a query. As described in greater detail above, the search manager 514 can receive the query from the search head 504, search master 512, etc. In some cases, the search manager 514 can receive the query from a client device 204. The query can be in a query language as described in greater detail above. In some cases, the query received by the search manager 514 can correspond to a query received and reviewed by the search head 504. For example, the search head 504 can determine whether the query was submitted by an authenticated user and/or review the query to determine that it is in a proper format for the data intake and query system 108, has correct semantics and syntax, etc. In some cases, the search head 504 can use a search master 512 to receive search queries, and in some cases, spawn the search manager 514 to process and execute the query.

At block 1504, the search manager 514 identifies one or more containerized search nodes, e.g., search nodes 506, to execute the query. As described herein, the query system 214 can include multiple containerized search nodes 506 to execute queries. One or more of the containerized search nodes 506 can be instantiated on the same computing device, and share the resources of the computing device. In addition, the containerized search nodes 506 can enable the query system 214 to provide a highly extensible and dynamic searching service. For example, based on resource availability and/or workload, the query system 214 can instantiate additional containerized search nodes 506 or terminate containerized search nodes 506. Furthermore, the query system 214 can dynamically assign containerized search nodes 506 to execute queries on data in common storage 216 based on a search node mapping policy.

As described herein, each search node 506 can be implemented using containerization or operating-system-level virtualization, or other virtualization technique. For example, the containerized search node 506, or one or more components of the search node 506 can be implemented as separate containers or container instances. Each container instance can have certain resources (e.g., memory, processor, etc.) of the underlying computing system assigned to it, but may share the same operating system and may use the operating system's system call interface. Further, each container may run the same or different computer applications concurrently or separately, and may interact with each other. It will be understood that other virtualization techniques can be used. For example, the containerized search nodes 506 can be implemented using virtual machines using full virtualization or paravirtualization, etc.

In some embodiments, the search node 506 can be implemented as a group of related containers or a pod, and the various components of the search node 506 can be implemented as related containers of a pod. Further, the search node 506 can assign different containers to execute different tasks. For example one container of a containerized search node 506 can receive and query instructions, a second container can obtain the data or buckets to be searched, and a third container of the containerized search node 506 can search the buckets and/or perform one or more transformations on the data. However, it will be understood that the containerized search node 506 can be implemented in a variety of configurations. For example, in some cases, the containerized search node 506 can be implemented as a single container and can include multiple processes to implement the tasks described above by the three containers. Any combination of containerization and processed can be used to implement the containerized search node 506 as desired.

In some cases, the search manager 514 can identify the search nodes 506 using the search node catalog 510. For example, as described herein a search node monitor 508 can monitor the status of the search nodes 506 instantiated in the query system 514 and monitor their status. The search node monitor can store the status of the search nodes 506 in the search node catalog 510.

In certain embodiments, the search manager 514 can identify search nodes 506 using a search node mapping policy, previous mappings, previous searches, or the contents of a data store associated with the search nodes 506. For example, based on the previous assignment of a search node 506 to search data as part of a query, the search manager 514 can assign the search node 506 to search the same data for a different query. As another example, as search nodes 506 search data, it can cache the data in a local or shared data store. Based on the data in the cache, the search manager 514 can assign the search node 506 to search the again as part of a different query.

In certain embodiments, the search manager 514 can identify search nodes 506 based on shared resources. For example, if the search manager 514 determines that a search node 506 shares a data store with a search node 506 that previously performed a search on data and cached the data in the shared data store, the search manager 514 can assign the search node 506 that share the data store to search the data stored therein as part of a different query.

In some embodiments, the search manager 514 can identify search nodes 506 using a hashing algorithm. For example, as described herein, the search manager 514 based can perform a hash on a bucket identifier of a bucket that is to be searched to identify a search node to search the bucket. In some implementations, that hash may be a consistent hash, to increase the chance that the same search node will be selected to search that bucket as was previously used, thereby reducing the chance that the bucket must be retrieved from common storage 216.

It will be understood that the search manger 514 can identify search nodes 506 based on any one or any combination of the aforementioned methods. Furthermore, it will be understood that the search manager 514 can identify search nodes 506 in a variety of ways.

At 1506, the search manager 514 instructs the search nodes 506 to execute the query. As described herein, the search manager 514 can process the query to determine portions of the query that it will execute and portions of the query to be executed by the search nodes 506. Furthermore, the search manager 514 can generate instructions or sub-queries for each search node 506 that is to execute a portion of the query. In some cases, the search manager 514 generates a DAG for execution by the search nodes 506. The instructions or sub-queries can identify the data or buckets to be searched by the search nodes 506. In addition, the instructions or sub-queries may identify one or more transformations that the search nodes 506 are to perform on the data.

Fewer, more, or different blocks can be used as part of the routine 1500. In some cases, one or more blocks can be omitted. For example, in certain embodiments, the search manager 514 can receive partial results from the search nodes 506, process the partial results, perform one or more transformation on the partial results or aggregated results, etc. Further, in some embodiments, the search manager 514 provide the results to a client device 204. In some embodiments, the search manager 514 can combine the results with results stored in the accelerated data store 222 or store the results in the accelerated data store 222 for combination with additional search results.

In some cases, the search manager 514 can identify the data or buckets to be searched by, for example, using the data store catalog 220, and map the buckets to the search nodes 506 according to a search node mapping policy. As described herein, the data store catalog 220 can receive updates from the indexing system 212 about the data that is stored in common storage 216. The information in the data store catalog 220 can include, but is not limited to, information about the location of the buckets in common storage 216, and other information that can be used by the search manager 514 to identify buckets that include data that satisfies at least a portion of the query.

In certain cases, as part of executing the query, the search nodes 506 can obtain the data to be searched from common storage 216 using the cache manager 516. The obtained data can be stored on a local or shared data store and searched as part of the query. In addition, the data can be retained on the local or shared data store based on a bucket caching policy as described herein.

Furthermore, it will be understood that the various blocks described herein with reference to FIG. 15 can be implemented in a variety of orders. In some cases, the search manager 514 can implement some blocks concurrently or change the order as desired. For example, the search manager 514 an concurrently identify search nodes 506 to execute the query and instruct the search nodes 506 to execute the query. As described herein, in some embodiments, the search manager 514 can instruct the search nodes 506 to execute the query at once. In certain embodiments, the search manager 514 can assign a first group of buckets for searching, and dynamically assign additional groups of buckets to search nodes 506 depending on which search nodes 506 complete their searching first or based on an updated status of the search nodes 506, etc.

4.3.2. Identifying Buckets and Search Nodes for Query

Figure 16:
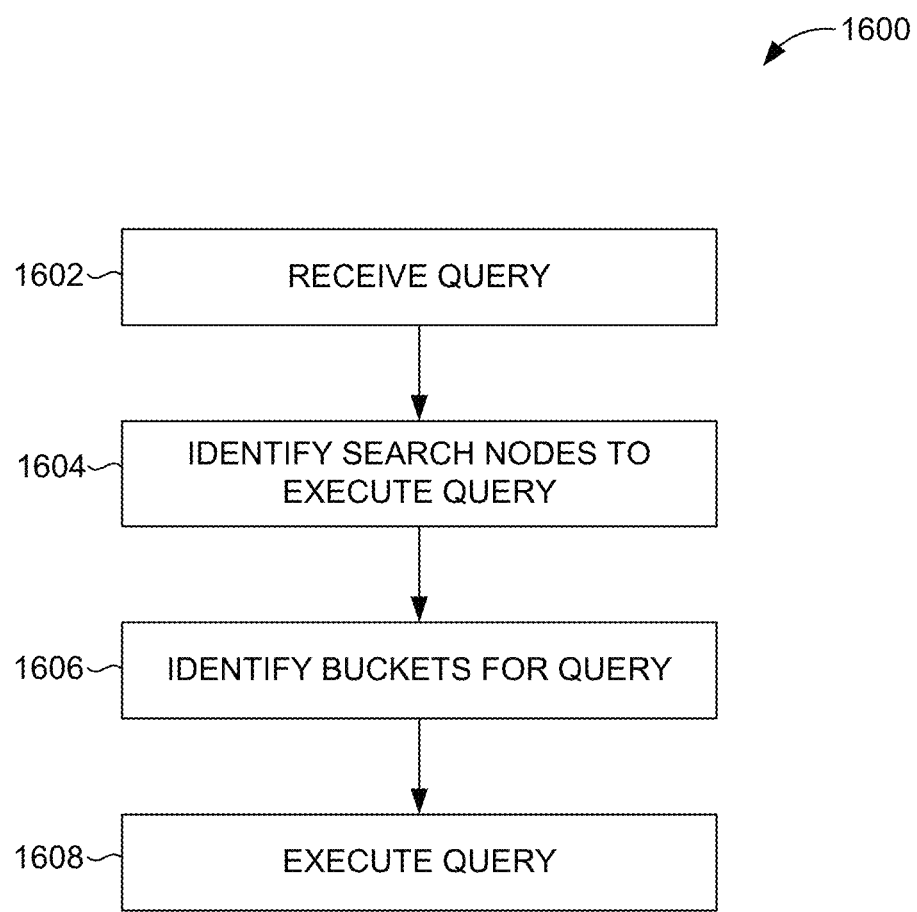
FIG. 16 is a flow diagram illustrative of an embodiment of a routine implemented by a query system to execute a query.

FIG. 16 is a flow diagram illustrative of an embodiment of a routine 1600 implemented by the query system 214 to execute a query. Although described as being implemented by the search manager 514, it will be understood that the elements outlined for routine 1600 can be implemented by one or more computing devices/components that are associated with the data intake and query system 108, such as, but not limited to, the query system manager 502, the search head 504, the search master 512, the search manager 514, the search nodes 506, etc. Thus, the following illustrative embodiment should not be construed as limiting.

At block 1602, the search manager 514 receives a query, as described in greater detail herein at least with reference to block 1502 of FIG. 15.

At block 1604, the search manager 514 identifies search nodes to execute the query, as described in greater detail herein at least with reference to block 1504 of FIG. 15. However, it will be noted, that in certain embodiments, the search nodes 506 may not be containerized.

At block 1606, the search manager 514 identifies buckets to query. As described herein, in some cases, the search manager 514 can consult the data store catalog 220 to identify buckets to be searched. In certain embodiments, the search manager 514 can use metadata of the buckets stored in common storage 216 to identify the buckets for the query. For example, the search manager 514 can compare a tenant identifier and/or partition identifier associated with the query with the tenant identifier and/or partition identifier of the buckets. The search manager 514 can exclude buckets that have a tenant identifier and/or partition identifier that does not match the tenant identifier and/or partition identifier associated with the query. Similarly, the search manager can compare a time range associate with the query with the time range associated with the buckets in common storage 216. Based on the comparison, the search manager 514 can identify buckets that satisfy the time range associated with the query (e.g., at least partly overlap with the time range from the query).

At 1608, the search manager 514 executes the query. As described herein, at least with reference to 1506 of FIG. 15, in some embodiments, as part of executing the query, the search manager 514 can process the search query, identify tasks for it to complete and tasks for the search nodes 506, generate instructions or sub-queries for the search nodes 506 and instruct the search nodes 506 to execute the query. Further, the search manager 514 can aggregate the results from the search nodes 506 and perform one or more transformations on the data.

Fewer, more, or different blocks can be used as part of the routine 1600. In some cases, one or more blocks can be omitted. For example, as described herein, the search manager 514 can map the search nodes 506 to certain data or buckets for the search according to a search node mapping policy. Based on the search node mapping policy, search manager 514 can instruct the search nodes to search the buckets to which they are mapped. Further, as described herein, in some cases, the search node mapping policy can indicate that the search manager 514 is to use a hashing algorithm, previous assignment, network architecture, cache information, etc., to map the search nodes 506 to the buckets.

As another example, the routine 1600 can include storing the search results in the accelerated data store 222. Furthermore, as described herein, the search nodes 506 can store buckets from common storage 216 to a local or shared data store for searching, etc.

In addition, it will be understood that the various blocks described herein with reference to FIG. 16 can be implemented in a variety of orders, or implemented concurrently. For example, the search manager 514 can identify search nodes to execute the query and identify bucket for the query concurrently or in any order.

4.3.3. Identifying Buckets for Query Execution

Figure 17:
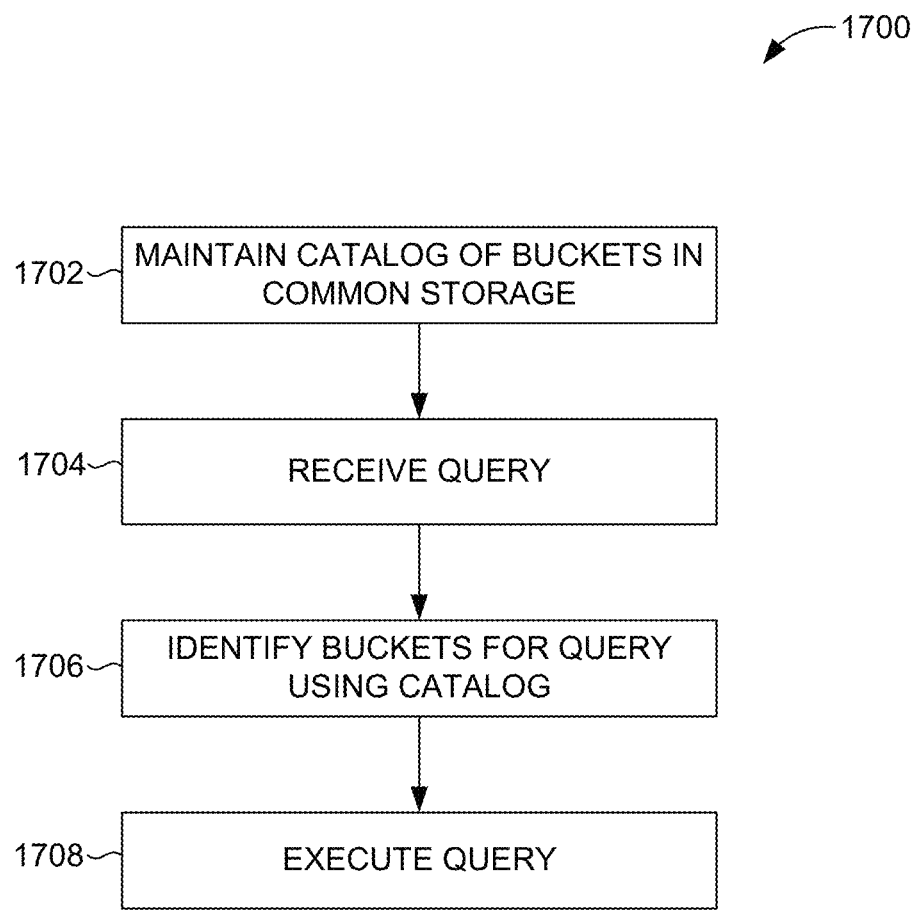
FIG. 17 is a flow diagram illustrative of an embodiment of a routine implemented by a query system to identify buckets for query execution.

FIG. 17 is a flow diagram illustrative of an embodiment of a routine 1700 implemented by the query system 214 to identify buckets for query execution. Although described as being implemented by the search manager 514, it will be understood that the elements outlined for routine 1700 can be implemented by one or more computing devices/components that are associated with the data intake and query system 108, such as, but not limited to, the query system manager 502, the search head 504, the search master 512, the search manager 514, the search nodes 506, etc. Thus, the following illustrative embodiment should not be construed as limiting.

At block 1702, the data intake and query system 108 maintains a catalog of bucket in common storage 216. As described herein, the catalog can also be referred to as the data store catalog 220, and can include information about the buckets in common storage 216, such as, but not limited to, location information, metadata fields, tenant and partition information, time range information, etc. Further, the data store catalog 220 can be kept up-to-date based on information received from the indexing system 212 as the indexing system 212 processes and stores data in the common storage 216.

At block 1704, the search manager 514 receives a query, as described in greater detail herein at least with reference to block 1502 of FIG. 15.

At block 1706, the search manager 514 identifies buckets to be searched as part of the query using the data store catalog 220. As described herein, the search manager 514 can use the data store catalog 220 to filter the universe of buckets in the common storage 216 to buckets that include data that satisfies at least a portion of the query. For example, if a query includes a time range of 4/23/18 from 03:30:50 to 04:53:32, the search manager 514 can use the time range information in the data store catalog to identify buckets with a time range that overlaps with the time range provided in the query. In addition, if the query indicates that only a _main partition is to be searched, the search manager 514 can use the information in the data store catalog to identify buckets that satisfy the time range and are associated with the _main partition. Accordingly, depending on the information in the query and the information stored in the data store catalog 220 about the buckets, the search manager 514 can reduce the number of buckets to be searched. In this way, the data store catalog 220 can reduce search time and the processing resources used to execute a query.

At block 1708, the search manager 514 executes the query, as described in greater detail herein at least with reference to block 1608 of FIG. 16.

Fewer, more, or different blocks can be used as part of the routine 1700. In some cases, one or more blocks can be omitted. For example, as described herein, the search manager 514 can identify and map search nodes 306 to the buckets for searching or store the search results in the accelerated data store 222. Furthermore, as described herein, the search nodes 506 can store buckets from common storage 216 to a local or shared data store for searching, etc. In addition, it will be understood that the various blocks described herein with reference to FIG. 16 can be implemented in a variety of orders, or implemented concurrently.

4.3.4. Identifying Search Nodes for Query Execution

Figure 18:
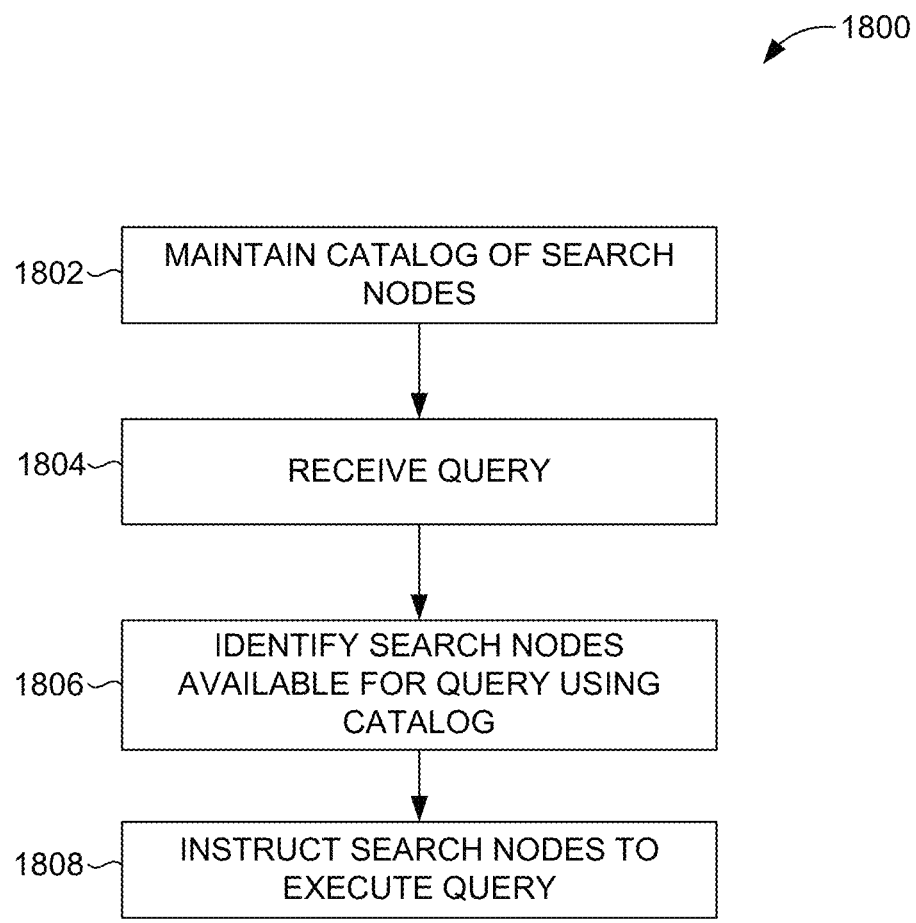
FIG. 18 is a flow diagram illustrative of an embodiment of a routine implemented by a query system to identify search nodes for query execution.

FIG. 18 is a flow diagram illustrative of an embodiment of a routine 1800 implemented by the query system 214 to identify search nodes for query execution. Although described as being implemented by the search manager 514, it will be understood that the elements outlined for routine 1800 can be implemented by one or more computing devices/components that are associated with the data intake and query system 108, such as, but not limited to, the query system manager 502, the search head 504, the search master 512, the search manager 514, the search nodes 506, etc. Thus, the following illustrative embodiment should not be construed as limiting.

At block 1802, the query system 214 maintains a catalog of instantiated search nodes 506. As described herein, the catalog can also be referred to as the search node catalog 510, and can include information about the search nodes 506, such as, but not limited to, availability, utilization, responsiveness, network architecture, etc. Further, the search node catalog 510 can be kept up-to-date based on information received by the search node monitor 508 from the search nodes 506.

At block 1804, the search manager 514 receives a query, as described in greater detail herein at least with reference to block 1502 of FIG. 15. At block 1806, the search manager 514 identifies available search nodes using the search node catalog 510, as described in greater detail herein at least with reference to block 1504 of FIG. 15 and block 1604 of FIG. 16.

At block 1808, the search manager 514 instructs the search nodes 506 to execute the query, as described in greater detail herein at least with reference to block 1506 of FIG. 15 and block 1608 of FIG. 16.

Fewer, more, or different blocks can be used as part of the routine 1800. In some cases, one or more blocks can be omitted. For example, in certain embodiments, the search manager can identify buckets in common storage 216 for searching. In addition, it will be understood that the various blocks described herein with reference to FIG. 18 can be implemented in a variety of orders, or implemented concurrently.

4.3.5. Hashing Bucket Identifiers for Query Execution

Figure 19:
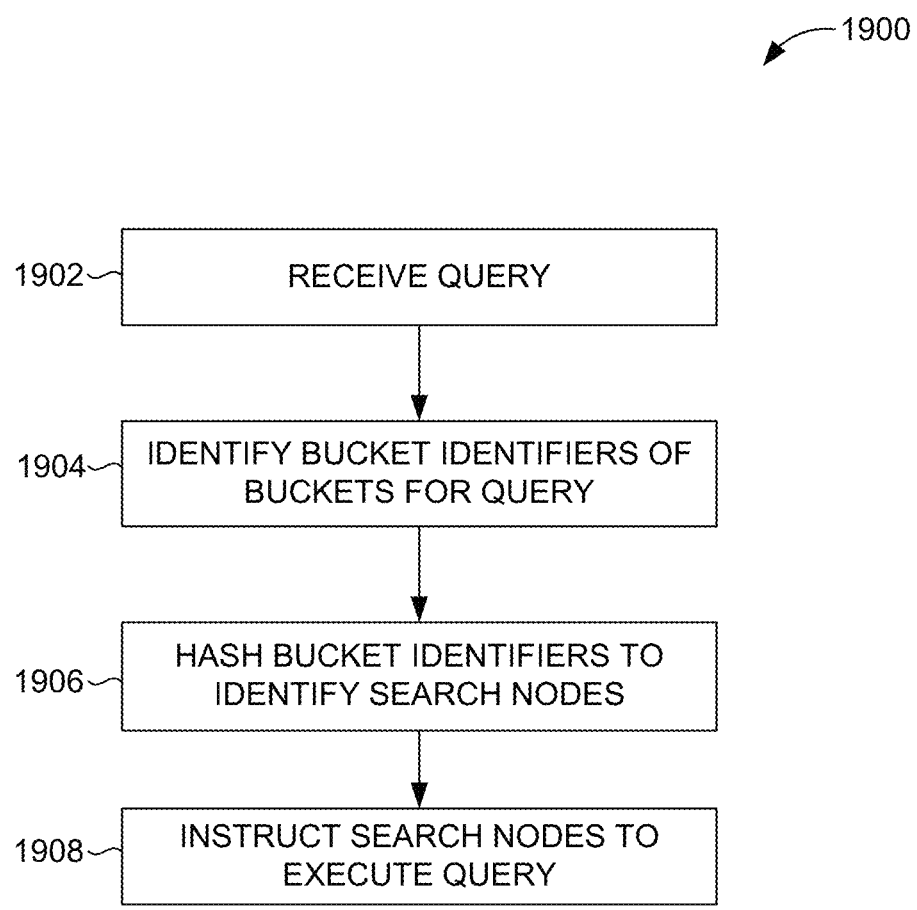
FIG. 19 is a flow diagram illustrative of an embodiment of a routine implemented by a query system to hash bucket identifiers for query execution.

FIG. 19 is a flow diagram illustrative of an embodiment of a routine 1900 implemented by the query system 214 to hash bucket identifiers for query execution. Although described as being implemented by the search manager 514, it will be understood that the elements outlined for routine 1900 can be implemented by one or more computing devices/components that are associated with the data intake and query system 108, such as, but not limited to, the query system manager 502, the search head 504, the search master 512, the search manager 514, the search nodes 506, etc. Thus, the following illustrative embodiment should not be construed as limiting.

At block 1902, the search manager 514 receives a query, as described in greater detail herein at least with reference to block 1502 of FIG. 15.

At block 1904, the search manager 514 identifies bucket identifiers associated with buckets to be searched as part of the query. The bucket identifiers can correspond to an alphanumeric identifier or other identifier that can be used to uniquely identify the bucket from other buckets stored in common storage 216. In some embodiments, the unique identifier may incorporate one or more portions of a tenant identifier, partition identifier, or time range of the bucket or a random or sequential (e.g., based on time of storage, creation, etc.) alphanumeric string, etc. As described herein, the search manager 514 can parse the query to identify buckets to be searched. In some cases, the search manager 514 can identify buckets to be searched and an associated bucket identifier based on metadata of the buckets and/or using a data store catalog 220. However, it will be understood that the search manager 514 can use a variety of techniques to identify buckets to be searched.

At block 1906, the search manager 514 performs a hash function on the bucket identifiers. The search manager can, in some embodiments, use the output of the hash function to identify a search node 506 to search the bucket. For example, as a non-limiting example, consider a scenario in which a bucket identifier is 4149 and the search manager 514 identified ten search nodes to process the query. The search manager 514 could perform a modulo ten operation on the bucket identifier to determine which search node 506 is to search the bucket. Based on this example, the search manager 514 would assign the ninth search node 506 to search the bucket, e.g., because the value 4149 modulo ten is 9, so the bucket having the identifier 4149 is assigned to the ninth search node. In some cases, the search manager can use a consistent hash to increase the likelihood that the same search node 506 is repeatedly assigned to the same bucket for searching. In this way, the search manager 514 can increase the likelihood that the bucket to be searched is already located in a local or shared data store of the search node 506, and reduce the likelihood that the bucket will be downloaded from common storage 216. It will be understood that the search manager can use a variety of techniques to map the bucket to a search node 506 according to a search node mapping policy. For example, the search manager 514 can use previous assignments, network architecture, etc., to assign buckets to search nodes 506 according to the search node mapping policy.

At block 1908, the search manager 514 instructs the search nodes 506 to execute the query, as described in greater detail herein at least with reference to block 1506 of FIG. 15 and block 1608 of FIG. 16.

Fewer, more, or different blocks can be used as part of the routine 1900. In some cases, one or more blocks can be omitted. In addition, it will be understood that the various blocks described herein with reference to FIG. 19 can be implemented in a variety of orders, or implemented concurrently.

4.3.6. Obtaining Data for Query Execution

Figure 20:
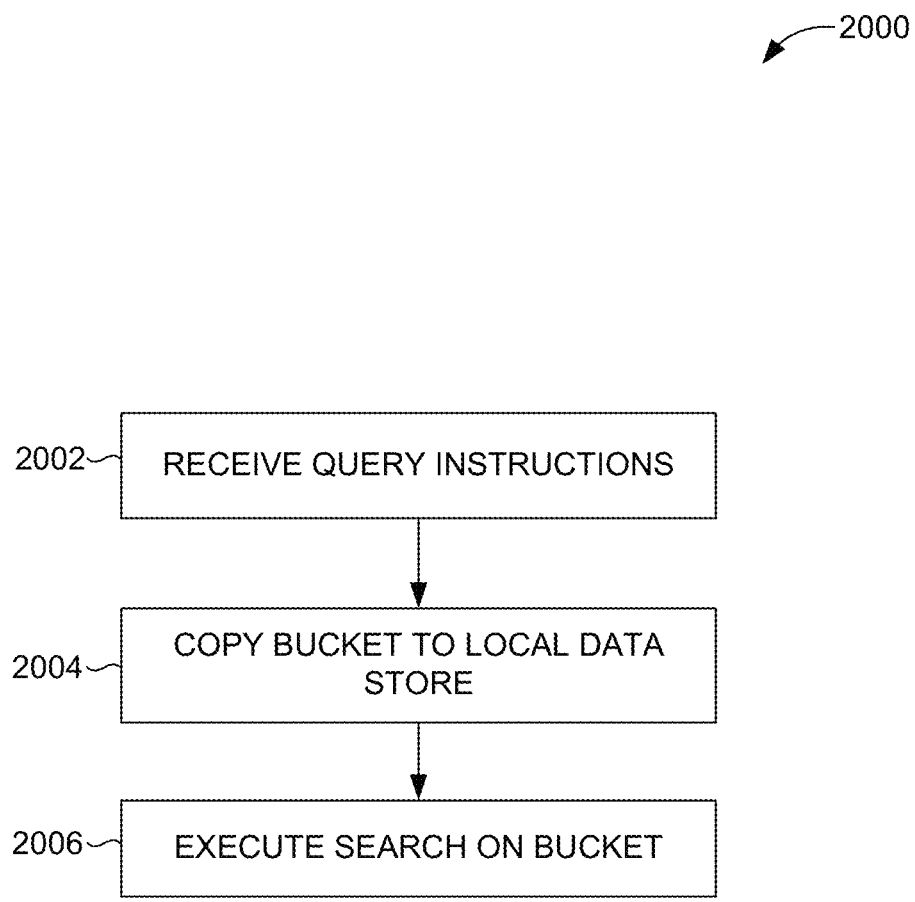
FIG. 20 is a flow diagram illustrative of an embodiment of a routine implemented by a search node to execute a search on a bucket.

FIG. 20 is a flow diagram illustrative of an embodiment of a routine 2000 implemented by a search node 506 to execute a search on a bucket. Although reference is made to downloading and searching a bucket, it will be understood that this can refer to downloading and searching one or more files associated within a bucket and does not necessarily refer to downloading all files associated with the bucket.

Further, although described as being implemented by the search node 506, it will be understood that the elements outlined for routine 2000 can be implemented by one or more computing devices/components that are associated with the data intake and query system 108, such as, but not limited to, the query system manager 502, the search head 504, the search master 512, search manager 514, cache manager 516, etc. Thus, the following illustrative embodiment should not be construed as limiting.

At block 2002, the search node 506 receives instructions for a query or sub-query. As described herein, a search manager 514 can receive and parse a query to determine the tasks to be assigned to the search nodes 506, such as, but not limited to, the searching of one or more buckets in common storage 216, etc. The search node 506 can parse the instructions and identify the buckets that are to be searched. In some cases, the search node 506 can determine that a bucket that is to be searched is not located in the search nodes local or shared data store.

At block 2004, the search node 506 obtains the bucket from common storage 216. As described herein, in some embodiments, the search node 506 obtains the bucket from common storage 216 in conjunction with a cache manager 516. For example, the search node 506 can request the cache manager 516 to identify the location of the bucket. The cache manager 516 can review the data stored in the local or shared data store for the bucket. If the cache manager 516 cannot locate the bucket in the local or shared data store, it can inform the search node 506 that the bucket is not stored locally and that it will be retrieved from common storage 216. As described herein, in some cases, the cache manager 516 can download a portion of the bucket (e.g., one or more files) and provide the portion of the bucket to the search node 506 as part of informing the search node 506 that the bucket is not found locally. The search node 506 can use the downloaded portion of the bucket to identify any other portions of the bucket that are to be retrieved from common storage 216.

Accordingly, as described herein, the search node 506 can retrieve all or portions of the bucket from common storage 216 and store the retrieved portions to a local or shared data store.

At block 2006, the search node 506 executes the search on the portions of the bucket stored in the local data store. As described herein, the search node 506 can review one or more files of the bucket to identify data that satisfies the query. In some cases, the search nodes 506 searches an inverted index to identify the data. In certain embodiments, the search node 506 searches the raw machine data, uses one or more configuration files, regex rules, and/or late binding schema to identify data in the bucket that satisfies the query.

Fewer, more, or different blocks can be used as part of the routine 2000. For example, in certain embodiments, the routine 2000 includes blocks for requesting a cache manager 516 to search for the bucket in the local or shared storage, and a block for informing the search node 506 that the requested bucket is not available in the local or shared data store. As another example, the routine 2000 can include performing one or more transformations on the data, and providing partial search results to a search manager 514, etc. In addition, it will be understood that the various blocks described herein with reference to FIG. 20 can be implemented in a variety of orders, or implemented concurrently.

4.3.7. Caching Search Results

Figure 21:
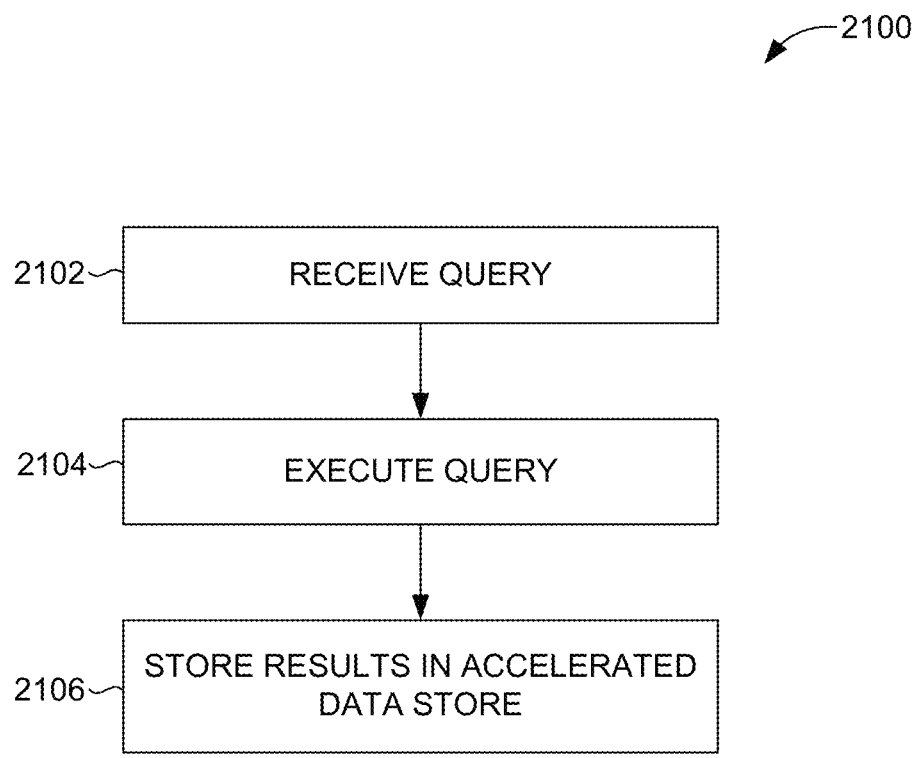
FIG. 21 is a flow diagram illustrative of an embodiment of a routine implemented by the query system to store search results.

FIG. 21 is a flow diagram illustrative of an embodiment of a routine 2100 implemented by the query system 212 to store search results. Although described as being implemented by the search manager 514, it will be understood that the elements outlined for routine 2100 can be implemented by one or more computing devices/components that are associated with the data intake and query system 108, such as, but not limited to, the query system manager 502, the search head 504, the search master 512, the search nodes 506, etc. Thus, the following illustrative embodiment should not be construed as limiting.

At block 2102, the search manager 514 receives a query, as described in greater detail herein at least with reference to block 1502 of FIG. 15, and at block 2104, the search manager 514 executes the query, as described in greater detail herein at least with reference to block 1608 of FIG. 16. For example, as described herein, the search manager 514 can identify buckets for searching assign the buckets to search nodes 506, and instruct the search nodes 506 to search the buckets. Furthermore, the search manager can receive partial results from each of the buckets, and perform one or more transformations on the received data.

At block 2106, the search manager 514 stores the results in the accelerated data store 222. As described herein, the results can be combined with results previously stored in the accelerated data store 222 and/or can be stored for combination with results to be obtained later in time. In some cases, the search manager 514 can receive queries and determine that at least a portion of the results are stored in the accelerated data store 222. Based on the identification, the search manager 514 can generate instructions for the search nodes 506 to obtain results to the query that are not stored in the accelerated data store 222, combine the results in the accelerated data store 222 with results obtained by the search nodes 506, and provide the aggregated search results to the client device 204, or store the aggregated search results in the accelerated data store 222 for further aggregation. By storing results in the accelerated data store 222, the search manager 514 can reduce the search time and computing resources used for future searches that rely on the query results.

Fewer, more, or different blocks can be used as part of the routine 2100. In some cases, one or more blocks can be omitted. For example, in certain embodiments, the search manager 514 can consult a data store catalog 220 to identify buckets, consult a search node catalog 510 to identify available search nodes, map buckets to search nodes 506, etc. Further, in some cases, the search nodes 506 can retrieve buckets from common storage 216. In addition, it will be understood that the various blocks described herein with reference to FIG. 21 can be implemented in a variety of orders, or implemented concurrently.

4.4. Querying Using Metadata Catalog

As described herein, the metadata catalog 221 can be used to stored information related to various datasets 608 and/or rules 610 used by the data intake and query system to process data. In some embodiments, the metadata catalog can be used to process and/or execute queries received by the data intake and query system 108.

4.4.1. Metadata Catalog Data Flow

Figure 22:
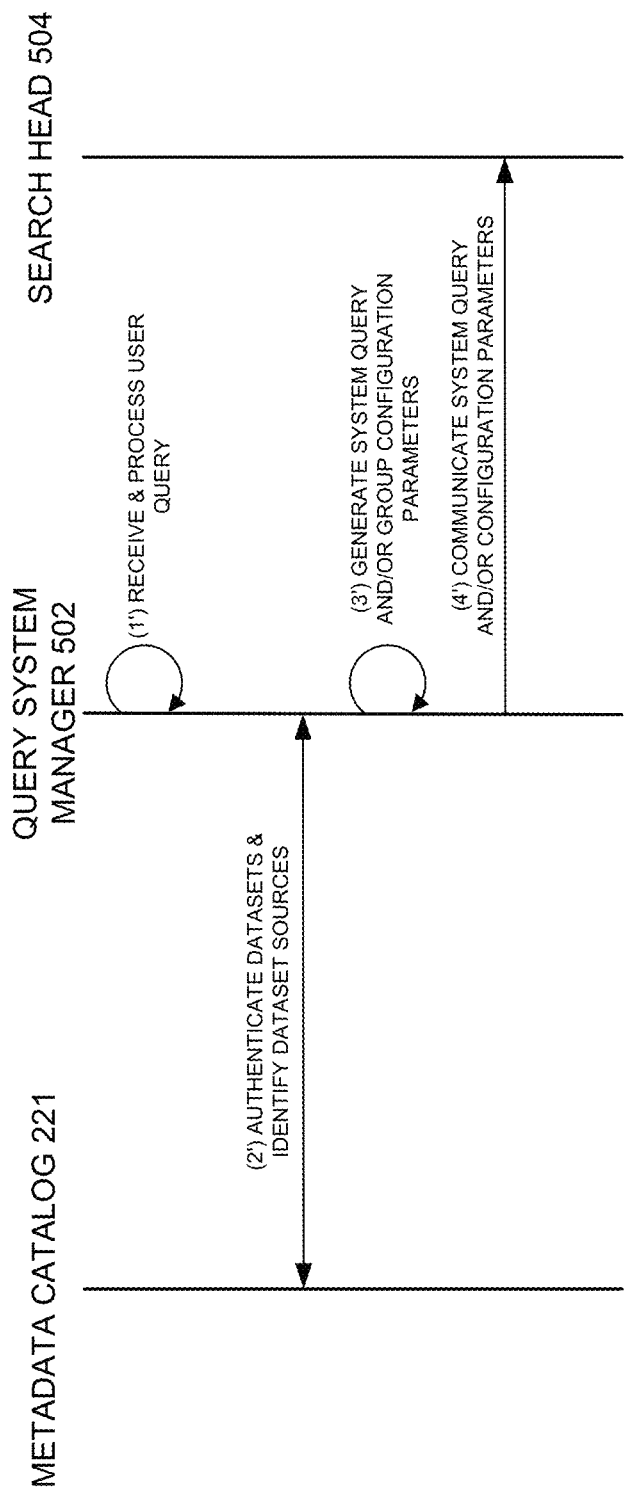
FIG. 22 is a data flow diagram illustrating an embodiment of the data flow and communications between a variety of the components of the data intake and query system to execute a query.

FIG. 22 is a data flow diagram illustrating an embodiment of the data flow and communications between a variety of the components of the data intake and query system 108 during execution of a query. Specifically, FIG. 22 is a data flow diagram illustrating an embodiment of the data flow and communications between the metadata catalog 221, the query system manager 502, and the search head 504. However, it will be understood, that in some of embodiments, one or more of the functions described herein with respect to FIG. 22 can be omitted, performed in a different order and/or performed by the same or a different component of the data intake and query system 108. For example, in some embodiments, the steps identified as being performed by the query system manager 502 and search head 504 can be performed by the same component (e.g., the query system manager 502, the search head 504, or another component of the data intake and query system 108). In some such embodiments, (4') can be omitted.

Furthermore, in some embodiments, the data flow diagram illustrated at FIG. 22 can be performed prior to (5) of the data flow diagram illustrated in FIG. 14. For example, (5) of FIG. 14 references receiving a query at the search head 504. In some embodiments, the query received at the search head 504 can correspond to the system query communicated to the search head 504 by the query system manager 502 at (4') of FIG. 22.

At (1'), a query system manager 502 receives and processes a user query. The user query can correspond to a query received from a client device 204. In some cases, the user query can be received via the gateway 215 and/or via the network 208. The query can identify a set of data and manner processing the set of data. Furthermore, the query can include at least one dataset identifier and/or dataset association record identifier. In some embodiments, the dataset identifier can be a logical identifier of a dataset. In certain embodiments, the dataset identifier and/or dataset association record identifier can follow a particular query parameter, such as "from" "datasetID," "moduleID," etc. In some embodiments, the dataset identifier and/or dataset association record identifier can be included as a parameter of a command received by the query system manager 502. For example, in some embodiments, the data intake and query system 108 can receive the query as one parameter and the dataset identifier and/or the dataset association record as another parameter.

As part of processing the user query, the query system manager 502 can identify the dataset identifier and/or the dataset association record identifier. In some embodiments, the query system manager 502 can parse the query to identify the dataset identifier and/or dataset association record identifier. For example, the dataset identifier can identify "from" (or some other query parameter) in the query and determine that the subsequent string is the dataset identifier.

At (2'), the query system manager 502 communicates with the metadata catalog 221 to authenticate the datasets identified in the query (and other datasets parsed during the query processing), identify query datasets, and/or identify query configuration parameters.

In some embodiments, upon identifying a dataset association record associated with the query, the query system manager 502 uses the dataset association record to identify additional information associated with the user query, such as one or more datasets (or dataset sources) and/or rules. In some embodiments, using the dataset association record, the query system manager 502 can determine whether a user associated with the query has the authorizations and/or permissions to access the datasets identified in the query.

Once the query system manager 502 identifies the dataset referenced in the query in the dataset association record, the query system manager 502 can determine whether the identified dataset identifies one or more additional datasets, includes additional query parameters, is a dataset source and/or will be used by the data intake and query system to execute the query (also referred to herein as a query dataset).

With each additional dataset identified, the query system manager 502 can recursively review information about the dataset to determine whether it is a query dataset and/or whether it identifies additional datasets. For example, as described in herein, the dataset identifier used in the user query may refer to a dataset that is from another dataset association record. Based on the determination that the dataset is inherited, the query system manager 502 can review the other dataset association record to identify any additional datasets, identify characteristics (e.g., access information, dataset type, etc.) of the inherited dataset, and/or determine whether the referenced dataset was inherited from a third dataset. The query system manager 502 can continue to review the dataset association records until it has identified the dataset association record where the dataset is native.

As another example, the dataset identifier in the user query may refer to a dataset that relies on one or more other datasets, such as a view dataset that refers to one or more index and/or lookup datasets. Accordingly, the query system manager 502 can recursively review the datasets referred to in the first dataset until it identifies datasets that do not rely on any other datasets and/or identifies the dataset sources that include the data that forms at least a portion of the set of data.

With each new dataset identified from the dataset association records, the query system manager 502 can authenticate the dataset. As part of authenticating the datasets, the query system manager 502 can determine whether the dataset referred to is inherited by the dataset association record and/or whether the user has the proper credentials, authorizations, and/or permissions to access the dataset.

In addition to identifying additional datasets, the query system manager 502 can identify additional query parameters. For example, one or more datasets, such as a view dataset, may include additional query parameters. Accordingly, as the query system manager 502 parses the various datasets, it can identify additional query parameters that are to be processed and/or executed.

Furthermore, as the query system manager 502 parses the dataset association records, it can identify one or more rules that are to be used to process data from one or more datasets. As described herein, the rules can be inherited by different dataset association records. Accordingly, the query system manager 502 can recursively parse the rules to identify the dataset association record from which the rule originated. Furthermore, as the query system manager 502 parses the dataset association records and identifies additional rules, it can determine whether the user has the proper credentials permissions etc. to access the identified rules. In addition, the query system manager 502 can identify one or more datasets that are referenced, or used by the additional rules. As described herein, in some embodiments these datasets may not be explicitly inherited in a dataset association record, but may be automatically included as part of the query processing process.

In addition to identifying the various datasets and/or rules associated with the query, the query system manager 502 can identify the configurations associated with the datasets and rules associated with the query. In some embodiments, the query system manager 502 can use the dataset configurations and/or rules configurations to identify the relevant configurations for the datasets and/or rules associated with the query. For example, the query system manager 502 can refer to the dataset configurations to identify the dataset types of the various datasets associated with the query. In some embodiments, based on the dataset type, the query system manager 502 can determine how to interact with or generate commands for the dataset.

As described herein, in some embodiments, the dataset configurations and rules configurations can include a physical identifier for the datasets and/or rules. Accordingly, in some embodiments, the query system manager 502 can obtain the physical identifiers for each of the datasets and/or rules associated with the query. In certain embodiments, the query system manager 502 can determine the physical identifiers for each of the datasets and/or rules associated with the query based on the logical name and dataset association record associated with the dataset or rule. For example, in certain embodiments, the physical identifier can correspond to a combination of the logical identifier of the dataset and the logical identifier of the associated dataset association record.

In some embodiments, when identifying the rules configurations and/or dataset configurations, the query system manager 502 can obtain a subset of the dataset configurations and/or rules configurations in the metadata catalog 221 and/or a subset of the dataset configurations and/or rules configurations associated with the dataset association records identified by the query or referenced while processing the query. In certain embodiments, the query system manager 502 obtains only the dataset configurations and/or rules configurations that are needed to process the query. For example, if the dataset association record includes references to three datasets, but the query only uses one of the datasets, the query system manager 502 can obtain the dataset configuration of the dataset referenced in the query but not the dataset configurations of the datasets that are not referenced in or used by the query.

At (3'), the query system manager 502 generates a system query and/or groups query configuration parameters. The query configuration parameters can include the dataset configurations corresponding to the query datasets and/or the rule configurations corresponding to the rules associated with the query.

In some embodiments, the system query can be based on the user query, one or more query datasets, the physical name of the query datasets, the dataset type of the query datasets, additional query parameters identified from the datasets, and/or based on information about the search head 504, etc. In certain embodiments, the system query corresponds to the user query modified to be compatible with the search head 504. For example, in some embodiments, the search head 504 may not be able to process one or more commands in the system query. Accordingly, the query system manager 502 can replace the commands unsupported by the search head 504 with commands that are supported by the search head 504.

In certain embodiments, the system query replaces the logical dataset identifier of the user query with the physical dataset identifier identified from the metadata catalog 221. For example, if the logical name is "main" and the dataset association record is "test," the query system manager 504 can replace "main" with "test.main" or "test_main," as the case may be. Accordingly, the query system manager 502 can generate the system query based on the physical identifier of the query datasets.

In some embodiments, the query system manager 502 modifies the user query based on the dataset type of the query datasets. For example, datasets of different types may be interacted with using different commands and/or procedures. Accordingly, the query system manager 502 can include the command associated with the dataset type. For example, if the dataset type is an index type, the query system manager 502 can replace a "from" command with a "search" command. Similarly, if the dataset type is a lookup type, the query system manager 502 can replace the "from" command with a "lookup" command. As yet another example, if the dataset type is a metrics data store type, the query system manager 502 can replace the "from" command with an "mstats" command. Accordingly, in certain embodiments, the query system manager 502 can generate the system query based on the dataset type of the query datasets.

In some embodiments, the query system manager 502 uses one or more query parameters identified from one or more datasets of a dataset association record to generate the system query. For example, if a view dataset includes one or more queries or search parameters, the query system manager 502 can include the queries or search parameters in the system query.

In certain embodiments, the query system manager 502 can identify query configuration parameters (configuration parameters associated with the query) based on the query datasets and/or rules associated with the query. For example, the query system manager 502 can obtain dataset configurations and/or rules configurations from the metadata catalog 221 for each query dataset and/or rule associated with the query. Accordingly, in some embodiments, the query system manager 502 can dynamically identify the query configuration parameters to be used to process and execute the query.

At (4'), the query system manager 502 communicates the system query and/or query configuration parameters to the search head 504. As described herein, in some embodiments, the query system manager can communicate the system query to the search head 504. In certain embodiments, the query system manager 502 can communicate the query configuration parameters to the search head 504. Accordingly, the query system manager 502 can communicate either the system query, the query configuration parameters, or both.

In certain embodiments, by dynamically determining and communicating the query configuration parameters to the search head 504, the query system manager 502 can provide a stateless search experience. For example, if the search head 504 become unavailable, the query system manager 502 can communicate the dynamically determined query configuration parameters (and/or query to be executed) to another search head 504 without data loss and/or with minimal time loss.

4.4.2. Example Metadata Catalog Processing

Figure 23:
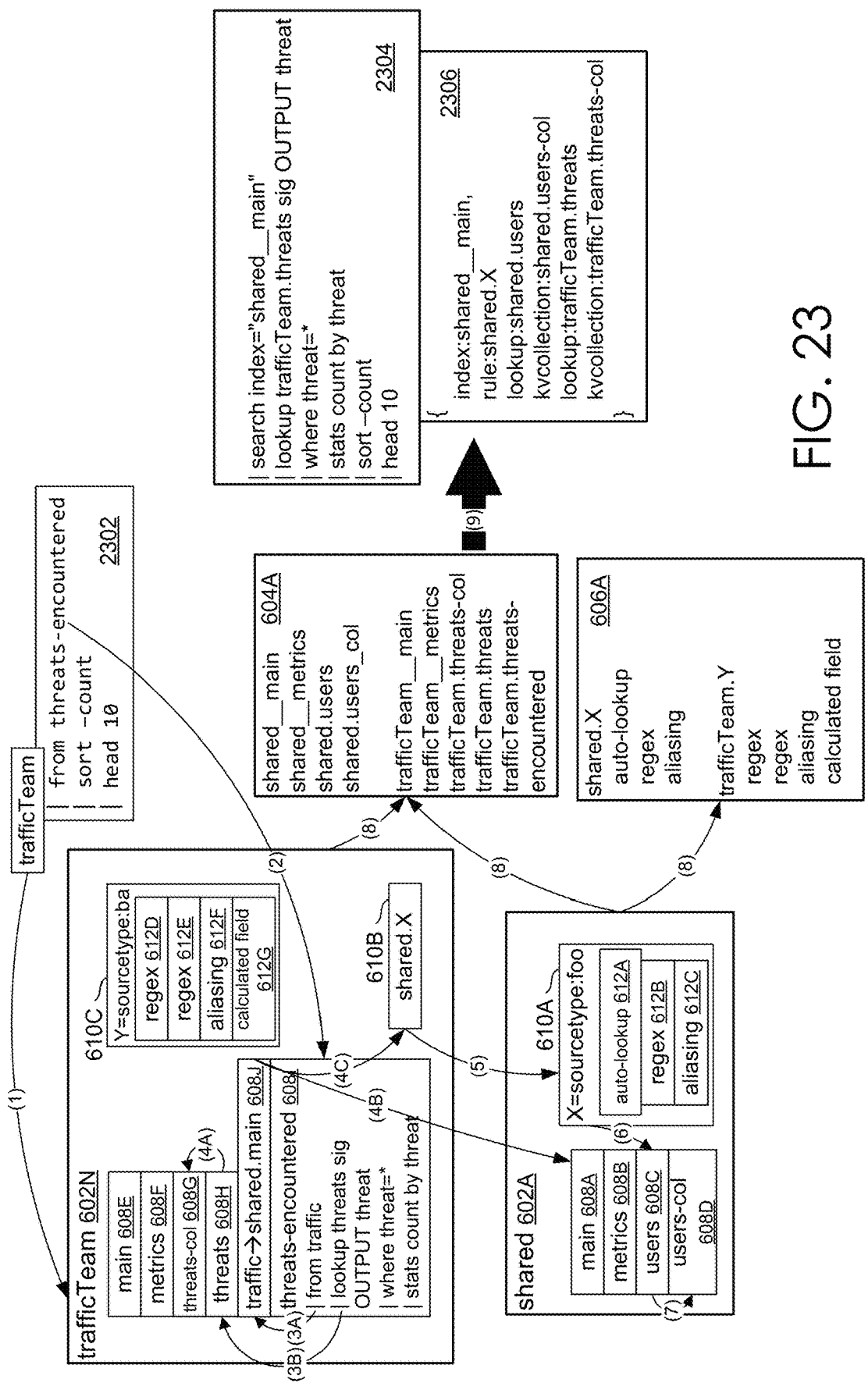
FIG. 23 is a data flow diagram illustrating an embodiment of the data flow for identifying query datasets and query configuration parameters for a particular query.

FIG. 23 is a data flow diagram illustrating an embodiment of the data flow for identifying query datasets and query configuration parameters for a particular query 2302. In the illustrated embodiment, the query system manager 502 receives the query 2302, which includes the following query parameters "|from threats-encountered|sourt-count|head 10." In addition, "trafficTeam" is identified as the identifier of a dataset association record 602N associated with the query 2302.

Based on the identification of "trafficTeam" as the dataset association record identifier, the query system manager 502 (1) determines that the "trafficTeam" dataset association record 602N is to be searched and/or determines a portion of the physical name for datasets to be searched. In addition, based on the query 2302, the query system manager 502 identifies "threats-encountered" as a logical dataset identifier.

Accordingly, at (2), the query system manager 502 parses the "threats-encountered" dataset 608I (or associated dataset configuration 604). As part of parsing the "threats-encountered" dataset 608I, the query system manager 502 determines that the "threats-encountered" dataset 608I references two additional datasets 608J and 608H ("traffic" and "threats"). Based on the identification of the additional datasets, the query system manager 502 parses the "traffic" dataset 608J and the "threats" dataset 608H (or associated dataset configurations 604) at (3A) and (3B), respectively. Based on parsing the "threats" dataset 608H, the query system manager 502 determines that the "threats" dataset 608H references or relies on the "threats-col" dataset 608G. Accordingly, at (4A) query system manager 502 parses the "threats-col" dataset 608G (or associated dataset configurations 604). Based on parsing the "threats-col" dataset 608G, the query system manager 502 determines that the "threats-col" dataset 608G does not reference any further datasets.

Based on parsing the "traffic" dataset 608J, the query system manager determines that the "traffic" dataset 608J is an inherited dataset that corresponds to the "main" dataset 608A of the "shared" dataset association record 602A, which may also be referred to as the "shared.main" dataset 608A. Accordingly, at (4B), the query system manager 502 parses the "shared.main" dataset 608A (or associated dataset configurations 604). Based on parsing the the "shared.main" dataset 608A, the query system manager 502 determines that the "shared.main" dataset 608A does not reference any further datasets.

However, as part of parsing the "traffic" dataset 608J, the query system manager 502 determines that the "shared.X" rule 610B is associated with the "traffic" dataset 608J, and at (4C), parses the "shared.X" rule 610B. Based on parsing the "shared.X" rule 610B, the query system manager 502 determines that the "shared.X" rule 610B is inherited from the "shared" dataset association record 602A and at (5) parses the "X" rule 610A of the dataset association record 602A. Based on parsing the "X" rule 610A, the query system manager 502 determines that the "X" rule 610A references the "users" dataset 608C, and at (6) parses the "users" dataset 608C. Based on parsing the "users" dataset 608C, the query system manager 502 determines that the "users" dataset 608C references the "users-col" dataset 608D and at (7) parses the "users-col" dataset 608D. Based on parsing the "users-col" dataset 608D, the query system manger 502 determines that the "users-col" dataset 608D does not reference any further datasets.

In some embodiments, each time the query system manager 502 identifies a new dataset, it can include the dataset as a potential query dataset. As the query system manager 502 processes the dataset, it can determine whether the dataset is a dataset source and/or will otherwise be used to execute the resulting query. For example, if a view dataset merely references other datasets or includes additional query parameters and the configurations of the view dataset will not be used (or needed) to execute the query parameters or access the referenced datasets, it can be omitted as a query dataset. With reference to the illustrated embodiment, the query system manager 502 may identify "threats-encountered" dataset 608I as being associated with the query based on its presence in the user query 2302. However, once the query system manager 502 determines that the "threats-encountered" dataset 608I adds additional query parameters to the query 2302, but does not include data and/or will not be used to execute the query, it can remove the "threats-encountered" dataset 608I as a query dataset (and may or may not keep the query parameters).

As described herein, in some cases, the query system manager 502 determines the physical names of the query datasets based on dataset association records 602A, 602N. For example, the query system manager 502 can use the names or identifiers of the dataset association records 602A, 602N to determine the physical names of the query datasets and/or rules association with the query. Using the physical names of the query datasets and/or rules association with the query, the query system manager 502 (8) parses the dataset configurations 604 and rules configurations 606. From the dataset configurations 604 and rules configurations 606, the query system manager 502 can determine the dataset types of the query datasets and other query configuration parameters of the query datasets, as well as the query configuration parameters associated with the identified rules.

In the illustrated embodiment, the query system manager 502 determines that the "shared_main," "shared.users," "shared.users-col," "trafficTeam.threats," and "trafficTeam.threat-col" datasets 608A, 608C, 608D, 608H, 608G, respectively, are query datasets (e.g., are dataset sources and/or will be used to process the system query). Similarly, using the rules configurations 606, the query system manager 502 determines that the rule "shared.X" is associated with the query and/or will be used to process/execute the system query. Conversely, the query system manager 502 determines that the datasets 608B, 608E, 608F, 608I, 608J are not datasets as they were either not referenced by the query, identified during the processing, or will not be used to execute the system query 2304. Similarly, the query system manager 502 determines that the rule 610C is not a query rule as it was not referenced by the query, associated with a query dataset, or will not be used to process data of a query dataset.

As mentioned, although, the "threats-encountered" and "traffic" datasets 608I, 608J, respectively, were identified as part of the processing, the query system manager 502 determines not to include them as query datasets as they are not dataset sources or will not be used to execute the system query. Rather, the "threats-encountered" and "traffic" datasets 608I, 608J were used to identify other datasets and query parameters. For example, the "threats-encountered" dataset 608I is a view dataset includes additional query parameters that reference two other datasets, and the "traffic" dataset 608J is merely the name of the "shared.main" dataset 608A imported into the "trafficTeam" dataset association record 602N.

Based on the acquired information, the query system manager 502 (9) generates the system query 2304 and/or the query configuration parameters 2306 for the query. With reference to the system query 2304, the query system manager 502 replaces the logical names of datasets with physical names of dataset sources (e.g., replaced "threats-encountered" with "shared_main" and "trafficTeam.threats"). In addition, the query system manager 502 includes commands specific to the dataset type of the dataset sources (e.g., "from" replaced with "search" for the "shared_main" dataset 608A and "lookup" for the lookup "trafficTeam.threats" dataset 608H). Furthermore, the query system manager 502 has included query parameters identified from the "threats-encountered dataset" in the system query 2304. Accordingly, the system query 2304 is configured to be communicated to the search head 504 for processing and execution.

Moreover, based on the information from the metadata catalog 221, the query system manager 502 is able to generate the query configuration parameters 2306 for the query to be executed by the data intake and query system 108. In some embodiments, the query configuration parameters 2306 include dataset configurations 604 associated with the identified dataset sources or query datasets. In certain embodiments, the query configuration parameters include rule configurations 606 associated with query rules. Less or additional information or configurations can be included in the query configuration parameters 2306.

In the illustrated embodiment, the query to be executed by the data intake and query system 108 corresponds to the system query 2304, however, it will be understood that in other embodiments, the query system manager 502 may identify the query configuration parameters 2306 for the query and may not translate the user query to the system query 2304. Thus, the query configuration parameters 2306 can be used to execute a system query, a user query, or some other query generated from the user query.

In the illustrated embodiment, the query system manager 502 determines that the datasets "shared_main," "shared.users," "shared.users-col," "trafficTeam.threats," and "trafficTeam.threat-col" are query datasets. Accordingly, the query system manager 502 includes the dataset configurations corresponding to the identified query datasets as part of the query configuration parameters 2306. Similarly, the query system manager 502 determines that the "shared.X" rule is associated with the query and/or will be used to process/execute the query and includes the corresponding rules configuration 606 as part of the query configuration parameters 2306.

As mentioned, in some embodiments, the metadata catalog 221 may not store separate dataset association records 602. Rather, the datasets association records 602 illustrated in FIG. 23 can be considered a logical association between one or more dataset configurations 604 and/or one or more rules configurations 606. In certain embodiments, the datasets 608 and/or rules 610 of each dataset association record 602 may be references to dataset configurations 604 and/or rules configurations 606. Accordingly, in some embodiments, rather than moving from or parsing different portions of a dataset association record 602, it will be understood that the query system manager 502 can parse different dataset configurations 604 and/or rules configurations 606 based on the identified physical identifier for the dataset or rule. For example, (2) may refer to parsing the "trafficTeam.threats-encountered" dataset configuration 604, (3A) and (3B) may refer to parsing the "trafficTeam.traffic" and "trafficTeam.threats" dataset configurations 604, respectively, (4A) and (4B) may refer to parsing the "trafficTeam.threats-col" and "shared.main," dataset configurations 604, respectively, (4C) may refer to parsing the "trafficTeam.shared.X" (or "shared.X") rule configuration 606, (5) may refer to parsing the "shared.X" rule configuration 606 (or be combined with (4C)), (6) may refer to parsing the "shared.users" dataset configuration 604, and (7) may refer to parsing the "shared.users-col" dataset configuration 604. Thus, as the query system manager 502 parses different datasets 608 or rules 610, it can do so using the dataset configurations 604 and rule configurations 606, respectively. Moreover, in some such embodiments (8) may be omitted (or considered as part of each parsing step) as the query system manager 502 references the relevant dataset configurations 604 and rule configurations 606 throughout the review or parsing process. Based on the review of the various dataset configurations 604 and rules configurations 606, the query system manager 502 can (9) generate the system query 2304 and/or the query configuration parameters 2306.

4.4.3. Metadata Catalog Flows

Figure 24:
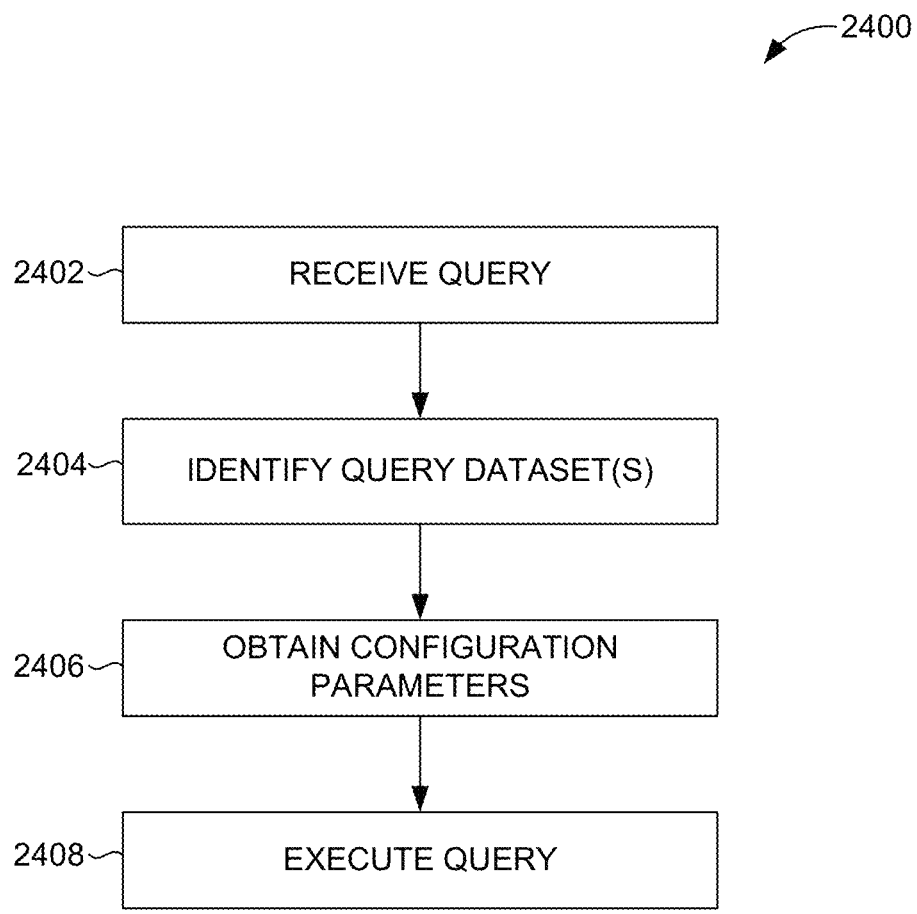
FIG. 24 is a flow diagram illustrative of an embodiment of a routine implemented by the query system to execute a query.

FIG. 24 is a flow diagram illustrative of an embodiment of a routine 2400 implemented by the query system 214 to execute a query. Although described as being implemented by the query system 214, it will be understood that the elements outlined for routine 2500 can be implemented by one or more computing devices/components that are associated with the data intake and query system 108, such as, but not limited to, the query system manager 502, the search head 504, the search master 512, the search manager 514, the search nodes 506, etc. Thus, the following illustrative embodiment should not be construed as limiting.

At block 2402, a query system 214 receives a search query. As described herein, the query system manager 502 can receive the query in a variety of ways. For example, the query can be received via the gateway 215 and/or network 208. The query can identify a set of data processing set of data. In addition, some embodiments, the query can include one or more commands to obtain data from a dataset, one or more dataset identifiers, and/or a dataset association record identifier.

At block 2404, query system 214 identifies one or more query datasets. As described herein, the query datasets can include one or more dataset sources and/or one or more datasets that are to be used to execute the query. In some embodiments, to identify the dataset sources, the query system 214 parses the query to identify the dataset identifier(s) and/or the dataset association record identifier. In certain embodiments, the query system 214 uses the dataset identifier(s) and/or the dataset association record identifier to identify the one or more query datasets.

In some embodiments, the query system 214 can iteratively process the dataset association record 602 associated with the identified dataset association record identifier to identify the query datasets. For example, as described herein, the query system 214 can parse datasets of the dataset association record. For each dataset that is parsed, the query system 214 can determine whether the dataset is a dataset source or will otherwise be used to execute the query. If the query system 214 determines that the dataset is a dataset source or will otherwise be used to execute the query, it can include the dataset as a query dataset.

In certain embodiments, the query system 214 can use the dataset associated with the dataset identifier to identify query datasets. For example, the query system 214 can parse the dataset (or corresponding dataset configuration) to determine whether the dataset includes at least a portion of the set of data of the query (or is a dataset source), includes one or more query parameters to be included as part of the query, references additional datasets (e.g., as part of a query parameter and/or as part of being inherited), and/or will be used (or its configuration parameters will be used) to execute the query.

Based on the parsing the query system 214 can determine whether the dataset is a query dataset. In some embodiments, if the query system determines that the dataset includes at least a portion of the set of data of the query, it can identify the dataset as a dataset source and a query dataset. In certain embodiments, if the dataset (or its configuration parameters) will be used to execute the query, the query system 214 can determine that the dataset is a query dataset. In some cases, if the dataset references other datasets, the query system 214 can parse the referenced datasets to determine whether they are query datasets. The query system 214 can iteratively process the datasets until any dataset referenced by the query or referenced by another dataset that was referenced by the (directly or indirectly) query, have been processed. In each case, the query system 214 can determine whether the dataset is a query dataset. In certain embodiments, if the dataset includes one or more query parameters and/or references one or more additional datasets but does not include at least a portion of the set of data or will not be used as part of the query, the query system 214 can determine that the dataset is not a query dataset.

In certain embodiments, the query system 214 can also identify query rules, such as rules that will be used to process at least a portion of the set of data or process data from a query dataset. In some embodiments, the query system 214 identifies the query rules similar to identifying query datasets. For example, the query system 214 can identify one or more rules in the query and/or one or more rules associated with a dataset that is referenced in the query or is referenced by another dataset that is referenced (directly or indirectly) by the query.

At 2406, the query system 214 obtains query configuration parameters. In some cases, the query system 214 can obtain the query configuration parameters based on the query datasets and/or query rules. In certain embodiments, the query system 214 can obtain the query configuration parameters from a metadata catalog 221. For example, as described herein, the metadata catalog 221 can include one or more dataset configurations. In certain embodiments, the query system 214 query configuration parameters include the dataset configurations associated with the query datasets. In certain embodiments, the query configuration parameters can include rules configurations associated with the query rules.

At 2408, the query system 214 executes the query. In some embodiments, the query system 214 executes the query based on the query configuration parameters. For example, the query configuration parameters can indicate how to access the dataset sources, how to process data from the dataset sources, etc. As described herein, the query system 214 can dynamically determine the query configuration parameters for the query. In certain embodiments, the query system 214 executes the query using only the query configuration parameters identified at block 2406. Furthermore, the query system 214 can execute the query, as described herein at least with reference to FIGS. 14-21.

Fewer, more, or different blocks can be used as part of the routine 2400. For example, in some embodiments, the query system 214 can generate a system query from a user query. In some cases, one or more blocks can be omitted. Furthermore, it will be understood that the various blocks described herein with reference to FIG. 24 can be implemented in a variety of orders, or can be performed concurrently. For example, the indexing node 404 can concurrently identify dataset sources and obtain query configuration parameters.

Figure 25:
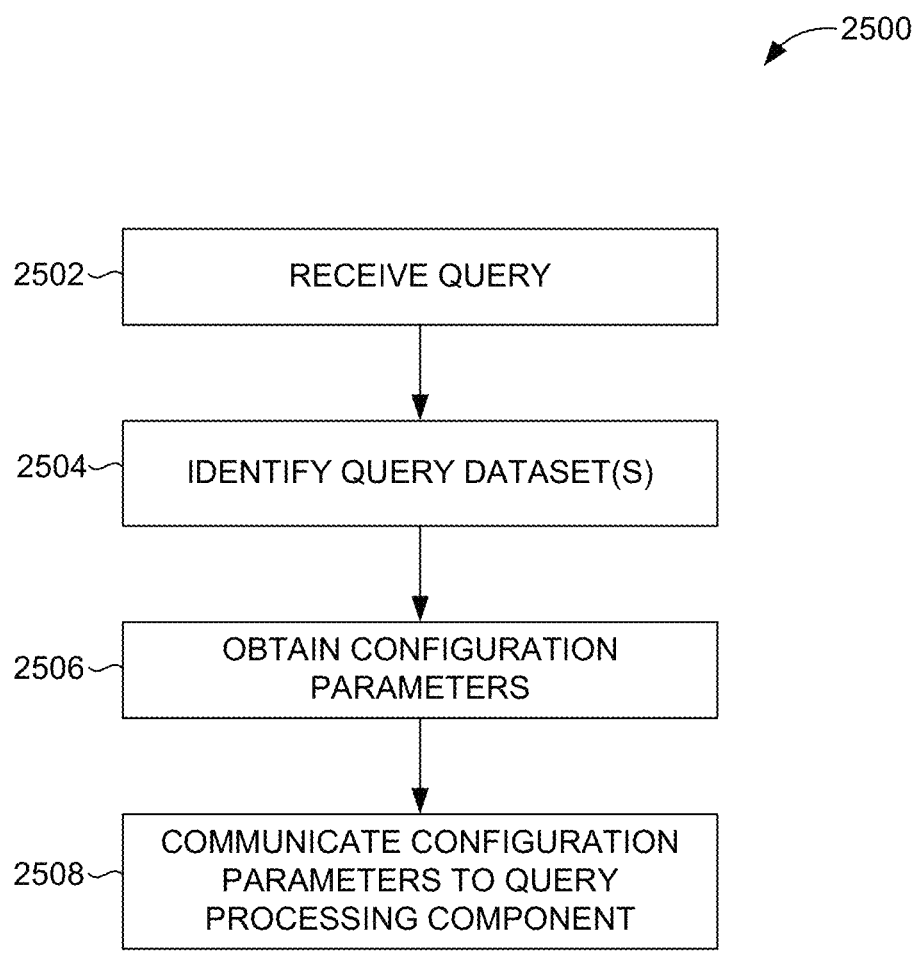
FIG. 25 is a flow diagram illustrative of an embodiment of a routine implemented by a query system manager to communicate query configuration parameters to a query processing component.

FIG. 25 is a flow diagram illustrative of an embodiment of a routine 2500 implemented by a query system manager 502 to communicate query configuration parameters to a query processing component. Although described as being implemented by the query system manager 502, it will be understood that the elements outlined for routine 2500 can be implemented by one or more computing devices/components that are associated with the data intake and query system 108, such as, but not limited to, query system 214, the search head 504, the search master 512, the search manager 514, the search nodes 506, etc. Thus, the following illustrative embodiment should not be construed as limiting.

At block 2502, the query system manager 502 receives a search query, as described in greater detail above at least with reference to block 2402 of FIG. 24 and (1') of FIG. 22. At block 2504, query system manager 502 identifies query datasets, as described herein at least with reference to block 2404 of FIG. 24 and (2') of FIG. 22. At 2506, the query system manager 502 obtains query configuration parameters, as described in greater detail above at least with reference to block 2406 of FIG. 24 and (2') of FIG. 22.

At 2508, the query system manager 502 communicates the query configuration parameters to a query processing component, such as the search head 504. As described herein, the query processing component can process and execute the query using the received query configuration parameters. Further, as described herein, in some embodiments, the query configuration parameters communicated to the query processing component include only the query configuration parameters of the query dataset and query rules, which, in some embodiments, form a subset of the dataset configurations and rule configurations of the metadata catalog 221 and, in certain embodiments, form a subset of the dataset configurations and rule configurations associated with the dataset association record(s) associated with the query.

In some embodiments, the query processing component does not store query configuration parameters. Accordingly, the search head 504 may be otherwise unable to process and execute the query without the query configuration parameters received from the query system manager 502. Similarly, in some embodiments, the indexers and/or search nodes do not include query configuration parameters. Accordingly, in some such embodiments, without the query configuration parameters received from the query system manager 502, the query system 214 would be unable to process and execute the query. Furthermore, by dynamically determining and providing the query configuration parameters to the query processing component, the query system 214 can provide a stateless query system. For example, if the query system 214 determines that multiple query processing components are to be used to process the query or if an assigned query processing component becomes unavailable, the query system can communicate the query configuration parameters to another query processing component without data loss.

Fewer, more, or different blocks can be used as part of the routine 2500. In some cases, one or more blocks can be omitted. Furthermore, it will be understood that the various blocks described herein with reference to FIG. 25 can be implemented in a variety of orders, or can be performed concurrently. For example, the indexing node 404 can concurrently identify dataset sources and obtain query configuration parameters.

Figure 26:
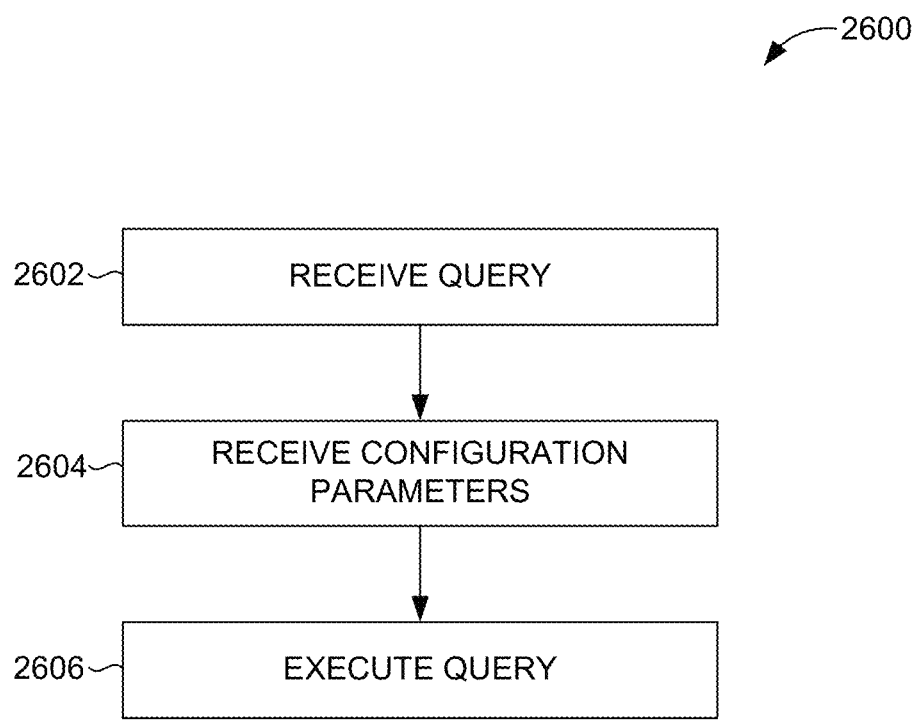
FIG. 26 is a flow diagram illustrative of an embodiment of a routine implemented by the query system to execute a query.

FIG. 26 is a flow diagram illustrative of an embodiment of a routine 2600 implemented by the query system 214 to execute a query. Although described as being implemented by the search head 504, it will be understood that the elements outlined for routine 2600 can be implemented by one or more computing devices/components that are associated with the data intake and query system 108, such as, but not limited to, the query system manager 502, the search master 512, the search manager 514, the search nodes 506, etc. Thus, the following illustrative embodiment should not be construed as limiting.

At block 2602, the search head 504 receives a query. In some embodiments the query received by the search head 504 can be a system query generated by a query system manager 502. In certain embodiments, the query received by the search head 504 can correspond to a query received by the query system 214 and/or a query received by the data intake and query system 108.

At block 2604, the search head 504 receives query configuration parameters. As described herein, in some embodiments, the query system manager 502 dynamically identifies the query configuration parameters to be used to process and execute query. The query configuration parameters can include dataset configurations associated with query datasets and/or rule configurations associated with query rules. In some such embodiments, the search head 504 does not store query configuration parameters locally. In certain embodiments, the query configuration parameters are concurrently received with the query. Furthermore, as described herein, in some embodiments, the query configuration parameters are dynamically generated at query time, or in other words are not determined prior to receipt of the query. In certain embodiments, the query configuration parameters correspond to a subset of the configuration parameters associated with a dataset association record and/or a metadata catalog 221.

In certain embodiments, by dynamically receiving the query configuration parameters associated with a query (or concurrently with the query), the query system 214 can provide a stateless search experience. For example, if the search head 504 becomes unavailable, the query system manager 502 can communicate the dynamically determined query configuration parameters (and/or query to be executed) to another search head 504 without data loss and/or with minimal time loss. At block 2606, the search head 504 executes the query, as described herein at least with reference to block 2408 of FIG. 24 and FIGS. 14-21.

Fewer, more, or different blocks can be used as part of the routine 2600. In some cases, one or more blocks can be omitted. Furthermore, it will be understood that the various blocks described herein with reference to FIG. 26 can be implemented in a variety of orders, or can be performed concurrently.

Figure 27:
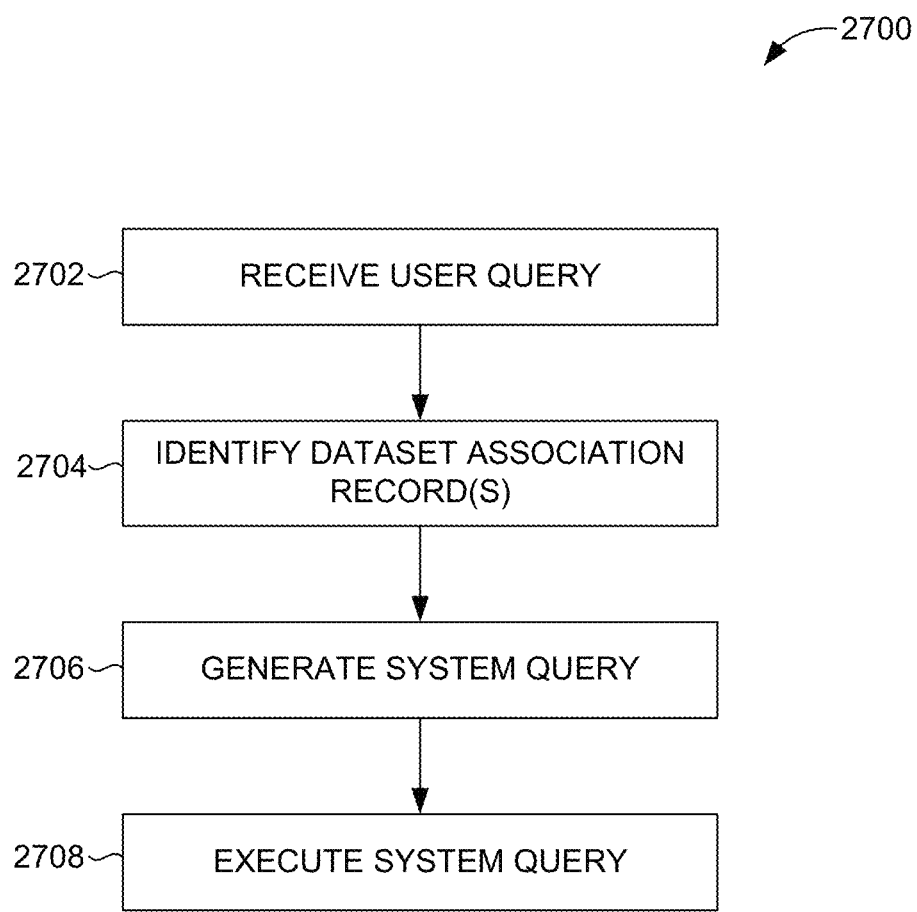
FIG. 27 is a flow diagram illustrative of an embodiment of a routine implemented by the query system to execute a query.

FIG. 27 is a flow diagram illustrative of an embodiment of a routine 2700 implemented by the query system 214 to execute a query. Although described as being implemented by the query system manager 502, it will be understood that the elements outlined for routine 2700 can be implemented by one or more computing devices/components that are associated with the data intake and query system 108, such as, but not limited to, the search head 504, the search master 512, the search manager 514, the search nodes 506, etc. Thus, the following illustrative embodiment should not be construed as limiting.

At block 2702, the query system manager 502 receives a user query, as described herein at least with reference to (1') of FIG. 22 and block 2502 of FIG. 25. At block 2704, the query system manager 502 identifies one or more dataset association records. In some embodiments, the query system manager 502 identifies the more dataset association records by parsing the user query and/or via command received with the user query.

In certain embodiments, as described herein, the dataset association records identify a subset of datasets of a plurality of datasets in a metadata catalog and/or one or more rules for processing data from at least one dataset of the subset of datasets. In certain embodiments, the datasets of a dataset association record include dataset sources, datasets that reference additional datasets, and/or datasets that reference one or more rules. In some embodiments, if the dataset references another dataset or rule, the query system manager 502 can recursively analyze the referenced datasets and rules until it identifies the query datasets and query rules. In certain embodiments, the query system manager 502 parses multiple dataset association records to identify query datasets and/or query rules.

At block 2706, the query system manager 502 generates a system query. In some embodiments, the query system manager 502 generates a system query based on the dataset association records identified at block 2704. For example, using the dataset association records, the query system manager 502 can determine a physical identifier for query datasets and query rules. The query system manager 502 can use the physical dataset identifiers to generate the system query. For example, the query system manager 502 can reference the physical dataset identifiers in the system query and/or remove all logical dataset identifiers from the user query. In addition, as described herein, in some embodiments, datasets of a dataset association record 602 may reference one or more query parameters. Accordingly, in certain embodiments, the query system manager 502 can include the query parameters referenced by a dataset in the system query.

Furthermore, using the dataset association records, the query system manager can identify one or more rules related to the dataset sources. As described herein, in certain embodiments, the query system manager 502 analyzes multiple dataset association records to identify datasets associated with the query.

At block 2708, the query system manager 502 communicates the system query to a query execution component of the data intake and query system. In certain embodiments, query system manager 502 communicates the system query to a search head 504, as described herein at least with reference to the (4') of FIG. 22. Furthermore, the query execution component can process and execute the system query, as described herein at least with reference to FIGS. 14-21.

Fewer, more, or different blocks can be used as part of the routine 2700. In some cases, one or more blocks can be omitted. Furthermore, it will be understood that the various blocks described herein with reference to FIG. 27 can be implemented in a variety of orders, or can be performed concurrently.

Figure 28:
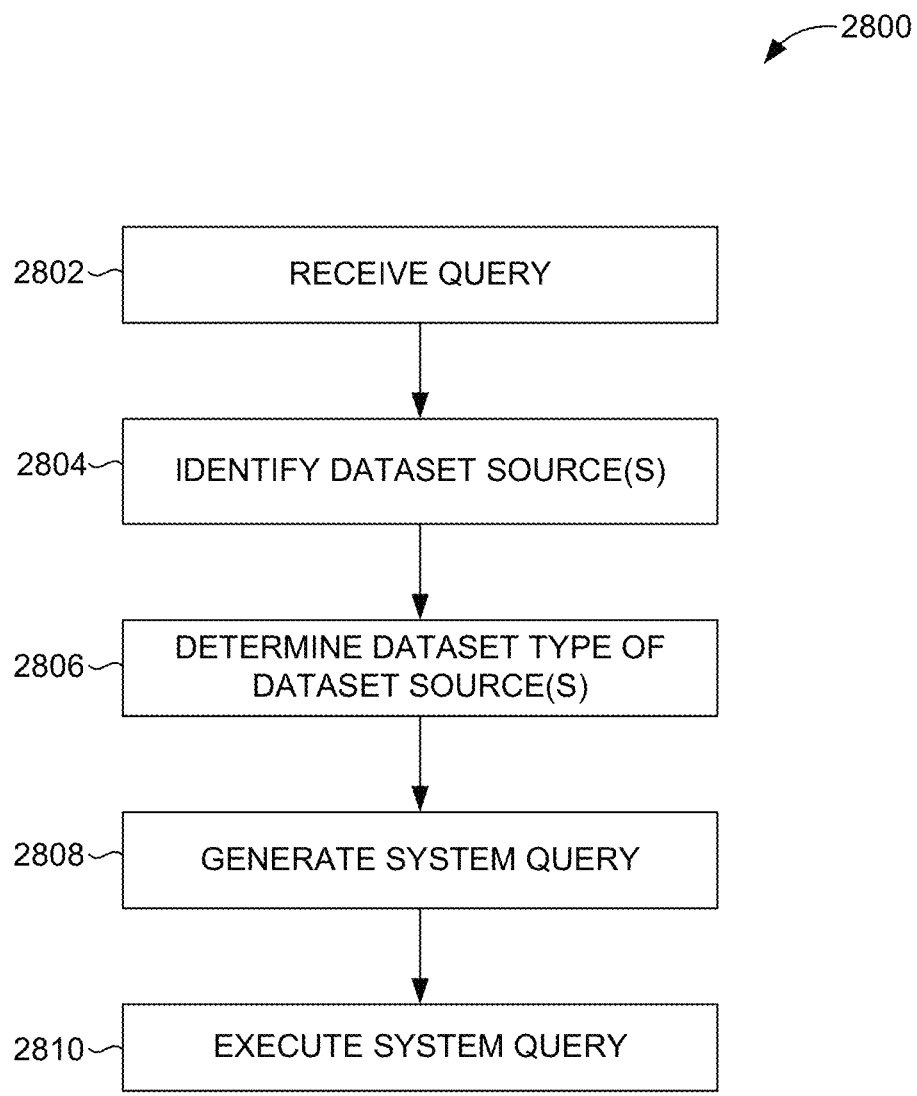
FIG. 28 is a flow diagram illustrative of an embodiment of a routine 2800 implemented by the query system to execute a query.

FIG. 28 is a flow diagram illustrative of an embodiment of a routine 2800 implemented by the query system 214 to execute a query. Although described as being implemented by the query system manager 502, it will be understood that the elements outlined for routine 2800 can be implemented by one or more computing devices/components that are associated with the data intake and query system 108, such as, but not limited to, the search head 504, the search master 512, the search manager 514, the search nodes 506, etc. Thus, the following illustrative embodiment should not be construed as limiting.

At block 2802, the query system manager 502 receives a user query, as described in herein at least with reference to block 2702 of FIG. 27. At block 2804, the query system manager 502 identifies one or more dataset sources and at block 2806 the query system manager 502 identifies a dataset type of the dataset sources, as described herein at least with reference to (2') of FIG. 22 and FIG. 23. For example, the query system manager 502 can identify one or more query datasets that include or reference at least a portion of the set of data of the query and identify dataset configurations associated with the identified datasets. Furthermore, the query system manager 502 can parse the identified dataset configurations to identify the dataset type of the dataset sources.

At block 2808, the query system manager 502 generates a system query, as described herein at least with reference to (3') of FIG. 22 and FIG. 23. In some embodiments, different commands can be associated with different query datasets. For example, an index dataset type can be associated with a "search" command, a lookup dataset type can be associated with a "lookup," command, etc. Accordingly, based on the dataset type, the query system manager 502 can determine a command to be used to search or retrieve data from the particular dataset source or query dataset. The query system manager 502 can include the determined commands for the identified dataset source in the system query.

At block 2810, the query system manager 502 communicates the system query to a query execution component of the data intake and query system, as described herein at least with reference to block 2708 of FIG. 27.

Fewer, more, or different blocks can be used as part of the routine 2800. In some cases, one or more blocks can be omitted. Furthermore, it will be understood that the various blocks described herein with reference to FIG. 28 can be implemented in a variety of orders, or can be performed concurrently.

4.5. Data Ingestion, Indexing, and Storage Flow

Figure 29A:
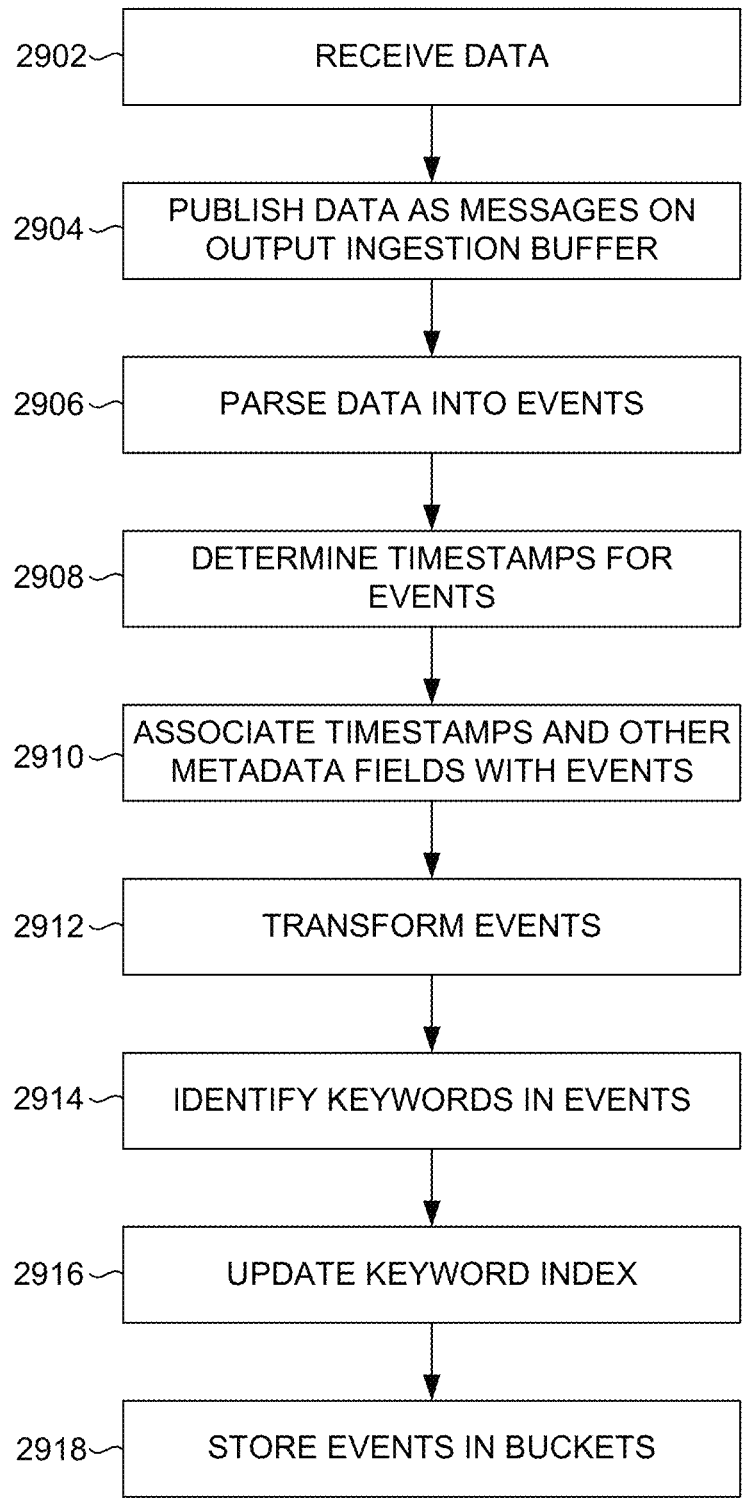
FIG. 29A is a flowchart of an example method that illustrates how indexers process, index, and store data received from intake system, in accordance with example embodiments.

FIG. 29A is a flow diagram of an example method that illustrates how a data intake and query system 108 processes, indexes, and stores data received from data sources 202, in accordance with example embodiments. The data flow illustrated in FIG. 29A is provided for illustrative purposes only; it will be understood that one or more of the steps of the processes illustrated in FIG. 29A may be removed or that the ordering of the steps may be changed. Furthermore, for the purposes of illustrating a clear example, one or more particular system components are described in the context of performing various operations during each of the data flow stages. For example, the intake system 210 is described as receiving and processing machine data during an input phase; the indexing system 212 is described as parsing and indexing machine data during parsing and indexing phases; and a query system 214 is described as performing a search query during a search phase. However, other system arrangements and distributions of the processing steps across system components may be used.

4.5.1. Input

At block 2902, the intake system 210 receives data from an input source, such as a data source 202 shown in FIG. 2. The intake system 210 initially may receive the data as a raw data stream generated by the input source. For example, the intake system 210 may receive a data stream from a log file generated by an application server, from a stream of network data from a network device, or from any other source of data. In some embodiments, the intake system 210 receives the raw data and may segment the data stream into messages, possibly of a uniform data size, to facilitate subsequent processing steps. The intake system 210 may thereafter process the messages in accordance with one or more rules, as discussed above for example with reference to FIGS. 7 and 8, to conduct preliminary processing of the data. In one embodiment, the processing conducted by the intake system 210 may be used to indicate one or more metadata fields applicable to each message. For example, the intake system 210 may include metadata fields within the messages, or publish the messages to topics indicative of a metadata field. These metadata fields may, for example, provide information related to a message as a whole and may apply to each event that is subsequently derived from the data in the message. For example, the metadata fields may include separate fields specifying each of a host, a source, and a source type related to the message. A host field may contain a value identifying a host name or IP address of a device that generated the data. A source field may contain a value identifying a source of the data, such as a pathname of a file or a protocol and port related to received network data. A source type field may contain a value specifying a particular source type label for the data. Additional metadata fields may also be included during the input phase, such as a character encoding of the data, if known, and possibly other values that provide information relevant to later processing steps.

At block 504, the intake system 210 publishes the data as messages on an output ingestion buffer 310. Illustratively, other components of the data intake and query system 108 may be configured to subscribe to various topics on the output ingestion buffer 310, thus receiving the data of the messages when published to the buffer 310.

4.5.2. Parsing

At block 2906, the indexing system 212 receives messages from the intake system 210 (e.g., by obtaining the messages from the output ingestion buffer 310) and parses the data of the message to organize the data into events. In some embodiments, to organize the data into events, the indexing system 212 may determine a source type associated with each message (e.g., by extracting a source type label from the metadata fields associated with the message, etc.) and refer to a source type configuration corresponding to the identified source type. The source type definition may include one or more properties that indicate to the indexing system 212 to automatically determine the boundaries within the received data that indicate the portions of machine data for events. In general, these properties may include regular expression-based rules or delimiter rules where, for example, event boundaries may be indicated by predefined characters or character strings. These predefined characters may include punctuation marks or other special characters including, for example, carriage returns, tabs, spaces, line breaks, etc. If a source type for the data is unknown to the indexing system 212, the indexing system 212 may infer a source type for the data by examining the structure of the data. Then, the indexing system 212 can apply an inferred source type definition to the data to create the events.

At block 2908, the indexing system 212 determines a timestamp for each event. Similar to the process for parsing machine data, an indexing system 212 may again refer to a source type definition associated with the data to locate one or more properties that indicate instructions for determining a timestamp for each event. The properties may, for example, instruct the indexing system 212 to extract a time value from a portion of data for the event, to interpolate time values based on timestamps associated with temporally proximate events, to create a timestamp based on a time the portion of machine data was received or generated, to use the timestamp of a previous event, or use any other rules for determining timestamps.

At block 2910, the indexing system 212 associates with each event one or more metadata fields including a field containing the timestamp determined for the event. In some embodiments, a timestamp may be included in the metadata fields. These metadata fields may include any number of "default fields" that are associated with all events, and may also include one more custom fields as defined by a user. Similar to the metadata fields associated with the data blocks at block 2904, the default metadata fields associated with each event may include a host, source, and source type field including or in addition to a field storing the timestamp.

At block 2912, the indexing system 212 may optionally apply one or more transformations to data included in the events created at block 2906. For example, such transformations can include removing a portion of an event (e.g., a portion used to define event boundaries, extraneous characters from the event, other extraneous text, etc.), masking a portion of an event (e.g., masking a credit card number), removing redundant portions of an event, etc. The transformations applied to events may, for example, be specified in one or more configuration files and referenced by one or more source type definitions.

FIG. 29C illustrates an illustrative example of how machine data can be stored in a data store in accordance with various disclosed embodiments. In other embodiments, machine data can be stored in a flat file in a corresponding bucket with an associated index file, such as a time series index or "TSIDX." As such, the depiction of machine data and associated metadata as rows and columns in the table of FIG. 29C is merely illustrative and is not intended to limit the data format in which the machine data and metadata is stored in various embodiments described herein. In one particular embodiment, machine data can be stored in a compressed or encrypted formatted. In such embodiments, the machine data can be stored with or be associated with data that describes the compression or encryption scheme with which the machine data is stored. The information about the compression or encryption scheme can be used to decompress or decrypt the machine data, and any metadata with which it is stored, at search time.

As mentioned above, certain metadata, e.g., host 2936, source 2937, source type 2938 and timestamps 2935 can be generated for each event, and associated with a corresponding portion of machine data 2939 when storing the event data in a data store, e.g., data store 218. Any of the metadata can be extracted from the corresponding machine data, or supplied or defined by an entity, such as a user or computer system. The metadata fields can become part of or stored with the event. Note that while the time-stamp metadata field can be extracted from the raw data of each event, the values for the other metadata fields may be determined by the indexing system 212 or indexing node 404 based on information it receives pertaining to the source of the data separate from the machine data.

While certain default or user-defined metadata fields can be extracted from the machine data for indexing purposes, all the machine data within an event can be maintained in its original condition. As such, in embodiments in which the portion of machine data included in an event is unprocessed or otherwise unaltered, it is referred to herein as a portion of raw machine data. In other embodiments, the port of machine data in an event can be processed or otherwise altered. As such, unless certain information needs to be removed for some reasons (e.g. extraneous information, confidential information), all the raw machine data contained in an event can be preserved and saved in its original form. Accordingly, the data store in which the event records are stored is sometimes referred to as a "raw record data store." The raw record data store contains a record of the raw event data tagged with the various default fields.

In FIG. 29C, the first three rows of the table represent events 2931, 2932, and 2933 and are related to a server access log that records requests from multiple clients processed by a server, as indicated by entry of "access.log" in the source column 2936.

In the example shown in FIG. 29C, each of the events 2931-2933 is associated with a discrete request made from a client device. The raw machine data generated by the server and extracted from a server access log can include the IP address of the client 2940, the user id of the person requesting the document 2941, the time the server finished processing the request 2942, the request line from the client 2943, the status code returned by the server to the client 2945, the size of the object returned to the client (in this case, the gif file requested by the client) 2946 and the time spent to serve the request in microseconds 2944. As seen in FIG. 29C, all the raw machine data retrieved from the server access log is retained and stored as part of the corresponding events, 2931-2933 in the data store.

Event 2934 is associated with an entry in a server error log, as indicated by "error.log" in the source column 2937 that records errors that the server encountered when processing a client request. Similar to the events related to the server access log, all the raw machine data in the error log file pertaining to event 2934 can be preserved and stored as part of the event 2934.

Saving minimally processed or unprocessed machine data in a data store associated with metadata fields in the manner similar to that shown in FIG. 29C is advantageous because it allows search of all the machine data at search time instead of searching only previously specified and identified fields or field-value pairs. As mentioned above, because data structures used by various embodiments of the present disclosure maintain the underlying raw machine data and use a late-binding schema for searching the raw machines data, it enables a user to continue investigating and learn valuable insights about the raw data. In other words, the user is not compelled to know about all the fields of information that will be needed at data ingestion time. As a user learns more about the data in the events, the user can continue to refine the late-binding schema by defining new extraction rules, or modifying or deleting existing extraction rules used by the system.

4.5.3. Indexing

At blocks 2914 and 2916, the indexing system 212 can optionally generate a keyword index to facilitate fast keyword searching for events. To build a keyword index, at block 2914, the indexing system 212 identifies a set of keywords in each event. At block 2916, the indexing system 212 includes the identified keywords in an index, which associates each stored keyword with reference pointers to events containing that keyword (or to locations within events where that keyword is located, other location identifiers, etc.). When the data intake and query system 108 subsequently receives a keyword-based query, the query system 214 can access the keyword index to quickly identify events containing the keyword.

In some embodiments, the keyword index may include entries for field name-value pairs found in events, where a field name-value pair can include a pair of keywords connected by a symbol, such as an equals sign or colon. This way, events containing these field name-value pairs can be quickly located. In some embodiments, fields can automatically be generated for some or all of the field names of the field name-value pairs at the time of indexing. For example, if the string "dest=10.0.1.2" is found in an event, a field named "dest" may be created for the event, and assigned a value of "10.0.1.2".

At block 2918, the indexing system 212 stores the events with an associated timestamp in a local data store 218 and/or common storage 216. Timestamps enable a user to search for events based on a time range. In some embodiments, the stored events are organized into "buckets," where each bucket stores events associated with a specific time range based on the timestamps associated with each event. This improves time-based searching, as well as allows for events with recent timestamps, which may have a higher likelihood of being accessed, to be stored in a faster memory to facilitate faster retrieval. For example, buckets containing the most recent events can be stored in flash memory rather than on a hard disk. In some embodiments, each bucket may be associated with an identifier, a time range, and a size constraint.

The indexing system 212 may be responsible for storing the events contained in various data stores 218 of common storage 216. By distributing events among the data stores in common storage 216, the query system 214 can analyze events for a query in parallel. For example, using map-reduce techniques, each search node 506 can return partial responses for a subset of events to a search head that combines the results to produce an answer for the query. By storing events in buckets for specific time ranges, the indexing system 212 may further optimize the data retrieval process by enabling search nodes 506 to search buckets corresponding to time ranges that are relevant to a query.

In some embodiments, each indexing node 404 (e.g., the indexer 410 or data store 412) of the indexing system 212 has a home directory and a cold directory. The home directory stores hot buckets and warm buckets, and the cold directory stores cold buckets. A hot bucket is a bucket that is capable of receiving and storing events. A warm bucket is a bucket that can no longer receive events for storage but has not yet been moved to the cold directory. A cold bucket is a bucket that can no longer receive events and may be a bucket that was previously stored in the home directory. The home directory may be stored in faster memory, such as flash memory, as events may be actively written to the home directory, and the home directory may typically store events that are more frequently searched and thus are accessed more frequently. The cold directory may be stored in slower and/or larger memory, such as a hard disk, as events are no longer being written to the cold directory, and the cold directory may typically store events that are not as frequently searched and thus are accessed less frequently. In some embodiments, an indexing node 404 may also have a quarantine bucket that contains events having potentially inaccurate information, such as an incorrect time stamp associated with the event or a time stamp that appears to be an unreasonable time stamp for the corresponding event. The quarantine bucket may have events from any time range; as such, the quarantine bucket may always be searched at search time. Additionally, an indexing node 404 may store old, archived data in a frozen bucket that is not capable of being searched at search time. In some embodiments, a frozen bucket may be stored in slower and/or larger memory, such as a hard disk, and may be stored in offline and/or remote storage.

In some embodiments, an indexing node 404 may not include a cold directory and/or cold or frozen buckets. For example, as warm buckets and/or merged buckets are copied to common storage 216, they can be deleted from the indexing node 404. In certain embodiments, one or more data stores 218 of the common storage 216 can include a home directory that includes warm buckets copied from the indexing nodes 404 and a cold directory of cold or frozen buckets as described above.

Moreover, events and buckets can also be replicated across different indexing nodes 404 and data stores 218 of the common storage 216.

Figure 29B:
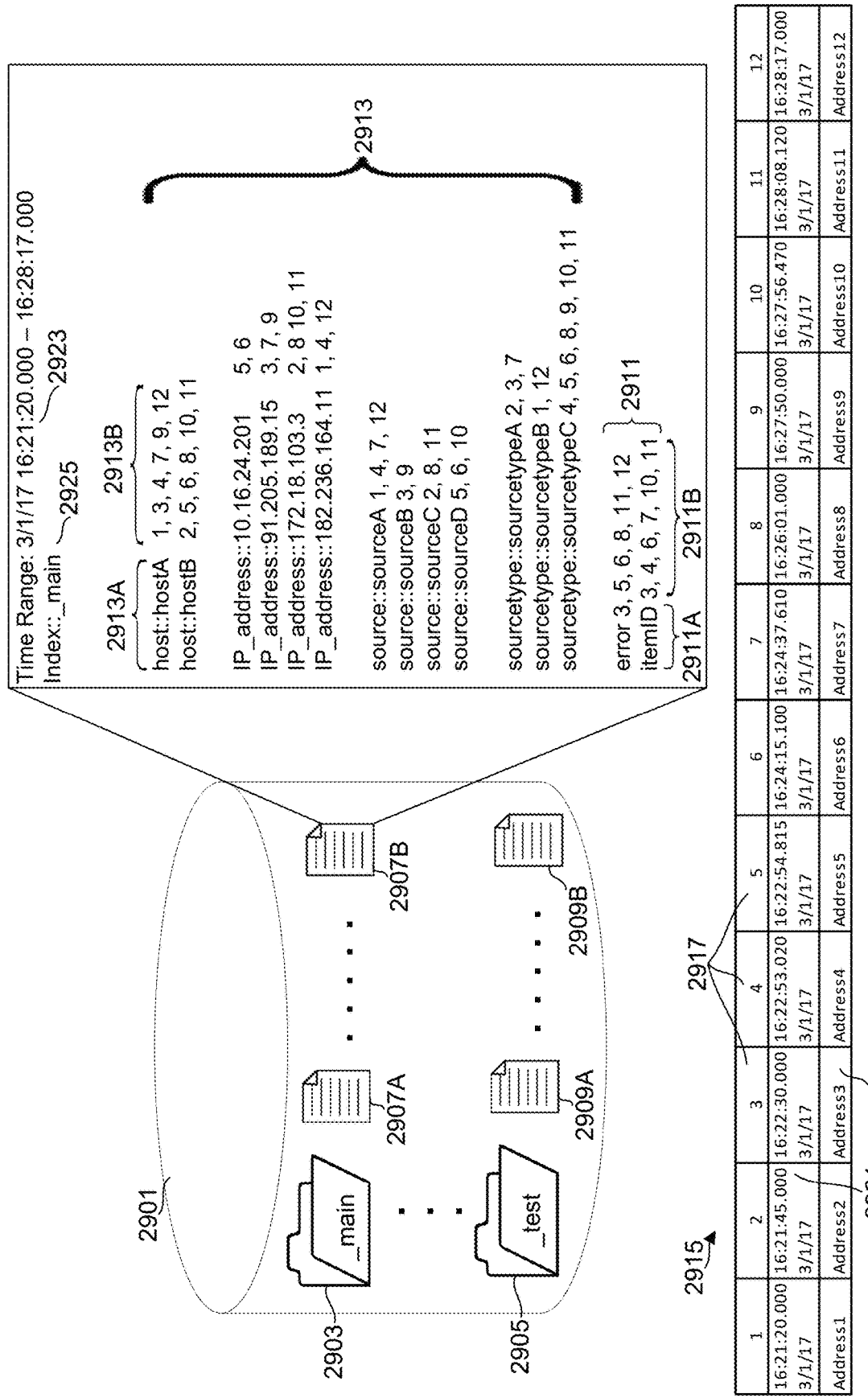
FIG. 29B is a block diagram of a data structure in which time-stamped event data can be stored in a data store, in accordance with example embodiments.

FIG. 29B is a block diagram of an example data store 2901 that includes a directory for each index (or partition) that contains a portion of data stored in the data store 2901. FIG. 29B further illustrates details of an embodiment of an inverted index 2907B and an event reference array 2915 associated with inverted index 2907B.

The data store 2901 can correspond to a data store 218 that stores events in common storage 216, a data store 412 associated with an indexing node 404, or a data store associated with a search peer 506. In the illustrated embodiment, the data store 2901 includes a _main directory 2903 associated with a _main partition and a _test directory 2905 associated with a _test partition. However, the data store 2901 can include fewer or more directories. In some embodiments, multiple indexes can share a single directory or all indexes can share a common directory. Additionally, although illustrated as a single data store 2901, it will be understood that the data store 2901 can be implemented as multiple data stores storing different portions of the information shown in FIG. 29B. For example, a single index or partition can span multiple directories or multiple data stores, and can be indexed or searched by multiple search nodes 506.

Furthermore, although not illustrated in FIG. 29B, it will be understood that, in some embodiments, the data store 2901 can include directories for each tenant and sub-directories for each partition of each tenant, or vice versa. Accordingly, the directories 2901 and 2903 illustrated in FIG. 29B can, in certain embodiments, correspond to sub-directories of a tenant or include sub-directories for different tenants.

In the illustrated embodiment of FIG. 29B, the partition-specific directories 2903 and 2905 include inverted indexes 2907A, 2907B and 2909A, 2909B, respectively. The inverted indexes 2907A . . . 2907B, and 2909A . . . 2909B can be keyword indexes or field-value pair indexes described herein and can include less or more information than depicted in FIG. 29B.

In some embodiments, the inverted index 2907A . . . 2907B, and 2909A . . . 2909B can correspond to a distinct time-series bucket stored in common storage 216, a search node 506, or an indexing node 404 and that contains events corresponding to the relevant partition (e.g., _main partition, _test partition). As such, each inverted index can correspond to a particular range of time for a partition. Additional files, such as high performance indexes for each time-series bucket of a partition, can also be stored in the same directory as the inverted indexes 2907A . . . 2907B, and 2909A . . . 2909B. In some embodiments, inverted index 2907A ... 2907B, and 2909A ... 2909B can correspond to multiple time-series buckets or inverted indexes 2907A ... 2907B, and 2909A ... 2909B can correspond to a single time-series bucket.

Each inverted index 2907A ... 2907B, and 2909A ... 2909B can include one or more entries, such as keyword (or token) entries or field-value pair entries. Furthermore, in certain embodiments, the inverted indexes 2907A ... 2907B, and 2909A ... 2909B can include additional information, such as a time range 2923 associated with the inverted index or a partition identifier 2925 identifying the partition associated with the inverted index 2907A ... 2907B, and 2909A ... 2909B. However, each inverted index 2907A ... 2907B, and 2909A ... 2909B can include less or more information than depicted.

Token entries, such as token entries 2911 illustrated in inverted index 2907B, can include a token 2911A (e.g., "error," "itemID," etc.) and event references 2911B indicative of events that include the token. For example, for the token "error," the corresponding token entry includes the token "error" and an event reference, or unique identifier, for each event stored in the corresponding time-series bucket that includes the token "error." In the illustrated embodiment of FIG. 29B, the error token entry includes the identifiers 3, 5, 6, 8, 11, and 12 corresponding to events located in the time-series bucket associated with the inverted index 2907B that is stored in common storage 216, a search node 506, or an indexing node 404 and is associated with the partition _main 2903.

In some cases, some token entries can be default entries, automatically determined entries, or user specified entries. In some embodiments, the indexing system 212 can identify each word or string in an event as a distinct token and generate a token entry for the identified word or string. In some cases, the indexing system 212 can identify the beginning and ending of tokens based on punctuation, spaces, as described in greater detail herein. In certain cases, the indexing system 212 can rely on user input or a configuration file to identify tokens for token entries 2911, etc. It will be understood that any combination of token entries can be included as a default, automatically determined, a or included based on user-specified criteria.

Similarly, field-value pair entries, such as field-value pair entries 29B shown in inverted index 2907B, can include a field-value pair 2913A and event references 2913B indicative of events that include a field value that corresponds to the field-value pair. For example, for a field-value pair sourcetype::sendmail, a field-value pair entry can include the field-value pair sourcetype::sendmail and a unique identifier, or event reference, for each event stored in the corresponding time-series bucket that includes a sendmail sourcetype.

In some cases, the field-value pair entries 2913 can be default entries, automatically determined entries, or user specified entries. As a non-limiting example, the field-value pair entries for the fields host, source, sourcetype can be included in the inverted indexes 2907A ... 2907B, and 2909A ... 2909B as a default. As such, all of the inverted indexes 2907A ... 2907B, and 2909A ... 2909B can include field-value pair entries for the fields host, source, sourcetype. As yet another non-limiting example, the field-value pair entries for the IP_address field can be user specified and may only appear in the inverted index 2907B based on user-specified criteria. As another non-limiting example, as the indexing system 212 indexes the events, it can automatically identify field-value pairs and create field-value pair entries. For example, based on the indexing system's 212 review of events, it can identify IP_address as a field in each event and add the IP_address field-value pair entries to the inverted index 2907B. It will be understood that any combination of field-value pair entries can be included as a default, automatically determined, or included based on user-specified criteria.

With reference to the event reference array 2915, each unique identifier 2917, or event reference, can correspond to a unique event located in the time series bucket. However, the same event reference can be located in multiple entries of an inverted index. For example if an event has a sourcetype "splunkd," host "www1" and token "warning," then the unique identifier for the event will appear in the field-value pair entries sourcetype::splunkd and host::www1, as well as the token entry "warning." With reference to the illustrated embodiment of FIG. 29B and the event that corresponds to the event reference 3, the event reference 3 is found in the field-value pair entries 2913 host::hostA, source::sourceB, sourcetype::sourcetypeA, and IP_address::91.205.189.15 indicating that the event corresponding to the event references is from hostA, sourceB, of sourcetypeA, and includes 91.205.189.15 in the event data.

For some fields, the unique identifier is located in only one field-value pair entry for a particular field. For example, the inverted index may include four sourcetype field-value pair entries corresponding to four different sourcetypes of the events stored in a bucket (e.g., sourcetypes: sendmail, splunkd, web_access, and web_service). Within those four sourcetype field-value pair entries, an identifier for a particular event may appear in only one of the field-value pair entries. With continued reference to the example illustrated embodiment of FIG. 29B, since the event reference 7 appears in the field-value pair entry sourcetype::sourcetypeA, then it does not appear in the other field-value pair entries for the sourcetype field, including sourcetype::sourcetypeB, sourcetype::sourcetypeC, and sourcetype::sourcetypeD.

The event references 2917 can be used to locate the events in the corresponding bucket. For example, the inverted index can include, or be associated with, an event reference array 2915. The event reference array 2915 can include an array entry 2917 for each event reference in the inverted index 2907B. Each array entry 2917 can include location information 2919 of the event corresponding to the unique identifier (non-limiting example: seek address of the event), a timestamp 2921 associated with the event, or additional information regarding the event associated with the event reference, etc.

For each token entry 2911 or field-value pair entry 2913, the event reference 2901B or unique identifiers can be listed in chronological order or the value of the event reference can be assigned based on chronological data, such as a timestamp associated with the event referenced by the event reference. For example, the event reference 1 in the illustrated embodiment of FIG. 29B can correspond to the first-in-time event for the bucket, and the event reference 12 can correspond to the last-in-time event for the bucket. However, the event references can be listed in any order, such as reverse chronological order, ascending order, descending order, or some other order, etc. Further, the entries can be sorted. For example, the entries can be sorted alphabetically (collectively or within a particular group), by entry origin (e.g., default, automatically generated, user-specified, etc.), by entry type (e.g., field-value pair entry, token entry, etc.), or chronologically by when added to the inverted index, etc. In the illustrated embodiment of FIG. 29B, the entries are sorted first by entry type and then alphabetically.

As a non-limiting example of how the inverted indexes 2907A . . . 2907B, and 2909A . . . 2909B can be used during a data categorization request command, the query system 214 can receive filter criteria indicating data that is to be categorized and categorization criteria indicating how the data is to be categorized. Example filter criteria can include, but is not limited to, indexes (or partitions), hosts, sources, sourcetypes, time ranges, field identifier, tenant and/or user identifiers, keywords, etc.

Using the filter criteria, the query system 214 identifies relevant inverted indexes to be searched. For example, if the filter criteria includes a set of partitions (also referred to as indexes), the query system 214 can identify the inverted indexes stored in the directory corresponding to the particular partition as relevant inverted indexes. Other means can be used to identify inverted indexes associated with a partition of interest. For example, in some embodiments, the query system 214 can review an entry in the inverted indexes, such as a partition-value pair entry 2913 to determine if a particular inverted index is relevant. If the filter criteria does not identify any partition, then the query system 214 can identify all inverted indexes managed by the query system 214 as relevant inverted indexes.

Similarly, if the filter criteria includes a time range, the query system 214 can identify inverted indexes corresponding to buckets that satisfy at least a portion of the time range as relevant inverted indexes. For example, if the time range is last hour then the query system 214 can identify all inverted indexes that correspond to buckets storing events associated with timestamps within the last hour as relevant inverted indexes.

When used in combination, an index filter criterion specifying one or more partitions and a time range filter criterion specifying a particular time range can be used to identify a subset of inverted indexes within a particular directory (or otherwise associated with a particular partition) as relevant inverted indexes. As such, the query system 214 can focus the processing to only a subset of the total number of inverted indexes in the data intake and query system 108.

Once the relevant inverted indexes are identified, the query system 214 can review them using any additional filter criteria to identify events that satisfy the filter criteria. In some cases, using the known location of the directory in which the relevant inverted indexes are located, the query system 214 can determine that any events identified using the relevant inverted indexes satisfy an index filter criterion. For example, if the filter criteria includes a partition main, then the query system 214 can determine that any events identified using inverted indexes within the partition main directory (or otherwise associated with the partition main) satisfy the index filter criterion.

Furthermore, based on the time range associated with each inverted index, the query system 214 can determine that any events identified using a particular inverted index satisfies a time range filter criterion. For example, if a time range filter criterion is for the last hour and a particular inverted index corresponds to events within a time range of 50 minutes ago to 35 minutes ago, the query system 214 can determine that any events identified using the particular inverted index satisfy the time range filter criterion. Conversely, if the particular inverted index corresponds to events within a time range of 59 minutes ago to 62 minutes ago, the query system 214 can determine that some events identified using the particular inverted index may not satisfy the time range filter criterion.

Using the inverted indexes, the query system 214 can identify event references (and therefore events) that satisfy the filter criteria. For example, if the token "error" is a filter criterion, the query system 214 can track all event references within the token entry "error." Similarly, the query system 214 can identify other event references located in other token entries or field-value pair entries that match the filter criteria. The system can identify event references located in all of the entries identified by the filter criteria. For example, if the filter criteria include the token "error" and field-value pair sourcetype::web_ui, the query system 214 can track the event references found in both the token entry "error" and the field-value pair entry sourcetype::web_ui. As mentioned previously, in some cases, such as when multiple values are identified for a particular filter criterion (e.g., multiple sources for a source filter criterion), the system can identify event references located in at least one of the entries corresponding to the multiple values and in all other entries identified by the filter criteria. The query system 214 can determine that the events associated with the identified event references satisfy the filter criteria.

In some cases, the query system 214 can further consult a timestamp associated with the event reference to determine whether an event satisfies the filter criteria. For example, if an inverted index corresponds to a time range that is partially outside of a time range filter criterion, then the query system 214 can consult a timestamp associated with the event reference to determine whether the corresponding event satisfies the time range criterion. In some embodiments, to identify events that satisfy a time range, the query system 214 can review an array, such as the event reference array 2115 that identifies the time associated with the events. Furthermore, as mentioned above using the known location of the directory in which the relevant inverted indexes are located (or other partition identifier), the query system 214 can determine that any events identified using the relevant inverted indexes satisfy the index filter criterion.

In some cases, based on the filter criteria, the query system 214 reviews an extraction rule. In certain embodiments, if the filter criteria includes a field name that does not correspond to a field-value pair entry in an inverted index, the query system 214 can review an extraction rule, which may be located in a configuration file, to identify a field that corresponds to a field-value pair entry in the inverted index.

For example, the filter criteria includes a field name "sessionID" and the query system 214 determines that at least one relevant inverted index does not include a field-value pair entry corresponding to the field name sessionID, the query system 214 can review an extraction rule that identifies how the sessionID field is to be extracted from a particular host, source, or sourcetype (implicitly identifying the particular host, source, or sourcetype that includes a sessionID field). The query system 214 can replace the field name "sessionID" in the filter criteria with the identified host, source, or sourcetype. In some cases, the field name "sessionID" may be associated with multiples hosts, sources, or sourcetypes, in which case, all identified hosts, sources, and sourcetypes can be added as filter criteria. In some cases, the identified host, source, or sourcetype can replace or be appended to a filter criterion, or be excluded. For example, if the filter criteria includes a criterion for source S1 and the "sessionID" field is found in source S2, the source S2 can replace S1 in the filter criteria, be appended such that the filter criteria includes source S1 and source S2, or be excluded based on the presence of the filter criterion source S1. If the identified host, source, or sourcetype is included in the filter criteria, the query system 214 can then identify a field-value pair entry in the inverted index that includes a field value corresponding to the identity of the particular host, source, or sourcetype identified using the extraction rule.

Once the events that satisfy the filter criteria are identified, the query system 214 can categorize the results based on the categorization criteria. The categorization criteria can include categories for grouping the results, such as any combination of partition, source, sourcetype, or host, or other categories or fields as desired.

The query system 214 can use the categorization criteria to identify categorization criteria-value pairs or categorization criteria values by which to categorize or group the results. The categorization criteria-value pairs can correspond to one or more field-value pair entries stored in a relevant inverted index, one or more partition-value pairs based on a directory in which the inverted index is located or an entry in the inverted index (or other means by which an inverted index can be associated with a partition), or other criteria-value pair that identifies a general category and a particular value for that category. The categorization criteria values can correspond to the value portion of the categorization criteria-value pair.

As mentioned, in some cases, the categorization criteria-value pairs can correspond to one or more field-value pair entries stored in the relevant inverted indexes. For example, the categorization criteria-value pairs can correspond to field-value pair entries of host, source, and sourcetype (or other field-value pair entry as desired). For instance, if there are ten different hosts, four different sources, and five different sourcetypes for an inverted index, then the inverted index can include ten host field-value pair entries, four source field-value pair entries, and five sourcetype field-value pair entries. The query system 214 can use the nineteen distinct field-value pair entries as categorization criteria-value pairs to group the results.

Specifically, the query system 214 can identify the location of the event references associated with the events that satisfy the filter criteria within the field-value pairs, and group the event references based on their location. As such, the query system 214 can identify the particular field value associated with the event corresponding to the event reference. For example, if the categorization criteria include host and sourcetype, the host field-value pair entries and sourcetype field-value pair entries can be used as categorization criteria-value pairs to identify the specific host and sourcetype associated with the events that satisfy the filter criteria.

In addition, as mentioned, categorization criteria-value pairs can correspond to data other than the field-value pair entries in the relevant inverted indexes. For example, if partition or index is used as a categorization criterion, the inverted indexes may not include partition field-value pair entries. Rather, the query system 214 can identify the categorization criteria-value pair associated with the partition based on the directory in which an inverted index is located, information in the inverted index, or other information that associates the inverted index with the partition, etc. As such a variety of methods can be used to identify the categorization criteria-value pairs from the categorization criteria.

Accordingly, based on the categorization criteria (and categorization criteria-value pairs), the query system 214 can generate groupings based on the events that satisfy the filter criteria. As a non-limiting example, if the categorization criteria includes a partition and sourcetype, then the groupings can correspond to events that are associated with each unique combination of partition and sourcetype. For instance, if there are three different partitions and two different sourcetypes associated with the identified events, then the six different groups can be formed, each with a unique partition value-sourcetype value combination. Similarly, if the categorization criteria includes partition, sourcetype, and host and there are two different partitions, three sourcetypes, and five hosts associated with the identified events, then the query system 214 can generate up to thirty groups for the results that satisfy the filter criteria. Each group can be associated with a unique combination of categorization criteria-value pairs (e.g., unique combinations of partition value sourcetype value, and host value).

In addition, the query system 214 can count the number of events associated with each group based on the number of events that meet the unique combination of categorization criteria for a particular group (or match the categorization criteria-value pairs for the particular group). With continued reference to the example above, the query system 214 can count the number of events that meet the unique combination of partition, sourcetype, and host for a particular group.

The query system 214, such as the search head 504 can aggregate the groupings from the buckets, or search nodes 506, and provide the groupings for display. In some cases, the groups are displayed based on at least one of the host, source, sourcetype, or partition associated with the groupings. In some embodiments, the query system 214 can further display the groups based on display criteria, such as a display order or a sort order as described in greater detail above.

As a non-limiting example and with reference to FIG. 29B, consider a request received by the query system 214 that includes the following filter criteria: keyword=error, partition=main, time range=3/1/17 16:22.00.000-16:28.00.000, sourcetype=sourcetypeC, host=hostB, and the following categorization criteria: source.

Based on the above criteria, a search node 506 of the query system 214 that is associated with the data store 2901 identifies _main directory 2903 and can ignore test directory 2905 and any other partition-specific directories. The search node 506 determines that inverted index 2907B is a relevant index based on its location within the _main directory 2903 and the time range associated with it. For sake of simplicity in this example, the search node 506 determines that no other inverted indexes in the _main directory 2903, such as inverted index 2907A satisfy the time range criterion.

Having identified the relevant inverted index 2907B, the search node 506 reviews the token entries 2911 and the field-value pair entries 2913 to identify event references, or events, that satisfy all of the filter criteria.

With respect to the token entries 2911, the search node 506 can review the error token entry and identify event references 3, 5, 6, 8, 11, 12, indicating that the term "error" is found in the corresponding events. Similarly, the search node 506 can identify event references 4, 5, 6, 8, 9, 10, 11 in the field-value pair entry sourcetype::sourcetypeC and event references 2, 5, 6, 8, 10, 11 in the field-value pair entry host::hostB. As the filter criteria did not include a source or an IP_address field-value pair, the search node 506 can ignore those field-value pair entries.

In addition to identifying event references found in at least one token entry or field-value pair entry (e.g., event references 3, 4, 5, 6, 8, 9, 10, 11, 12), the search node 506 can identify events (and corresponding event references) that satisfy the time range criterion using the event reference array 2915 (e.g., event references 2, 3, 4, 5, 6, 7, 8, 9, 10). Using the information obtained from the inverted index 2907B (including the event reference array 2915), the search node 506 can identify the event references that satisfy all of the filter criteria (e.g., event references 5, 6, 8).

Having identified the events (and event references) that satisfy all of the filter criteria, the search node 506 can group the event references using the received categorization criteria (source). In doing so, the search node 506 can determine that event references 5 and 6 are located in the field-value pair entry source::sourceD (or have matching categorization criteria-value pairs) and event reference 8 is located in the field-value pair entry source::sourceC. Accordingly, the search node 506 can generate a sourceC group having a count of one corresponding to reference 8 and a sourceD group having a count of two corresponding to references 5 and 6. This information can be communicated to the search head 504. In turn the search head 504 can aggregate the results from the various search nodes 506 and display the groupings. As mentioned above, in some embodiments, the groupings can be displayed based at least in part on the categorization criteria, including at least one of host, source, sourcetype, or partition.

It will be understood that a change to any of the filter criteria or categorization criteria can result in different groupings. As a one non-limiting example, consider a request received by a search node 506 that includes the following filter criteria: partition=main, time range=3/1/17 3/1/17 16:21:20.000-16:28:17.000, and the following categorization criteria: host, source, sourcetype can result in the search node 506 identifying event references 1-12 as satisfying the filter criteria. The search node 506 can generate up to 24 groupings corresponding to the 24 different combinations of the categorization criteria-value pairs, including host (hostA, hostB), source (sourceA, sourceB, sourceC, sourceD), and sourcetype (sourcetypeA, sourcetypeB, sourcetypeC). However, as there are only twelve events identifiers in the illustrated embodiment and some fall into the same grouping, the search node 506 generates eight groups and counts as follows:

Group 1 (hostA, sourceA, sourcetypeA): 1 (event reference 7)
Group 2 (hostA, sourceA, sourcetypeB): 2 (event references 1, 12)
Group 3 (hostA, sourceA, sourcetypeC): 1 (event reference 4)
Group 4 (hostA, sourceB, sourcetypeA): 1 (event reference 3)
Group 5 (hostA, sourceB, sourcetypeC): 1 (event reference 9)
Group 6 (hostB, sourceC, sourcetypeA): 1 (event reference 2)
Group 7 (hostB, sourceC, sourcetypeC): 2 (event references 8, 11)
Group 8 (hostB, sourceD, sourcetypeC): 3 (event references 5, 6, 10)

As noted, each group has a unique combination of categorization criteria-value pairs or categorization criteria values. The search node 506 communicates the groups to the search head 504 for aggregation with results received from other search nodes 506. In communicating the groups to the search head 504, the search node 506 can include the categorization criteria-value pairs for each group and the count. In some embodiments, the search node 506 can include more or less information. For example, the search node 506 can include the event references associated with each group and other identifying information, such as the search node 506 or inverted index used to identify the groups.

As another non-limiting example, consider a request received by an search node 506 that includes the following filter criteria: partition=main, time range=3/1/17 3/1/17 16:21:20.000-16:28:17.000, source=sourceA, sourceD, and keyword=itemID and the following categorization criteria: host, source, sourcetype can result in the search node identifying event references 4, 7, and 10 as satisfying the filter criteria, and generate the following groups:

Group 1 (hostA, sourceA, sourcetypeC): 1 (event reference 4)
Group 2 (hostA, sourceA, sourcetypeA): 1 (event reference 7)
Group 3 (hostB, sourceD, sourcetypeC): 1 (event references 10)

The search node 506 communicates the groups to the search head 504 for aggregation with results received from other search node 506s. As will be understand there are myriad ways for filtering and categorizing the events and event references. For example, the search node 506 can review multiple inverted indexes associated with a partition or review the inverted indexes of multiple partitions, and categorize the data using any one or any combination of partition, host, source, sourcetype, or other category, as desired.

Further, if a user interacts with a particular group, the search node 506 can provide additional information regarding the group. For example, the search node 506 can perform a targeted search or sampling of the events that satisfy the filter criteria and the categorization criteria for the selected group, also referred to as the filter criteria corresponding to the group or filter criteria associated with the group.

In some cases, to provide the additional information, the search node 506 relies on the inverted index. For example, the search node 506 can identify the event references associated with the events that satisfy the filter criteria and the categorization criteria for the selected group and then use the event reference array 2915 to access some or all of the identified events. In some cases, the categorization criteria values or categorization criteria-value pairs associated with the group become part of the filter criteria for the review.

With reference to FIG. 29B for instance, suppose a group is displayed with a count of six corresponding to event references 4, 5, 6, 8, 10, 11 (i.e., event references 4, 5, 6, 8, 10, 11 satisfy the filter criteria and are associated with matching categorization criteria values or categorization criteria-value pairs) and a user interacts with the group (e.g., selecting the group, clicking on the group, etc.). In response, the search head 504 communicates with the search node 506 to provide additional information regarding the group.

In some embodiments, the search node 506 identifies the event references associated with the group using the filter criteria and the categorization criteria for the group (e.g., categorization criteria values or categorization criteria-value pairs unique to the group). Together, the filter criteria and the categorization criteria for the group can be referred to as the filter criteria associated with the group. Using the filter criteria associated with the group, the search node 506 identifies event references 4, 5, 6, 8, 10, 11.

Based on a sampling criteria, discussed in greater detail above, the search node 506 can determine that it will analyze a sample of the events associated with the event references 4, 5, 6, 8, 10, 11. For example, the sample can include analyzing event data associated with the event references 5, 8, 10. In some embodiments, the search node 506 can use the event reference array 2915 to access the event data associated with the event references 5, 8, 10. Once accessed, the search node 506 can compile the relevant information and provide it to the search head 504 for aggregation with results from other search nodes. By identifying events and sampling event data using the inverted indexes, the search node can reduce the amount of actual data this is analyzed and the number of events that are accessed in order to generate the summary of the group and provide a response in less time.

4.6. Query Processing Flow

Figure 30A:
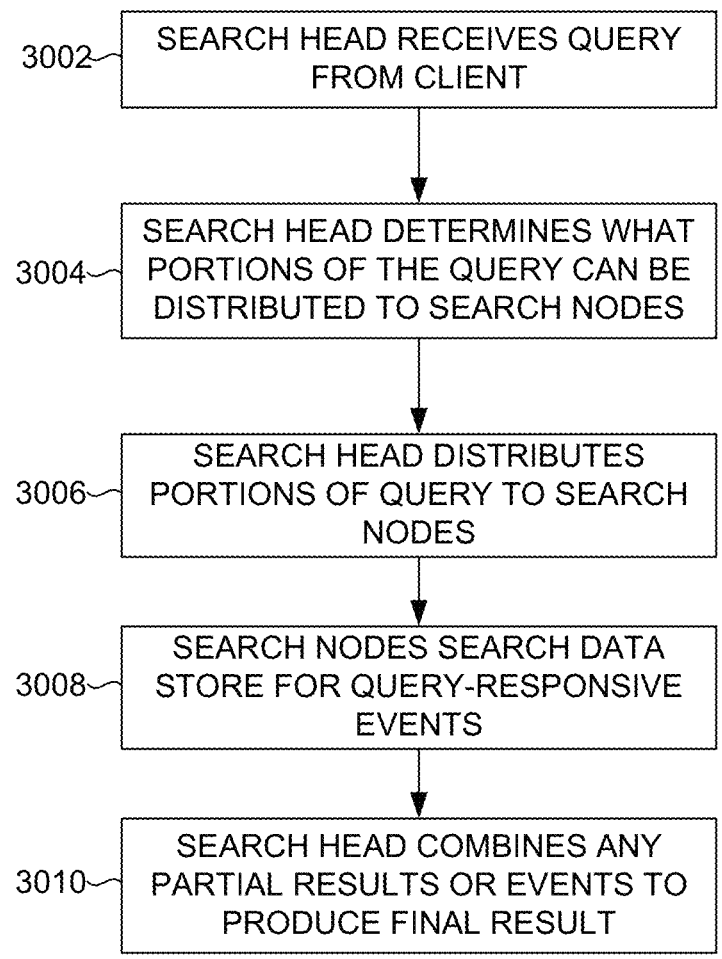
FIG. 30A is a flow diagram of an example method that illustrates how a search head and indexers perform a search query, in accordance with example embodiments.

FIG. 30A is a flow diagram illustrating an embodiment of a routine implemented by the query system 214 for executing a query. At block 3002, a search head 504 receives a search query. At block 3004, the search head 504 analyzes the search query to determine what portion(s) of the query to delegate to search nodes 506 and what portions of the query to execute locally by the search head 504. At block 3006, the search head distributes the determined portions of the query to the appropriate search nodes 506. In some embodiments, a search head cluster may take the place of an independent search head 504 where each search head 504 in the search head cluster coordinates with peer search heads 504 in the search head cluster to schedule jobs, replicate search results, update configurations, fulfill search requests, etc. In some embodiments, the search head 504 (or each search head) consults with a search node catalog 510 that provides the search head with a list of search nodes 506 to which the search head can distribute the determined portions of the query. A search head 504 may communicate with the search node catalog 510 to discover the addresses of active search nodes 506.

At block 3008, the search nodes 506 to which the query was distributed, search data stores associated with them for events that are responsive to the query. To determine which events are responsive to the query, the search node 506 searches for events that match the criteria specified in the query. These criteria can include matching keywords or specific values for certain fields. The searching operations at block 3008 may use the late-binding schema to extract values for specified fields from events at the time the query is processed. In some embodiments, one or more rules for extracting field values may be specified as part of a source type definition in a configuration file. The search nodes 506 may then either send the relevant events back to the search head 504, or use the events to determine a partial result, and send the partial result back to the search head 504.

At block 3010, the search head 504 combines the partial results and/or events received from the search nodes 506 to produce a final result for the query. In some examples, the results of the query are indicative of performance or security of the IT environment and may help improve the performance of components in the IT environment. This final result may comprise different types of data depending on what the query requested. For example, the results can include a listing of matching events returned by the query, or some type of visualization of the data from the returned events. In another example, the final result can include one or more calculated values derived from the matching events.

The results generated by the system 108 can be returned to a client using different techniques. For example, one technique streams results or relevant events back to a client in real-time as they are identified. Another technique waits to report the results to the client until a complete set of results (which may include a set of relevant events or a result based on relevant events) is ready to return to the client. Yet another technique streams interim results or relevant events back to the client in real-time until a complete set of results is ready, and then returns the complete set of results to the client. In another technique, certain results are stored as "search jobs" and the client may retrieve the results by referring the search jobs.

The search head 504 can also perform various operations to make the search more efficient. For example, before the search head 504 begins execution of a query, the search head 504 can determine a time range for the query and a set of common keywords that all matching events include. The search head 504 may then use these parameters to query the search nodes 506 to obtain a superset of the eventual results. Then, during a filtering stage, the search head 504 can perform field-extraction operations on the superset to produce a reduced set of search results. This speeds up queries, which may be particularly helpful for queries that are performed on a periodic basis.

4.7. Pipelined Search Language

Various embodiments of the present disclosure can be implemented using, or in conjunction with, a pipelined command language. A pipelined command language is a language in which a set of inputs or data is operated on by a first command in a sequence of commands, and then subsequent commands in the order they are arranged in the sequence. Such commands can include any type of functionality for operating on data, such as retrieving, searching, filtering, aggregating, processing, transmitting, and the like. As described herein, a query can thus be formulated in a pipelined command language and include any number of ordered or unordered commands for operating on data.

Splunk Processing Language (SPL) is an example of a pipelined command language in which a set of inputs or data is operated on by any number of commands in a particular sequence. A sequence of commands, or command sequence, can be formulated such that the order in which the commands are arranged defines the order in which the commands are applied to a set of data or the results of an earlier executed command. For example, a first command in a command sequence can operate to search or filter for specific data in particular set of data. The results of the first command can then be passed to another command listed later in the command sequence for further processing.

In various embodiments, a query can be formulated as a command sequence defined in a command line of a search UI. In some embodiments, a query can be formulated as a sequence of SPL commands. Some or all of the SPL commands in the sequence of SPL commands can be separated from one another by a pipe symbol "|". In such embodiments, a set of data, such as a set of events, can be operated on by a first SPL command in the sequence, and then a subsequent SPL command following a pipe symbol "|" after the first SPL command operates on the results produced by the first SPL command or other set of data, and so on for any additional SPL commands in the sequence. As such, a query formulated using SPL comprises a series of consecutive commands that are delimited by pipe "|" characters. The pipe character indicates to the system that the output or result of one command (to the left of the pipe) should be used as the input for one of the subsequent commands (to the right of the pipe). This enables formulation of queries defined by a pipeline of sequenced commands that refines or enhances the data at each step along the pipeline until the desired results are attained. Accordingly, various embodiments described herein can be implemented with Splunk Processing Language (SPL) used in conjunction with the SPLUNK® ENTERPRISE system.

While a query can be formulated in many ways, a query can start with a search command and one or more corresponding search terms at the beginning of the pipeline. Such search terms can include any combination of keywords, phrases, times, dates, Boolean expressions, fieldname-field value pairs, etc. that specify which results should be obtained from an index. The results can then be passed as inputs into subsequent commands in a sequence of commands by using, for example, a pipe character. The subsequent commands in a sequence can include directives for additional processing of the results once it has been obtained from one or more indexes. For example, commands may be used to filter unwanted information out of the results, extract more information, evaluate field values, calculate statistics, reorder the results, create an alert, create summary of the results, or perform some type of aggregation function. In some embodiments, the summary can include a graph, chart, metric, or other visualization of the data. An aggregation function can include analysis or calculations to return an aggregate value, such as an average value, a sum, a maximum value, a root mean square, statistical values, and the like.

Due to its flexible nature, use of a pipelined command language in various embodiments is advantageous because it can perform "filtering" as well as "processing" functions. In other words, a single query can include a search command and search term expressions, as well as data-analysis expressions. For example, a command at the beginning of a query can perform a "filtering" step by retrieving a set of data based on a condition (e.g., records associated with server response times of less than 1 microsecond). The results of the filtering step can then be passed to a subsequent command in the pipeline that performs a "processing" step (e.g. calculation of an aggregate value related to the filtered events such as the average response time of servers with response times of less than 1 microsecond). Furthermore, the search command can allow events to be filtered by keyword as well as field value criteria. For example, a search command can filter out all events containing the word "warning" or filter out all events where a field value associated with a field "clientip" is "10.0.1.2."

The results obtained or generated in response to a command in a query can be considered a set of results data. The set of results data can be passed from one command to another in any data format. In one embodiment, the set of result data can be in the form of a dynamically created table. Each command in a particular query can redefine the shape of the table. In some implementations, an event retrieved from an index in response to a query can be considered a row with a column for each field value. Columns contain basic information about the data and also may contain data that has been dynamically extracted at search time.

Figure 30B:
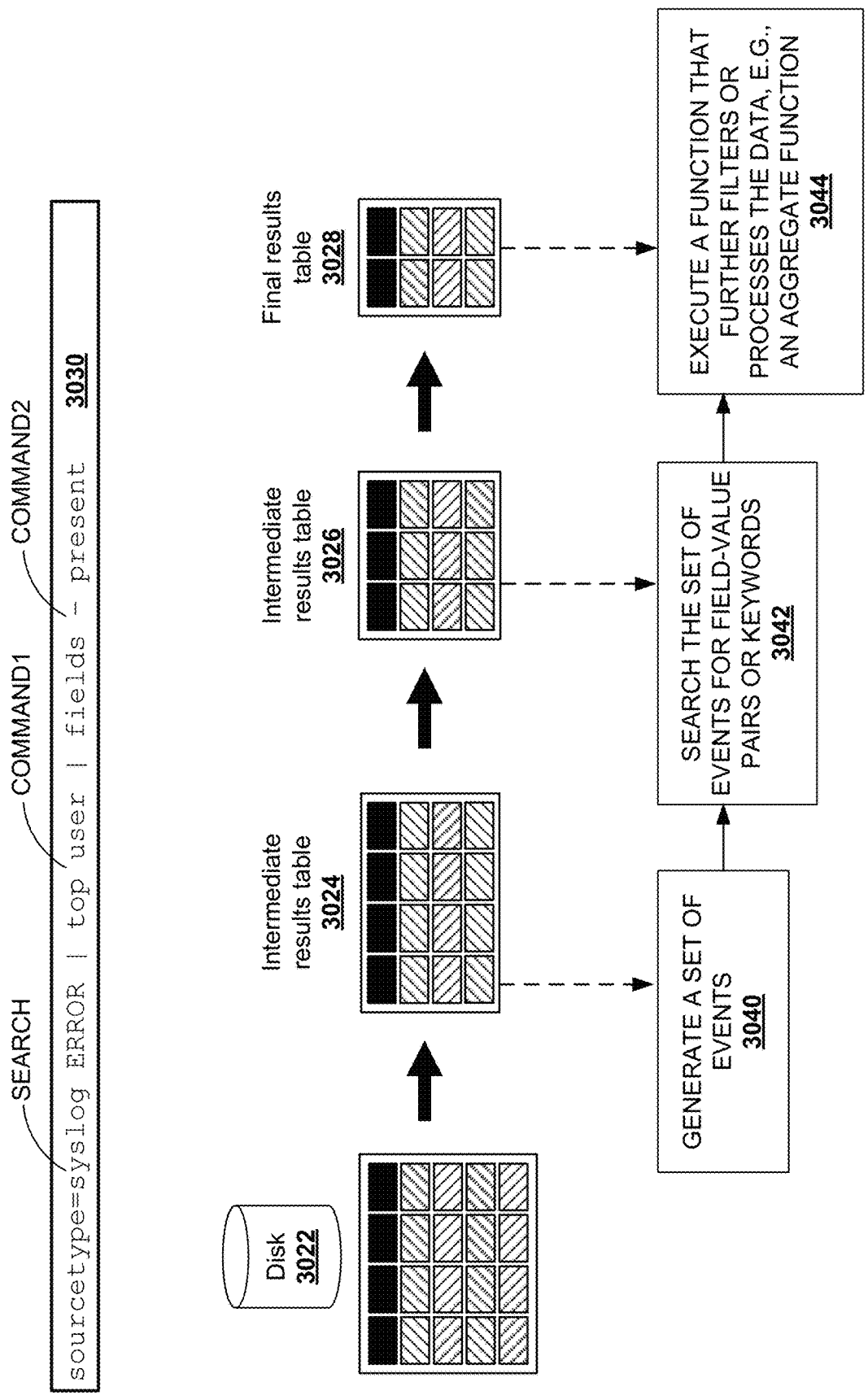
FIG. 30B provides a visual representation of an example manner in which a pipelined command language or query operates, in accordance with example embodiments.

FIG. 30B provides a visual representation of the manner in which a pipelined command language or query operates in accordance with the disclosed embodiments. The query 3030 can be inputted by the user into a search. The query comprises a search, the results of which are piped to two commands (namely, command 1 and command 2) that follow the search step.

Disk 3022 represents the event data in the raw record data store.

When a user query is processed, a search step will precede other queries in the pipeline in order to generate a set of events at block 3040. For example, the query can comprise search terms "sourcetype=syslog ERROR" at the front of the pipeline as shown in FIG. 30B. Intermediate results table 3024 shows fewer rows because it represents the subset of events retrieved from the index that matched the search terms "sourcetype=syslog ERROR" from search command 3030. By way of further example, instead of a search step, the set of events at the head of the pipeline may be generating by a call to a pre-existing inverted index (as will be explained later).

At block 3042, the set of events generated in the first part of the query may be piped to a query that searches the set of events for field-value pairs or for keywords. For example, the second intermediate results table 3026 shows fewer columns, representing the result of the top command, "top user" which summarizes the events into a list of the top 10 users and displays the user, count, and percentage.

Finally, at block 3044, the results of the prior stage can be pipelined to another stage where further filtering or processing of the data can be performed, e.g., preparing the data for display purposes, filtering the data based on a condition, performing a mathematical calculation with the data, etc. As shown in FIG. 30B, the "fields—percent" part of command 3030 removes the column that shows the percentage, thereby, leaving a final results table 3028 without a percentage column. In different embodiments, other query languages, such as the Structured Query Language ("SQL"), can be used to create a query.

4.8. Field Extraction

The query system 214 allows users to search and visualize events generated from machine data received from homogenous data sources. The query system 214 also allows users to search and visualize events generated from machine data received from heterogeneous data sources. The query system 214 includes various components for processing a query, such as, but not limited to a query system manager 502, one or more search heads 504 having one or more search masters 512 and search managers 514, and one or more search nodes 506. A query language may be used to create a query, such as any suitable pipelined query language. For example, Splunk Processing Language (SPL) can be utilized to make a query. SPL is a pipelined search language in which a set of inputs is operated on by a first command in a command line, and then a subsequent command following the pipe symbol "|" operates on the results produced by the first command, and so on for additional commands. Other query languages, such as the Structured Query Language ("SQL"), can be used to create a query.

In response to receiving the search query, a search head 504 (e.g., a search master 512 or search manager 514) can use extraction rules to extract values for fields in the events being searched. The search head 504 can obtain extraction rules that specify how to extract a value for fields from an event. Extraction rules can comprise regex rules that specify how to extract values for the fields corresponding to the extraction rules. In addition to specifying how to extract field values, the extraction rules may also include instructions for deriving a field value by performing a function on a character string or value retrieved by the extraction rule. For example, an extraction rule may truncate a character string or convert the character string into a different data format. In some cases, the query itself can specify one or more extraction rules.

The search head 504 can apply the extraction rules to events that it receives from search nodes 506. The search nodes 506 may apply the extraction rules to events in an associated data store or common storage 216. Extraction rules can be applied to all the events in a data store or common storage 216 or to a subset of the events that have been filtered based on some criteria (e.g., event time stamp values, etc.). Extraction rules can be used to extract one or more values for a field from events by parsing the portions of machine data in the events and examining the data for one or more patterns of characters, numbers, delimiters, etc., that indicate where the field begins and, optionally, ends.

Figure 31A:
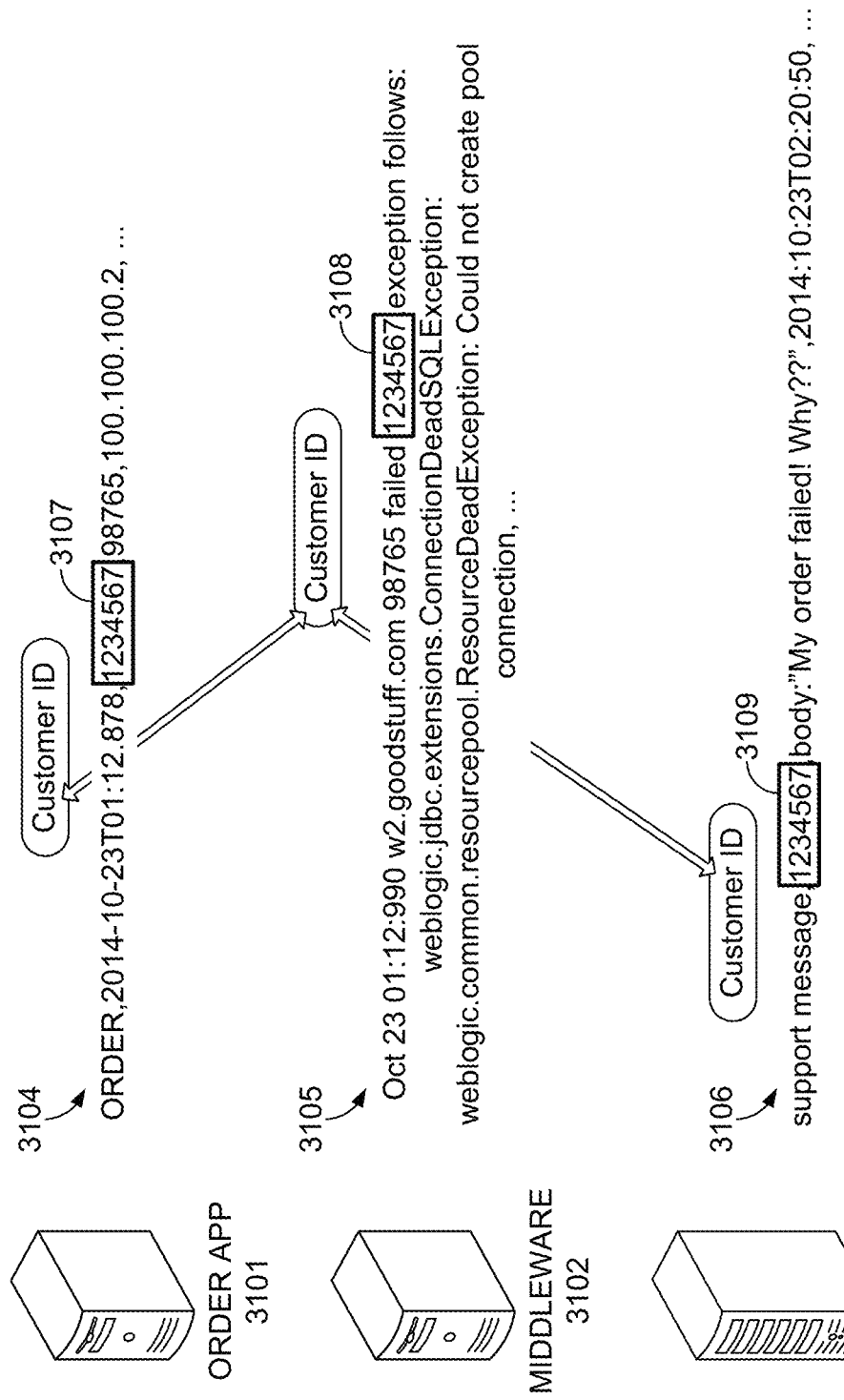
FIG. 31A is a diagram of an example scenario where a common customer identifier is found among log data received from three disparate data sources, in accordance with example embodiments.

FIG. 31A is a diagram of an example scenario where a common customer identifier is found among log data received from three disparate data sources, in accordance with example embodiments. In this example, a user submits an order for merchandise using a vendor's shopping application program 3101 running on the user's system. In this example, the order was not delivered to the vendor's server due to a resource exception at the destination server that is detected by the middleware code 3102. The user then sends a message to the customer support server 3103 to complain about the order failing to complete. The three systems 3101, 3102, and 3103 are disparate systems that do not have a common logging format. The order application 3101 sends log data 3104 to the data intake and query system 108 in one format, the middleware code 3102 sends error log data 3105 in a second format, and the support server 3103 sends log data 3106 in a third format.

Using the log data received at the data intake and query system 108 from the three systems, the vendor can uniquely obtain an insight into user activity, user experience, and system behavior. The query system 214 allows the vendor's administrator to search the log data from the three systems, thereby obtaining correlated information, such as the order number and corresponding customer ID number of the person placing the order. The system also allows the administrator to see a visualization of related events via a user interface. The administrator can query the query system 214 for customer ID field value matches across the log data from the three systems that are stored in common storage 216. The customer ID field value exists in the data gathered from the three systems, but the customer ID field value may be located in different areas of the data given differences in the architecture of the systems. There is a semantic relationship between the customer ID field values generated by the three systems. The query system 214 requests events from the one or more data stores 218 to gather relevant events from the three systems. The search head 504 then applies extraction rules to the events in order to extract field values that it can correlate. The search head 504 may apply a different extraction rule to each set of events from each system when the event format differs among systems. In this example, the user interface can display to the administrator the events corresponding to the common customer ID field values 3107, 3108, and 3109, thereby providing the administrator with insight into a customer's experience.

Note that query results can be returned to a client, a search head 504, or any other system component for further processing. In general, query results may include a set of one or more events, a set of one or more values obtained from the events, a subset of the values, statistics calculated based on the values, a report containing the values, a visualization (e.g., a graph or chart) generated from the values, and the like.

Figure 31B:
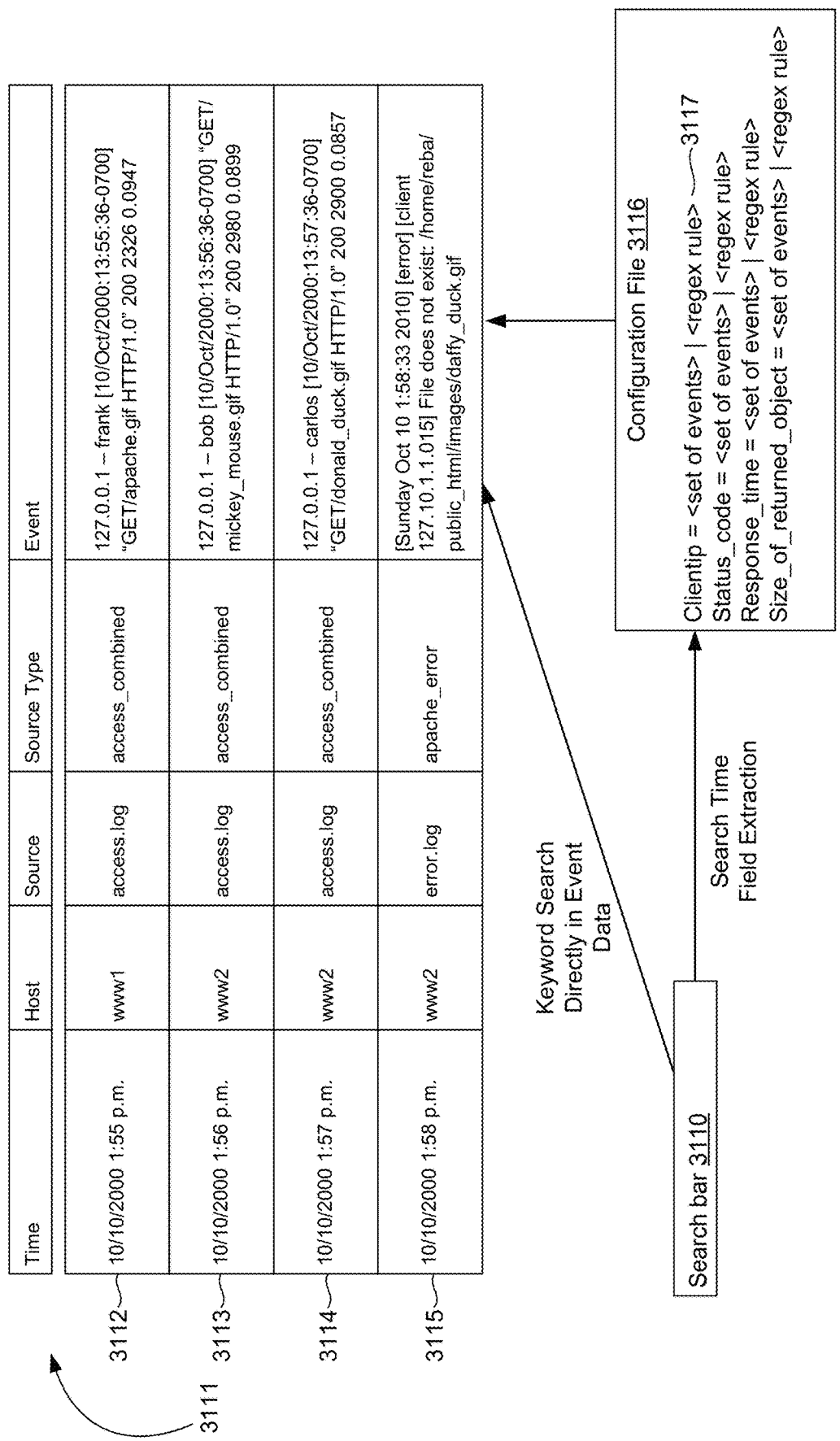
FIG. 31B illustrates an example of processing keyword searches and field searches, in accordance with disclosed embodiments.
Figure 31C:
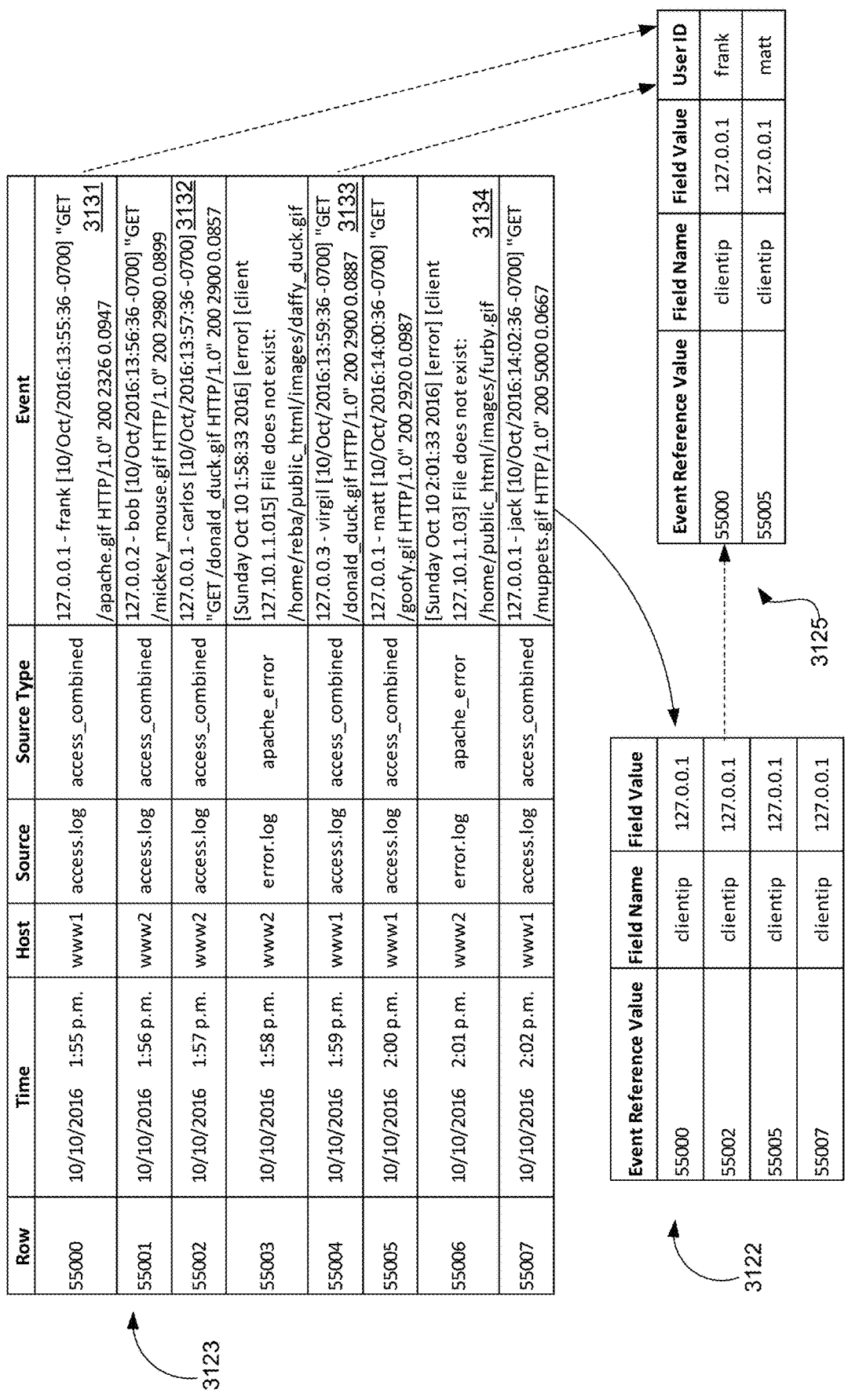
FIG. 31C illustrates an example of creating and using an inverted index, in accordance with example embodiments.
Figure 31D:
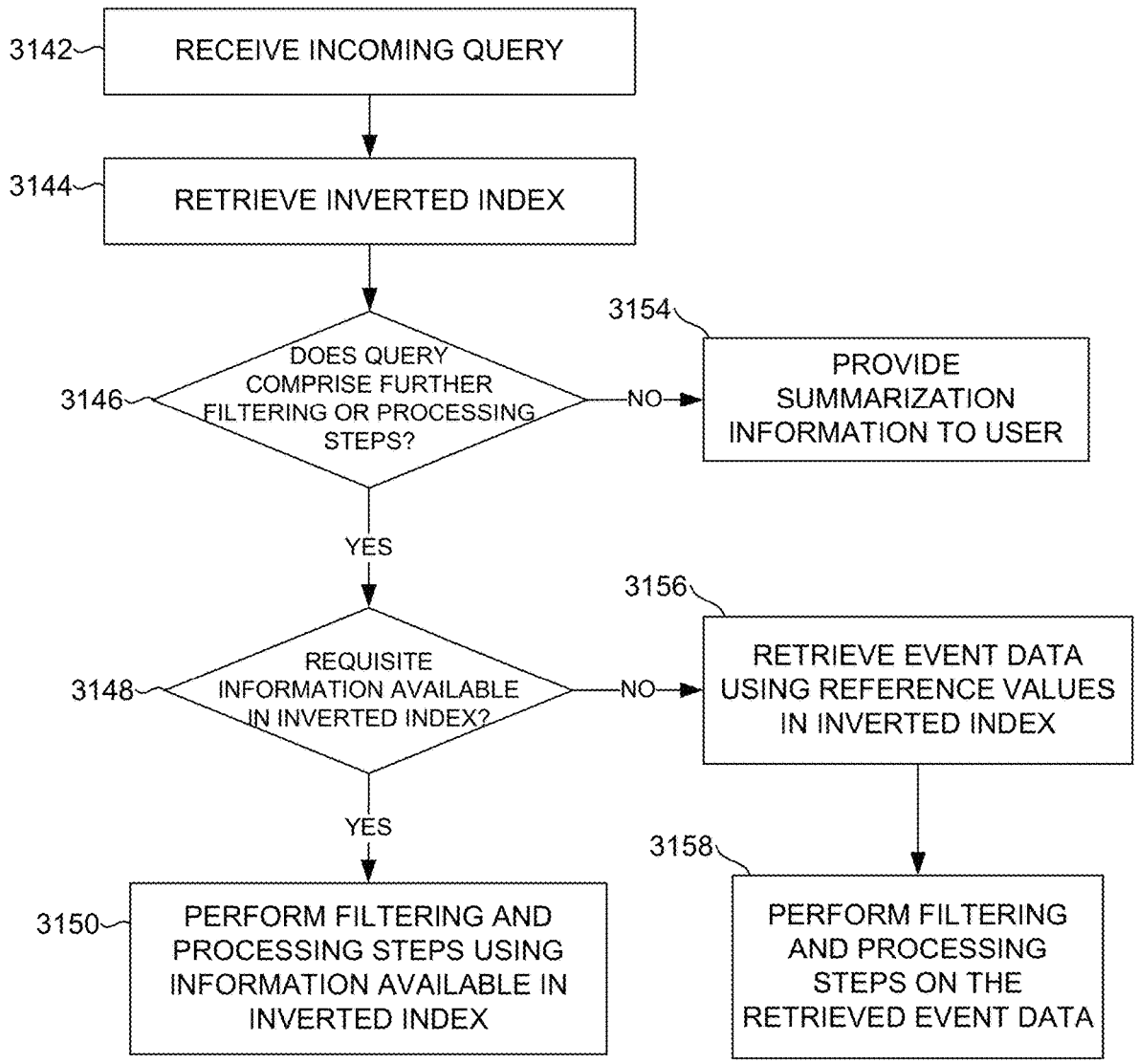
FIG. 31D depicts a flowchart of example use of an inverted index in a pipelined search query, in accordance with example embodiments.

The query system 214 enables users to run queries against the stored data to retrieve events that meet criteria specified in a query, such as containing certain keywords or having specific values in defined fields. FIG. 31B illustrates the manner in which keyword searches and field searches are processed in accordance with disclosed embodiments.

If a user inputs a search query into search bar 3110 that includes only keywords (also known as "tokens"), e.g., the keyword "error" or "warning", the query system 214 of the data intake and query system 108 can search for those keywords directly in the event data 3111 stored in the raw record data store. Note that while FIG. 31B only illustrates four events 3112, 3113, 3114, 3115, the raw record data store (corresponding to data store 218 in FIG. 2) may contain records for millions of events.

As disclosed above, the indexing system 212 can optionally generate a keyword index to facilitate fast keyword searching for event data. The indexing system 212 can include the identified keywords in an index, which associates each stored keyword with reference pointers to events containing that keyword (or to locations within events where that keyword is located, other location identifiers, etc.). When the query system 214 subsequently receives a keyword-based query, the query system 214 can access the keyword index to quickly identify events containing the keyword. For example, if the keyword "HTTP" was indexed by the indexing system 212 at index time, and the user searches for the keyword "HTTP", the events 3112, 3113, and 3114, will be identified based on the results returned from the keyword index. As noted above, the index contains reference pointers to the events containing the keyword, which allows for efficient retrieval of the relevant events from the raw record data store.

If a user searches for a keyword that has not been indexed by the indexing system 212, the data intake and query system 108 may nevertheless be able to retrieve the events by searching the event data for the keyword in the raw record data store directly as shown in FIG. 31B. For example, if a user searches for the keyword "frank", and the name "frank" has not been indexed at search time, the query system 214 can search the event data directly and return the first event 3112. Note that whether the keyword has been indexed at index time or search time or not, in both cases the raw data with the events 3111 is accessed from the raw data record store to service the keyword search. In the case where the keyword has been indexed, the index will contain a reference pointer that will allow for a more efficient retrieval of the event data from the data store. If the keyword has not been indexed, the query system 214 can search through the records in the data store to service the search.

In most cases, however, in addition to keywords, a user's search will also include fields. The term "field" refers to a location in the event data containing one or more values for a specific data item. Often, a field is a value with a fixed, delimited position on a line, or a name and value pair, where there is a single value to each field name. A field can also be multivalued, that is, it can appear more than once in an event and have a different value for each appearance, e.g., email address fields. Fields are searchable by the field name or field name-value pairs. Some examples of fields are "clientip" for IP addresses accessing a web server, or the "From" and "To" fields in email addresses.

By way of further example, consider the search, "status=404". This search query finds events with "status" fields that have a value of "404." When the search is run, the query system 214 does not look for events with any other "status" value. It also does not look for events containing other fields that share "404" as a value. As a result, the search returns a set of results that are more focused than if "404" had been used in the search string as part of a keyword search. Note also that fields can appear in events as "key=value" pairs such as "user name=Bob." But in most cases, field values appear in fixed, delimited positions without identifying keys. For example, the data store may contain events where the "user name" value always appears by itself after the timestamp as illustrated by the following string: "Nov 15 09:33:22 johnmedlock."

The data intake and query system 108 advantageously allows for search time field extraction. In other words, fields can be extracted from the event data at search time using late-binding schema as opposed to at data ingestion time, which was a major limitation of the prior art systems.

In response to receiving the search query, a search head 504 of the query system 214 can use extraction rules to extract values for the fields associated with a field or fields in the event data being searched. The search head 504 can obtain extraction rules that specify how to extract a value for certain fields from an event. Extraction rules can comprise regex rules that specify how to extract values for the relevant fields. In addition to specifying how to extract field values, the extraction rules may also include instructions for deriving a field value by performing a function on a character string or value retrieved by the extraction rule. For example, a transformation rule may truncate a character string, or convert the character string into a different data format. In some cases, the query itself can specify one or more extraction rules.

FIG. 31B illustrates the manner in which configuration files may be used to configure custom fields at search time in accordance with the disclosed embodiments. In response to receiving a search query, the data intake and query system 108 determines if the query references a "field." For example, a query may request a list of events where the "clientip" field equals "127.0.0.1." If the query itself does not specify an extraction rule and if the field is not a metadata field, e.g., time, host, source, source type, etc., then in order to determine an extraction rule, the query system 214 may, in one or more embodiments, need to locate configuration file 3116 during the execution of the search as shown in FIG. 31B.

Configuration file 3116 may contain extraction rules for all the various fields that are not metadata fields, e.g., the "clientip" field. The extraction rules may be inserted into the configuration file in a variety of ways. In some embodiments, the extraction rules can comprise regular expression rules that are manually entered in by the user. Regular expressions match patterns of characters in text and are used for extracting custom fields in text.

In one or more embodiments, as noted above, a field extractor may be configured to automatically generate extraction rules for certain field values in the events when the events are being created, indexed, or stored, or possibly at a later time. In one embodiment, a user may be able to dynamically create custom fields by highlighting portions of a sample event that should be extracted as fields using a graphical user interface. The system can then generate a regular expression that extracts those fields from similar events and store the regular expression as an extraction rule for the associated field in the configuration file 3116.

In some embodiments, the indexing system 212 can automatically discover certain custom fields at index time and the regular expressions for those fields will be automatically generated at index time and stored as part of extraction rules in configuration file 3116. For example, fields that appear in the event data as "key=value" pairs may be automatically extracted as part of an automatic field discovery process. Note that there may be several other ways of adding field definitions to configuration files in addition to the methods discussed herein.

The search head 504 can apply the extraction rules derived from configuration file 3116 to event data that it receives from search nodes 506. The search nodes 506 may apply the extraction rules from the configuration file to events in an associated data store or common storage 216. Extraction rules can be applied to all the events in a data store, or to a subset of the events that have been filtered based on some criteria (e.g., event time stamp values, etc.). Extraction rules can be used to extract one or more values for a field from events by parsing the event data and examining the event data for one or more patterns of characters, numbers, delimiters, etc., that indicate where the field begins and, optionally, ends.

In one more embodiments, the extraction rule in configuration file 3116 will also need to define the type or set of events that the rule applies to. Because the raw record data store will contain events from multiple heterogeneous sources, multiple events may contain the same fields in different locations because of discrepancies in the format of the data generated by the various sources. Furthermore, certain events may not contain a particular field at all. For example, event 3115 also contains "clientip" field, however, the "clientip" field is in a different format from events 3112, 3113, and 3114. To address the discrepancies in the format and content of the different types of events, the configuration file will also need to specify the set of events that an extraction rule applies to, e.g., extraction rule 3117 specifies a rule for filtering by the type of event and contains a regular expression for parsing out the field value. Accordingly, each extraction rule can pertain to only a particular type of event. If a particular field, e.g., "clientip" occurs in multiple types of events, each of those types of events can have its own corresponding extraction rule in the configuration file 3116 and each of the extraction rules would comprise a different regular expression to parse out the associated field value. The most common way to categorize events is by source type because events generated by a particular source can have the same format.

The field extraction rules stored in configuration file 3116 perform search-time field extractions. For example, for a query that requests a list of events with source type "access_combined" where the "clientip" field equals "127.0.0.1," the query system 214 can first locate the configuration file 3116 to retrieve extraction rule 3117 that allows it to extract values associated with the "clientip" field from the event data 3120 "where the source type is "access_combined. After the "clientip" field has been extracted from all the events comprising the "clientip" field where the source type is "access_combined," the query system 214 can then execute the field criteria by performing the compare operation to filter out the events where the "clientip" field equals "127.0.0.1." In the example shown in FIG. 31B, the events 3112, 3113, and 3114 would be returned in response to the user query. In this manner, the query system 214 can service queries containing field criteria in addition to queries containing keyword criteria (as explained above).

In some embodiments, the configuration file 3116 can be created during indexing. It may either be manually created by the user or automatically generated with certain predetermined field extraction rules. As discussed above, the events may be distributed across several data stores in common storage 216, wherein various indexing nodes 404 may be responsible for storing the events in the common storage 216 and various search nodes 506 may be responsible for searching the events contained in common storage 216.

The ability to add schema to the configuration file at search time results in increased efficiency. A user can create new fields at search time and simply add field definitions to the configuration file. As a user learns more about the data in the events, the user can continue to refine the late-binding schema by adding new fields, deleting fields, or modifying the field extraction rules in the configuration file for use the next time the schema is used by the system. Because the data intake and query system 108 maintains the underlying raw data and uses late-binding schema for searching the raw data, it enables a user to continue investigating and learn valuable insights about the raw data long after data ingestion time.

The ability to add multiple field definitions to the configuration file at search time also results in increased flexibility. For example, multiple field definitions can be added to the configuration file to capture the same field across events generated by different source types. This allows the data intake and query system 108 to search and correlate data across heterogeneous sources flexibly and efficiently.

Further, by providing the field definitions for the queried fields at search time, the configuration file 3116 allows the record data store to be field searchable. In other words, the raw record data store can be searched using keywords as well as fields, wherein the fields are searchable name/value pairings that distinguish one event from another and can be defined in configuration file 3116 using extraction rules. In comparison to a search containing field names, a keyword search does not need the configuration file and can search the event data directly as shown in FIG. 31B.

It should also be noted that any events filtered out by performing a search-time field extraction using a configuration file 3116 can be further processed by directing the results of the filtering step to a processing step using a pipelined search language. Using the prior example, a user can pipeline the results of the compare step to an aggregate function by asking the query system 214 to count the number of events where the "clientip" field equals "127.0.0.1."

The foregoing paragraphs describe an example data intake and query system 108 operating in a containerized, cloud-based environment, according to various embodiments. The following description also may be implemented on other data intake and query systems, including a data intake and query system that includes one or more forwarders that receive data from a variety of input data sources, one or more indexers that process and store the data in one or more data stores, and directed by a search head, as described in U.S. patent application Ser. No. 16/146,933, titled "GENERATING JOURNEY FLOW VISUALIZATION WITH NODE PLACEMENT BASED ON SHORTEST DISTANCE TO JOURNEY START," filed on Sep. 28, 2018, the entirety of which is incorporated herein by reference.

5.0. Medication Security and Healthcare Privacy Analytics Applications

As indicated herein, analyzing and searching large amounts of machine data presents a number of challenges that can be addressed using an event-based data intake and query system, such as the SPLUNK® ENTERPRISE system. In addition to facilitating the collection and indexing of any type of machine data, a data intake and query system further enables users to search for and process data stored by such systems in a variety of ways. One source of such data is the wide variety of systems and applications used by various healthcare providers and other healthcare-related entities. Users within the healthcare industry may often desire the ability to analyze healthcare-related data generated by such systems and applications to support initiatives such as protecting patient records, optimizing existing systems to improve patient care, complying with regulatory requirements, among numerous other challenges within the healthcare industry.

As an example, one such challenge relates to monitoring user interactions with medication dispensing systems. Medication dispensing systems, for example, are used in many hospitals and other healthcare environments to help manage processes related to dispensing medications to patients. In some cases, such medication dispensing systems may generate electronic logs or other data reflecting various types of user interactions (e.g., healthcare provider interactions) with the medication dispensing systems over time (e.g., where the log data may record instances of users accessing certain types of drugs, as well as instances of other types of user interactions such as logging in, opening bins, returning drugs to a bin, forced entries into bins, etc.). The data generated by such systems, particularly in large hospitals and other similar environments, can be voluminous. As such, deriving meaningful insights from the generated data, and detecting interesting patterns in the data across time, can be challenging. Furthermore, the ability to correlate such data with data generated by other systems and applications, such as employee records databases, patient care databases, and often many other types of systems, presents additional challenges.

Many of these challenges can be addressed by a data intake and query system, as described herein. In one embodiment, a data intake and query system obtains user behavior data generated by a medication dispensing system. The user behavior data, for example, may include first data indicating instances of a user checking out a drug from a medication dispensing system and second data indicating instances of a user interacting with the medication dispensing system. The data intake and query system generates a first plurality of timestamped events based on the first data and a second plurality of timestamped events based on the second data. In some embodiments, the data intake and query system further obtains data from other sources, including additional medication dispensing systems, an employee records database, an employee attendance records database (e.g., KRONOS®), patient care databases (e.g., Allscripts®, EPIC®, Cerner® CompuRecords, Provation®, etc.), where the data intake and query system can identify correlations among such data to generate various dashboards and other interfaces as described herein. In some embodiments, prior to correlating the data from multiple sources, the data intake and query system normalizes the data from the multiple sources using a healthcare common information model. Although many of the examples described herein relate to deriving insights involving data obtained from a medication dispensing systems, the described techniques can be applied broadly to various types of data obtained from the wide range of healthcare-related applications and systems.

In some embodiments, medication security and healthcare privacy analytics systems are implemented as an application or "app" component of a data intake and query system 108. As indicated above, for example, a data intake and query system 108 provides various schemas, dashboards, and visualizations that simplify developers' tasks to create applications with additional capabilities. In some embodiments, a medication security analytics app and a healthcare privacy analytics app each interface with the data intake and query system 108 via one or more APIs. The APIs, for example, can include methods that enable the medication security analytics and healthcare privacy analytics apps to search for event data stored by the data intake and query system 108, to access user information, to store data related to saved search queries, search results, interface customizations, and so forth. In other embodiments, the medication security analytics and healthcare privacy analytics apps can be implemented as a standalone application, or as separate standalone applications, that enables users to search and analyze virtually any types of healthcare-related datasets (including, for example, event data, data stored in databases, raw machine data, and so forth). In one embodiment, the medication security analytics and healthcare privacy analytics apps are comprised of one or more software modules executed by one or more electronic devices, and users using one or more electronic device(s) can interact with the medication security analytics and healthcare privacy analytics apps via one or more networks, such as the internet.

Figure 32:
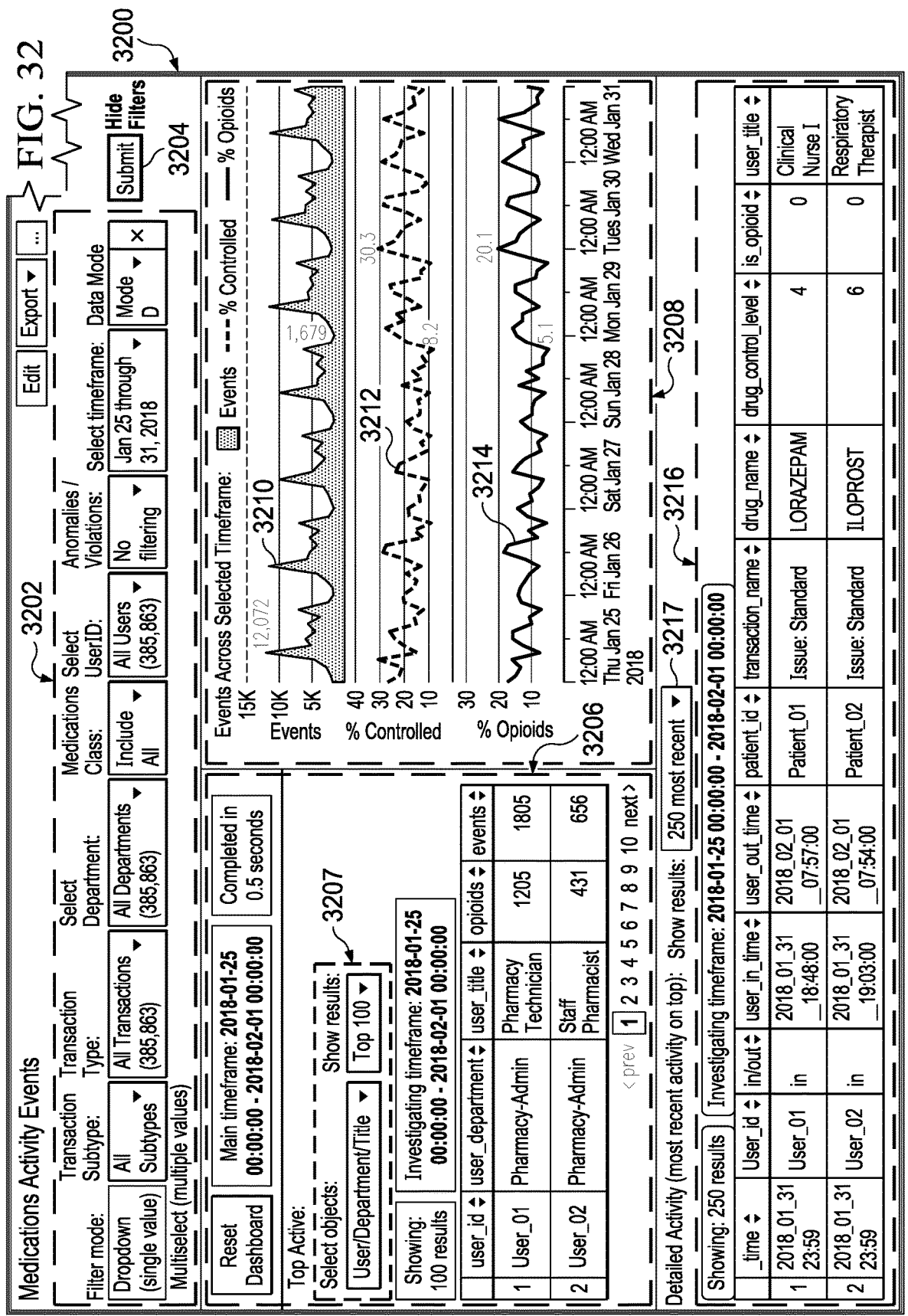
FIG. 32 illustrates an example graphical user interface of a medication security analytics application displaying interactions with a medication dispensing system in accordance with the disclosed embodiments.
Figure 33:
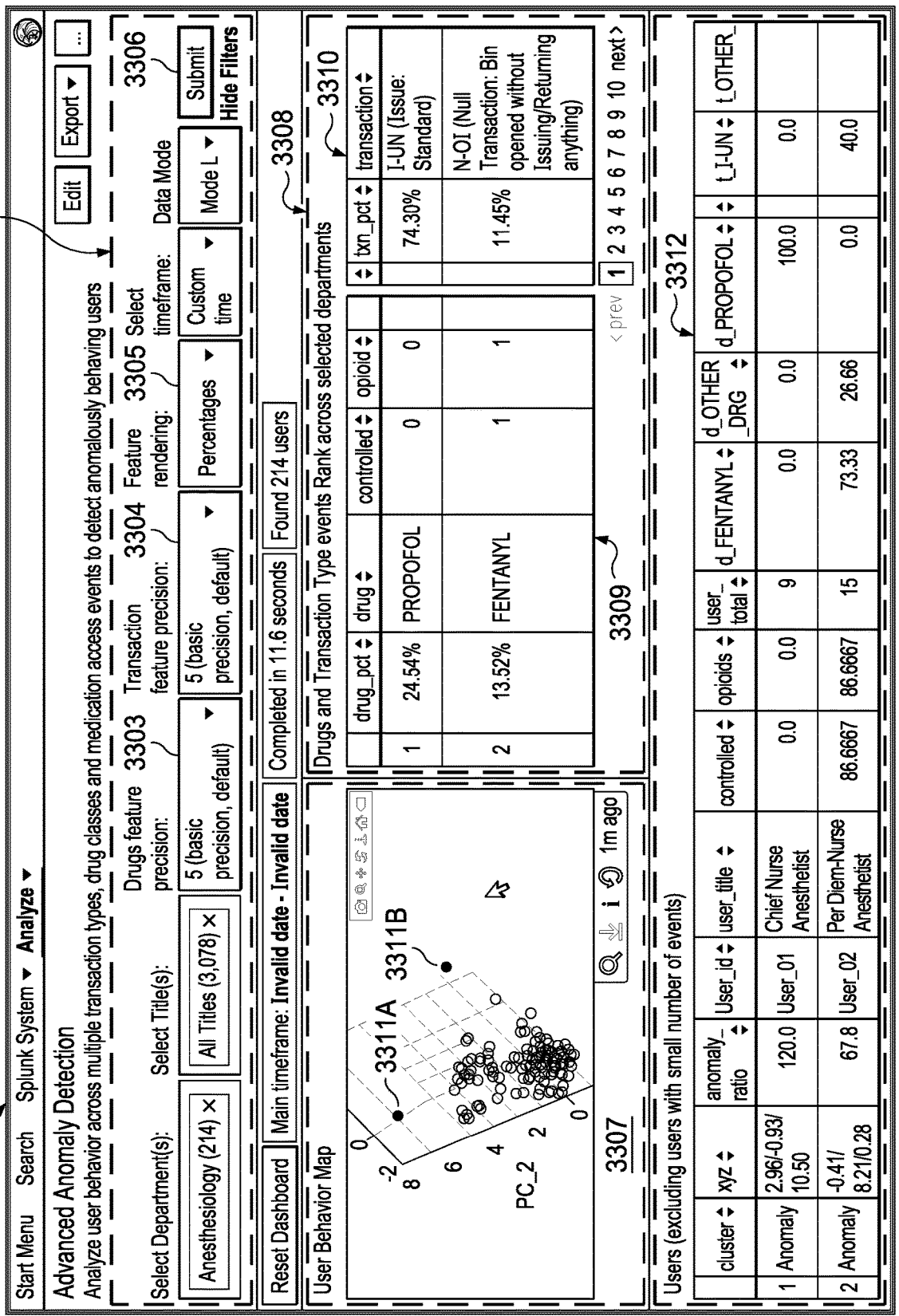
FIG. 33 illustrates an example graphical user interface of a medication security analytics application displaying user behavior information with respect to a medication dispensing system in accordance with the disclosed embodiments.

In some embodiments, the medication security analytics and healthcare privacy analytics apps are configured to correlate data from two or more of the multiple sources described above to generate the datasets used in one or more of the following graphical user interfaces of the medication security analytics application and healthcare privacy analytics application. In one embodiment, the medication security analytics application provides a collection of graphical user interfaces (e.g., dashboards) configured to enable users to filter correlated data associated with the issuance and administration of medications (e.g., drugs, narcotics, controlled substances, etc.) to patients in a healthcare environment. For example, the medication security analytics application can correlate healthcare data received from the medication dispensing system with employee records to determine how each employee is interacting with the medication dispensing system and to identify users with anomalous types or numbers of interactions in comparison to other users (e.g., as depicted in FIGS. 32 and 33). In other examples, the medication security analytics application correlates healthcare data received from the medication dispensing system with patient data from a patient records system to identify similar drugs accesses (e.g., as depicted in FIG. 34), to detect unaccounted narcotic removals (as depicted in FIG. 35), and to identify unjustified narcotics administrations (e.g., as depicted in FIG. 36).

Figure 38:
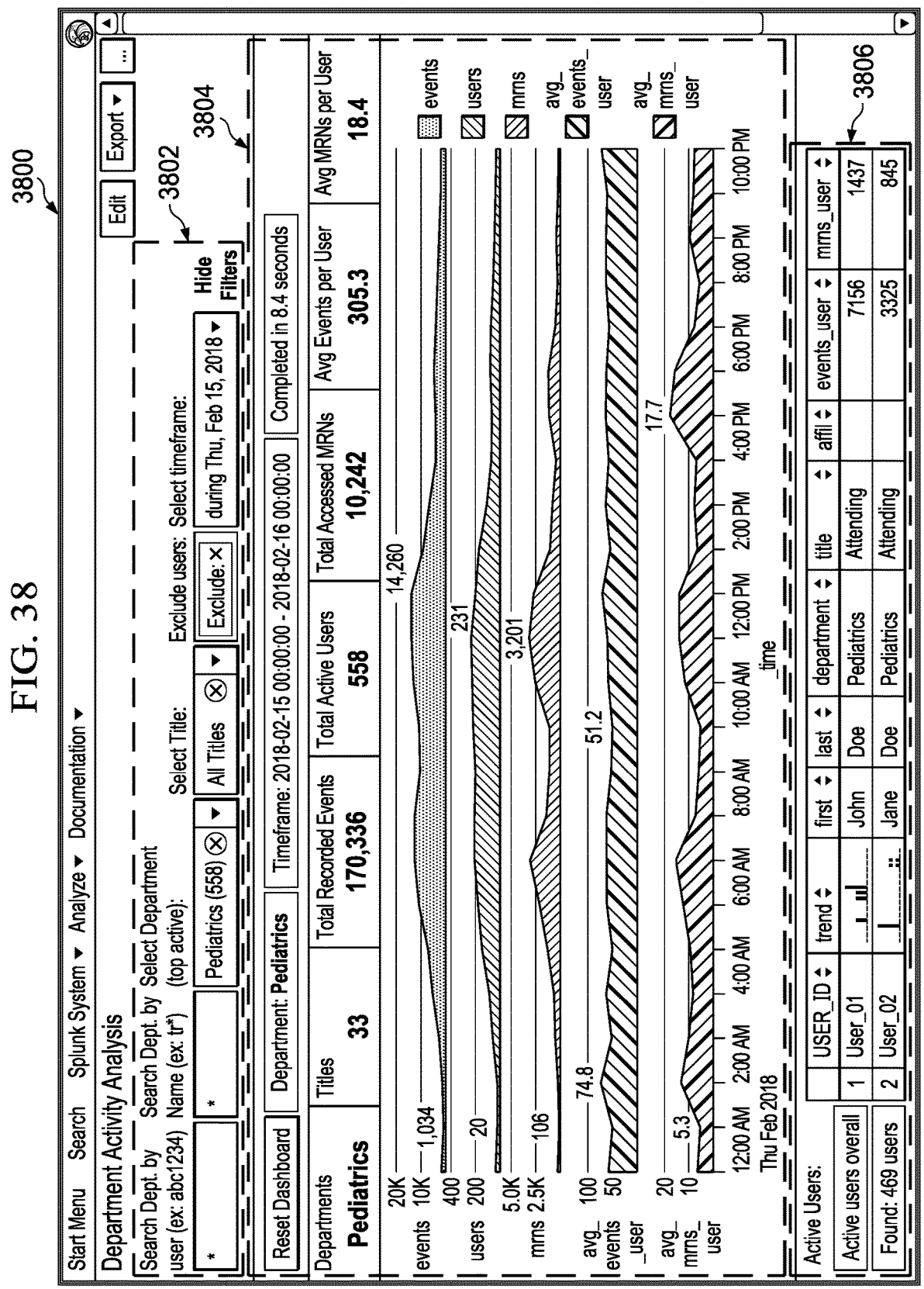
FIG. 38 illustrates an example graphical user interface of a healthcare privacy analytics application displaying user/peer group activity in accordance with the disclosed embodiments.
Figure 39:
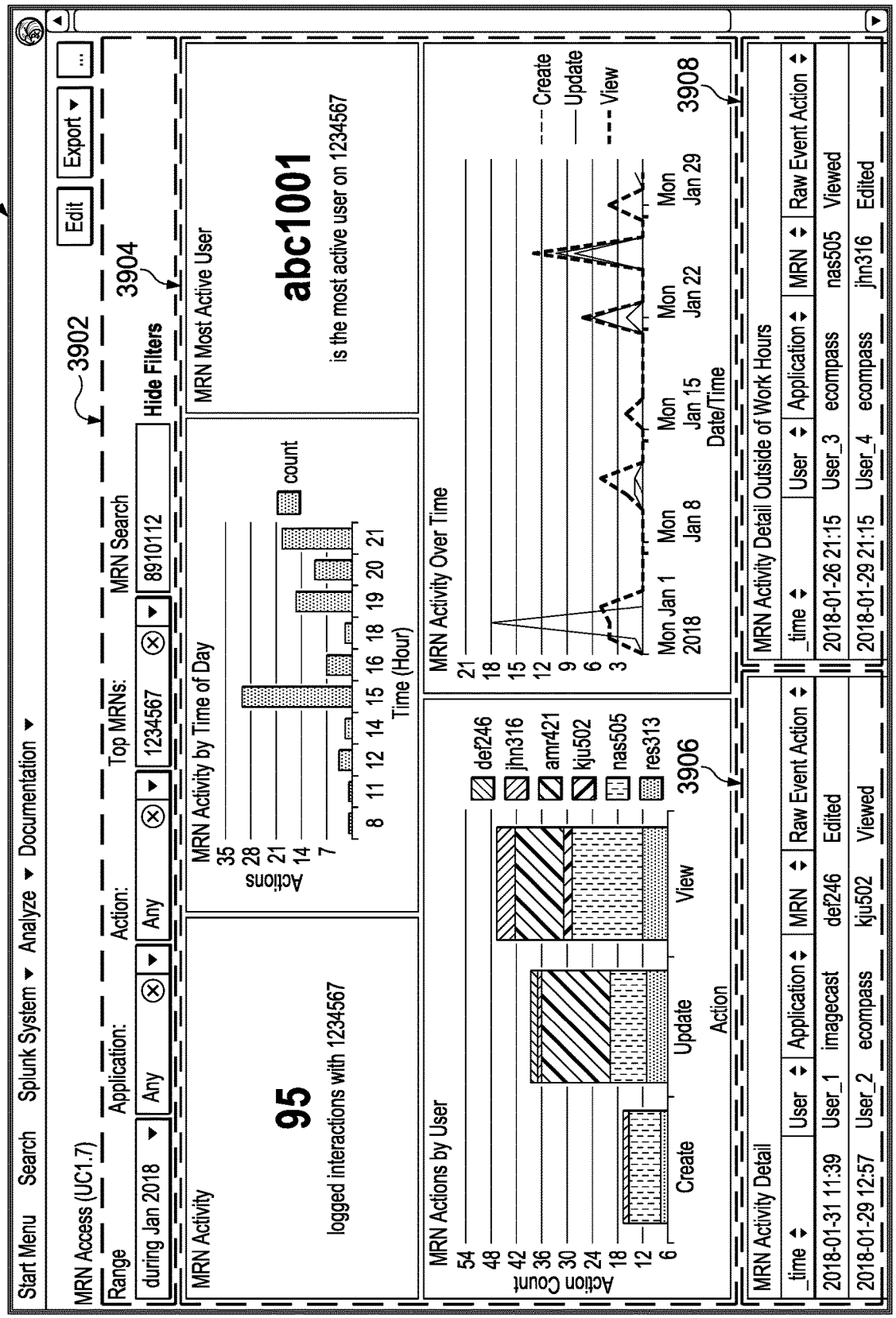
FIG. 39 illustrates an example graphical user interface of a healthcare privacy analytics application displaying data of interactions with medical records in accordance with the disclosed embodiments.
Figure 40:
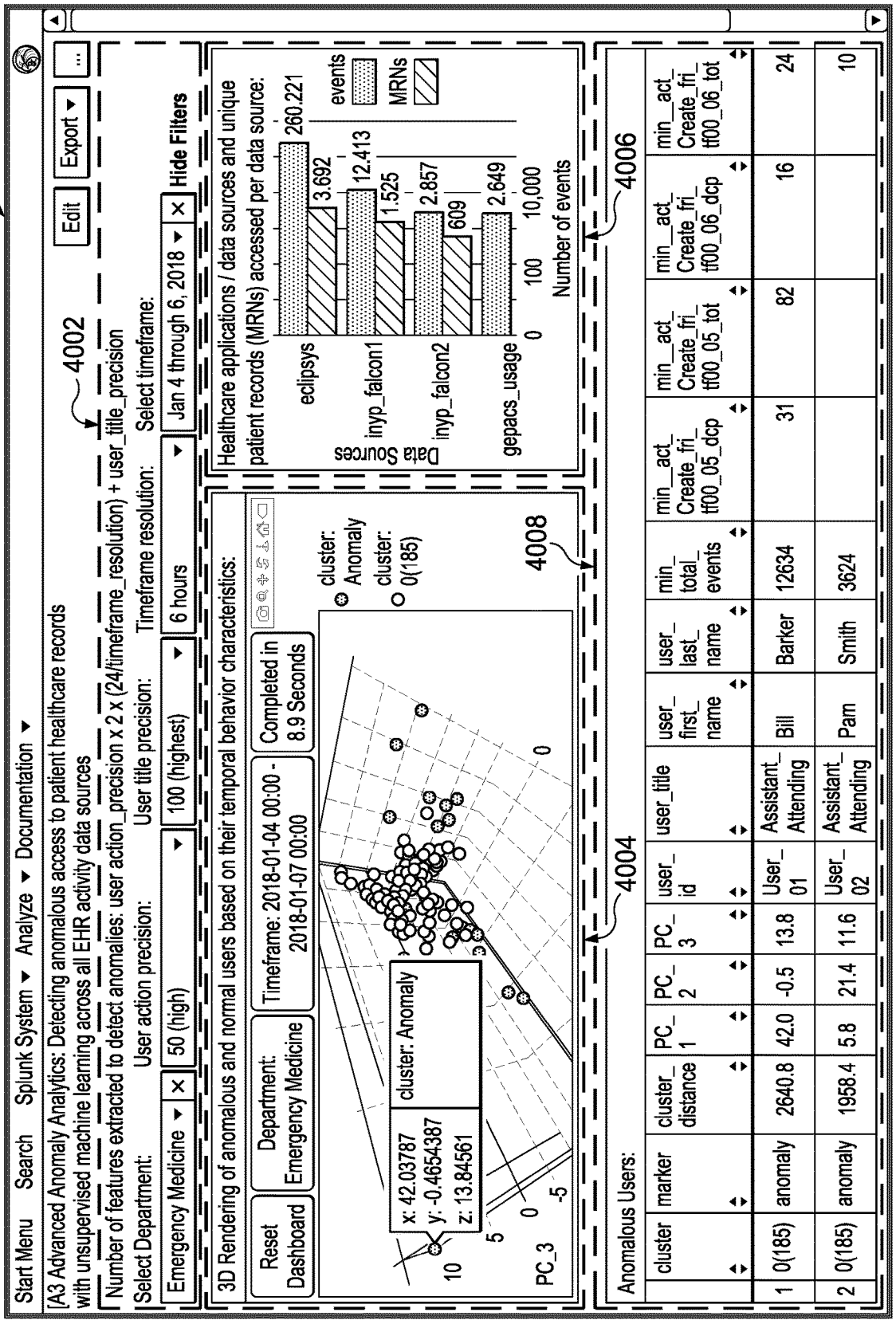
FIG. 40 illustrates an example graphical user interface of a healthcare privacy analytics application displaying user behavior information in accordance with the disclosed embodiments.

In one embodiment, the healthcare privacy analytics application provides a collection of graphical user interfaces (e.g., dashboards) configured to enable users to filter correlated data associated with user accesses to healthcare information, including patient records. For example, the healthcare privacy analytics application can correlate healthcare data received from one or more patient care databases storing patient records with employee records and an employee attendance records database to determine how each employee is interacting with the patient records and to identify employees with anomalous numbers of interactions with patient records in comparison to other users (e.g., as depicted in FIGS. 38, 39, and 40).

5.1. Medication Security Analytics Application Interfaces

FIG. 32 illustrates an example graphical user interface of a medication security analytics application displaying user interactions with a medication dispensing system in accordance with the disclosed embodiments. As shown in FIG. 32, a graphical user interface 3200 includes a set of dataset filters 3202, an interface element 3204 that can be selected to cause execution of a filtering specified through the selection of filter elements from the set of dataset filters 3202, a dataset results list 3206, a set of dataset results graphs 3208, and a detailed dataset results list 3216. In the embodiment depicted in FIG. 32, the set of dataset filters 3202 includes separate filters for transaction subtype, transaction type, department, medication class, user identifier, anomalies/variations, timeframe, and data mode.

In one embodiment, the dataset results list 3206 displays the most active users based on a received selection of the set of dataset filters 3202. In one embodiment, the contents of the dataset results list 3206 can be displayed based on interface elements 3207, which allow the selection of the types of information to display and the number of results to display. In the example of FIG. 32, the dataset results list 3206 displays the top 100 users based on the number of interactions with the medication dispensing system involving opioids within the selected timeframe. In one embodiment, the dataset results list 3206 includes user identifier information, user department information, user title information, the total number of interactions involving opioids, and the total number of interactions. In this example, the total number of interactions involving opioids and the total number of interactions are equal because of the filtering specified through the selection of filter elements from the set of dataset filters 3202.

In one embodiment, the set of dataset results graphs 3208 displays the results of the filtering specified by the selection of filter elements from the set of dataset filters 3202 in a graph form. In the example depicted in FIG. 32, graph 3210 depicts the number of events plotted over the specified timeframe (e.g., the previous 14 days as selected in the set of dataset filters 3202) involving the medication class selected from the set of data filters 3202 (e.g., opioids). Graphs 3212 and 3214 depict the number of interactions recorded over the same specified timeframe involving controlled substances and opioids, respectively.

In one embodiment, the detailed dataset results list 3216 displays all or a subset of all interactions with the medication dispensing system involving opioids within the selected timeframe based on the filtering specified by the selection of filter elements from the set of dataset filters 3202. In one embodiment, the contents of the detailed dataset results list 3216 can be displayed based on interface element 3217 which allows selection of the number of results to display. In the example of FIG. 32, the detailed dataset results list 3216 displays the 250 most recent interactions with the medication dispensing system involving opioids within the selected timeframe. In one embodiment, the detailed dataset results list 3216 includes the interaction time, user identifier information, an in/out indication, in/out time information, witness user identifier, patient identifier, transaction type, medication/prescription order identifier, medication name, medication control level, an opioid indicator, medication location, user department information, user title, etc.

FIG. 33 illustrates an example graphical user interface of a medication security analytics application displaying user behavior information with respect to a medication dispensing system in accordance with the disclosed embodiments. In one embodiment, the user behavior information is based on data obtained from a medication dispensing system, where the data indicates recorded interactions with the medication dispensing system. As shown in FIG. 33, a graphical user interface 3300 includes a set of dataset filters 3302, a visualization of user behavior information 3307, a dataset results lists 3308, and a detailed user dataset results list 3312.

In one embodiment, the set of dataset filters 3302 includes separate filters for transaction type, user department, user title, timeframe, data mode. In some embodiments, the set of dataset filters 3302 also includes a separate filter for additional data, including medication classification type. The set of dataset filters 3302 also includes a first feature filter 3303, a second feature filter 3304, and a feature rendering filter 3305 allowing a user to select whether the dataset results lists 3308 should be ordered based on percentages of total medications issued and transaction types or based on the number of medications issued and transaction types. The graphical user interface 3300 also includes an interface element 3306 that can be selected to cause data displayed in the graphical user interface 3300 to be filtered according to the selection of filter elements from the set of dataset filters 3302. In one embodiment, the first feature filter 3303 allows for selection of a numerical value, where the selected numerical value indicates a number of different medications issued from the medication dispensing system to include as part of generating the visualization of user behavior information 3307. Similarly, the second feature filter 3304 allows for selection of another numerical value, where the selected numerical value indicates a number of types of transactions (e.g., interactions) performed with the medication dispensing system to include as part of generating the visualization of user behavior information 3307.

Based on the filtering options specified using the set of dataset filters 3302, the medication security analytics application generates the visualization of user behavior information 3307, the dataset results lists 3308, and the detailed user dataset results list 3312. As indicated above, the medication security analytics application may generate the visualization in response to user selection of an interface element 3306; in other examples, the medication security analytics application updates the display of graphical user interface 3300 dynamically in response to user selection of the various filtering options.

In one embodiment, the visualization of user behavior information 3307 displays information about a plurality of users having interactions with the medication dispensing system and, in some instances, provides indications of users having anomalous interactions with the medication dispensing system. To generate the visualization, in some embodiments, the medication security analytics application generates a plurality of feature vectors, where each feature vector corresponds to one of a plurality of users having interactions with the medication dispensing system. Each feature of a user's feature vector is generally associated with a numerical value indicating a characteristic of the user's interactions with the medication dispensing system (e.g., one feature might indicate a percentage of the user's interactions involving a particular type of drug, another feature might indicate a percentage of the user's transactions that were of a certain type, etc.). As described above, the number and type of features included in the users' features vectors can be configured using first feature filters 3303 and second feature filters 3304 and the feature rendering filter 3305 of the dataset filters 3302.

In one embodiment, the plurality of feature vectors are generated based on execution of a filter query against timestamped event data stored by the data intake and query system (e.g., a first plurality of timestamped events based on data indicating instances of users checking out various medications from a medication dispensing system and a second plurality of timestamped events based on data indicating instances of various types of user interactions with the medication dispensing system). As depicted in FIG. 33, the visualization of user behavior information 3307 is a three-dimensional mapping showing a clustered representation of the plurality of feature vectors (where the feature vectors may be clustered using k-means clustering or any other clustering algorithm). As indicated above, the number of dimensions of the plurality of feature vectors is initially based on a combined number of features selected using the dataset filters 3302 (or based on a default number of features). For example, if the medication security analytics application receives a numerical selection of five for the first feature filter 3303 and a numerical selection of five for the second feature filter 3304, the medication security analytics application generates each of the plurality of feature vectors with ten dimensions. In such embodiments, the medication security analytics application uses a machine learning or other type of algorithm to generate the visualization of user behavior information 3307 by reducing the number of dimensions of the clustered plurality of feature vectors to three dimensions. While the number of first features and second features is the same in the example depicted in FIG. 33, in other examples, the number of first features and second features can be different (for example, a user might specify a drugs feature precision of 4 and a transaction feature precision of 6).

The dataset results lists 3308 displays two lists: a first dataset results list 3309 based, at least in part, on the first plurality of timestamped events generated based on data reflecting instances of a user checking out medications from a medication dispensing system, and a second dataset results list 3310 based, at least in part on the second plurality of timestamped events generated based on data reflecting instances of various types of user interactions with the medication dispensing system. As depicted in FIG. 33, the first dataset results list 3309 displays the most frequently issued medications (based on a percentage of total issued medications) over a selected timeframe, ranked from most frequently to least frequently issued. The second dataset results list 3310 displays the most frequently performed interactions with the medication dispensing system over the same selected timeframe, ranked from most frequently to least frequently performed interactions. Continuing the example described above, the five most frequently issued medications from the medication dispensing system and the five most frequently performed interactions with the medication dispensing system, as displayed in the first dataset results list 3309 and the second dataset results list 3310, respectively, are the features used to generate the plurality of feature vectors. In an alternative embodiment, the medication security analytics application selects the M−1 most frequently issued medications from the medication dispensing system and the N−1 most frequently performed interactions with the medication dispensing system, where M and N are the numerical selection of the first feature filter 3303 and the numerical selection of the second feature filter 3304, respectively. In such an embodiment, the medication security analytics application buckets the remaining issued medications and performed interactions into an "other" category as the last features used to generate the plurality of feature vectors.

In one embodiment, the medication security analytics application can identify one or more anomalous vertices in the visualization of user behavior information 3307 (e.g., where each of the one or more anomalous vertices represents a user associated with anomalous user behavior with respect to the medication dispensing system). As indicated above, in one embodiment, the medication security analytics application uses a k-means clustering or other algorithm to cluster the plurality of feature vectors. Using the clustering algorithm, the medication security analytics application identifies a centroid of the cluster, determines each vertices' distances away from the centroid of the cluster, and compares the determined distance value for each vertex with a threshold value. In one embodiment, the medication security analytics application flags, or otherwise indicates, each vertex having a distance from the centroid of the cluster that is less than the threshold value as being "Typical" or "Expected" (for example, by displaying these vertices using a same color, shape, or other graphical representation). In contrast, the medication security analytics application flags, or otherwise indicates, each vertex having a distance from the centroid of the cluster are greater than the threshold value as an "Anomaly" (for example, by displaying these vertices using a different color, shape, or other graphical representation). In this example, the anomalous vertices may indicate users issuing medications and/or interacting with the medication dispensing system in ways that are different (e.g., beyond an expected variance) from the other users in the visualized set. In the example of FIG. 33, the visualization of user behavior information 3307 includes two vertices (3311A and 3311B) that are identified as being outliers within the cluster of vertices.

The detailed user dataset results list 3312 in graphical user interface 3300 displays an entry for all or a subset of users having recorded interactions with the medication dispensing system based on the filtering specified using the set of dataset filters 3302. In one embodiment, the medication security analytics application excludes users with a number of interactions with the medication dispensing system that is below a threshold value. The entries in the detailed user dataset results list 3312 can be sorted based on one of a plurality of fields. As shown in FIG. 33, the detailed user dataset results list 3312 is sorted by a cluster indicator that indicates, for each user, whether the user's corresponding vertex in the clustered visualization was typical or anomalous.

FIG. 34 illustrates an example graphical user interface of a medication security analytics application displaying user behavior information of accesses of similar medications in accordance with the disclosed embodiments. As shown in FIG. 34, a graphical user interface 3400 includes a dataset filter 3402 and a detailed dataset results list 3404. In one embodiment, the dataset filter 3402 includes a filter, which allows for selection of a specified timeframe.

In one embodiment, the user behavior information of accesses of similar medications is generated using information obtained from a medication dispensing system, where the information reflects recorded user interactions with the medication dispensing system. For example, the medication security analytics application can generate the entries in the detailed dataset results list 3404 using a plurality of timestamped events. The plurality of timestamped events is generated using the first data indicating instances of a user checking out a drug from a medication dispensing system. In one embodiment, the medication security analytics application correlates the plurality of timestamped events with another plurality of timestamped events from an employee records database. For example, the plurality of timestamped events generated from the data from the medication dispensing system can be correlated to another plurality of timestamped events generated from data from employee attendance records.

In one embodiment, the medication security analytics application associates the issuance of similar medications or drugs when the amount of time passing between the issuances is less than a pre-defined amount of time. In the example of FIG. 34, the detailed dataset results list 3404 displays pairs of accesses for a specified user of two similar medications: acetaminophen (e.g., Tylenol®) and acetaminophen-oxycodone (an opioid). The detailed dataset results list 3404 can identify users who are accessing the two similar medications more often, anomalously, than other users. This can assist in detecting drug diversions, that is, the transfer of legally prescribed controlled substance from the individual for whom it was prescribed to another individual for an illicit use.

FIG. 35 illustrates an example graphical user interface of a medication security analytics application displaying unaccounted narcotic removals in accordance with the disclosed embodiments. As shown in FIG. 35, a graphical user interface 3500 includes a dataset filter 3502 and a detailed dataset results list 3504. In one embodiment, the dataset filter 3502 includes a filter, which allows for selection of a specified timeframe.

In one embodiment, the unaccounted narcotic removals entries in the detailed dataset results list 3504 are generated using information obtained from a medication dispensing system of recorded interactions with the medication dispensing system and patient medical records. For example, the medication security analytics application can generate the entries in the detailed dataset results list 3504 by correlating sets of timestamped events. In one embodiment, a first plurality of timestamped events is generated using the first data indicating instances of a user checking out a drug from a medication dispensing system, and a second plurality of timestamped events is generated using second data indicating the administration of medications to patients, e.g., by accessing patient records data. In one embodiment, the medication security analytics application associates the issuance of medications or narcotics with patient records by matching patient identifiers or another identifier (e.g., user identifier, etc.) occurring in the timeframe specified using the dataset filter 3502.

In the example of FIG. 35, each entry in the detailed dataset results list 3504 displays a timeframe, user information (e.g., a user identifier, name, etc.) indicating the user who removed narcotics from the medication dispensing system, the narcotics removed, patient information (e.g., a patient number or identifier), the number of narcotics removed, the number of narcotics administered to the patient, and the number of unaccounted narcotics (the difference between the number of narcotics removed and the number of narcotics administered). The entries in the detailed dataset results list 3504 can be sorted based on one of a plurality of fields. In FIG. 35, the detailed dataset results list 3504 is sorted by the values of the number of unaccounted narcotics to identify the users who have the largest number of unaccounted narcotics, information useful for detecting drug diversions.

FIG. 36 illustrates an example graphical user interface of a medication security analytics application displaying unjustified narcotics administration in accordance with the disclosed embodiments. As shown in FIG. 36, a graphical user interface 3600 includes a dataset filter 3602 and a detailed dataset results list 3604. In one embodiment, the dataset filter 3602 includes a filter, which allows for selection of a specified timeframe.

In one embodiment, the unjustified narcotics administration entries in the detailed dataset results list 3604 are generated using information obtained from patient medical records. For example, the medication security analytics application identifies the patient pain score information and information regarding narcotics administered to the patient from the individual patient records to generate the detailed dataset results list 3604.

In the example of FIG. 36, each entry in the detailed dataset results list 3604 displays a user identifier indicating the user who administered narcotics, the number of times the user administered narcotics, the medications removed, the user's title, the user's first and last name, the narcotics administered, patient information (e.g., a patient number and/or identifier), and the patient's pain score. The entries in the detailed dataset results list 3604 can be sorted based on one of a plurality of fields. In FIG. 36, the detailed dataset results list 3604 is sorted by the values of the number of times the user administered narcotics.

Figure 37:
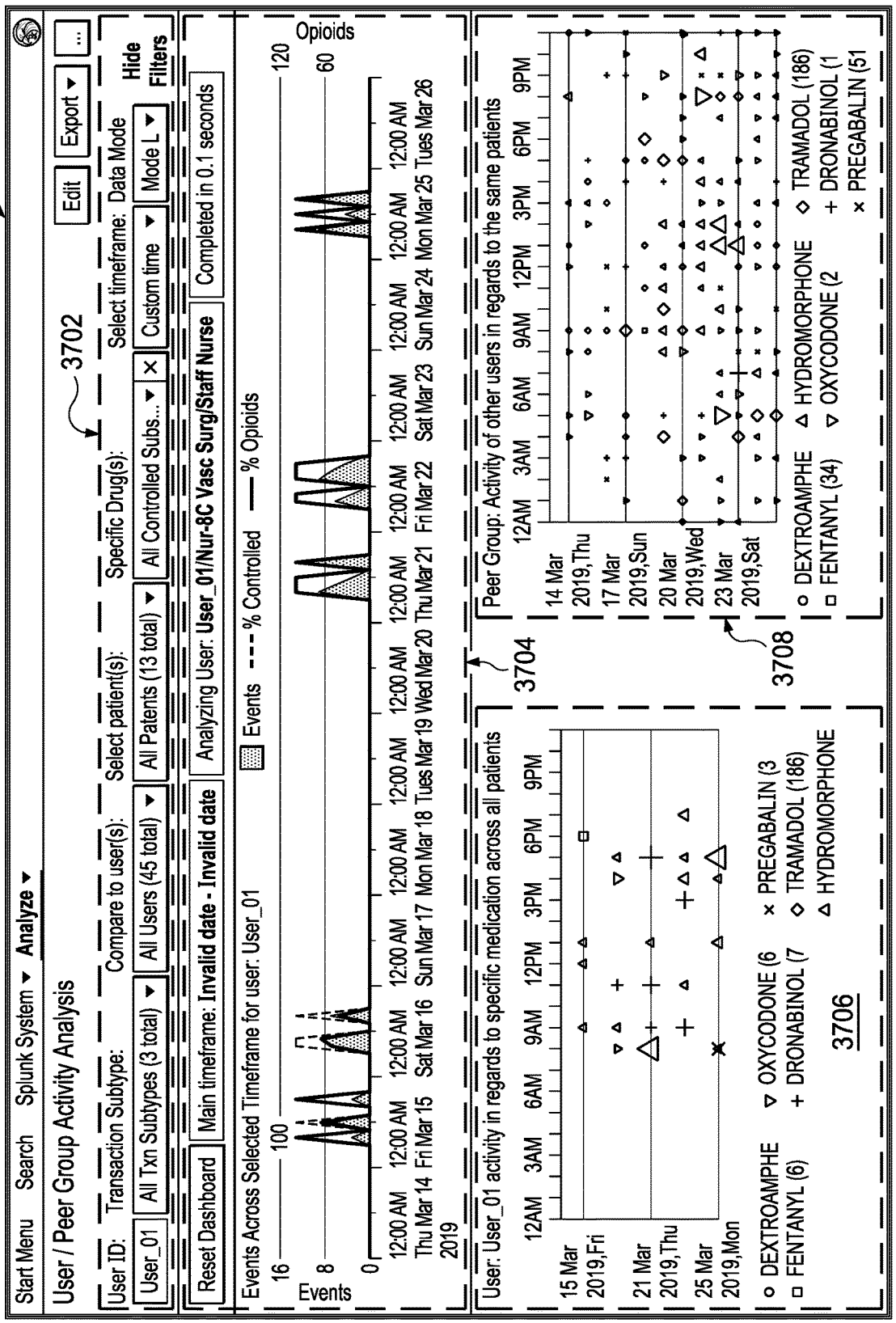
FIG. 37 illustrates an example graphical user interface of a medication security analytics application displaying user/peer group activity in accordance with the disclosed embodiments.

FIG. 37 illustrates an example graphical user interface of a medication security analytics application displaying user/peer group activity in accordance with the disclosed embodiments. As shown in FIG. 37, a graphical user interface 3700 includes a set of dataset filters 3702, a first visualization of dataset results for a specified user 3704, a second visualization of dataset results for the specified user 3706, and a third visualization of dataset results for a peer group of the specified user 3708. In one embodiment, the set of dataset filters 3702 includes a field for entry of a specific user (e.g., using a user identifier) and separate filters, which allow for selection of a transaction type, a peer group, a patient, a medication, a timeframe, and a data mode.

In one embodiment, the first visualization of dataset results for a specified user 3704 is a representation of interactions performed by the specified user over the timeframe indicated in the set of dataset filters 3702 involving controlled substances and opioids. As depicted in FIG. 37, the first visualization of dataset results for a specified user 3704 is a line graph with time as the x-axis and the number of medications administered and the number of opioids administered as the y-axis. In one embodiment, the second visualization of dataset results for the specified user 3706 is a representation of the specific medications administered by the specified user over the timeframe indicated in the set of dataset filters 3702. As depicted in FIG. 37, the second visualization of dataset results for a specified user 3704 is a heatmap where the larger the indicator, the larger the number of administrations of the indicated medications.

In one embodiment, the third visualization of dataset results for a peer group of the specified user 3708 is a representation of the specific medications administered by users within the peer group of the specified user and over the specified timeframe, both selected in the set of dataset filters 3702. As depicted in FIG. 37, the third visualization of dataset results for a peer group of the specified user 3708 is a heatmap. The data presented in the third visualization of dataset results for a peer group of the specified user 3708 can indicate whether a user of the plurality of users in the peer group is administering certain medications anomalously, e.g., in a manner inconsistent with the other users in the peer group.

5.2. Healthcare Privacy Analytics Application Interfaces

FIG. 38 illustrates an example graphical user interface of a healthcare privacy analytics application displaying user/peer group activity in accordance with the disclosed embodiments. As shown in FIG. 38, a graphical user interface 3800 includes a set of dataset filters 3802, a visualization of dataset results 3804, detailed dataset results list 3806. In one embodiment, the set of dataset filters 3802 includes fields for entry of a specific user using a user identifier or a name, and a plurality of filters, which allow for selection of department, title, and timeframe.

In one embodiment, the visualization of dataset results 3804 includes multiple line graphs charting data based on the inputs and selections of the set of dataset filters 3802. In one embodiment, the healthcare privacy analytics application correlates a plurality of timestamped events generated from one or more patient records databases with a plurality of timestamped events generated from employee records and/or an employee attendance records database to generate the user/peer group patient record activity data. In the example of FIG. G, the visualization of dataset results 3804 includes line graphs charting data for the pediatrics department on Thursday, Feb. 15, 2018. The five graphs chart the total number of events recorded with a medical records system, the total number of users, the total number of accessed medical record numbers (MRNs), the average number of events per user, and the average number of MRNs access per user, respectively.

In one embodiment, the detailed dataset results list 3806 utilizes the same data used to generate the visualization of dataset results 3804 to generate a plurality of entries in a table. In the detailed dataset results list 3806, each entry corresponds to one of a plurality of active users. In one embodiment, each entry includes a user identifier, a visualization of the user's activity (e.g., a bar graph), the user's first and last name, the user's department, the user's title, an affiliation, the number of events corresponding to the user, and the number of MRNs accessed by the user. As depicted in FIG. 38, the entries in the detailed dataset results list 3806 are sorted based on the number of MRNs accessed. In one embodiment, the healthcare privacy analytics application identifies users having user activity (e.g., MRNs accessed) that is anomalous as compared to the other users, e.g., by comparing the user to an average computed based on the information from all users. For example, the healthcare privacy analytics application may identify the first two entries in the detailed dataset results list 3806 as being anomalous because of the larger number of MRNs accessed.

FIG. 39 illustrates an example graphical user interface of a healthcare privacy analytics application displaying data of interactions with medical records in accordance with the disclosed embodiments. As shown in FIG. 39, a graphical user interface 3900 includes a set of dataset filters 3902, a set of visualizations of dataset results 3904, a first detailed dataset results list 3906, and a second detailed dataset results list 3908. In one embodiment, the set of dataset filters 3902 includes separate filters, which allowing the selection of time range, application, action, top medical record numbers (MRNs), and a field for entry of an MRN.

In one embodiment, the set of visualizations of dataset results 3904 includes information associated with a selected MRN (e.g., 3154399). In the example of FIG. 39, the set of visualizations of dataset results 3904 include an indication of a total number of logged interactions, a total number of logged interactions by time of data, the most active user interacting with the selected MRN, a bar graph and line graph displaying types of actions performed on the selected MRN and the user performing the actions. In one embodiment, the healthcare privacy analytics application correlates a plurality of timestamped events generated from one or more patient records databases with a plurality of timestamped events generated from employee records and/or an employee attendance records database.

In one embodiment, the first detailed dataset results lists 3906 includes entries for all logged interactions with the selected MRN. In one embodiment, the second detailed dataset results lists 3908 includes entries for the subset of all logged interactions with the selected MRN that occurred outside of work hours. In the example of FIG. 39, each entry in both the first detailed dataset results lists 3906 and the second detailed dataset results lists 3908 include a time of interaction, a user identifier, an application, the MRN, and the event action or interaction type.

FIG. 40 illustrates an example graphical user interface of a healthcare privacy analytics application displaying user behavior information in accordance with the disclosed embodiments. In one embodiment, the user behavior information is generated using information obtained from a healthcare records system of recorded interactions by users with the healthcare record system. As shown in FIG. 40, a graphical user interface 4000 includes a set of dataset filters 4002, a visualization of user behavior information 4004, a dataset results lists 4006, and a detailed dataset results list 4008.

In one embodiment, the set of dataset filters 4002 include separate filter, which allow for the selection of department, user action precision, user title precision, timeframe resolution, and timeframe. Based on the filtering specified through the selection of filter elements from the set of dataset filters 4002, the healthcare privacy analytics application generates the visualization of user behavior information 4004, the dataset results lists 4006, and the detailed dataset results list 4008. In one embodiment, the healthcare privacy analytics application correlates a plurality of timestamped events generated from one or more patient records databases with a plurality of timestamped events generated from employee records and/or an employee attendance records database.

In one embodiment, the visualization of user behavior information 4004 is a mapping of vertices, where each vertex corresponds to one of a plurality of users having interactions with the healthcare records system. The healthcare privacy analytics application generates a plurality of feature vectors, where each vector corresponds to one of a plurality of user having interactions with the healthcare records system. As depicted in FIG. 40, the visualization of user behavior information 4004 is a three-dimensional mapping showing a clustered representation of the plurality of feature vectors.

In one embodiment, the healthcare privacy analytics application can identify one or more vertices (e.g., users) that are anomalies as compared to the other vertices in the clustered representation of the plurality of feature vectors in the visualization of user behavior information 4004. In one embodiment, the healthcare privacy analytics application uses a k-means clustering algorithm to cluster the plurality of feature vectors. In other embodiments, the healthcare privacy analytics application uses other algorithms to perform the clustering of the plurality of feature vectors. Using the clustering algorithm, the healthcare privacy analytics application identifies a centroid of the cluster and determines each vertices' distances away from the centroid of the cluster and compares the determined value with a threshold value. In one embodiment, the healthcare privacy analytics application flags, or otherwise indicates, each vertex whose distance from the centroid of the cluster are less than the threshold value as being "Typical" or "Expected." In contrast, the healthcare privacy analytics application flags, or otherwise indicates, each vertex whose distance from the centroid of the cluster are greater than the threshold value as an "Anomaly," which indicates that the corresponding users are accessing, or otherwise interacting, with the patient records in the patient record systems in ways that are different, beyond an expected variance, from the rest of the plurality of users. In FIG. 40, the visualization of user behavior information 4004 includes multiple vertices, that are outliers from the cluster of vertices and considered anomalies by the healthcare privacy analytics application.

The detailed dataset results lists 4008 displays a visualization of healthcare applications (e.g., data sources) and the number of unique patient records accessed per data source (e.g., events or interactions). The detailed dataset results list 4008 in graphical user interface 4000 displays an entry for all or a subset of users who interacted with the healthcare records system, based on the filtering specified through the selection of filter elements from the set of dataset filters 4002. In one embodiment, each entry can include a plurality of fields, including: a cluster identifier, an anomaly indicator, a cluster distance value, user title, user first and last name, total number of events or interactions by the user with the healthcare records system, etc. The entries in the detailed dataset results list 4008 can be sorted based on one of the plurality of fields. As shown in FIG. 40, the detailed dataset results list 4008 is sorted by a cluster distance value, where the value is the distance from the centroid of the cluster.

Figure 41:
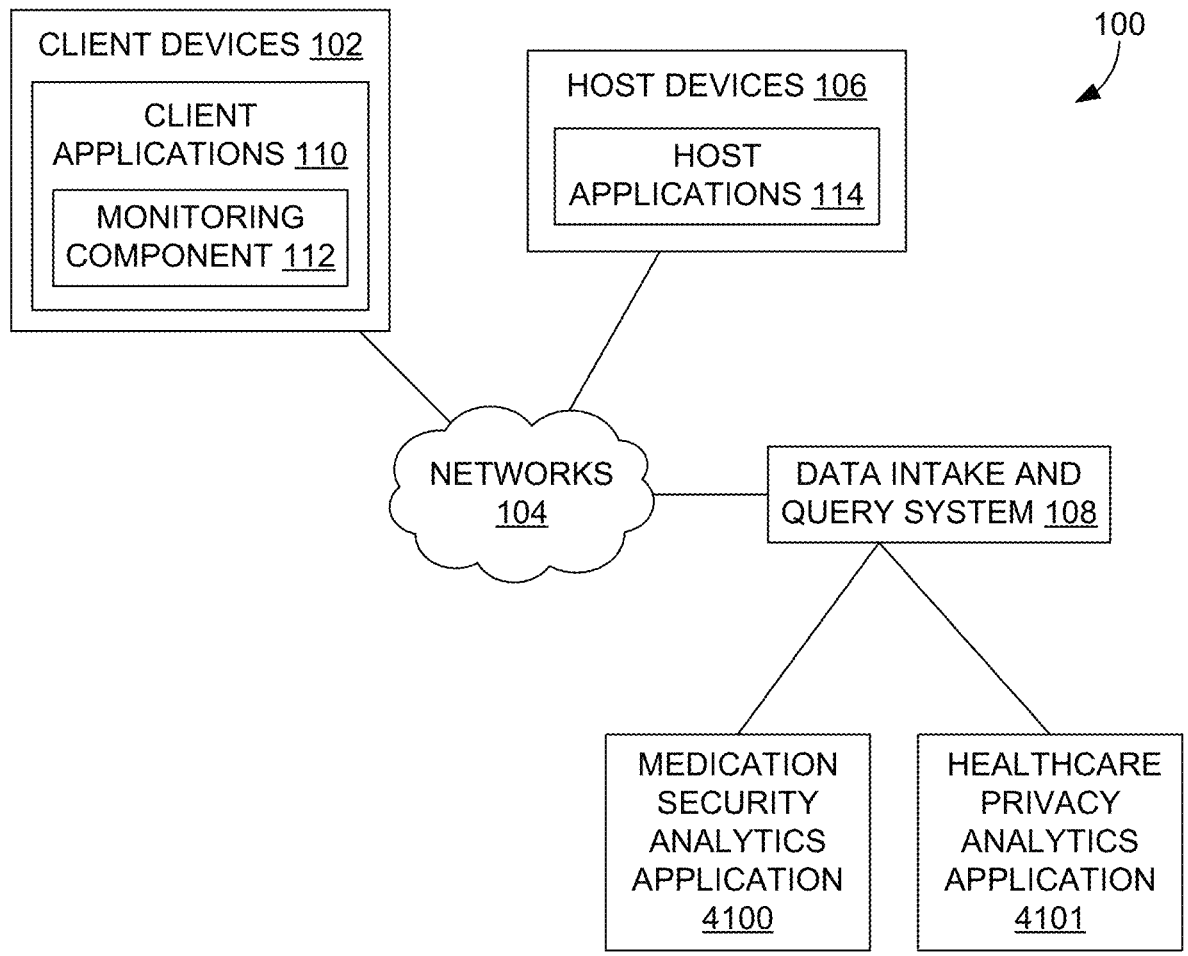
FIG. 41 illustrates a block diagram of an example application environment including medication security and healthcare privacy analytics applications in accordance with the disclosed embodiments.

FIG. 41 illustrates a networked computer environment 100 including medication security and healthcare privacy analytics applications. As described in reference to FIG. 2, an application environment 205 generally includes tools, software modules (e.g., compute executable instructions to perform a particular function, etc.), to enable application developers to create computer executable applications to interface with a data intake and query system 108. Application developers can use the application environment to build a particular application to interface with the data intake and query system 108 to obtain the relevant data that they seek, process the relevant data, and display it in a manner that is consumable by a user. The applications developed using the application environment can include their own backend services, middleware logic, front-end user interface, etc., and can provide facilities for ingesting use case specific data and interacting with that data. In some embodiments, the development of applications using the application environment can make use of an application platform, including an application framework and API gateway, which provide tools that developers can use to create such applications and for developed applications to interface with the data intake and query system 108.

In one embodiment, a medication security analytics application 4100 and a healthcare privacy analytics application 4101 can be implemented to store and access various types of data used to provide the functionality of search and filtering interfaces, and other features described herein. For example, the medication security analytics application 4100 and the healthcare privacy analytics application 4101 can use an API gateway or other interface to access storage provided by the data intake and query system 108, use another application of the application environment that provides controlled access to data storage, use storage resources local the medication security analytics application 4100 and the healthcare privacy analytics application 4101, or use any other type of storage available to the medication security analytics application 4100 and healthcare privacy analytics application 4101.

As shown in the previous figures, various embodiments may refer to a data intake and query system 108 that includes one or more of a search head 210, an indexer 206, and a forwarder 204. In other implementations, data intake and query system 108 may have a different architecture, but may carry out indexing and searching in a way that is indistinguishable or functionally equivalent from the perspective of the end user. For example, data intake and query system 108, as well as the medication security and healthcare privacy analytics applications, may be re-architected to run in a stateless, containerized environment. In some of these embodiments, data intake and query system 108 may be run in a computing cloud provided by a third party or provided by the operator of the data intake and query system 108. This type of cloud-based data intake and query system may have several benefits, including, but not limited to, lossless data ingestion, more robust disaster recovery, and faster or more efficient processing, searching, and indexing. A cloud-based data intake and query system as described in this section may provide separately scalable storage resources and compute resources, or separately scalable search and index resources. Additionally, the cloud-based data intake and query system may allow for applications to be developed on top of the data intake and query system, to extend or enhance functionality, through a gateway layer or one or more APIs, which may provide customizable access control or targeted exposure to the workings of data intake and query system 108.

In some embodiments, a cloud-based data intake and query system may include an intake system. Such an intake system can include, but is not limited to an intake buffer, such as Apache Kafka (R) or Amazon Kinesis (R), or an extensible compute layer, such as Apache Spark™ or Apache Flink (R). In some embodiments, the search function and the index function may be separated or containerized, so that search functions and index functions may run or scale independently. In some embodiments, data that is indexed may be stored in buckets, which may be stored in a persistent storage once certain bucket requirements have been met, and retrieved as needed for searching. In some embodiments, the search functions and index functions run in stateless containers, which may be coordinated by an orchestration platform. These containerized search and index functions may retrieve data needed to carry out searching and indexing from the buckets or various other services that may also run in containers, or within other components of the orchestration platform. In this manner, loss of a single container, or even multiple containers, does not result in data loss, because the data can be quickly recovered from the various services or components or the buckets in which the data is persisted.

In some embodiments, the cloud-based data intake and query system and the medication security and healthcare privacy analytics systems may implement tenant-based and user-based access control. In some embodiments, the cloud-based data intake and query system may implement an abstraction layer, through a gateway portal, an API, or some combination thereof, to control or limit access to the functionality of the cloud-based data intake and query system.

Figure 42:
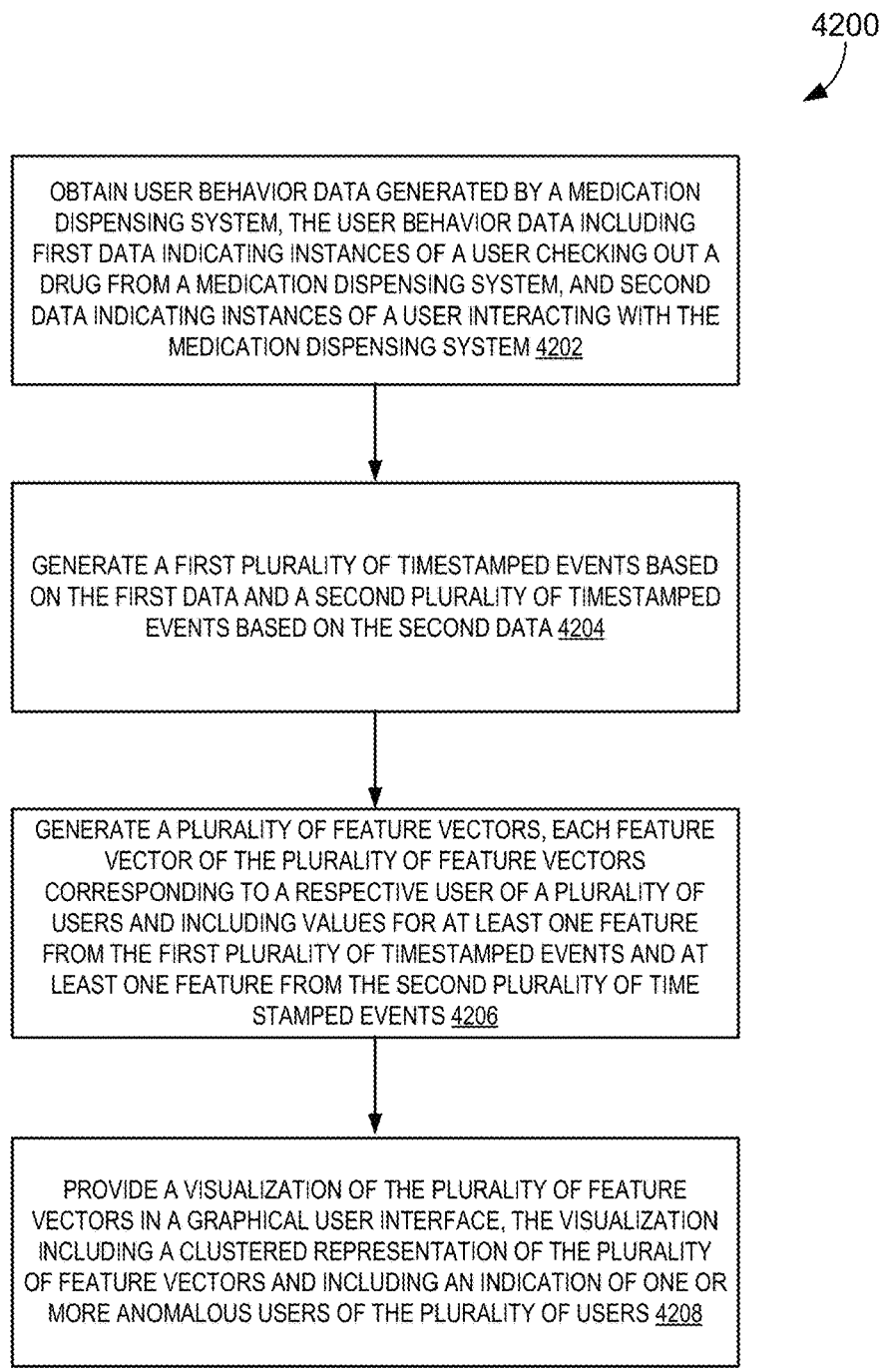
FIG. 42 is a flow diagram illustrating operations of a method for providing medication security and healthcare privacy analytics applications as part of a data intake and query system according to some embodiments.

FIG. 42 is a flow diagram illustrating operations 4200 of a method for providing medication security and healthcare privacy analytics applications as part of a data intake and query system according to some embodiments. Some or all of the operations 4200 (or other processes described herein, or variations, and/or combinations thereof) are performed under the control of one or more computer systems configured with executable instructions and are implemented as code (e.g., executable instructions, one or more computer programs, or one or more applications) executing collectively on one or more processors, by hardware or combinations thereof. The code is stored on a computer-readable storage medium, for example, in the form of a computer program comprising instructions executable by one or more processors. The computer-readable storage medium is non-transitory. In some embodiments, one or more (or all) of the operations 4200 are performed by a medication security analytics application 4100 and a healthcare privacy analytics application 4101 of the other figures.

The operations 4200 include, at block 4202, obtaining, by a data intake and query system, user behavior data generated by a medication dispensing system, the user behavior data including first data indicating instances of a user checking out a drug from a medication dispensing system, and second data indicating instances of a user interacting with the medication dispensing system.

The operations 4200 further include, at block 4204, generating a first plurality of timestamped events based on the first data and a second plurality of timestamped events based on the second data.

The operations 4200 further include, at block 4206, generating a plurality of feature vectors, each feature vector of the plurality of feature vectors corresponding to a respective user of a plurality of users and including values for at least one feature from the first plurality of timestamped events and at least one feature from the second plurality of time stamped events.

The operations 4200 further include, at block 4208, providing a visualization of the plurality of feature vectors in a graphical user interface (GUI), the visualization including a clustered representation of the plurality of feature vectors and including an indication of one or more anomalous users of the plurality of users.

Figure 43:
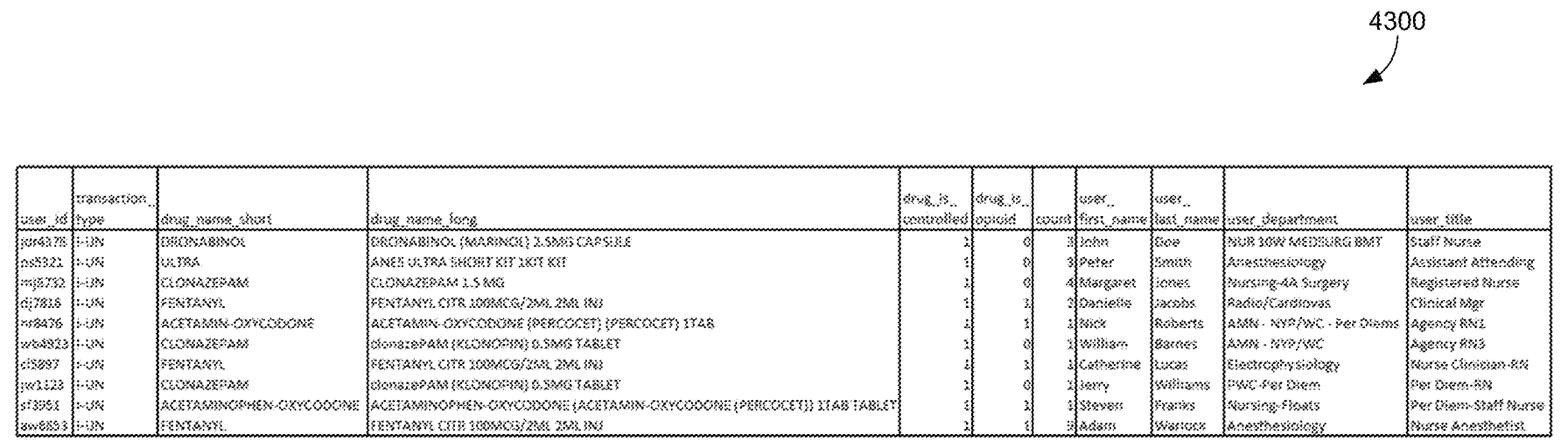

FIG. 43 is a table of sample data from a medication dispensing system according to some embodiments. In one embodiment, the medication security analytics app receives raw data from the medication dispensing system and processes the raw data to generate the data in table 4300. In the example of FIG. 43, each entry for table 4300 includes fields for a user identifier, a transaction type, a short drug name, a long drug name, a controlled drug indicator, an opioid indicator, a count of the number of doses removed, a user first and last name, a user department, and a user title.

Figure 44A:
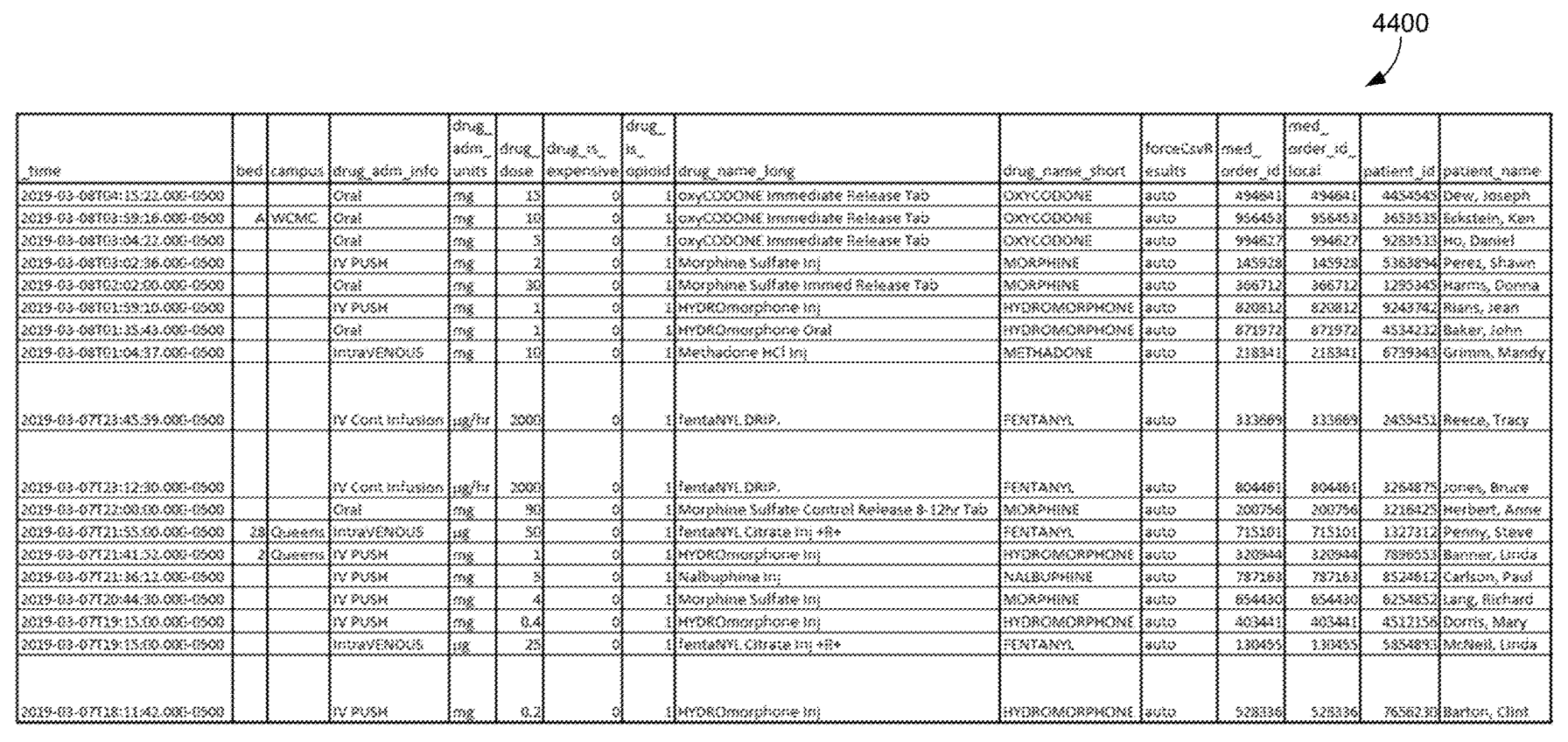

FIGS. 44A-B are tables of sample data from an electronic health records system according to some embodiments. In one embodiment, the medication security analytics app receives raw data from electronic health records or electronic medical records systems and processes the raw data to generate the data in table 4400 and 4410. In the example of FIG. 44A, each entry for table 4400 includes fields for a time, a bed, a campus, method of drug administration, a unit type of the drug administered, a drug dosage, an expensive drug indicator, a short drug name, a long drug name, a force CSV results indicator, a medication order identifier, a local medication order identifier, a patient identifier, and a patient name. Continuing in FIG. 44B, each entry for table 4410 includes fields for a patient pain score, patient pain score notations, a user affiliation, a user department, a user email address, a user first name, a user identifier, a user inactive date, a user last name, a user middle name, a user role, a user status, a user title, and visit identifier.

In the preceding description, various embodiments are described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Reference numerals with suffix letters may be used to indicate that there can be one or multiple instances of the referenced entity in various embodiments, and when there are multiple instances, each does not need to be identical but may instead share some general traits or act in common ways. Further, the particular suffixes used are not meant to imply that a particular amount of the entity exists unless specifically indicated to the contrary. Thus, two entities using the same or different suffix letters may or may not have the same number of instances in various embodiments.

References to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Moreover, in the various embodiments described above, unless specifically noted otherwise, disjunctive language such as the phrase "at least one of A, B, or C" is intended to be understood to mean either A, B, or C, or any combination thereof (e.g., A, B, and/or C). As such, disjunctive language is not intended to, nor should it be understood to, imply that a given embodiment requires at least one of A, at least one of B, or at least one of C to each be present.

What is claimed is:

1. A computer-implemented method, comprising:
    obtaining, by a data intake and query system, user behavior data, wherein the user behavior data includes:
        first data indicating instances of medications checked out from a medication dispensing system by a plurality of users, and
        second data indicating types of interactions performed by the plurality of users with the medication dispensing system,
    generating a first plurality of timestamped events based on the first data and a second plurality of timestamped events based on the second data;
    generating a plurality of feature vectors, each feature vector of the plurality of feature vectors corresponding to a respective user of the plurality of users, wherein each of the plurality of feature vectors is multi-dimensional and includes values for a first plurality of features from the first plurality of timestamped events associated with the respective user and a second plurality of features from the second plurality of timestamped events associated with the respective user;
    using a machine learning algorithm to reduce a number of dimensions of each feature vector of the plurality of feature vectors to three dimensions; and
    generating a visualization plotting the plurality of feature vectors in a three-dimensional space displayed in a graphical user interface (GUI), the visualization including a clustered representation of the plurality of feature vectors and including an indication of one or more anomalous users of the plurality of users.

2. The method of claim 1, wherein a number of dimensions of the plurality of feature vectors is based on a sum of a first number of the first plurality of features from the first plurality of timestamped events and a second number of the second plurality of features from the second plurality of timestamped events.

3. The method of claim 1, wherein the indication of the one or more anomalous users of the plurality of users includes user information for at least one user associated with one or more anomalous user interactions.

4. The method of claim 1, wherein a first numerical value indicating a number of features from the first plurality of timestamped events comprising the first plurality of features from the first plurality of timestamped events indicates a first number of most frequently checked-out drugs from the medication dispensing system to include for each of the plurality of feature vectors, and wherein a second numerical value indicating a number of features from the second plurality of timestamped events comprising the second plurality of features from the second plurality of timestamped events indicates a second number of most frequently performed user interactions with the medication dispensing system to include for each of the plurality of feature vectors.

5. The method of claim 4, wherein the GUI includes an element enabling selection of a feature rendering type, the feature rendering type modifying a features visualization on the GUI of the most frequently checked-out drugs from the medication dispensing system and the most frequently performed user interactions with the medication dispensing system.

6. The method of claim 1, further comprising:
    causing display in the GUI of a representation of the second plurality of timestamped events based on the second data.

7. The method of claim 1, wherein the types of interactions performed by the plurality of users with the medication dispensing system include interactions initiated by the plurality of users logging in, opening bins, returning drugs to a bin, and forced entries into bins.

8. The method of claim 1, wherein the GUI includes a first element enabling selection of a first numerical value indicating a number of features from the first plurality of timestamped events comprising the first plurality of features from the first plurality of timestamped events, and wherein the GUI includes a second element enabling selection of a second numerical value indicating a number of features from the second plurality of timestamped events comprising the second plurality of features from the second plurality of timestamped events.

9. The method of claim 8, further comprising:
    receiving, via the first element, a selection of a third numerical value indicating an updated number of features from the first plurality of timestamped events comprising the first plurality of features from the first plurality of timestamped events;
    generating an updated plurality of feature vectors based on the updated number of features from the first plurality of timestamped events; and
    generating an updated visualization plotting the updated plurality of feature vectors in the three-dimensional space displayed in the GUI.

10. The method of claim 1, wherein the GUI includes an element enabling selection of a subset of a total number of users interacting with the medication dispensing system.

11. The method of claim 1, wherein the GUI includes an element enabling selection of a timeframe.

12. The method of claim 1, wherein the GUI includes an element enabling selection of a medication classification type.

13. The method of claim 1, wherein the indication of the one or more anomalous users of the plurality of users is displayed as a first graphical representation on the visualization, and wherein an indication of one or more non-anomalous users of the plurality of users is displayed as a second graphical representation on the visualization, the first graphical representation different from the second graphical representation.

14. The method of claim 13, wherein the first graphical representation of the indication of the one or more anomalous users is a first color, and the second graphical representation of the indication of one or more non-anomalous users is a second color.

15. The method of claim 1, further comprising:
    normalizing the first data and the second data using a healthcare common information model.

16. The method of claim 1, further comprising:
generating a first dataset results list based on the first plurality of timestamped events, the first dataset results list indicating most frequently checked-out drugs from the medication dispensing system;
generating a second dataset results list based on the second plurality of timestamped events, the second dataset results list indicating most frequently performed user interactions with the medication dispensing system; and
causing a display of the first and second dataset results lists in the GUI.

17. The method of claim 1, further comprising:
receiving third data from a patient medical records database indicating instances of medication administrations to a plurality of patients;
correlating the first data indicating instances of a user checking out a drug from the medication dispensing system by the plurality of users and the third data from the patient medical records database indicating the instances of medication administrations to the plurality of patients; and
generating a third plurality of timestamped events based on the correlation.

18. A non-transitory computer-readable storage medium storing instructions which, when executed by one or more processors, cause performance of operations comprising:
obtaining, by a data intake and query system, user behavior data, wherein the user behavior data includes:
first data indicating instances of medications checked out from a medication dispensing system by a plurality of users, and
second data indicating types of interactions performed by the plurality of users with the medication dispensing system;
generating a first plurality of timestamped events based on the first data and a second plurality of timestamped events based on the second data;
generating a plurality of feature vectors, each feature vector of the plurality of feature vectors corresponding to a respective user of the plurality of users, wherein each of the plurality of feature vectors is multi-dimensional and includes values for a first plurality of features from the first plurality of timestamped events associated with the respective user and a second plurality of features from the second plurality of timestamped events associated with the respective user;
using a machine learning algorithm to reduce a number of dimensions of each feature vector of the plurality of feature vectors to three dimensions; and
generating a visualization plotting the plurality of feature vectors in a three-dimensional space displayed in a graphical user interface (GUI), the visualization including a clustered representation of the plurality of feature vectors and including an indication of one or more anomalous users of the plurality of users.

19. The non-transitory computer-readable storage medium of claim 18, wherein a number of dimensions of the plurality of feature vectors is based on a sum of a first number of the first plurality of features from the first plurality of timestamped events and a second number of the second plurality of features from the second plurality of timestamped events.

20. The non-transitory computer-readable storage medium of claim 18, wherein the indication of the one or more anomalous users of the plurality of users includes user information for at least one user associated with one or more anomalous user interactions.

21. The non-transitory computer-readable storage medium of claim 18, wherein a first numerical value indicating a number of features from the first plurality of timestamped events comprising the first plurality of features from the first plurality of timestamped events indicates a first number of most frequently checked-out drugs from the medication dispensing system to include for each of the plurality of feature vectors, and wherein a second numerical value indicating a number of features from the second plurality of timestamped events comprising the second plurality of features from the second plurality of timestamped events indicates a second number of most frequently performed user interactions with the medication dispensing system to include for each of the plurality of feature vectors.

22. The non-transitory computer-readable storage medium of claim 21, wherein the GUI includes an element enabling selection of a feature rendering type, the feature rendering type modifying a features visualization on the GUI of the most frequently checked-out drugs from the medication dispensing system and the most frequently performed user interactions with the medication dispensing system.

23. The non-transitory computer-readable storage medium of claim 18, wherein the GUI includes a first element enabling selection of a first numerical value indicating a number of features from the first plurality of timestamped events comprising the first plurality of features from the first plurality of timestamped events, and wherein the GUI includes a second element enabling selection of a second numerical value indicating a number of features from the second plurality of timestamped events comprising the second plurality of features from the second plurality of timestamped events.

24. The non-transitory computer-readable storage medium of claim 23, wherein the instructions, when executed by the one or more processors, further cause performance of operations comprising:
receiving, via the first element, a selection of a third numerical value indicating an updated number of features from the first plurality of timestamped events comprising the first plurality of features from the first plurality of timestamped events;
generating an updated plurality of feature vectors based on the updated number of features from the first plurality of timestamped events; and
generating an updated visualization plotting the updated plurality of feature vectors in the three-dimensional space displayed in the GUI.

25. An apparatus, comprising:
one or more processors; and
a non-transitory computer-readable storage medium storing instructions which, when executed by the one or more processors, causes the apparatus to:
obtain, by a data intake and query system, user behavior data, wherein the user behavior data includes:
first data indicating instances of medications checked out from a medication dispensing system by a plurality of users, and
second data indicating types of interactions performed by the plurality of users with the medication dispensing system;
generate a first plurality of timestamped events based on the first data and a second plurality of timestamped events based on the second data;

generate a plurality of feature vectors, each feature vector of the plurality of feature vectors corresponding to a respective user of the plurality of users, wherein each of the plurality of feature vectors is multi-dimensional and includes values for a first plurality of features from the first plurality of timestamped events associated with the respective user and a second plurality of features from the second plurality of timestamped events associated with the respective user;

use a machine learning algorithm to reduce a number of dimensions of each feature vector of the plurality of feature vectors to three dimensions; and generate a visualization plotting the plurality of feature vectors in a three-dimensional space displayed in a graphical user interface (GUI), the visualization including a clustered representation of the plurality of feature vectors and including an indication of one or more anomalous users of the plurality of users.

26. The apparatus of claim 25, wherein a number of dimensions of the plurality of feature vectors is based on a sum of a first number of the first plurality of features from the first plurality of timestamped events and a second number of the second plurality of features from the second plurality of timestamped events.

27. The apparatus of claim 25, wherein the indication of the one or more anomalous users of the plurality of users includes user information for at least one user associated with one or more anomalous user interactions.

28. The apparatus of claim 25, wherein a first numerical value indicating a number of features from the first plurality of timestamped events comprising the first plurality of features from the first plurality of timestamped events indicates a first number of most frequently checked-out drugs from the medication dispensing system to include for each of the plurality of feature vectors, and wherein a second numerical value indicating a number of features from the second plurality of timestamped events comprising the second plurality of features from the second plurality of timestamped events indicates a second number of most frequently performed user interactions with the medication dispensing system to include for each of the plurality of feature vectors.

29. The apparatus of claim 25, wherein the GUI includes a first element enabling selection of a first numerical value indicating a number of features from the first plurality of timestamped events comprising the first plurality of features from the first plurality of timestamped events, and wherein the GUI includes a second element enabling selection of a second numerical value indicating a number of features from the second plurality of timestamped events comprising the second plurality of features from the second plurality of timestamped events.

30. The apparatus of claim 29, wherein the instructions, when executed by the one or more processors, further causes the apparatus to:
receive, via the first element, a selection of a third numerical value indicating an updated number of features from the first plurality of timestamped events comprising the first plurality of features from the first plurality of timestamped events;

generate an updated plurality of feature vectors based on the updated number of features from the first plurality of timestamped events; and generate an updated visualization plotting the updated plurality of feature vectors in the three-dimensional space displayed in the GUI.

\* \* \* \* \*